US007754450B2

(12) United States Patent
Grasso et al.

(10) Patent No.: US 7,754,450 B2
(45) Date of Patent: *Jul. 13, 2010

(54) METHODS OF GENERATING HIGH-PRODUCTION OF ANTIBODIES FROM HYBRIDOMAS CREATED BY IN VITRO IMMUNIZATION

(75) Inventors: Luigi Grasso, Bala Cynwyd, PA (US); Shaohong Liang, West Chester, PA (US); Nicholas C. Nicolaides, Boothwyn, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 1789 days.

This patent is subject to a terminal disclaimer.

(21) Appl. No.: 10/714,228

(22) Filed: Nov. 14, 2003

(65) Prior Publication Data

US 2004/0214288 A1    Oct. 28, 2004

Related U.S. Application Data

(60) Provisional application No. 60/427,165, filed on Nov. 15, 2002, provisional application No. 60/501,650, filed on Sep. 10, 2003.

(51) Int. Cl.
*C12P 21/08* (2006.01)
(52) U.S. Cl. .................................. 435/69.6; 435/70.21
(58) Field of Classification Search ........................ None
See application file for complete search history.

(56) References Cited

U.S. PATENT DOCUMENTS

| | | | |
|---|---|---|---|
| 3,687,808 A | 8/1972 | Merigan, Jr. et al. | |
| 4,376,110 A | 3/1983 | David et al. | 436/548 |
| 4,469,863 A | 9/1984 | Ts'o et al. | 536/27 |
| 4,476,301 A | 10/1984 | Imbach et al. | 536/27 |
| 4,587,044 A | 5/1986 | Miller et al. | 530/211 |
| 4,605,735 A | 8/1986 | Miyoshi et al. | 536/27 |
| 4,667,025 A | 5/1987 | Miyoshi et al. | 536/27 |
| 4,720,459 A | 1/1988 | Winkelhake | 435/240.2 |
| 4,762,779 A | 8/1988 | Snitman | 435/6 |
| 4,789,737 A | 12/1988 | Miyoshi et al. | 536/27 |
| 4,824,941 A | 4/1989 | Gordon et al. | 530/403 |
| 4,828,979 A | 5/1989 | Klevan et al. | 435/6 |
| 4,835,263 A | 5/1989 | Nguyen et al. | 536/27 |
| 4,845,205 A | 7/1989 | Huynh Dinh et al. | 536/28 |
| 4,876,335 A | 10/1989 | Yamane et al. | 536/27 |
| 4,904,582 A | 2/1990 | Tullis | 435/6 |
| 4,948,882 A | 8/1990 | Ruth | 536/27 |
| 4,958,013 A | 9/1990 | Letsinger | 536/27 |
| 4,981,957 A | 1/1991 | Lebleu et al. | 536/27 |
| 5,013,830 A | 5/1991 | Ohtsuka et al. | 536/27 |
| 5,023,243 A | 6/1991 | Tullis | 514/44 |
| 5,034,506 A | 7/1991 | Summerton et al. | 528/391 |
| 5,082,830 A | 1/1992 | Brakel et al. | 514/44 |
| 5,109,124 A | 4/1992 | Ramachandran et al. | 536/27 |
| 5,112,963 A | 5/1992 | Pieles et al. | 536/27 |
| 5,118,800 A | 6/1992 | Smith et al. | 536/23 |
| 5,118,802 A | 6/1992 | Smith et al. | 536/27 |
| 5,130,302 A | 7/1992 | Spielvogel et al. | 514/45 |
| 5,134,066 A | 7/1992 | Rogers et al. | 435/91 |
| 5,138,045 A | 8/1992 | Cook et al. | 536/27 |
| 5,149,797 A | 9/1992 | Pederson et al. | 536/27 |
| 5,166,315 A | 11/1992 | Summerton et al. | 528/406 |
| 5,175,273 A | 12/1992 | Bischofberger et al. | 536/27 |
| 5,177,196 A | 1/1993 | Meyer, Jr. et al. | 536/22.1 |
| 5,185,444 A | 2/1993 | Summerton et al. | 544/81 |
| 5,188,897 A | 2/1993 | Suhadolnik et al. | 428/402.2 |
| 5,194,599 A | 3/1993 | Froehler et al. | 536/26.72 |
| 5,214,134 A | 5/1993 | Weis et al. | 536/25.3 |
| 5,214,136 A | 5/1993 | Lin et al. | 514/44 |
| 5,216,141 A | 6/1993 | Benner | 536/27.13 |
| 5,218,105 A | 6/1993 | Cook et al. | 536/25.31 |
| 5,220,007 A | 6/1993 | Pederson et al. | 536/23.1 |
| 5,235,033 A | 8/1993 | Summerton et al. | 528/391 |
| 5,245,022 A | 9/1993 | Weis et al. | 536/24.5 |
| 5,254,469 A | 10/1993 | Warren, III et al. | 435/188 |
| 5,256,775 A | 10/1993 | Froehler | 536/25.6 |
| 5,258,506 A | 11/1993 | Urdea et al. | 536/23.1 |

(Continued)

FOREIGN PATENT DOCUMENTS

CA    2240609 A1    10/1999

(Continued)

OTHER PUBLICATIONS

Herbert et al, Dictionary of Immunology, 1985, p. 221.*

(Continued)

*Primary Examiner*—Karen A Canella
(74) *Attorney, Agent, or Firm*—Woodcock Washburn, LLP

(57) ABSTRACT

The invention provides methods for generating high titers of high-affinity antibodies from hybridoma cells produced by fusing myeloma cells with in vitro immunized donor cells. The hybridoma cells or mammalian expression cells with cloned antibody genes from the hybridomas producing the high-affinity antibodies may be mismatch repair defective due to defects of endogenous mismatch repair subunits of through expression of a dominant negative allele of a mismatch repair gene which allows the hybridoma cell to be hypermutable, may be rendered hypermutable by chemical means, or may be naturally mismatch repair deficient. High-affinity antibodies and high titer producer cells producing antibodies may be prepared by the methods of the invention.

45 Claims, 10 Drawing Sheets

U.S. PATENT DOCUMENTS

| | | | |
|---|---|---|---|
| 5,262,536 A | 11/1993 | Hobbs, Jr. | 546/25 |
| 5,264,423 A | 11/1993 | Cohen et al. | 514/44 |
| 5,264,562 A | 11/1993 | Matteucci | 536/23.1 |
| 5,272,250 A | 12/1993 | Spielvogel et al. | 530/300 |
| 5,264,564 A | 1/1994 | Cohen et al. | 514/44 |
| 5,276,019 A | 1/1994 | Cohen et al. | 514/44 |
| 5,276,423 A | 1/1994 | Breit et al. | 338/308 |
| 5,278,302 A | 1/1994 | Caruthers et al. | 536/24.5 |
| 5,286,717 A | 2/1994 | Cohen et al. | 514/44 |
| 5,292,873 A | 3/1994 | Rokita et al. | 536/24.3 |
| 5,317,098 A | 5/1994 | Shizuya et al. | 536/23.1 |
| 5,319,080 A | 6/1994 | Leumann | 536/27.1 |
| 5,321,131 A | 6/1994 | Agrawal et al. | 536/25.34 |
| 5,359,044 A | 10/1994 | Cook et al. | 536/23.1 |
| 5,366,878 A | 11/1994 | Pederson et al. | 435/91.3 |
| 5,367,066 A | 11/1994 | Urdea et al. | 536/24.3 |
| 5,371,241 A | 12/1994 | Brush | 549/220 |
| 5,391,723 A | 2/1995 | Priest | 536/23.1 |
| 5,393,878 A | 2/1995 | Leumann | 536/28.2 |
| 5,399,676 A | 3/1995 | Froehler | 536/23.1 |
| 5,403,711 A | 4/1995 | Walder et al. | 435/6 |
| 5,405,938 A | 4/1995 | Summerton et al. | 528/406 |
| 5,405,939 A | 4/1995 | Suhadolnik et al. | 530/322 |
| 5,414,077 A | 5/1995 | Lin et al. | 536/24.3 |
| 5,416,203 A | 5/1995 | Letsinger | 536/25.34 |
| 5,432,272 A | 7/1995 | Benner | 536/25.3 |
| 5,434,257 A | 7/1995 | Matteucci et al. | 536/24.3 |
| 5,446,137 A | 8/1995 | Maag et al. | 536/23.1 |
| 5,451,463 A | 9/1995 | Nelson et al. | 428/402 |
| 5,453,496 A | 9/1995 | Caruthers et al. | 536/24.5 |
| 5,455,233 A | 10/1995 | Spielvogel et al. | 514/44 |
| 5,457,187 A | 10/1995 | Gmeiner et al. | 536/25.5 |
| 5,459,255 A | 10/1995 | Cook et al. | 536/27.13 |
| 5,466,677 A | 11/1995 | Baxter et al. | 514/44 |
| 5,466,786 A | 11/1995 | Buhr et al. | 536/26.26 |
| 5,470,967 A | 11/1995 | Huie et al. | 536/24.3 |
| 5,476,925 A | 12/1995 | Letsinger et al. | 536/23.1 |
| 5,484,908 A | 1/1996 | Froehler et al. | 536/24.31 |
| 5,486,603 A | 1/1996 | Buhr | 536/24.3 |
| 5,489,677 A | 2/1996 | Sanghvi et al. | 536/22.1 |
| 5,491,133 A | 2/1996 | Walder et al. | 514/44 |
| 5,502,177 A | 3/1996 | Matteucci et al. | 536/26.6 |
| 5,510,475 A | 4/1996 | Agrawal et al. | 536/24.3 |
| 5,512,439 A | 4/1996 | Hornes et al. | 435/6 |
| 5,512,667 A | 4/1996 | Reed et al. | 536/24.31 |
| 5,514,785 A | 5/1996 | Van Ness et al. | 536/22.1 |
| 5,519,126 A | 5/1996 | Hecht | 536/24.3 |
| 5,519,134 A | 5/1996 | Acevedo et al. | 544/243 |
| 5,525,465 A | 6/1996 | Haralambidis et al. | 435/6 |
| 5,525,711 A | 6/1996 | Hawkins et al. | 536/22.1 |
| 5,527,899 A | 6/1996 | Froehler | 536/25.3 |
| 5,530,101 A | 6/1996 | Queen et al. | 530/387.3 |
| 5,536,821 A | 7/1996 | Agrawal et al. | 536/22.1 |
| 5,539,082 A | 7/1996 | Nielsen et al. | 530/300 |
| 5,541,306 A | 7/1996 | Agrawal et al. | 536/22.1 |
| 5,541,307 A | 7/1996 | Cook et al. | 536/23.1 |
| 5,541,313 A | 7/1996 | Ruth | 536/24.3 |
| 5,545,730 A | 8/1996 | Urdea et al. | 536/28.51 |
| 5,550,111 A | 8/1996 | Suhadolnik et al. | 514/44 |
| 5,552,538 A | 9/1996 | Urdea et al. | 536/24.3 |
| 5,552,540 A | 9/1996 | Haralambidis | 536/25.34 |
| 5,561,225 A | 10/1996 | Maddry et al. | 536/23.1 |
| 5,563,253 A | 10/1996 | Agrawal et al. | 536/22.1 |
| 5,565,350 A | 10/1996 | Kmiec | 435/172.3 |
| 5,565,552 A | 10/1996 | Magda et al. | 534/11 |
| 5,565,555 A | 10/1996 | Froehler et al. | 536/26.22 |
| 5,567,810 A | 10/1996 | Weis et al. | 536/25.3 |
| 5,567,811 A | 10/1996 | Misiura et al. | 536/25.34 |
| 5,571,799 A | 11/1996 | Tkachuk et al. | 514/47 |
| 5,574,142 A | 11/1996 | Meyer, Jr. et al. | 536/23.1 |
| 5,576,427 A | 11/1996 | Cook et al. | 536/23.1 |
| 5,578,717 A | 11/1996 | Urdea et al. | 536/26.1 |
| 5,578,718 A | 11/1996 | Cook et al. | 536/27.21 |
| 5,580,731 A | 12/1996 | Chang et al. | 435/6 |
| 5,585,481 A | 12/1996 | Arnold, Jr. et al. | 536/25.33 |
| 5,587,361 A | 12/1996 | Cook et al. | 514/44 |
| 5,587,371 A | 12/1996 | Sessler et al. | 514/185 |
| 5,587,469 A | 12/1996 | Cook et al. | 536/23.1 |
| 5,591,584 A | 1/1997 | Chang et al. | 435/6 |
| 5,591,722 A | 1/1997 | Montgomery et al. | 514/45 |
| 5,594,121 A | 1/1997 | Froehler et al. | 536/23.5 |
| 5,595,726 A | 1/1997 | Magda et al. | 424/9.61 |
| 5,596,086 A | 1/1997 | Matteucci et al. | 536/22.1 |
| 5,596,091 A | 1/1997 | Switzer | 536/24.5 |
| 5,597,696 A | 1/1997 | Linn et al. | 435/6 |
| 5,597,909 A | 1/1997 | Urdea et al. | 536/24.3 |
| 5,599,923 A | 2/1997 | Sessler et al. | 540/145 |
| 5,599,928 A | 2/1997 | Hemmi et al. | 540/474 |
| 5,602,240 A | 2/1997 | De Mesmaeker et al. | 536/22.1 |
| 5,608,046 A | 3/1997 | Cook et al. | 536/23.1 |
| 5,610,289 A | 3/1997 | Cook et al. | 536/25.34 |
| 5,610,300 A | 3/1997 | Altmann et al. | 544/244 |
| 5,614,617 A | 3/1997 | Cook et al. | 536/23.1 |
| 5,618,704 A | 4/1997 | Sanghvi et al. | 435/91.5 |
| 5,623,065 A | 4/1997 | Cook et al. | 536/23.1 |
| 5,623,070 A | 4/1997 | Cook et al. | 536/27.6 |
| 5,625,050 A | 4/1997 | Beaton et al. | 536/24.1 |
| 5,627,053 A | 5/1997 | Usman et al. | 435/91.1 |
| 5,633,360 A | 5/1997 | Bischofberger et al. | 536/22.1 |
| 5,639,873 A | 6/1997 | Barascut et al. | 536/25.3 |
| 5,645,985 A | 7/1997 | Froehler et al. | 435/6 |
| 5,646,265 A | 7/1997 | McGee | 536/25.34 |
| 5,646,269 A | 7/1997 | Matteucci et al. | 536/26.7 |
| 5,652,355 A | 7/1997 | Metelev et al. | 536/24.5 |
| 5,652,356 A | 7/1997 | Agrawal | 536/24.5 |
| 5,658,873 A | 8/1997 | Bertsch-Frank et al. | 510/375 |
| 5,663,312 A | 9/1997 | Chaturvedula | 536/22.1 |
| 5,670,633 A | 9/1997 | Cook et al. | 536/23.1 |
| 5,672,697 A | 9/1997 | Buhr et al. | 536/26.7 |
| 5,677,437 A | 10/1997 | Teng et al. | 536/23.1 |
| 5,677,439 A | 10/1997 | Weis et al. | 536/23.1 |
| 5,681,941 A | 10/1997 | Cook et al. | 536/23.1 |
| 5,688,941 A | 11/1997 | Cook et al. | 536/25.3 |
| 5,700,920 A | 12/1997 | Altmann et al. | 536/221 |
| 5,700,922 A | 12/1997 | Cook | 536/23.1 |
| 5,714,331 A | 2/1998 | Buchardt et al. | 435/6 |
| 5,719,262 A | 2/1998 | Buchardt et al. | 530/300 |
| 5,721,218 A | 2/1998 | Froehler | 514/44 |
| 5,750,692 A | 5/1998 | Cook et al. | 544/253 |
| 5,763,588 A | 6/1998 | Matteucci et al. | 536/22.1 |
| 5,792,608 A | 8/1998 | Swaminathan et al. | 435/6 |
| 5,792,747 A | 8/1998 | Schally et al. | 514/12 |
| 5,830,653 A | 11/1998 | Froehler et al. | 435/6 |
| 6,005,096 A | 12/1999 | Matteucci et al. | 536/26.6 |
| 6,146,894 A | 11/2000 | Nicolaides et al. | 435/440 |
| 6,333,318 B1 * | 12/2001 | Evans et al. | 514/171 |
| 2003/0143682 A1 | 7/2003 | Nicolaides et al. | 435/69.1 |

FOREIGN PATENT DOCUMENTS

| | | |
|---|---|---|
| WO | PCT/US92/09196 | 10/1992 |
| WO | 93/21952 A1 | 11/1993 |
| WO | WO 98/39352 | 9/1998 |
| WO | WO 99/14226 | 3/1999 |
| WO | WO 01/59092 A2 | 8/2001 |
| WO | WO01/88192 A3 | 11/2001 |
| WO | WO 02/37967 A1 | 5/2002 |
| WO | WO 02/054856 A1 | 7/2002 |
| WO | WO 03/012130 A1 | 2/2003 |
| WO | WO 03/062435 A1 | 7/2003 |
| WO | WO2004/009782 A3 | 1/2004 |
| WO | 2004024871 A2 | 3/2004 |

WO 2005/011735 A1 2/2005

OTHER PUBLICATIONS

Sharon (PNAS, 1990, vol. 87, pp. 4814-4817).*
Yelton et al (Journal of Immunology, 1995, vol. 155, pp. 1994-2004).*
Borrebaeck (Adv Drug Delivery Reviews, 1988, vol. 2, pp. 143-165).*
Zan et al (Immunity, 2001, vol. 14, pp. 643-653).*
Allen, D.J., et al., "MutS mediates heteroduplex loop formation by a translocation mechanism," *EMBO J.*, 1997, 16(14), 4467-4476.
Antoni, G., et al., "An interactive computer program for the determination of the binding constants of monoclonal antibodies by nonlinear regression analysis of radioimmunoassay data," *J. of Immunol. Meth.*, 1985, 83, 61-68.
Ausubel, et al., Current Protocols in Molecular Biology, *John Wiley & Sons, NY*, 1998.
Belmont, P., et al., "Synthesis and study of a new adenine—acridine tandem, inhibitor of exonuclease III," *Bioorg. Med. Chem. Lett.*, 2000, 10, 293-295.
Bjornson, K.P., et al., "Modulation of MutS ATP hydrolysis by DNA cofactors," *Biochem.* 2000, 39, 3176-3183.
Borrebaeck, C.A.K., "Human mAbs produced by primary in-vitro immunization," *Immunol. Today*, 1988, 9(11), 355-359.
Brown, J.P., et al., "Protein antigens of normal and malignant human cells identified by immunoprecipitation with monoclonal antibodies," *J. Biol. Chem.*, Jun. 10, 1980, 255(11), 4980-4983.
Brown, J.P., et al., "Structural characterization of human melanoma-associated antigen p97 with monoclonal antibodies," *J. of Immunol.*, Aug. 1981, 127(2), 539-546.
Chino, M., et al., "Effect of a novel antibiotic, heliquinomycin, on DNA helicase and cell growth," *J. Antibiot. (Tokyo)*, May 1998, 51(5), 480-486.
Cole, S.P.C., et al., "The EBV-hybridoma technique and its application to human lung cancer," Monoclonal Antibodies and Cancer Therapy, *Alan R. Liss, Inc.*, 1985, 77-96.
Cote, R.J., et al., "Generation of human monoclonal antibodies reactive with cellular antigens," *Proc. Natl. Acad. Sci. USA*, Apr. 1983, 80, 2026-2030.
Crooke, S.T., et al., "Pharmacokinetic properties of several novel oligonucleotide analogs in mice," *J. Pharmacol. Exp. Ther.*, 1996, 277(2), 923-937.
Emery, S.C., et al., "Strategies for humanizing antibodies," in: Antibody Engineering, Borrebaeck, C.A.K. (Ed.), *Oxford University Press, NY*, 1995, 159-183.
Englisch, U., et al., "Chemically modified oligonucleotides as probes and inhibitors," *Angewandte Chemie (International Edition)*, Jun. 1991, 30(6), 613-722.
Fiedler, U., et al., "High-level production and long-term storage of engineered antibodies in transgenic tobacco seeds," *Bio/Technology*, Oct. 1995, 13, 1090-1093.
Fire, A., et al., "Potent and specific genetic interference by double-stranded RNA in *Caenorhabditis elegans*," *Nature*, Feb. 19, 1998, 391 806-811.
Gait, M.J., "Oligoribonucleotides as drugs?," Antisense Research and Applications, Crooke, S.T., et al. (Eds.), CRC Press, 1993, Chapt. 16, 289-302.
Galfre, G., et al., "Antibodies to major histocompatibility antigens produced by hybrid cell lines," *Nature*, Apr. 7, 1977, 266, 550-552.
Galio, L., et al., "ATP hydrolysis-dependent formation of a dynamic ternary nucleoprotein complex with MutS and MutL," *Nucl. Acids Res.*, 1999, 27(11), 2325-2331.
Gefter, M.L., et al., "A simple method for polyethylene glycol-promoted hybridization of mouse myeloma cells," *Somatic Cell Genet.*, 1977, 3(2), 231-236.
Glaser, V., "Can ReoPro repolish tarnished monoclonal therapeutics?," *Nat. Biotechnol.*, Oct. 1996, 14, 1216-1217.
Graham, F.L., et al., "Characteristics of a human cell line transformed by DNA from human adenovirus type 5," *J. Gen. Virol.*, 1977, 36, 59-72.
Grishok, A., et al.,"Genetic requirements for inheritance of RNAi in C. elegans," *Science*, Mar. 31, 2001, 287, 2494-2497.

Horii, A., et al., "Cloning, characterization and chromosomal assignment of the human genes homologous to yeast PMS1, a member of mismatch repair genes," *Biochem. Biophys. Res. Commun.*, 1994, 204(3), 1257-1264.
Huang, Y.-C., et al., "$N$-ethylmaleimide profiling of yeast NADP-dependent isocitrate dehydrogenase," *Arch. Biochem. Biophys.*, Jan. 10, 1995, 316(1), 485-492.
Kabanov, A.V., et al., "A new class of antivirals: antisense olgonucleotides combined with a hydrophobic substituent effectively inhibit influenza virus reproduction and synthesis of virus-specific proteins in MDCK cells," *FEBS Lett.*, 1990, 259, 327-330.
Kaufman, et al. (Eds.), Handbook of Molecular and Cellular Methods in Biology and Medicine, *CRC Press, Boca Raton*, 1995.
Kenneth, in Monoclonal Antibodies: A New Dimension in Biological Analyses, *Plenum Publishing Corp., NY, NY*, 1980.
Khazaeli, M.B., et al., "Human immune response to monoclonal antibodies," *J. of Immunother.*, 1994, 15, 42-52.
Kitagawa, T., et al., "Enzyme coupled immunoassay of insulin using a novel reagent," *J. Biochem.*, 1976, 79, 233-236.
Köhler, G., et al., "Continuous cultures of fused cells secreting antibody of predefined specificity," *Nature*, Aug. 7, 1975, 256, 495-497.
Kozbor, D., et al., "The production of monoclonal antibodies from human lymphocytes," *Immunology Today*, 1983, 4(3), 72-79.
Kroschwitz, J.I.(Ed.), "Polynucleotides," The Concise Encyclopedia of Polymer Science and Engineering, *John Wiley & Sons*, 1990, 858-859.
Kukhanova M., et al., "Unique inhibitory effect of 1-(2'-deoxy-2'-fluoro-β-L-arabinofuranosyl_-5-methyluracil 5'-triphosphate on Epstein-barr virus nd human DNA polymerases," *Biochem. Pharmacol.*, 1998, 55, 1181-1187.
Kuwakado, K., et al., "Aphidicolin potentiates apoptosis induced by arabinosyl nucleosides in human myeloid leukemia cell lines," *Biochem. Pharmacol.*, 1993, 46(11), 1909-1916.
Lehninger, A.L., "The molecular basis of cell structure and function," Biochemistry, $2^{nd}$ Ed., *Worth Publishers, Inc.*, 1975, 72-77.
Lerner, E.A., "How to make a hybridoma," *Yale J. Biol. and Med.*, 1981, 54, 387-402.
Letsinger, R.L., et al., "Cholesteryl-conjugated oligonucleotides: synthesis, properties and activity as inhibitors of replication of human immunodeficiency virus in cell culture," *Proc. Natl. Acad. Sci. USA*, 1989, 86, 6553-6556.
Manoharan, M., et al., "Chemical modifications to improve uptake and bioavailability of antisense oligonucleotides," *Ann. NY Acad. Sci.*, 1992, 660, 306-309.
Manoharan, M., et al., "Introduction of a lipophilic thioether tether in the mirror groove of nucleic acids for antisense applications," *Bioorg. Med. Chem. Let.*, 1993, 3, 2765-2770.
Manoharan, M., et al., "Cholic acid-oligonucliotide conjugates for antisense applications," *Bioorg. Med. Chem. Let.*, 1994, 4, 1053-1060.
Manoharan, M., et al., "Oligonucleotide conjugates: alteration of the pharmacokinetic properties of antisense agents," *Nucleosides & Nucleotides*, 1995, 14, 969-973.
Manoharan, M., et al., "Lipidic nucleic acids," *Tetrahedron Lett.*, 1995, 36(21), 3651-3654.
Martin, v.-P., et al., "Ein neuer zugang zu 2'-O-alkylribonucleosiden und eigenschaften deren oligonucleotide," *Helv. Chim. Acta*, 1995, 78, 486-504 (English abstract).
Martin, S.J., et al., "Induction of apoptosis (programmed cell death) in human leukemic HL-60 cells by inhibition of RNA or protein synthesis," *J. of Immunol.*, Sep. 15, 1990, 145(6), 1859-1867.
Marx, J., "Interfering with gene expression," *Science*, May 26, 2000, 288, 1370-1372.
Mather, J.P., "Establishment and characterization of two distinct mouse testicular epithelial cell lines," *Biol. of Reprod.*, 1980, 23, 243-252.
Mather, J.P., et al., "culture of testicular cells in hormone-supplemented serum-free medium," *Annals N.Y. Acad. Sci.*, 1982, 383, 44-68.
McPherson (Ed.), Directed Mutagenesis: A Practical Approach, *IRL Press, Oxford*, 1991.

Mishra, R.K., et al., "Improved leishmanicidal effect of phosphorotioate antisense oligonucleotides by LDL-medicated delivery," *Biochim. Et Biophysica*, 1995, 1264, 229-237.

Müller, R., "calculation of average antibody affinity in anti-hapten sera from data obtained by competitive radioimmunoassay," *J. Immunol. Meth.*, 1980, 34, 345-352.

Neuberger, M., et al., "Mice perform a human repertoire," *Nature*, Mar. 6, 1997, 386, 25-26.

Nicolaides, N.C., et al., "Genomic organization of the human *PMS2* gene family," *Genomics*, 1995, 30, 195-206.

Nicolaides, N.C., et al., "A naturally occurring *hPMS2* mutation can confer a dominant negative mutator phenotype," *Mol. Cell. Biol.*, XP-002165242, Mar. 1998, 18(3), 1635-1641.

Nielsen, P.E., et al., "Sequence-selective recognition of DNA by strand displacement with a thymine-substituted polymide," *Science*, 1991, 254, 1497-1500.

Oberhauser, B., et al., "Effective incorporation of 2'-O-methyl-oligoribonucleotides into liposomes and enhanced cell association through modification with thiocholesterol," *Nucl. Acids Res.*, 1992, 20(3), 533-538.

Ono, K., et al., "Inhibition of DNA polymerase α by 2',3'-dideoxyribonucleoside 5'- triphosphates: effect of manganese ion," *Biomed. & Pharmacother.*, 1984, 38, 382-389.

Reff, M.E., "High-level production of recombinant immunoglobulins in mammalian cells," *Curr. Opin. Biotechnol.*, 1993, 4, 573-576.

Saez-Llorens, X., et al., "Safety and pharmacokinetics of an intramuscular humanized monoclonal antibody to respiratory syncytial virus in premature infants and infants with bronchopulmonary dysplasia," *Pediat. Infect. Disc. J.*, Sep. 1998, 17(9), 787-791.

Saison-Behmoaras, T., et al., "Short modified antisense oligonucleotides directed against Ha-*ras* point mutation induced selective cleavage of the mRNA and inhibit T24 cells proliferation," *Embo J.*, 1991, 10(5), 1111-1118.

Sambrook, et al., Molecular Cloning: A Laboratory Manual, $2^{nd}$ Ed., *Cold Spring Harbor Laboratory Press, Plainview, NY*, 1989.

Sanghvi, Y.S., "Heterocyclic base modifications in nucleic acids and their applications in antisense oligonucleotides," Antisense Research and Applications, Crooke, et al. (Eds.), *CRC Press*, 1993, 273-288.

Sharp, P.A., et al., "RNA Interference," *Science*, Mar. 31, 2000, 287, 2431-2433.

Shea, R.G., et al., "Synthesis, hybridization properties and antiviral activity of lipidoligodeoxynucleotide conjugates," *Nucl. Acids Res.*, 1990, 18, 3777-3783.

Shield, C.F., III, et al., "A cost-effectiveness analysis of OKT3 induction therapy in cadaveric kidney transplantation," *Am. J. Kidney Dis.*, Jun. 1996, 27(6), 855-864.

Svinarchuk, F.P., et al., "Inhibition of HIV proliferation in MT-4 cells by antisense oligonucleotide conjugated to lipophilic groups," *Biochimie*, 1993, 79, 49-54.

Thorell, et al., Radioimmunoassay and Related Techniques: Methodology and Clinical Applications, 1978.

Urlaub, G., et al., "Isolation of chinese hamster cell mutants deficient in dihydrofolate," *Proc. Natl. Acad. Sci. USA*, Jul. 1980, 77(7), 4216-4220.

Waldman, T., et al., "p21 is necessary for the p53-mediated $G_1$ arrest in human cancer cells," *Cancer Res.*, Nov. 15, 1995, 55, 5187-5190.

Weiner, L.M., "Monoclonal antibody therapy of cancer," *Semin. In Oncol.*, Oct. 1999, 26(5), 43-51.

Yeh, M.-Y., et al., "A cell-surface antigen which is present in the ganglioside fraction and shared by human melanomas," *Int. J. Cancer*, 1982, 29, 269-275.

Yeh, M.-Y., et al., "Cell surface antigens of human melanoma identified by monoclonal antibody," *Proc. Natl. Acad. Sci. USA*, Jun. 1979, 76(6), 2927-2931.

Zafiropoulos, A., et al., "Induction of antigen-specific isotype switching by in vitro immunization of human naïve B lymphocytes," *J. of Immunological Methods*, 1997, 200, 181-190.

Guzman, J., et al., "In vitro immunization: generation of neutralizing monoclonal antibodies to human interleukin-10," J. of Immunological Methods, 1995, 179(2), 265-268.

Ho, M.K., et al., "In vitro immunization of human lymphocytes. I. Production of human monoclonal antibodies against bombes in and tetanus toxoid," J. of Immunology, 1985, 135(6), 3831-3838.

Kim, N., et al., "The role of DNA repair in somatic hypermutation of immunoglobulin genes," J. of Experimental medicine, 1998, 187(11), 1729-1733.

Martin, A., et al., "Aid and mismatch repair in antibody diversification," Nature Reviews, Immunology, 2002, 2(8), 605-614.

Pardue, R.L., et al., "Production of monoclonal antibodies against calmodulin by in vitro immunization of spleen cells," J. of Cell Biology, 1983, 96(4), 1149-1154.

Spencer, J. et al., "Characteristics of Sequences Around Individual Nucleotide Substitutions I $IgV_H$ Genes Suggest different GC and AT Mutators," *Journal of Immunology*, 1999, 162, 6596-6601.

Reynaud, C-A. et al., "Mismatch repair and immunoglobulin gene hypermutation: did we learn something?" *Immunology Today*, Nov. 1999, 20, 522-527.

Bigger, C. A. H. et al., "Mutational spectra for polycyclic aromatic hydrocarbons in the *supF* target gene," *Mutation Research*, 2000, 450, 75-93.

Guzman, J., et al., "In vitro immunization: generation of neutralizing monoclonal antibodies to human interleukin-10," J. of Immunol. Methods, 1995, 179, 265-268.

Mironov, N., et al., "Introduction of mutations in mismatch repair-proficient and—deficient human colon cancer cell lines by carcinogens producing different types of DNA damage," Proc. Of the Amer. Assoc. for Cancer Res., 1999, 40, p. 625.

Borrebaeck et al., "Human monoclonal antibodies produced by primary in vitro immunization of peripheral blood lymphocytes," Proc. Natl. Acad. Sci, USA, 1998, 85, 3995-3999.

MA, A-H., "Creation of Isogenic Mismatch Repair Deficient Cell Lines From a Non-RER Human Colon Cancer," Environmental and Molecular Mutagenesis, 1998, vol. 31(Suppl 29), p. 31.

Irving, R.A. et al, "Affinity maturation of recombinant antibodies using *E. coli* mutator cells," Immunotechnology, 1996, 2, 127-143.

Wiesendanger, M. et al., "Somatic Hypermutation, Transcription, and DNA Mismatch Repair", Cell, 1998, 94, 415-418.

Nicolaides N.C. et al., "Morphogenics as a Tool for Target Discovery and Drug Development", Ann. N.Y. Acad. Sci, 2005, 1059, 86-96.

Green, N.S. et al., "Immunoglobulin hypermutation in cultured cells," Immunol. Rev., 1998, 162, 77-87.

Cascalho, M. et al., "Mismatch Repair Co-opted by Hermutation," Science, 1998, 279, 1207-1210.

\* cited by examiner

Fig. 6A
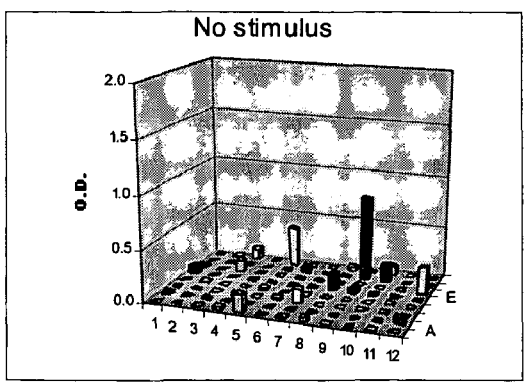
Fig. 6B
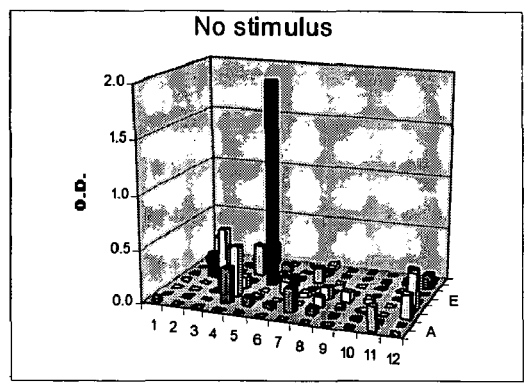
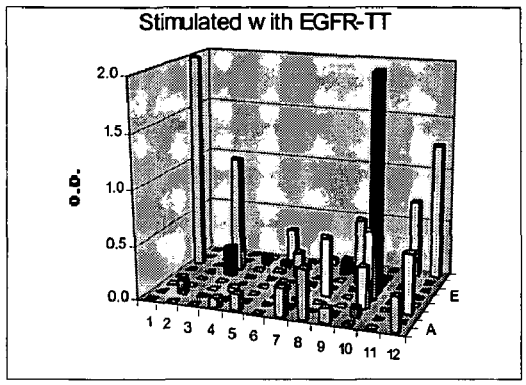
Fig. 6C
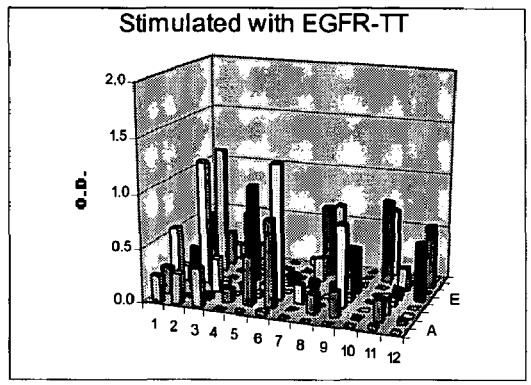
Fig. 6D

METHODS OF GENERATING HIGH-PRODUCTION OF ANTIBODIES FROM HYBRIDOMAS CREATED BY IN VITRO IMMUNIZATION

CROSS-REFERENCE TO RELATED APPLICATIONS

This Application claims the benefit of U.S. Provisional Application No. 60/427,165 filed Nov. 15, 2002 and U.S. Provisional Application No. 60/501,650 filed Sep. 10, 2003, the disclosures of which are hereby incorporated by reference in their entirety.

FIELD OF THE INVENTION

The invention relates to the generation of hybridoma cells that produce high-affinity antibodies in high titers. More specifically, the invention relates to the use of an in vitro immunization method in conjunction with hybridoma technology using dominant negative mismatch repair genes or chemical inhibitors of mismatch repair to produce high titers of antigen specific antibodies of the IgG subclass, that bind to the antigen with high affinity.

BACKGROUND OF THE RELATED ART

The use of antibodies to block the activity of foreign and/or endogenous polypeptides provides an effective and selective strategy for treating the underlying cause of disease. In particular is the use of monoclonal antibodies (MAb) as effective therapeutics such as the FDA approved ReoPro (Glaser, (1996) *Nat. Biotechnol.* 14:1216-1217), an anti-platelet MAb from Centocor; Herceptin (Weiner, (1999) *Semin. Oncol.* 26:43-51), an anti-Her2/neu MAb from Genentech; and Synagis (SaezLlorens, et al. (1998) *Pediat. Infect. Dis. J.* 17:787-791), an anti-respiratory syncytial virus MAb produced by Medimmune.

Standard methods for generating MAbs against candidate protein targets are known by those skilled in the art. Briefly, rodents such as mice or rats are injected with a purified antigen in the presence of adjuvant to generate an immune response (Shield, et al. (1996) *Am. J. Kidney Dis.* 27: 855-864). Rodents with positive immune sera are sacrificed and splenocytes are isolated. Isolated splenocytes are fused to melanomas to produce immortalized cell lines that are then screened for antibody production. Positive lines are isolated and characterized for antibody production. The direct use of rodent MAbs as human therapeutic agents were confounded by the fact that human anti-rodent antibody (HARA) responses occurred in a significant number of patients treated with the rodent-derived antibody (Khazaeli, et al., (1994) *Immunother.* 15:42-52). In order to circumvent the problem of HARA, the grafting of the complementarity determining regions (CDRs), which are the critical motifs found within the heavy and light chain variable regions of the immunoglobulin (Ig) subunits making up the antigen binding domain, onto a human antibody backbone found these chimeric molecules are able to retain their binding activity to antigen while lacking the HARA response (Emery and Harris, "Strategies for humanizing antibodies" In: ANTIBODY ENGINEERING, C. A. K. Borrebaeck (Ed.) Oxford University Press, NY, 1995. pp. 159-183. A common problem that exists during the "humanization" of rodent-derived MAbs (referred to hereafter as HAb) is the loss of binding affinity due to conformational changes in the three-dimensional structure of the CDR domain upon grafting onto the human Ig backbone (U.S. Pat. No. 5,530,101 to Queen et al.). To overcome this problem, additional HAb vectors are usually needed to be engineered by inserting or deleting additional amino acid residues within the framework region and/or within the CDR coding region itself in order to recreate high affinity HAbs (U.S. Pat. No. 5,530,101 to Queen et al.). This process is a very time consuming procedure that involves the use of expensive computer modeling programs to predict changes that may lead to a high affinity HAb. In some instances the affinity of the HAb is never restored to that of the MAb, rendering them of little therapeutic use.

Another problem that exists in antibody engineering is the generation of stable, high yielding producer cell lines that is required for manufacturing of the molecule for clinical materials. Several strategies have been adopted in standard practice by those skilled in the art to circumvent this problem. One method is the use of Chinese Hamster Ovary (CHO) cells transfected with exogenous Ig fusion genes containing the grafted human light and heavy chains to produce whole antibodies or single chain antibodies, which are a chimeric molecule containing both light and heavy chains that form an antigen-binding polypeptide (Reff, M. E. (1993) *Curr. Opin. Biotechnol.* 4:573-576). Another method employs the use of human lymphocytes derived from transgenic mice containing a human grafted immune system or transgenic mice containing a human Ig gene repertoire. Yet another method employs the use of monkeys to produce primate MAbs, which have been reported to lack a human anti-monkey response (Neuberger and Gruggermann (1997) *Nature* 386:25-26). In all cases, the generation of a cell line that is capable of generating sufficient amounts of high affinity antibody poses a major limitation for producing sufficient materials for clinical studies. Because of these limitations, the utility of other recombinant systems such as plants are currently being explored as systems that will lead to the stable, high-level production of humanized antibodies (Fiedler and Conrad (1995) *Bio/Technology* 13:1090-1093).

One strategy to overcome the problem of human reactions against foreign antibodies is to stimulate human immunoglobulin-producing cells in vitro. Various attempts to stimulate human antibody production in vitro typically have resulted in low affinity antibodies of the IgM subclass (Zafiropoulos et al (1997) *J. Immunological Methods* 200:181-190).

A method for generating diverse antibody sequences within the variable domain that results in HAbs and MAbs with high binding affinities to antigens would be useful for the creation of more potent therapeutic and diagnostic reagents respectively. Moreover, the generation of randomly altered nucleotide and polypeptide residues throughout an entire antibody molecule will result in new reagents that are less antigenic and/or have beneficial pharmacokinetic properties. The invention described herein is directed to the use of random genetic mutation throughout an antibody structure in vitro by blocking the endogenous mismatch repair (MMR) activity of a host cell producing immunoglobulins that encode biochemically active antibodies. The invention also relates to methods for repeated in vitro genetic alterations and selection for antibodies with enhanced binding and pharmacokinetic profiles.

In addition, the ability to develop genetically altered host cells that are capable of secreting increased amounts of antibody also will provide a valuable method for creating cell hosts for product development. The invention described herein is further directed to the creation of genetically altered cell hosts with increased antibody production via the blockade of MMR. The invention facilitates the generation of high affinity antibodies and the production of cell lines with elevated levels of antibody production derived from hybridoma cells. The invention described herein provides methods for generating antigen-specific monoclonal antibodies (mAbs). Other advantages of the present invention are described in the examples and figures described herein.

SUMMARY OF THE INVENTION

The invention provides methods for producing hybridoma cells producing high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

In some embodiments, the dominant negative allele of a mismatch repair gene comprises a truncation mutation of the PMS2 gene (e.g., a PMS2-134 gene). In some embodiments of the method of the invention, antibodies are screened using an ELISA-based assay or other assays that can measure antibody-antigen binding. In some embodiments, the screening assays screen for hypermutated hybridomas that produce higher affinity antibodies than those produced by the parental hybridomas. In other embodiments, the screening assays screen for hypermutated hybridomas that produce antibodies in higher titers than the parental hybridomas.

In some embodiments of the method of the invention, the method further comprises inactivation of the dominant negative allele of the mismatch repair gene, thereby stabilizing the genome of said hypermutated hybridoma.

In some embodiments of the method of the invention, the dominant negative mismatch repair gene is introduced into the hybridoma cell after the fusion of said myeloma with the immunoglobulin-producing cells. In other embodiments, the dominant negative mismatch repair gene is introduced into the myeloma cell prior to the fusion with the immunoglobulin-producing cells.

The invention also comprises antibodies produced by the hybridoma cells.

The invention also comprises methods for producing hybridoma cells that produce high titers of antibodies from in vitro immunized immunoglobulin-producing cells comprising: (a) combining donor blood cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by the parental hybridoma cells.

In some embodiments, the dominant negative allele of a mismatch repair gene comprises a truncation mutation of the PMS2 gene (e.g., a PMS2-134 gene). In some embodiments of the method of the invention, antibodies are screened using an ELISA-based assay. In some embodiments, the screening assays screen for hypermutated hybridomas that produce higher affinity antibodies than those produced by the parental hybridomas. In other embodiments, the screening assays screen for hypermutated hybridomas that produce antibodies in higher titers than the parental hybridomas.

In some embodiments of the method of the invention, the method further comprising inactivation of the dominant negative allele of the mismatch repair gene, thereby stabilizing the genome of said hypermutated hybridoma.

In some embodiments of the method of the invention, the dominant negative mismatch repair gene is introduced into the hybridoma cell after the fusion of said myeloma with the immunoglobulin-producing cells. In other embodiments, the dominant negative mismatch repair gene is introduced into the myeloma cell prior to the fusion with the immunoglobulin-producing cells.

In some embodiments of the method of the invention, the dominant negative allele of the mismatch repair gene is subsequently inactivated in order to restabilize the genome of the cell.

The dominant negative allele of the mismatch repair gene may be introduced into the myeloma cell prior to fusion with the immunoglobulin producing cells. Thus, the resulting hybridoma cells express the same dominant negative allele of the mismatch repair gene as the myeloma cells. Alternatively, the dominant negative allele of the mismatch repair gene may be introduced into the hybridoma cells.

The invention also comprises antibodies produced by the hybridoma cells.

The invention further provides recombinant myeloma cells comprising a polynucleotide sequence encoding a dominant negative mismatch repair protein. The dominant negative mismatch repair protein may be a dominant negative form of, for example, a PMS2, PMS1, PMSR3, PMSR2, PMSR6, MLH1, GTBP, MSH3, MSH2, MLH3, or MSH1, and PMSR proteins encoded by homologs of the PMSR genes as described in Nicolaides et al. (1995) *Genomics* 30:195-206 and Horii et al. (1994) *Biochem. Biophys. Res. Commun.* 204:1257-1264. In some embodiments, the recombinant myeloma cell expresses a polynucleotide encoding a dominant negative allele of a PMS2 gene (e.g., a truncation mutation of the PMS2 gene, such as the PMS2-134 gene).

In some embodiments, the recombinant myeloma cell is a human cell. In other embodiments, the recombinant myeloma cell does not express immunoglobulin genes and/or Epstein-Barr virus. In other embodiments, the myeloma cells are HAT sensitive.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; (d) cloning immunoglobulin genes from said hybridoma into a mammalian expression cell, wherein said mammalian expression cell expresses a dominant negative allele of a mismatch repair gene; (e) performing a screen for mammalian expression cells that secrete antibodies with higher affinity for antigen as compared to antibodies produced from said hybridoma cells; thereby producing mammalian expression cells that produce high titers of high-affinity antibodies from in vitro immunized immunoglobulin-producing cells.

In some embodiments, the dominant negative allele of a mismatch repair gene is introduced into said mammalian expression cell prior to introduction of the immunoglobulin genes. In other embodiments, the dominant negative allele of a mismatch repair gene is introduced into said mammalian expression cell after introduction of said immunoglobulin genes. In other embodiments, the dominant negative allele of a mismatch repair gene is introduced into the mammalian expression cell with the immunoglobulin genes simultaneously.

The invention also comprises antibodies produced by the mammalian expression cells.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells, wherein said hybridoma cells express a dominant negative allele of a mismatch repair gene; (c) incubating said parental hybridoma cells to allow for mutagenesis, thereby forming hypermutated hybridoma cells; (d) performing a screen for binding of antibodies to antigen for antibodies produced from said hypermutated hybridoma cells; (e) selecting hypermutated hybridoma cells that produce antibodies with greater affinity for said antigen than antibodies produced by said parental hybridoma cells; (f) cloning immunoglobulin genes from said hybridoma into a mammalian expression cell; thereby producing mammalian expression cells that produce high titers of high-affinity antibodies from in vitro immunized human immunoglobulin-producing cells.

In some embodiments, the dominant negative allele of a mismatch repair gene is present in the myeloma cell prior to cell fusion In other embodiments, the dominant negative allele of the mismatch repair gene is introduced into the hybridoma cell after cell fusion.

The invention also comprises antibodies produced by the mammalian expression cells.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form hybridoma cells; (c) performing a screen for binding of antibodies produced from the hybridoma cells to antigen; (d) cloning immunoglobulin genes from the hybridoma into a parental mammalian expression cell, wherein the mammalian expression cell expresses a dominant negative allele of a mismatch repair gene; (e) incubating the parental mammalian expression cell to allow for mutagenesis, thereby forming hypermutated mammalian expression cells; (f) performing a screen of hypermutable mammalian expression cells that secrete antibodies with higher affinity for antigen as compared to antibodies produced from the hybridoma cells; and (g) performing a screen of hypermutable mammalian expression cells that secrete higher titers of antibodies than parental mammalian expression cells; thereby producing mammalian expression cells that produce high titers of high-affinity antibodies from in vitro immunized immunoglobulin-producing cells.

In some embodiments, the dominant negative allele of a mismatch repair gene is introduced into said mammalian expression cell prior to introduction of the immunoglobulin genes. In other embodiments, the dominant negative allele of a mismatch repair gene is introduced into said mammalian expression cell after introduction of said immunoglobulin genes. In other embodiments, the dominant negative allele of a mismatch repair gene is introduced into the mammalian expression cell with the immunoglobulin genes simultaneously.

The invention also provides antibodies produced by the mammalian expression cells.

The invention also provides recombinant, hypermutable mammalian expression cells comprising a polynucleotide sequence encoding a dominant negative mismatch repair protein.

The mismatch repair gene may be a dominant negative mismatch repair gene, including, but not limited to a dominant negative form of PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264. A non-limiting example includes a dominant negative truncation mutant of PMS2 (e.g., a PMS2-134 gene).

The invention also provides methods for producing hybridoma cells producing high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen for antigen binding for antibodies produced from the hypermutated hybridoma cells; and (e) selecting hypermutated hybridoma cells that produce antibodies with greater affinity for the antigen than antibodies produced by said parental hybridoma cells; thereby producing hybridoma cells producing high-affinity antibodies.

The invention also comprises antibodies produced by the hybridoma cells.

The invention also provides methods for producing hybridoma cells that produce high titers of antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by said parental hybridoma cells; thereby producing hybridoma cells producing high titers of antibodies.

In some embodiments of the method of the invention, the hypermutated hybridoma cells also are screened for the production of higher titers of antibodies than that produced by the parental hybridomas. The screening may be using an ELISA-based assay, or any other means to measure antibody-antigen binding.

The invention also comprises antibodies produced by the hybridoma cells.

The invention also provides methods for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form hybridoma cells; (c) performing a screen for antigen binding of antibodies produced from the hybridoma cells; (d) cloning immunoglobulin genes from the hybridoma cells into a mammalian expression cell; (e) incubating the mammalian expression cell in the presence of at least one chemical inhibitor of mismatch repair; (f) performing a screen for mammalian expression cells that secrete antibodies with higher affinity for antigen as compared to antibodies produced from the hybridoma cells; thereby producing mammalian expression cells that produce high titers of high-affinity antibodies from in vitro immunized immunoglobulin-producing cells.

In some embodiments of the method of the invention the method may further comprise the removal of the chemical inhibitor from the hypermutated mammalian expression cells, thereby stabilizing the genome of said hypermutated mammalian expression cells.

The invention also comprises antibodies produced by the mammalian expression cells The invention also provides methods for producing mammalian expression cells that produce high titers of high affinity antibodies to a selected antigen from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form hybridoma cells; (c) incubating the hybridoma cells in the presence of at least one chemical inhibitor of mismatch repair to form hypermutated hybridoma cells; (d) performing a screen for antigen binding for antibodies produced from the hypermutated hybridoma cells; (e) selecting hypermutated hybridoma cells that produce antibodies with greater affinity for the antigen than antibodies produced by the parental hybridoma cells; (f) cloning immunoglobulin genes from the hypermutated hybridoma cells into a mammalian expression cell, thereby forming parental mammalian expression cells; thereby producing mammalian expression cells that produce high titers of high-affinity antibodies from in vitro immunized immunoglobulin-producing cells.

In some embodiments, the parental mammalian expression cell is further incubated in the presence of at least one chemical inhibitor of mismatch repair, thereby forming a hypermutated mammalian expression cell; and the hypermutated mammalian expression cells are screened for higher production of antibodies than that of the parental mammalian expression cells.

In some embodiments of the method of the invention the method may further comprise the removal of the chemical inhibitor from the hypermutated hybridoma and/or hypermutated mammalian expression cells, thereby stabilizing the genome of said hypermutated hybridoma cells and/or hypermutated mammalian expression cells.

The invention also comprises antibodies produced by the mammalian expression cells.

The invention also provides a method for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; (d) cloning immunoglobulin genes from said hybridoma into a mammalian expression cell; (e) incubating said mammalian expression cell in the presence of at least one chemical inhibitor of mismatch repair, thereby forming a hypermutated mammalian expression cell; (f) performing a screen for hypermutated mammalian expression cells that secrete antibodies with higher affinity for antigen as compared to antibodies produced from said parental mammalian expression cells; and (g) performing a second screen for hypermutated mammalian expression cells that produce higher titers of antibodies than that produced by parental mammalian expression cells; thereby producing mammalian expression cells that produce high titers of high-affinity antibodies from in vitro immunized immunoglobulin-producing cells.

In some embodiments of the method of the invention the method may further comprise the removal of the chemical inhibitor from the hypermutated hybridoma and/or hypermutated mammalian expression cells, thereby stabilizing the genome of said hypermutated hybridoma cells and/or hypermutated mammalian expression cells.

The invention also comprises antibodies produced by the mammalian expression cells.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; (g) selecting hypermutated hybridoma cells that produce antibodies in higher titers than produced by the parental hybridoma cells; thereby producing hybridoma cells producing high titers of high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; (g) selecting hypermutated hybridoma cells that produce antibodies in higher titers than produced by the parental hybridoma cells; thereby producing hybridoma cells producing high titers of high-affinity antibodies.

The method may further comprise introducing a wild-type gene for mismatch repair into said selected hypermutated hybridoma cell to complement the mismatch repair deficiency, thereby restabilizing the genome of said selected hypermutated hybridoma cell.

The invention also comprises antibodies produced by the hybridoma cells.

In another embodiment, the invention comprises a method for producing mammalian expression cells that produce high-affinity antibodies in high titers from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) cloning immunoglobulin genes from said hypermutated hybridoma into a mammalian expression cell; thereby producing a mammalian expression cell that produces high titers of high-affinity antibodies in high titer from in vitro immunized immunoglobulin-producing cells.

In some embodiments, the parental mammalian expression cell is further incubated in the presence of at least one chemical inhibitor of mismatch repair, thereby forming a hypermutated mammalian expression cell; and the hypermutated mammalian expression cells are screened for higher production of antibodies than that of the parental mammalian expression cells.

In some embodiments of the method of the invention the method may further comprise the removal of the chemical inhibitor from the hypermutated mammalian expression cells, thereby stabilizing the genome of said hypermutated mammalian expression cells.

The invention also comprises antibodies produced by the mammalian expression cells.

In another embodiment, the invention comprises a method for producing mammalian expression cells that produce high-affinity antibodies in high titer from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; and (f) cloning immunoglobulin genes from said hypermutated hybridoma cell into a mammalian expression cell; thereby producing mammalian expression cells that produce high titers of high-affinity antibodies from in vitro immunized immunoglobulin-producing cells.

In some embodiments, the parental mammalian expression cell is further incubated in the presence of at least one chemical inhibitor of mismatch repair, thereby forming a hypermutated mammalian expression cell; and the hypermutated mammalian expression cells are screened for higher production of antibodies than that of the parental mammalian expression cells.

In some embodiments of the method of the invention the method may further comprise the removal of the chemical inhibitor from the hypermutated mammalian expression cells, thereby stabilizing the genome of said hypermutated mammalian expression cells.

The invention also comprises antibodies produced by the hybridoma cells.

In some embodiments of the methods of the invention, the immunoglobulin-producing cells are mammalian cells, including but not limited to, mouse cells, rat cells, goat cells, cow cells, horse cells, dog cells, cat cells, rabbit cells, bird cells, monkey cells and human cells. In preferred embodiments, the cells are human cells.

In some embodiments the dominant negative allele of a mismatch repair gene is a dominant negative allele of PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264. However, the mismatch repair genes are not limit to these examples.

In some embodiments of the method of the invention, the immunogenic antigen is conjugated to a mitogenic polypeptide comprising at least a portion of a polypeptide including, but not limited to tetanus toxoid, ovalbumin, bovine serum albumen, thyroglobulin, diptheria toxoid, BCG, and cholera toxin. In some embodiments, the antigen is generated by denaturing the mature protein.

In some embodiments of the method of the invention, the antibodies produced have an affinity of at least about $1\times10^7$ $M^{-1}$. In other embodiments, the antibodies have an affinity of at least about $1\times10^8$ $M^{-1}$. In other embodiments, the antibodies have an affinity of at least about $1\times10^9$ $M^{-1}$. In other embodiments, the antibodies have an affinity of at least about $1\times10^{10}$ $M^{-1}$. In other embodiments, the antibodies have an affinity of at least about $1\times10^{11}$ $M^{-1}$. In other embodiments, the antibodies have an affinity of at least about $1\times10^{12}$ $M^{-1}$. In other embodiments, the antibodies have an affinity of at least about $1\times10^{13}$ $M^{-1}$. In other embodiments, the antibodies have an affinity of at least about $1\times10^{14}$ $M^{-1}$.

In some embodiments, the antibodies are produced in a higher titer than the parental cell lines, such as in an amount of at least about 1.5 fold higher than the parental cell line. In other embodiments, the titer is at least about 1.5-3 fold higher than the parental cell line. In other embodiments, the titer is at least about 3-5 fold higher than the parental cell line. In other embodiments, the titer is at least about 5-7 fold higher than the parental cell line. In other embodiments, the titer is at least about 7-9 fold higher than the parental cell line. In other embodiments, the titer is at least about 9-10 fold higher than the parental cell line.

In some embodiments of the method of the invention, mutation rates are further enhanced by incubating the hybridoma cells with a chemical mutagen, such as, but not limited to N-ethyl-N-nitrosourea, N-methyl-N-nitrosourea, procarbazine hydrochloride, chlorambucil, cyclophosphamide, methyl methanesulfonate, ethyl methanesulfonate, diethyl sulfate, acrylamide monomer, triethylene melamin, melphalan, nitrogen mustard, vincristine, dimethylnitrosamine, N-methyl-N'-nitro-nitrosoguanidine, 7,12 dimethylbenz (a) anthracene, ethylene oxide, hexamethylphosphoramide, and bisulfan.

The chemical inhibitors of mismatch repair used in certain embodiments of the methods of the invention include, but are not limited to, at least one of an anthracene, an ATPase inhibitor, a nuclease inhibitor, an RNA interference molecule, a polymerase inhibitor and an antisense oligonucleotide that specifically hybridizes to a nucleotide encoding a mismatch repair protein. In some embodiments, the chemical inhibitor is an anthracene having the formula:

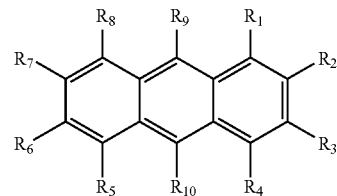

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups; wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or lower alkyl groups. In certain embodiments, $R_5$ and $R_6$ are hydrogen. In other embodiments, $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl. Non-limiting examples of the anthracenes include 1,2-dimethylanthracene, 9,10-dimethylanthracene, 7,8-dimethylanthracene, 9,10-duphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, and 9,10-di-m-tolylanthracene.

The chemical inhibitor may be introduced into the growth medium of the cells. In some embodiments, the chemical inhibitor may be withdrawn from the hypermutated hybridoma cells in order to re-stabilize the genome of the cells.

The invention also comprises a method for in vitro production of antigen-specific immunoglobulin-producing cells comprising: (a) isolating donor cells from an animal; (b) treating said cells with L-leucyl-L-leucine methy ester hydrobromide; (c) incubating said donor cells with an immunogenic antigen in vitro, at 25-37° C., 5-10% $CO_2$, in medium supplemented with 5-15% serum, and a growth promoting cytokine for 4 days; (d) washing said cells in medium; and (e) culturing said cells in medium supplemented with 5-15% serum an additional 8 days; thereby stimulating the production of antigen-specific immunoglobulin-producing cells.

In some embodiments, the immunoglobulin-producing cells are human cells.

In some embodiments of the method of the invention, the immunogenic antigen is conjugated to a mitogenic polypeptide comprising at least a portion of a polypeptide including, but not limited to tetanus toxoid, ovalbumin, bovine serum albumen, thyroglobulin, diptheria toxoid, BCG, and cholera toxin. In some embodiments, the antigen is generated by denaturing the mature protein.

In some embodiments of the method of the invention, the antibodies produced have an affinity of at least about $1 \times 10^7$ $M^{-1}$. In other embodiments, the antibodies have an affinity of at least about $1 \times 10^8$ $M^{-1}$. In other embodiments, the antibodies have an affinity of at least about $1 \times 10^9$ $M^{-1}$. In other embodiments, the antibodies have an affinity of at least about $1 \times 10^{10}$ $M^{-1}$. In other embodiments, the antibodies have an affinity of at least about $1 \times 10^{11}$ $M^{-1}$. In other embodiments, the antibodies have an affinity of at least about $1 \times 10^{12}$ $M^{-1}$. In other embodiments, the antibodies have an affinity of at least about $1 \times 10^{13}$ $M^{-1}$. In other embodiments, the antibodies have an affinity of at least about $1 \times 10^{14}$ $M^{-1}$.

In some embodiments, the antibodies are produced in a higher titer than the parental cell lines, such as in an amount of at least about 1.5 fold higher than the parental cell line. In other embodiments, the titer is at least about 1.5-3 fold higher than the parental cell line. In other embodiments, the titer is at least about 3-5 fold higher than the parental cell line. In other embodiments, the titer is at least about 5-7 fold higher than the parental cell line. In other embodiments, the titer is at least about 7-9 fold higher than the parental cell line. In other embodiments, the titer is at least about 9-10 fold higher than the parental cell line.

In some embodiments of the method of the invention, mutation rates are further enhanced by incubating the hybridoma cells and/or mammalian expression cells with a chemical mutagen, such as, but not limited to N-ethyl-N-nitrosourea, N-methyl-N-nitrosourea, procarbazine hydrochloride, chlorambucil, cyclophosphamide, methyl methanesulfonate, ethyl methanesulfonate, diethyl sulfate, acrylamide monomer, triethylene melamin, melphalan, nitrogen mustard, vincristine, dimethylnitrosamine, N-methyl-N'-nitro-nitrosoguanidine, 7,12 dimethylbenz (a) anthracene, ethylene oxide, hexamethylphosphoramide, and bisulfan.

The mammalian expression cells used in the methods of the invention may include, but are not limited to, Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK$^{31}$ cells, mouse sertoli cells, human cervical carcinoma cells, buffalo rat liver cells, human lung cells, human liver cells, mouse mammary tumor cells, TRI cells, MRC 5 cells, and FS4 cells.

These and other embodiments are described more fully in the next section and include certain non-limiting examples.

BRIEF DESCRIPTION OF THE DRAWINGS

FIG. 6A shows the reactivity of unstimulated PBMCs to EGFR. FIG. 6B shows the reactivity of PBMCs to EGFR after immunization with EGFR-TT. FIG. 6C shows the reactivity of unstimulated PBMCs to EGFR-TT. FIG. 6D shows the reactivity of PBMCs to EGFR-TT after immunization with EGFR-TT.

DETAILED DESCRIPTION OF THE INVENTION

Figure 1:
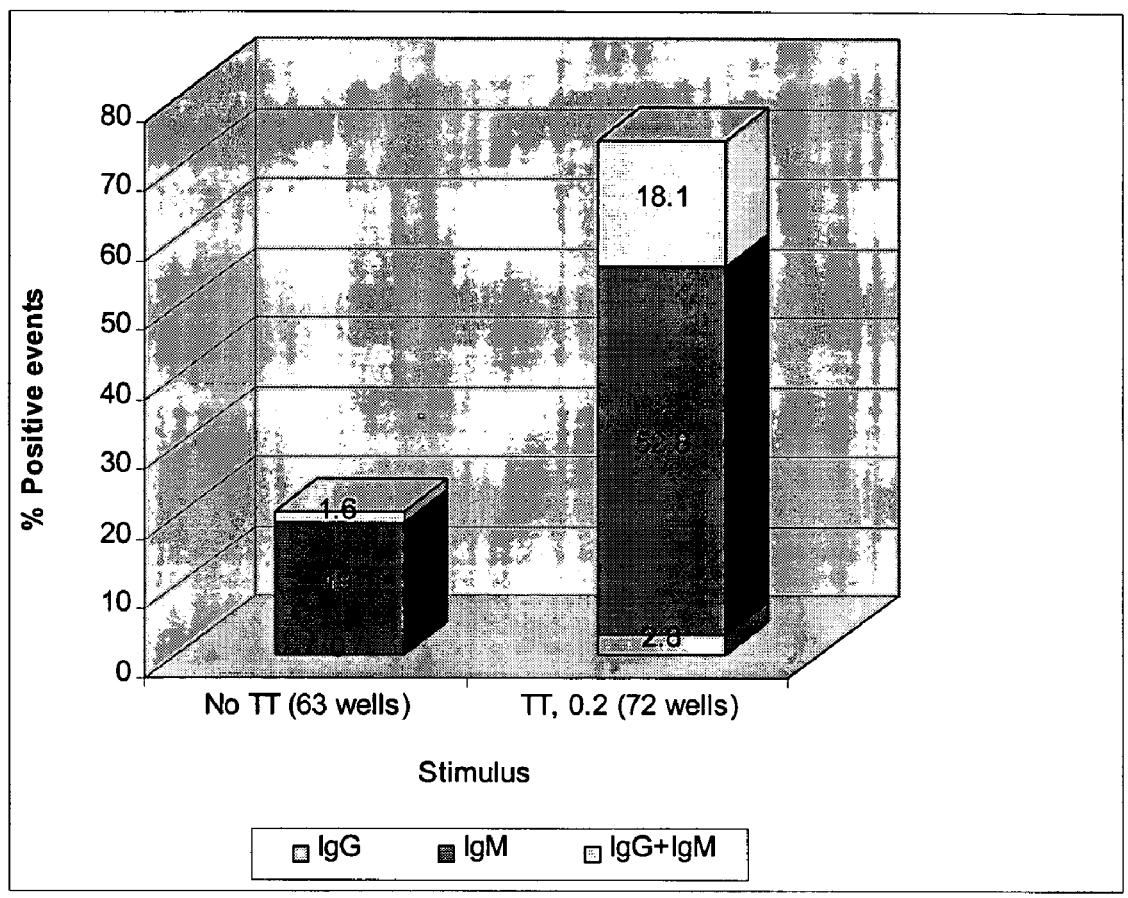
FIG. 1 shows the immune response of PBMCs to antigen stimulation. PBMCs were cultured in the presence or absence of TT for 4 days then washed with medium and cultured in the presence or absence of TT for an additional eight days. Culture supernates were collected and tested for the presence of antibody reactive to TT. Antibodies bound to TT pre-coated on the solid phase were detected with HRP-labeled goat anti-human IgG, or HRP-labeled goat anti-human IgM.

The referenced patents, patent applications, and scientific literature, including accession numbers to GenBank database sequences, referred to herein are hereby incorporated by reference in their entirety. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include, but are not limited to Ausubel et al. CURRENT PROTOCOLS IN MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR and CELLUAR METHODS IN BIOLOGY AND MEDICINE, CRC Press, Boca Raton (1995); McPherson, Ed., DIRECTED MUTAGENESIS: A PRATICAL APPROACH, IRL Press, Oxford (1991).

The invention provides various embodiments of a method for producing antibody-producing cells and antibodies from in vitro immunized cells with high affinity, and/or increased production. In some embodiments, the cells that produce the antibodies are hybridoma cells, formed by fusing myeloma cells with the lymphoid cells that have been immunized against an antigen in vitro. In other embodiments, the cells that produce the antibodies are mammalian cells that have been transfected with immunoglobulin genes cloned from lymphoid cells that have been immunized against an antigen in vitro. In some embodiments, the method employs both hybridoma cells and mammalian cells. Some basic embodiments of the method of the invention may be described as follows.

In one embodiment, the invention provides a method for generating hybridoma cells producing high-affinity antibodies from in vitro immunized, immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with greater affinity for the antigen than antibodies produced by the parental hybridoma cells; thereby producing hybridoma cells producing high-affinity antibodies.

In another embodiment, the invention provides methods of producing hybridoma cells that produce high titers of antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells to form parental hybridoma cells, wherein the hybridoma cells express a dominant negative allele of a mismatch repair gene; (c) incubating the parental hybridoma cells to allow for mutagenesis, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by the parental hybridoma cells; thereby producing hybridoma cells that produce high titers of antibodies.

In another embodiment, the invention provides a method for producing hybridoma cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; (d) cloning immunoglobulin genes from said hybridoma into a mammalian expression cell, wherein said mammalian expression cell expresses a dominant negative allele of a mismatch repair gene; and (e) performing a screen for mammalian expression cells that secrete antibodies with higher affinity for antigen as compared to antibodies produced from said hybridoma cells; thereby producing hybridoma cells that produce high titers of high-affinity antibodies from in vitro immunized immunoglobulin-producing cells.

In another embodiment, the invention provides a method for producing mammalian expression cells that produce high titers of high-affinity antibodies from in vitro immunized immunoglobulin-producing cells are produced by: (a) combining donor cells comprising immunoglobulin-producing cells with an immunogenic antigen in vitro; (b) fusing said immunoglobulin-producing cells with myeloma cells to form hybridoma cells, wherein said hybridoma cells express a dominant negative allele of a mismatch repair gene; (c) incubating said parental hybridoma cells to allow for mutagenesis, thereby forming hypermutated hybridoma cells; (d) performing a screen for binding of antibodies to antigen for antibodies produced from said hypermutated hybridoma cells; (e) selecting hypermutated hybridoma cells that produce antibodies with greater affinity for said antigen than antibodies produced by said parental hybridoma cells; and (f) cloning immunoglobulin genes from said hybridoma into a mammalian expression cell; thereby producing high titers of high-affinity antibodies from in vitro immunized immunoglobulin-producing cells.

In yet another embodiment, the invention provides mammalian expression cells that produce high titers of high-affinity antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form hybridoma cells; (c) performing a screen for binding of antibodies produced from the hybridoma cells to antigen; (d) cloning immunoglobulin genes from the hybridoma into a parental mammalian expression cell, wherein the mammalian expression cell expresses a dominant negative allele of a mismatch repair gene; (e) incubating the parental mammalian expression cell to allow for mutagenesis, thereby forming hypermutated mammalian expression cells; (f) performing a screen of hypermutable mammalian expression cells that secrete antibodies with higher affinity for antigen as compared to antibodies produced from the hybridoma cells; and (g) performing a screen of hypermutable mammalian expression cells that secrete higher titers of antibodies than parental mammalian expression cells; thereby producing mammalian expression cells that produce high titers of high-affinity antibodies from in vitro immunized immunoglobulin-producing cells.

In yet another embodiment, the invention provides a method of producing hybridoma cells that produce high-affinity antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen for antigen binding for antibodies produced from the hypermutated hybridoma cells; and (e) selecting hypermutated hybridoma cells that produce antibodies with greater affinity for the antigen than antibodies produced by said parental hybridoma cells; thereby producing hybridoma cells that produce high-affinity antibodies.

In still another embodiment, the invention provides a method of producing hybridoma cells that produce high titers of antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form parental hybridoma cells; (c) incubating the parental hybridoma cells in the presence of at least one chemical inhibitor of mismatch repair, thereby forming hypermutated hybridoma cells; (d) performing a screen of the hypermutated hybridoma cells for antigen-specific antibodies produced in higher titers than that produced by the parental hybridoma cells; and (e) selecting hypermutated hybridoma cells that produce higher titers of antibodies than that produced by said parental hybridoma cells; thereby producing hybridoma cells producing high titers of antibodies.

In another embodiment, the invention provides methods for producing mammalian expression cells that produce high titers of high-affinity antibodies from in vitro immunized immunoglobulin-producing cells are produced by: (a) combining donor cells comprising immunoglobulin-producing cells with an immunogenic antigen in vitro; (b) fusing the immunoglobulin-producing cells with myeloma cells to form hybridoma cells; (c) performing a screen for antigen binding of antibodies produced from the hybridoma cells; (d) cloning immunoglobulin genes from the hybridoma cells into a mammalian expression cell; (e) incubating the mammalian expression cell in the presence of at least one chemical inhibitor of mismatch repair; and (f) performing a screen for mammalian expression cells that secrete antibodies with higher affinity for antigen as compared to antibodies produced from the hybridoma cells; thereby producing mammalian expression cells that produce high titers of high-affinity antibodies from in vitro immunized immunoglobulin-producing cells.

In yet another embodiment, the invention provides a method for producing mammalian expression cells that produce high affinity antibodies to a selected antigen from in vitro immunized immunoglobulin-producing cells are produced in high titers by: (a) combining donor cells comprising immunoglobulin-producing cells with an immunogenic antigen in vitro; (b) fusing the immunoglobulin-producing cells with myeloma cells to form hybridora cells; (c) incubating the hybridoma cells in the presence of at least one chemical inhibitor of mismatch repair to form hypermutated hybridoma cells; (d) performing a screen for antigen binding for antibodies produced from the hypermutated hybridoma cells; (e) selecting hypermutated hybridoma cells that produce antibodies with greater affinity for the antigen than antibodies produced by the parental hybridoma cells; and (f) cloning immunoglobulin genes from the hypermutated hybridoma cells into a mammalian expression cell, thereby forming parental mammalian expression cells; thereby producing mammalian expression cells that produce high titers of high-affinity antibodies from in vitro immunized immunoglobulin-producing cells.

In yet another embodiment, the invention also provides methods for producing mammalian expression cells that produce high titers of high-affinity antibodies from in vitro immunized immunoglobulin-producing cells comprising: (a) combining donor cells comprising immunoglobulin-producing cells with an immunogenic antigen in vitro; (b) fusing said immunoglobulin-producing cells with myeloma cells to form hybridoma cells; (c) performing a screen for binding of antibodies produced from said hybridoma cells to antigen; —(d) cloning immunoglobulin genes from said hybridoma into a mammalian expression cell; (e) incubating said mammalian expression cell in the presence of at least one chemical inhibitor of mismatch repair, thereby forming a hypermutated mammalian expression cell; (f) performing a screen for hypermutated mammalian expression cells that secrete antibodies with higher affinity for antigen as compared to antibodies produced from said parental mammalian expression cells; and (g) performing a second screen for hypermutated mammalian expression cells that produce higher titers of antibodies that produced by parental mammalian expression cells; thereby producing mammalian expression cells that produce high titers of high-affinity antibodies from in vitro immunized immunoglobulin-producing cells.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

In another embodiment, the invention comprises a method for producing hybridoma cells that produce high-affinity antibodies from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; and (e) selecting hypermutated hybridoma cells that produce antibodies with enhanced affinity for the antigen than antibodies produced by the parental hybridoma cells; thereby producing hybridoma cells producing high-affinity antibodies.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro, wherein the donor cells are derived from a donor that is naturally deficient in mismatch repair; (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; and (g) selecting hypermutated hybridoma cells that produce antibodies in higher titers than produced by the parental hybridoma cells; thereby producing hybridoma cells producing high titers of high-affinity antibodies.

In another embodiment, the invention comprises a method for producing hybridoma cells that produce high-affinity antibodies from in vitro immunized immunoglobulin-producing cells in high titers comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; (f) performing a second screen for hypermutated hybridoma cells that produce increased titers of antibodies as compared with parental hybridoma cells; and (g) selecting hypermutated hybridoma cells that produce antibodies in higher titers than produced by the parental hybridoma cells; thereby producing hybridoma cells producing high titers of high-affinity antibodies.

In another embodiment, the invention comprises a method for producing mammalian expression cells that produce high-affinity antibodies in high titers from in vitro immunized immunoglobulin-producing cells comprising: (a) combining donor cells comprising immunoglobulin-producing cells with an immunogenic antigen in vitro, wherein the donor cells are derived from a donor that is naturally deficient in mismatch repair, (b) fusing the immunoglobulin-producing cells with myeloma cells to form parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; and (f) cloning immunoglobulin genes from said hypermutated hybridoma into a mammalian expression cell; thereby producing a mammalian expression cell that produce high titers of high-affinity antibodies in high titer from in vitro immunized immunoglobulin-producing cells.

In another embodiment, the invention comprises a method for producing mammalian expression cells that produce high-affinity antibodies in high titer from in vitro immunized immunoglobulin-producing cells comprising: (a) combining donor cells comprising immunoglobulin-producing cells with an immunogenic antigen in vitro; (b) fusing the immunoglobulin-producing cells with myeloma cells, wherein the myeloma cells are naturally deficient in mismatch repair, thereby forming parental hybridoma cells, wherein the hybridoma cells are deficient in mismatch repair; (c) incubating the parental hybridoma cells to allow for mutagenesis, thereby forming hypermutated hybridoma cells; (d) performing a screen for binding of antibodies to antigen for antibodies produced from the hypermutated hybridoma cells; (e) selecting hypermutated hybridoma cells that produce antibodies with enhanced affinity for the antigen than antibodies produced by the parental hybridoma cells; and (f) cloning immunoglobulin genes from said hypermutated hybridoma cell into a mammalian expression cell; thereby producing mammalian expression cells that produce high titers of high-affinity antibodies from in vitro immunized immunoglobulin-producing cells.

The invention also provides hybridoma cells, expression cells produced by any of the methods of the invention, as well as antibodies produced by any of the hybridoma cells and expression cells of the invention.

In still another embodiment, antigen-specific immunoglobulin-producing cells are produced by: (a) isolating donor cells from an animal; (b) treating said cells with L-leucyl-L-leucine methy ester hydrobromide; (c) incubating said donor cells with an immunogenic antigen in vitro, at 25-37° C., 5-10% $CO_2$, in medium supplemented with 5-15% serum, and a growth promoting cytokine for 4 days; (d) washing said cells in medium; and (e) culturing said cells in medium supplemented with 5-15% serum an additional 8 days; thereby stimulating the production of antigen-specific immunoglobulin-producing cells.

The blood cells used in the methods of the invention may be derived from any animal that produces antibodies. Preferably, the donor cells are derived from mammals, including, but not limited to humans, monkeys, mice, rats, guinea pigs, hamsters, gerbils, birds, rabbits, sheep, goats, pigs, horses, and cows. The source of blood is not necessarily limited, but may be whole blood or fractions containing lymphocytes. The blood may be donor or cord blood, for example. In some embodiments, the blood cells are preferably human donor cells.

The myeloma cells used to create the hybridoma cells in the method of the invention may be derived from any species known to have suitable myeloma cells. For example, but not by way of limitation, the myeloma cells may be conveniently derived from humans or mice. Suitable examples of myeloma cells include, but are not limited to the HuNS1 myeloma as described in U.S. Pat. No. 4,720,459 to Winkelhake, and deposited with the American Type Culture Collection (ATCC) as CRL 8644; GM4672; RPMI 8226; and murine myeloma cell lines (e.g., P3-NS1/1-Ag4-1; P3-x63-Ag8.653; Sp2/O-Ag14; NS/O, NS/1, SP2 and S194).

The mammalian expression cells suitable for use in certain embodiments of the method of the invention include, but are not limited to Chinese Hamster Ovary cells (CHO cells, Urlaub and Chasin (1980) *Proc. Natl. Acad. Sci. USA*, 77: 4216), baby hamsterkidney (BHK cells), human embryonic kidney line 293 (HeLa cells, Graham et al., (1977) *J. Gen Virol.*, 36: 59), normal dog kidney cell line (e.g., MDCK, ATCC CCL 34), normal cat kidney cell line (CRFK cells), monkey kidney cells (CVI ATCC CCL 70); African green monkey kidney cells (VERO-76, ATCC CRL-1587), COS (e.g., COS-7) cells, and non-tumorigenic mouse myoblast G8 cells (e.g., ATCC CRL 1246), fibroblast cell lines (e.g., human, murine or chicken embryo fibroblast cell lines), myeloma cell lines, mouse NIH/3T3 cells, $LMTK^{31}$ cells, mouse sertoli cells (TM4, Mather, (1980) *Biol. Reprod.*, 23:243-251); human cervical carcinoma cells (HELA, ATCC CCL 2); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51), TRI cells (Mather et al (1982) *Annals N.Y. Acad. Sci.* 383:44-68); MRC 5 cells; FS4 cells; and the human hepatoma line (Hep G2).

As an alternative to mammalian expression cells, other non-mammalian cells may be used to express the cloned immunoglobulin genes. Such non-mammalian cells include, but are not limited to insect cells (e.g., *Spodoptera frugiperda* cells and the like). Vectors and non-mammalian host cells are well known in the art and are continually being optimized and developed. Any host cell system capable of expressing antibodies may be used in the methods of the invention.

As used herein, "dominant negative allele of a mismatch repair gene" refers to an allele of a mismatch repair gene that, when expressed, exerts a dominant phenotype in the cell or organism that leads to an inhibition of the mismatch repair system, even in the presence of a wild-type allele. Cells expressing a dominant negative allele of a mismatch repair gene are hypermutable and accumulate mutations at a higher rate than wild-type cells. Examples of nucleic acid sequences encoding mismatch repair proteins useful in the method of the invention include, but are not limited to the following: PMS1 (SEQ ID NO:1); PMS2 (SEQ ID NO:3); PMS2-134 (SEQ ID NO:5); PMSR2 (SEQ ID NO:7); PMSR3 (SEQ ID NO:9); MLH1 (SEQ ID NO:11); MLH3 (SEQ ID NO:13); MSH2 (SEQ ID NO:15); MSH3 (SEQ ID NO:17); MSH4 (SEQ ID NO:19); MSH5 (SEQ ID NO:21); MSH6 (SEQ ID NO:23); PMSR6 (SEQ ID NO:25); PMSL9 (SEQ ID NO:27); yeast MLH1 (SEQ ID NO:29); mouse PMS2 (SEQ ID NO:31); mouse PMS2-134 (SEQ ID NO:33); *Arabidopsis thaliana* PMS2 (SEQ ID NO:35); *A. thaliana* PMS2-134 (SEQ ID NO:37) *A. thaliana* PMS1 (SEQ ID NO:39); *A. thaliana* MSH7 (SEQ ID NO:41) *A. thaliana* MSH2 (SEQ ID NO:43); *A thaliana* MSH3 (SEQ ID NO:45); *A. thaliana* MSH6-1 (SEQ ID NO:47); and *Oryza satvia* MLH1 (SEQ ID NO:49).

The corresponding amino acid sequences for the listed nucleic acid sequences are: PMS1 (SEQ ID NO:2); PMS2 (SEQ ID NO:4); PMS2-134 (SEQ ID NO:6); PMSR2 (SEQ ID NO:8); PMSR3 (SEQ ID NO:10); MLH1 (SEQ ID NO:12); MLH3 (SEQ ID NO:14); MSH2 (SEQ ID NO:16); MSH3 (SEQ ID NO:18); MSH4 (SEQ ID NO:20); MSH5 (SEQ ID NO:22); MSH6 (SEQ ID NO:24); PMSR6 (SEQ ID NO:26); PMSL9 (SEQ ID NO:28); yeast MLH1 (SEQ ID NO:30); mouse PMS2 (SEQ ID NO:32); mouse PMS2-134 (SEQ ID NO:34); Arabidopsis thaliana PMS2 (SEQ ID NO:36); A. thaliana PMS2-134 (SEQ ID NO:38); A. thaliana PMS1 (SEQ ID NO:40); A. thaliana MSH7 (SEQ ID NO:42) A. thaliana MSH2 (SEQ ID NO:44); A. thaliana MSH3 (SEQ ID NO:46); A. thaliana MSH6-1 (SEQ ID NO:48); and Oryza satvia MLH1 (SEQ ID NO:50).

As used herein, "high titer" refers to an titer of at least about 1.5 fold higher than the parental cell line. In some embodiments, the titer is at least about 1.5-3 fold higher, 3-5 fold higher, 5-7 fold higher, 7-9 fold higher, or 9-10 fold higher than the parental cell line.

As used herein, "high affinity" refers to a high antibody binding affinity, that may be calculated according to standard methods by the formula $K_a=8/3$ (It-Tt) where "It" is the total molar concentration of inhibitor uptake at 50% tracer and "Tt" is the total molar concentration of tracer. See Muller (1980) J. Immunol. Meth. 34:345-352. Binding affinity may also be calculated using the formula $B/T=n*N_{Ab}*W^{108}[(V-V_m)K+Q*W]$ (See Antoni and Mariani (1985) J. Immunol. Meth. 83:61-68). As used herein, "high affinity" is at least about $1\times10^7$ $M^{-1}$. In some embodiments, the antibodies have an affinity of at least about $1\times10^8$ $M^{-1}$. In other embodiments, the antibodies have an affinity of at least about $1\times10^9$ $M^{-1}$. In other embodiments, the antibodies have an affinity of at least about $1\times10^{10}$ $M^{-1}$. In other embodiments, the antibodies have an affinity of at least about $1\times10^{11}$ $M^{-1}$. In other embodiments, the antibodies have an affinity of at least about $1\times10^{12}$ $M^{-1}$. In other embodiments, the antibodies have an affinity of at least about $1\times10^{13}$ $M^{-1}$. In other embodiments, the antibodies have an affinity of at least about $1\times10^{14}$ $M^{-1}$.

As used herein, "antigen-specific" refers to an interaction between the CDR regions of the immunoglobulin molecule with an epitope of the antigen wherein the CDR regions of the immunoglobulin molecule binds to the epitope.

As used herein, "cured" refers to a state of the cells wherein the dominant negative mismatch repair gene has been eliminated from the cell or wherein the expression of the dominant negative allele has been turned off, leading to a stabilized genome, producing stable biological products such as immunoglobulins.

In some embodiments of the methods of the invention, mismatch repair is inhibited by introducing a dominant negative allele of a mismatch repair gene into a cell.

In other embodiments of the methods of the invention, mismatch repair is inhibited by exposing cells that express an antibody to a compound that inhibits mismatch repair. In some embodiments, the compound is an ATPase inhibitor. Suitable ATPase inhibitors include, but not limited to ATP analogs that are capable of blocking the ATPase activity necessary for mismatch repair in the cell. Examples of ATP analogs that may be used in the methods of the invention, include, but are not limited to non-hydrolyzable forms of ATP, such as AMP-PNP and ATPγS, which block mismatch repair activity (Galio et al. (1999) Nucl. Acids Res. 27:2325-2331; Allen et al. (1997) EMBO J. 16:4467-4476; Bjornson et al. (2000) Biochem. 39:3176-3183). Other suitable ATPase inhibitors may be identified using mismatch repair reporter cells that may be screened with candidate ATPase inhibitors to identify those compounds which effectively block ATPase activity in the cells.

In other embodiments of the methods of the invention, mismatch repair is inhibited by exposing cells that express an antibody to a nuclease inhibitor. The nuclease inhibitors are capable of blocking exonuclease activity in the mismatch repair biochemical pathway. Mismatch repair reporter cells may be screened with candidate nuclease inhibitors to identify compounds that effectively block the exonuclease activity of the mismatch repair system. Suitable nuclease inhibitors which may be used in the methods of the invention include, but are not limited to analogs of N-ethylmaleimide, an endonuclease inhibitor (Huang et al. (1995) Arch. Biochem. Biophys. 316:485); heterodimeric adenosine-chain-acridine compounds, exonuclease III inhibitors (Belmont et al. (2000) Bioorg. Med. Chem Lett. 10:293-295); as well as antibiotic compounds such as heliquinomycin, which have helicase inhibitory activity (Chino et al. (1998) J. Antibiot. (Tokyo) 51:480-486). Other suitable nuclease inhibitors may be identified using mismatch repair reporter cells that may be screened with candidate nuclease inhibitors to identify those compounds which effectively block nuclease activity in the cells.

In other embodiments of the methods of the invention, mismatch repair is inhibited by exposing the cells producing antibodies to DNA polymerase inhibitors. DNA polymerase inhibitors are capable of blocking the polymerization of DNA which is required for functional mismatch repair. Examples of suitable DNA polymerase inhibitors include, but are not limited to actinomycin D (Martin et al. (1990) J. Immunol. 145:1859); aphidicolin (Kuwakado et al. (1993) Biochem. Pharmacol. 46:1909); 1-(2'-deoxy-2'-fluoro-beta-L-arabinofuranosyl)-5-methyluracil (L-FMAU) (Kukhanova et al. (1998) Biochem. Pharmacol. 55:1181-1187); and 2'3'-dideoxyribonucleoside 5'-triphosphates (ddNTPs) (Ono et al. (1984) Biomed. Pharmacother. 38:382-389). Other suitable DNA polymerase inhibitors may be identified using mismatch repair reporter cells that may be screened with candidate DNA polymerase inhibitors to identify those compounds which effectively block DNA polymerase activity in the cells.

In other embodiments of the methods of the invention, mismatch repair is inhibited by exposing the cells producing antibody to an anthracene. As used herein the term "anthracene" refers to the compound anthracene. However, when referred to in the general sense, such as "anthracenes," "an anthracene" or "the anthracene," such terms denote any compound that contains the fused triphenyl core structure of anthracene, i.e.,

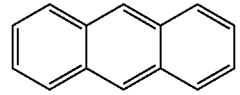

regardless of extent of substitution. The anthracene may be substituted or unsubstituted.

As used herein, "alkyl" refers to a hydrocarbon containing from 1 to about 20 carbon atoms. Alkyl groups may straight, branched, cyclic, or combinations thereof. Alkyl groups thus include, by way of illustration only, methyl, ethyl, propyl, isopropyl, butyl, isobutyl, cyclopentyl, cyclopentylmethyl, cyclohexyl, cyclohexylmethyl, and the like. Also included within the definition of "alkyl" are fused and/or polycyclic aliphatic cyclic ring systems such as, for example, adamantane. As used herein the term "alkenyl" denotes an alkyl group having at least one carbon-carbon double bond. As used herein the term "alkynyl" denotes an alkyl group having at least one carbon-carbon triple bond.

In some preferred embodiments, the alkyl, alkenyl, alkynyl, aryl, aryloxy, and heteroaryl substituent groups described above may bear one or more further substituent groups; that is, they may be "substituted". In some preferred embodiments these substituent groups can include halogens (for example fluorine, chlorine, bromine and iodine), CN, $NO_2$, lower alkyl groups, aryl groups, heteroaryl groups, aralkyl groups, aralkyloxy groups, guanidino, alkoxycarbonyl, alkoxy, hydroxy, carboxy and amino groups. In addition, the alkyl and aryl portions of aralkyloxy, arylalkyl, arylsulfonyl, alkylsulfonyl, alkoxycarbonyl, and aryloxycarbonyl groups also can bear such substituent groups. Thus, by way of example only, substituted alkyl groups include, for example, alkyl groups fluoro, chloro-, bromo- and iodoalkyl groups, aminoalkyl groups, and hydroxyalkyl groups, such as hydroxymethyl, hydroxyethyl, hydroxypropyl, hydroxybutyl, and the like. In some preferred embodiments such hydroxyalkyl groups contain from 1 to about 20 carbons.

As used herein the term "aryl" means a group having 5 to about 20 carbon atoms and which contains at least one aromatic ring, such as phenyl, biphenyl and naphthyl. Preferred aryl groups include unsubstituted or substituted phenyl and naphthyl groups. The term "aryloxy" denotes an aryl group that is bound through an oxygen atom, for example a phenoxy group.

In general, the prefix "hetero" denotes the presence of at least one hetero (i.e., non-carbon) atom, which is in some preferred embodiments independently one to three O, N, S, P, Si or metal atoms. Thus, the term "heteroaryl" denotes an aryl group in which one or more ring carbon atom is replaced by such a heteroatom. Preferred heteroaryl groups include pyridyl, pyrimidyl, pyrrolyl, furyl, thienyl, and imidazolyl groups.

The term "aralkyl" (or "arylalkyl") is intended to denote a group having from 6 to 15 carbons, consisting of an alkyl group that bears an aryl group. Examples of aralkyl groups include benzyl, phenethyl, benzhydryl and naphthylmethyl groups.

The term "alkylaryl" (or "alkaryl") is intended to denote a group having from 6 to 15 carbons, consisting of an aryl group that bears an alkyl group. Examples of aralkyl groups include methylphenyl, ethylphenyl and methylnaphthyl groups.

The term "arylsulfonyl" denotes an aryl group attached through a sulfonyl group, for example phenylsulfonyl. The term "alkylsulfonyl" denotes an alkyl group attached through a sulfonyl group, for example methylsulfonyl.

The term "alkoxycarbonyl" denotes a group of formula —C(═O)—O—R where R is alkyl, alkenyl, or alkynyl, where the alkyl, alkenyl, or alkynyl portions thereof can be optionally substituted as described herein.

The term "aryloxycarbonyl" denotes a group of formula —C(═O)—O—R where R is aryl, where the aryl portion thereof can be optionally substituted as described herein.

The terms "arylalkyloxy" or "aralkyloxy" are equivalent, and denote a group of formula —O—R'—R", where R' is R is alkyl, alkenyl, or alkynyl which can be optionally substituted as described herein, and wherein R" denotes a aryl or substituted aryl group.

The terms "alkylaryloxy" or "alkaryloxy" are equivalent, and denote a group of formula —O—R'—R", where R' is an aryl or substituted aryl group, and R" is alkyl, alkenyl, or alkynyl which can be optionally substituted as described herein.

As used herein, the term "aldehyde group" denotes a group that bears a moiety of formula —C(═O)—H. The term "ketone" denotes a moiety containing a group of formula —R—C(═O)—R═, where R and R═ are independently alkyl, alkenyl, alkynyl, aryl, heteroaryl, aralkyl, or alkaryl, each of which may be substituted as described herein.

As used herein, the term "ester" denotes a moiety having a group of formula —R—C(═O)—O—R═ or —R—O—C(═O)—R═ where R and R═ are independently alkyl, alkenyl, alkynyl, aryl, heteroaryl, aralkyl, or alkaryl, each of which may be substituted as described herein.

The term "ether" denotes a moiety having a group of formula —R—O—R═ or where R and R═ are independently alkyl, alkenyl, alkynyl, aryl, heteroaryl, aralkyl, or alkaryl, each of which may be substituted as described herein.

The term "crown ether" has its usual meaning of a cyclic ether containing several oxygen atoms. As used herein the term "organosulfur compound" denotes aliphatic or aromatic sulfur containing compounds, for example thiols and disulfides. The term "organometallic group" denotes an organic molecule containing at least one metal atom.

The term "organosilicon compound" denotes aliphatic or aromatic silicon containing compounds, for example alkyl and aryl silanes.

The term "carboxylic acid" denotes a moiety having a carboxyl group, other than an amino acid.

Suitable anthracenes that may be used in the method of the invention comprise compounds having the formula:

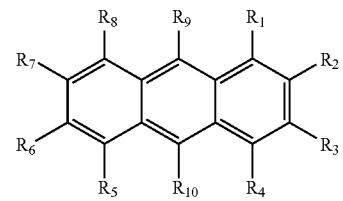

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups; wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or loweralkyl groups. In some embodiments, the $R_5$ and $R_6$ are hydrogen. In other embodiments, $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl. Suitable anthracenes for use in the methods of the invention include, but are not limited to 1,2-dimethylanthracene, 9,10-dimethylanthracene, 7,8-dimethylanthracene, 9,10-duphenylanthracene, 9,10-dihydroxymethylanthracene, 9-hydroxymethyl-10-methylanthracene, dimethylanthracene-1,2-diol, 9-hydroxymethyl-10-methylanthracene-1,2-diol, 9-hydroxymethyl-10-methylanthracene-3,4-diol, and 9,10-di-m-tolylanthracene.

Other suitable anthracenes may be identified using mismatch repair reporter cells that may be screened with candidate anthracenes to identify those compounds which effectively block mismatch repair activity in the cells. In some embodiments, the chemical inhibitor of mismatch repair is an RNA interference molecule that is homologous to a mismatch repair gene of the invention. The technique for generating sequence-specific RNA interference molecules is well-known in the art and may be found in, for example, Sharp et al. (2000) *Science* 287:2431-2433; Marx (2000) *Science* 288: 1370-1372; Grishok et al. (2001) *Science* 287:2494-2497; and Fire et al. (1998) *Nature* 391:806-811, the disclosures of which are specifically incorporated by reference in their entirety.

In other embodiments of the method of the invention, mismatch repair is inhibited by exposing the cells producing antibody to "antisense compounds" which specifically hybridize with one or more nucleic acids encoding a mismatch repair gene. As used herein, the terms "target nucleic acid" and "nucleic acid encoding a mismatch repair gene" encompass DNA encoding a mismatch repair gene, RNA (including pre-mRNA and mRNA) transcribed from such DNA, and also cDNA derived from such RNA. The specific hybridization of an antisense compound with its target nucleic acid interferes with the normal function of the nucleic acid, such as replication and transcription. The functions of RNA disrupted by antisense compounds include such functions as, for example, translocation of the RNA to the site of protein translation, translation of protein from the RNA, and splicing of the RNA to yield one or more mRNA species. The antisense compound thereby inhibits the expression or function of a mismatch repair gene.

It is preferred to target specific nucleic acids for antisense inhibition of mismatch repair in order to reversibly disrupt the function of a given mismatch repair gene. "Targeting" an antisense compound to a particular nucleic acid, in the context of this invention, is a multistep process, beginning with the identification of a nucleic acid sequence whose function is to be modulated. As disclosed herein, there are several mismatch repair genes that may be targeted by an antisense strategy. Among the various mismatch repair genes that may be targeted are PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264, including DNA or RNA. The next step of targeting involves the determination of a site or sites within this gene for the antisense interaction to occur, such that inhibition of the function of the mismatch repair gene occurs. In one embodiment, an intragenic site is targeted. An "intragenic site" is a region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding a mismatch repair gene, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. Complementarity of the antisense oligonucleotide is preferably 100%, however, degeneracy may be introduced into the oligonucleotide such that the complementarity, in some embodiments, is 80-85%, 85-90%, 90-95% or 95-100%.

Antisense and other compounds of the invention which hybridize to the target and inhibit expression of the target are identified through experimentation, and the sequences of these compounds are herein below identified as preferred embodiments of the invention. The target sites to which these preferred sequences are complementary comprise the region of PMS2, for example, which inhibits the translation of the C-terminal portion of the PMS2 protein, effectively forming a truncation mutant. The region targeted comprises a portion of the PMS2 gene that encodes the 134 amino acid of PMS2, for example.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e., from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. In some embodiments, the oligonucleotides are at least about 15 nucleotides in length and may be at least 20, 25, 30, 35, 40, 45, 50, 55, 60, 65, 70, 75, 80, 85, 90, 95, 100 or more nucleotides in length.

In some embodiments, the antisense oligonucleotides comprise a sequence that is complementary to a portion of the mismatch repair sequence shown in SEQ ID NO:1; SEQ ID NO:3; SEQ ID NO:5; SEQ ID NO:7; SEQ ID NO:9; SEQ ID NO:11; SEQ ID NO:13; SEQ ID NO:15; SEQ ID NO:17; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; SEQ ID NO:41; SEQ ID NO:43; SEQ ID NO:45; SEQ ID NO:47; or SEQ ID NO:49. In certain embodiments, the oligonucleotide is at least 15-50 nucleotides in length with 85-100% complementarity.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage, i.e., a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., (1991) *Science* 254:1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al. (1995) *Helv. Chim. Acta* 78:486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples hereinbelow.

A further preferred modification includes Locked Nucleic Acids (LNAs) in which the 2'-hydroxyl group is linked to the 3' or 4' carbon atom of the sugarring thereby forming a bicyclic sugar moiety. The linkage is preferably a methelyne (—$CH_2$—)$_n$ group bridging the 2' oxygen atom and the 3' or 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_2$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in THE CONCISE ENCYCLOPEDIA OF POLYMER SCIENCE AND ENGINEERING, Kroschwitz, (Ed.) John Wiley & Sons, 1990, pages 858-859, those disclosed by Englisch et al. (1991) *Angewandte Chemie* (International Edition) 30:613, and those disclosed by Sanghvi, ANTISENSE RESEARCH AND APPLICATIONS, Crooke and Lebleu (Eds.), CRC Press, 1993, pages 289-302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, ANTISENSE RESEARCH AND APPLICATIONS, Crooke and Lebleu (Eds.), CRC Press, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,750,692; 5,830,653; 5,763,588; 6,005,096; and 5,681,941, each of which is herein incorporated by reference in its entirety.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al. (1989) *Proc. Natl. Acad. Sci. USA* 86:6553-6556), cholic acid (Manoharan et al. (1994) *Bioorg. Med. Chem. Let.* 4:1053-1060), a thioether, e.g., hexyl-S-tritylthiol (Manoharan et al. (1992) *Ann. N.Y. Acad. Sci.* 660: 306-309; Manoharan et al. (1993) *Bioorg. Med. Chem. Let.* 3:2765-2770), a thiocholesterol (Oberhauser et al. (1992) *Nucl. Acids Res.* 20:533-538), an aliphatic chain, e.g., dodecandiol or undecyl residues (Saison-Behmoaras et al. (1991) *EMBO J.* 10:1111-1118; Kabanov et al. (1990) *FEBS Lett.* 259:327-330; Svinarchuk et al. (1993) *Biochimie* 75:49-54), a phospholipid, e.g., di-hexadecyl-rac-glycerol or triethylammonium 1,2-di-O-hexadecyl-rac-glycero-3-H-phosphonate (Manoharan et al. (1995) *Tetrahedron Lett.* 36:3651-3654; Shea et al. (1990) *Nucl. Acids Res.* 18:3777-3783), a polyamine or a polyethylene glycol chain (Manoharan et al. (1995) *Nucleosides & Nucleotides* 14:969-973), or adamantane acetic acid (Manoharan et al. (1995) *Tetrahedron Lett.* 36:3651-3654), a palmityl moiety (Mishra et al. (1995) *Biochim. Biophys. Acta* 1264:229-237), or an octadecylamine or hexylamino-carbonyl-oxycholesterol moiety (Crooke et al. (1996) *J. Pharmacol. Exp. Ther.* 277:923-937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

As used herein "donor cells comprising immunoglobulin-producing cells" or "donor cells comprising immunoglobulin-producing cells" sometimes referred to simply as "donor cells" or "donor blood cells" refers to cells that are capable of producing antibodies when immunized with an antigenic compound. Examples of sources of such donor cells suitable for use in the invention include, but are not limited to spleen cells, lymph node cells, bone marrow cells, and immortalizing tumor infiltrating lymphocytes.

As used herein, the term "amino acid" denotes a molecule containing both an amino group and a carboxyl group. In some preferred embodiments, the amino acids are $\alpha$-, $\beta$-, $\gamma$- or $\delta$-amino acids, including their stereoisomers and racemates. As used herein the term "L-amino acid" denotes an $\alpha$-amino acid having the L configuration around the $\alpha$-carbon, that is, a carboxylic acid of general formula $CH(COOH)(NH_2)$-(side chain), having the L-configuration. The term "D-amino acid" similarly denotes a carboxylic acid of general formula $CH(COOH)(NH_2)$-(side chain), having the D-configuration around the $\alpha$-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, BIOCHEMISTRY, Second Edition, Worth Publishers, Inc., 1975, pages 72-77 (incorporated herein by reference). Amino acid substituents may be attached through their carbonyl groups through the oxygen or carbonyl carbon thereof, or through their amino groups, or through functionalities residing on their sidechain portions.

As used herein "polynucleotide" refers to a nucleic acid molecule and includes genomic DNA cDNA, RNA, mRNA and the like.

As used herein "inhibitor of mismatch repair" refers to an agent that interferes with at least one function of the mismatch repair system of a cell and thereby renders the cell more susceptible to mutation.

As used herein "hypermutable" refers to a state in which a cell in vitro or in vivo is made more susceptible to mutation through a loss or impairment of the mismatch repair system.

As used herein "agents," "chemicals," and "inhibitors" when used in connection with inhibition of MMR refers to chemicals, oligonucleotides, RNA interference molecules, analogs of natural substrates, and the like that interfere with normal function of MMR.

As used herein, "about" refers to an amount within a range of +/−10% of the cited value.

As used herein, "mitogenic polypeptide" refers to a polypeptide when in combination with the antigen provides stimulation of appropriate cells to increase the immune response against the subject antigen.

As used herein, "hybridoma" refers to the result of a cell fusion between an immunoglobulin-producing cell and a transformed cell, such as a myeloma cell.

As used herein, "IgG subclass" refers to a category of immunoglobulins comprising IgG1, IgG2, IgG2a, IgG2b, IgG3, and IgG4.

As used herein, "mismatch repair gene" refers to a gene that encodes one of the proteins of the mismatch repair complex. Although not wanting to be bound by any particular theory of mechanism of action, a mismatch repair complex is believed to detect distortions of the DNA helix resulting from non-complementary pairing of nucleotide bases. The non-complementary base on the newer DNA strand is excised, and the excised base is replaced with the appropriate base which is complementary to the older DNA strand. In this way, cells eliminate many mutations that occur as a result of mistakes in DNA replication. Dominant negative alleles cause a mismatch repair defective phenotype even in the presence of a wild-type allele in the same cell. A non-limiting example of a dominant negative allele of a mismatch repair gene is the human gene hPMS2-134, which carries a truncation mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations which accumulate in cells after DNA replication. Thus, expression of a dominant negative allele of a mismatch repair gene results in impairment of mismatch repair activity, even in the presence of the wild-type allele.

As used herein, "HAT-sensitive" refers to a lethal effect on cells when cultured in medium containing hypoxanthine, aminopterin and thymidine.

As used herein, "EBV-negative" refers to lack of infection of Epstein-Barr virus in a cell as measured by production of EBNA protein, or detection of EBV nucleic acids.

As used herein, "Ig-negative" refers to lack of production in a cell of any light or heavy chains of immunoglobulins.

As used herein, "screening" refers to an assay to assess the genotype or phenotype of a cell or cell product including, but not limited to nucleic acid sequence, protein sequence, protein function (e.g., binding, enzymatic activity, blocking activity, cross-blocking activity, neutralization activity, and the like). The assays include ELISA-based assays, Biacore analysis, and the like.

As used herein, "isolated" refers to a nucleic acid or protein that has been separated and/or recovered from a component of its natural environment. Contaminant components of its natural environment are materials which would interfere with diagnostic or therapeutic uses for the polypeptide, and may include enzymes, hormones, and other proteinaceous or non-proteinaceous solutes. In some embodiments, the nucleic acid or protein is purified to greater than 95% by weight of protein. In other embodiments, the nucleic acid or protein is purified to greater than 99% by weight of protein. Determination of protein purity may be by any means known in the art such as the Lowry method, by SDS-PAGE under reducing or non-reducing conditions using a stain such as a Coomassie blue or silver stain. Purification of nucleic acid may be assessed by any known method, including, but not limited to spectroscopy, agarose or polyacrylamide separation with fluorescent or chemical staining such as methylene blue, for example.

The invention provides an in vitro immunization method for obtaining antigen-specific immunoglobulin producing cells wherein the cells produce immunoglobulins of the IgG subclass, and cells produced by this method. The in vitro immunization procedure comprises combining donor cells with an immunogenic antigen in culture. In one embodiment, the buffy coat of donor cells is used. The donor may be from any source, including, but not limited to cord blood, venous blood, and the like. The source of the blood cells may be from any animal producing immune cells, particularly mammals. Non-limiting examples of blood cell sources include, mice, rats, humans, monkeys, dogs, cats, horses, pigs, sheep, goats, rabbits, birds, cows, guinea pigs and fish. The blood or buffy coat may be further enriched for lymphocytes by any known method, such as, but not limited to differential centrifugation, filtration, and the like.

Donor cells such as peripheral blood mononuclear cells (PBMC) may be incubated in L-leucyl-L-lysine methyl ester hydrobromide (LLOMe). While not wishing to be bound by any particular theory of operation, LLOme is believed to lysosomotropic and specifically kills cytotoxic cells in the PBMC pool such as NK cells, cytotoxic T cells, and CD8+ suppressor T cells, while not having an effect on B cells, T helper cells accessory cells and fibroblasts (Borrebaeck (1988) Immunol. Today 9(11):355-359). Generally, the PBMCs may be incubated with LLOMe for a period of 1-30 minutes. In some embodiments, the incubation is performed for 10-20 minutes. In other embodiments, the incubation is performed for 15 minutes. The LLOMe is generally a component of culture medium, such as, for example, RPMI 1640, and is provided in a concentration of about 0.10 to 1 mM. In some embodiments, LLOMe is provided in an amount of about 0.10 to 0.50 mM. In other embodiments, LLOMe is provided in an amount of about 0.25 mM.

The antigen may be any antigen provided that it is immunogenic. Whole proteins or peptides may be used. In addition, one may use, for example, membrane preparations (including those from tumors), lymphoma cells, whole cells, single cells, homogenized cells, pathogens, inclusion bodies, cell lysates, protein preparations, and minced tissue (including tumor tissue). Whole proteins may be in native or denatured conformation. Peptides may be conjugated to carrier molecules to provide immunogenicity. While not wishing to be bound by any particular theory of operation, carrier molecules may provide additional T cell epitopes which may be useful in stimulating a more robust in vitro antibody response. Examples of carriers that are suitable for use in the method of the invention include tetanus toxoid, diptheria toxin, thyroglobulin, cholera toxin, BCG, bovine serum albumen (BSA), ovalbumin (OVA), and the like. These carriers are referred to herein as "mitogenic polypeptides."

Antigens may be conjugated to mitogenic polypeptides in any way known in the art. For example, fusion proteins may be generated by expressing a polypeptide in a recombinant expression system comprising the polynucleotide encoding at least a portion of the antigen joined in-frame to a polynucleotide encoding at least a portion of the mitogenic polypeptide. The fusion protein may have the mitogenic polypeptide joined at either the amino- or carboxy terminus of the antigen. In some embodiments, more that one antigen may be expressed as a fusion protein in combination with a mitogenic polypeptide. In other embodiments, more than one mitogenic polypeptide may be expressed as a fusion protein with the antigen or antigens. In other embodiments, more than one mitigenic polypeptide and more than one antigen may be expressed together as a single fusion protein.

In an alternative embodiment, at least a portion of the mitogenic polypeptide is conjugated to at least a portion of the antigen using chemical cross-linkers. Examples of chemical cross-linkers include, but are not limited to gluteraldehyde, formaldehyde, 1,1-bis (diazoacetyl)-2-phenylethane, N-hydroxysuccinimide esters (e.g., esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane). Derivatizing agents such as methyl-3-[(p-azido-phenyl)dithio]propioimidate yield photoactivatable intermediates which are capable of forming cross-links in the presence of light. Alternatively, for example, a lysine residue in the mitogenic polypeptide or antigen may be coupled to a C-terminal or other cysteine residue in the antigen or mitogenic polypeptide, respectively, by treatment with N-γ-maleimidobutyryloxy-succinimide (Kitagawa and Aikawa (1976) J. Biochem. 79, 233-236). Alternatively, a lysine residue in the mitogenic polypeptide or antigen may be conjugated to a glutamic or aspartic acid residue in the antigen or mitogenic polypeptide, respectively, using isobutylchloroformate (Thorell and De Larson (1978) RADIOIMMUNOASSAY AND RELATED TECHNIQUES: METHODOLOGY AND CLUBUCAL APPLICATIONS, p. 288). Other coupling reactions and reagents have been described in the literature.

The conditions for the in vitro immunization procedure comprise incubating the cells at about 25-37° C., (preferably 37° C.) supplied with about 5-10% $CO_2$. In some embodiments, the incubation is performed with between about 6-9% $CO_2$. In other embodiments the incubation is performed in about 8% $CO_2$. The cell density is between about 2.5 to $5 \times 10^6$ cells/ml in culture medium. In some embodiments, the culture medium is supplemented with about 2-20% FBS. In other embodiments, the culture medium is supplemented with about 5-15% FBS. In other embodiments, the culture medium is supplemented with about 7-12% FBS. In other embodiments, the culture medium is supplemented with about 10% FBS.

The in vitro stimulation culture medium is supplemented with cytokines to stimulate the cells and increase the immune response. In general IL-2 is supplied in the culture medium. However, other cytokines and additives may also be included to increase the immune response. Such cytokines and factors may include, for example, IL-4 and anti-CD40 antibodies.

The fusion of myeloma cells with the immunoglobulin-producing cells may be by any method known in the art for the creation of hybridoma cells. These methods include, but are not limited to, the hybridoma technique of Kohler and Milstein, (1975, Nature 256:495-497; and U.S. Pat. No. 4,376, 110) (see also, Brown et al. (1981) J. Immunol. 127:539-546; Brown et al. (1980) J. Biol. Chem. 255 (11):4980-4983; Yeh et al. (1976) Proc. Natl. Acad. Sci. USA 76:2927-2931; and Yeh et al. (1982) Int. J. Cancer 29:269-275), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, MONOCLONAL ANTIBODIES AND CANCER THERAPY, Alan R. Liss, Inc., pp. 77-96). The hybridoma producing the mAb of this invention may be cultivated in vitro or in vivo.

The technology for producing monoclonal antibody hybridomas is well-known to those of skill in the art and is described, for example in Kenneth, in MONOCLONAL ANTIBODIES: ANALYSES, NEW DIMENTION IN BIOLOGICAL ANALYSES, Plenum Publishing Corp., New York, N.Y. (1980); Lerner (1981) Yale J. Biol. Med., 54:387-402; Galfre et al. (1977) Nature 266: 55052; and Gefter et al. (1977) Somatic Cell Genet. 3:231-236). However, many variations of such methods are possible and would be appreciated by one of skill in the art. Thus, the techniques for generation of hybridomas is not limited to the disclosures of these references.

Any myeloma cell may be used in the method of the invention. Preferably, the myeloma cells are human cells, but the invention is not limited thereto or thereby. In some embodiments, the cells are sensitive to medium containing hypoxanthine, aminopterin, an thymidine (HAT medium). In some embodiments, the myeloma cells do not express immunoglobulin genes. In some embodiments the myeloma cells are negative for Epstein-Barr virus (EBV) infection. In preferred embodiments, the myeloma cells are HAT-sensitive, EBV negative and Ig expression negative. Any suitable myeloma may be used. An example of such a myeloma is that described in U.S. Pat. No. 4,720,459 to Winkelhake, and deposited with the American Type Culture Collection (ATCC) as CRL 8644. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC.

In some embodiments of the method of the invention, the hybridoma cells and/or mammalian expression cells may be rendered hypermutable by the introduction of a dominant negative allele of a mismatch repair gene. The dominant negative allele of the mismatch repair gene may be introduced into the hybridoma cell (i.e., after the fusion of immunoglobulin-producing cells with the myeloma cells) or may be introduced into the myeloma cell prior to the fusions. The invention, therefore, also provides hypermutable myeloma cells for use in the generation of hybridoma cells. The dominant negative allele may also be introduced into the mammalian expression cells.

The dominant negative allele of the mismatch repair gene is in the form of a polynucleotide which may be in the form of genomic DNA, cDNA, RNA, or a chemically synthesized polynucleotide. The polynucleotide can be cloned into an expression vector containing a constitutively active promoter segment (such as, but not limited to, CMV, SV40, EF-1 Dor LTR sequences) or to inducible promoter sequences such as those from tetracycline, or ecdysone/glucocorticoid inducible vectors, where the expression of the dominant negative mismatch repair gene can be regulated. The polynucleotide can be introduced into the cell by transfection.

Transfection is any process whereby a polynucleotide is introduced into a cell. The process of transfection can be carried out in vitro, e.g., using a suspension of one or more isolated cells in culture. The cell can be any immortalized cell used for creating hybridomas for the production of monoclonal antibodies, or the cell may be the hybridoma itself. The hybridomas may be heterohybridoma cells (e.g. human-mouse cell fusions) or homohybridoma cells (e.g., human-human hybridoma cells and mouse-mouse hybridoma cells).

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the mismatch repair gene, the cell can be grown and reproduced in culture. If the transfection is stable, such that the gene is expressed at a consistent level for many cell generations, then a cell line results.

The dominant negative allele of the mismatch repair gene may be derived from any known mismatch repair gene including, but not limited to PMS2, PMS1, PMSR3, PMSR2, PMSR6, MLH1, GTBP, MSH3, MSH2, MLH3, or MSH1, and homologs of PMSR genes as described in Nicolaides et al. (1995) *Genomics* 30:195-206 and Horii et al. (1994) *Biochem. Biophys. Res. Commun.* 204:1257-1264 and the like. "Dominant negative alleles" as used herein, refers to the ability of the allele to confer a hypermutable status to the cell expressing the allele. Any allele which produces such effect can be used in this invention. The dominant negative alleles of a mismatch repair gene can be obtained from the cells of humans, animals, yeast, bacteria, or other organisms. Dominant negative alleles of mismatch repair genes that are suitable for use in the invention have certain functional characteristics associated with structural features. A non-limiting example of a dominant negative mismatch repair gene is the PMS2 truncation mutant, PMS2-134. This gene contains a mutation which truncates the PMS2 protein after amino acid 133. The lack of the C-terminus in the PMS2 protein is believed to interfere with the binding of PMS2 with Screening cells for defective mismatch repair activity can identify such alleles. Cells from animals or humans with cancer can be screened for defective mismatch repair. Cells from colon cancer patients may be particularly useful. Genomic DNA, cDNA, or mRNA from any cell encoding a mismatch repair protein can be analyzed for variations from the wild type sequence. Dominant negative alleles of a mismatch repair gene can also be created artificially, for example, by producing variants of the hPMS2-134 allele or other mismatch repair genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

Dominant negative alleles of such genes, when introduced into cells or transgenic animals, increase the rate of spontaneous mutations by reducing the effectiveness of DNA repair and thereby render the cells or animals hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The hypermutable hybridoma cells will accumulate new mutations in gene(s) to produce new output traits within the hybridoma. The hybridoma cells can be screened for desired characteristics and cell lines bearing these characteristics may be expanded. Furthermore, the hybridoma cells may be "cured" of the mismatch repair defect by eliminating the dominant negative mismatch repair gene in the cell or by turning of its expression, leading to stable biological products consisting of altered genes, RNAs, or polypeptides.

The dominant negative alleles of the mismatch repair gene may be introduced as part of a vector. The polynucleotide encoding the dominant negative mismatch repair protein allele may be operably linked to a promoter that functions in the cell to drive expression of the dominant negative allele of the mismatch repair gene. Other elements of the vector may include an origin of replication, one or more selectable markers, such as a drug resistance gene that allows the cells to grow in the presence of a growth inhibitory compound.

In embodiments of the invention that utilize myeloma cells or donor immunoglobulin-producing cells that are naturally deficient in mismatch repair, the invention may further comprise the step of restoring genetic stability of the hybridoma by introducing a wildtype mismatch repair gene into the cell to complement the deficiency and restore genetic stability.

Another aspect of the invention is the use of cells lacking MMR (either due to defects in endogenous mismatch repair genes, or due to the introduction of a dominant negative MMR gene) and chemical mutagens to cause an enhanced rate of mutations in a host's genome. The lack of MMR activity has been known to make cells more resistant to the toxic effects of DNA damaging agents. This invention comprises making proficient MMR cells mismatch repair defective via the expression of a dominant negative MMR gene allele and then enhancing the genomic hypermutability with the use of a DNA mutagen. Chemical mutagens are classifiable by chemical properties, e.g., alkylating agents, crosslinking agents, etc. The following chemical mutagens are useful, as are others not listed here, according to the invention and may be used to further enhance the rate of mutation in any of the embodiments of the method of the invention: N-ethyl-N-nitrosourea (ENU), N-methyl-N-nitrosourea (MNU), procarbazine hydrochloride, chlorambucil, cyclophosphamide, methyl methanesulfonate (MMS), ethyl methanesulfonate (EMS), diethyl sulfate, acrylamide monomer, triethylene melamin (TEM), melphalan, nitrogen mustard, vincristine, dimethylnitrosamine, N-methyl-N'-nitro-nitrosoguanidine (MNNG), 7,12 dimethylbenz (a) anthracene (DMBA), ethylene oxide, hexamethylphosphoramide, bisulfan. In a preferred aspect of the invention, a mutagenesis technique is employed that confers a mutation rate in the range of 1 mutation out of every 100 genes; 1 mutation per 1,000 genes. The use of such combination (MMR deficiency and chemical mutagens will allow for the generation of a wide array of genome alterations (such as but not limited to expansions or deletions of DNA segments within the context of a gene's coding region, a gene's intronic regions, or 5' or 3' proximal and/or distal regions, point mutations, altered repetitive sequences) that are preferentially induced by each particular agent.

Mutations can be detected by analyzing for alterations in the genotype of the cells or animals, for example by examining the sequence of genomic DNA, cDNA, messenger RNA, or amino acids associated with the gene of interest. Mutations can also be detected by screening the phenotype of the gene. An altered phenotype can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest, such as but not limited to measuring protein secretion, chemical-resistance, pathogen resistance, etc.

In some embodiments of the method of the invention, inducible vectors that control the expression of a dominant negative and normally functioning MMR gene are used. This strategy restores DNA stability once a host cell or organism exhibiting a new output trait, altered gene, RNA or polypeptide has been generated via trait selection with or without the combination of chemical mutagens to establish a genetically stable version of this cell or organism. In the case of MMR defective cells as a result of ectopically expressing a dominant negative MMR gene allele, the MMR activity is decreased or completely eliminated by removing the inducer molecule from the cell culture or organism's environment. In addition, the expression of a dominant negative MMR gene can be suppressed by knocking out the MMR gene allele using methods that are standard to those skilled in the art of DNA knockout technology in germ or somatic cells (Waldman et al. (1995) *Cancer Res*. 55:5187-5190).

The chiral position of the side chains of the anthracenes is not particularly limited and may be any chiral position and any chiral analog. The anthracenes may also comprise a stereoisomeric form of the anthracenes and include any isomeric analog.

Examples of hosts are but not limited to cells or whole organisms from human, primate, mammal, rodent, plant, fish, reptiles, amphibians, insects, fungi, yeast or microbes of prokaryotic origin.

A more detailed disclosure of particular embodiments of the invention follows in the specific examples, however, the invention is not limited thereto or thereby.

EXAMPLES

Example 1

Generation of Hybridomas Secreting Human Monoclonal Antibodies to Tetanus Toxin (TT)

A. Generation and Assaying of TT-Specific B Lymphocytes

Isolation of lymphocytes from Donor. Lymphocytes were isolated from whole blood by centrifugation through Ficoll-Paque according to the manufacturer's instructions. Isolated lymphocytes were incubated with 0.25 mM Leu-Leu methyl ester hydrobromide (LLOMe) prepared in RPMI 1640 medium containing 2% fetal bovine serum (FBS) for 15 minutes at room temperature. The cells were then washed three times with culture medium.

In vitro stimulation of isolated lymphocytes The cells were incubated at 37° C. in a incubator, supplied with 8% $CO_2$, at a density between 2.5 to $5\times10^6$ cells/ml in culture medium supplemented with 10% FBS and TT and IL-2 at various concentrations. After four days of culture, the cells were washed four times with medium and the culture was continued for additional eight days.

Measurement of the B cell response. Lymphocyte culture supernatants were collected on day 12 of the culture and tested in an ELISA for the presence of anti-TT antibodies. Briefly, TT or BSA at 0.5 µg/ml in 0.05 M carbonate-bicarbonate buffer was immobilized onto an EIA plate. After blocking with 1% bovine serum albumin (BSA) in PBS containing 0.05% Tween 20, the supernatant was added to the wells. Antibodies bound to TT were detected with peroxidase-labeled goat anti-human IgG or anti-human IgM. TMB was used for color development. The plate was read using a Microplate reader with a 450 nm filter. A supernatant sample that had antibody bound to TT, but not to BSA, and in which the signal was two times the assay background was considered positive. The positive cells were pooled, and used for hybridoma production (FIG. 1).

Figure 2A:
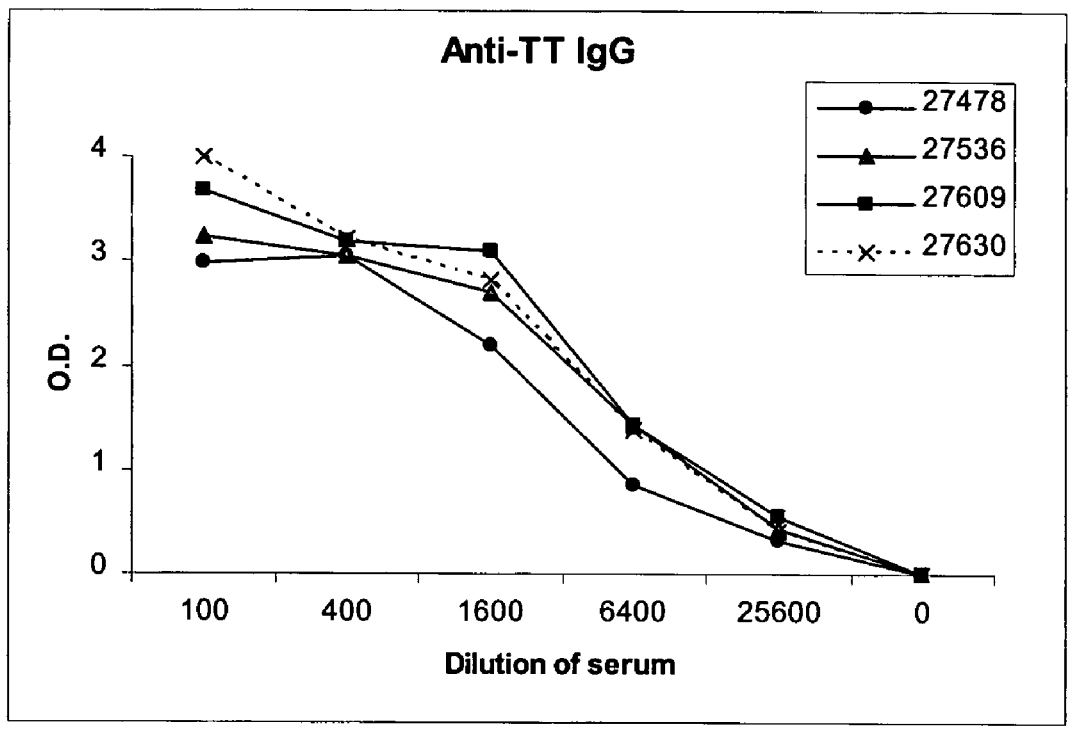
FIG. 2A shows reactivity of donor serum to TT by detection of donor anti-TT IgG.
Figure 2B:
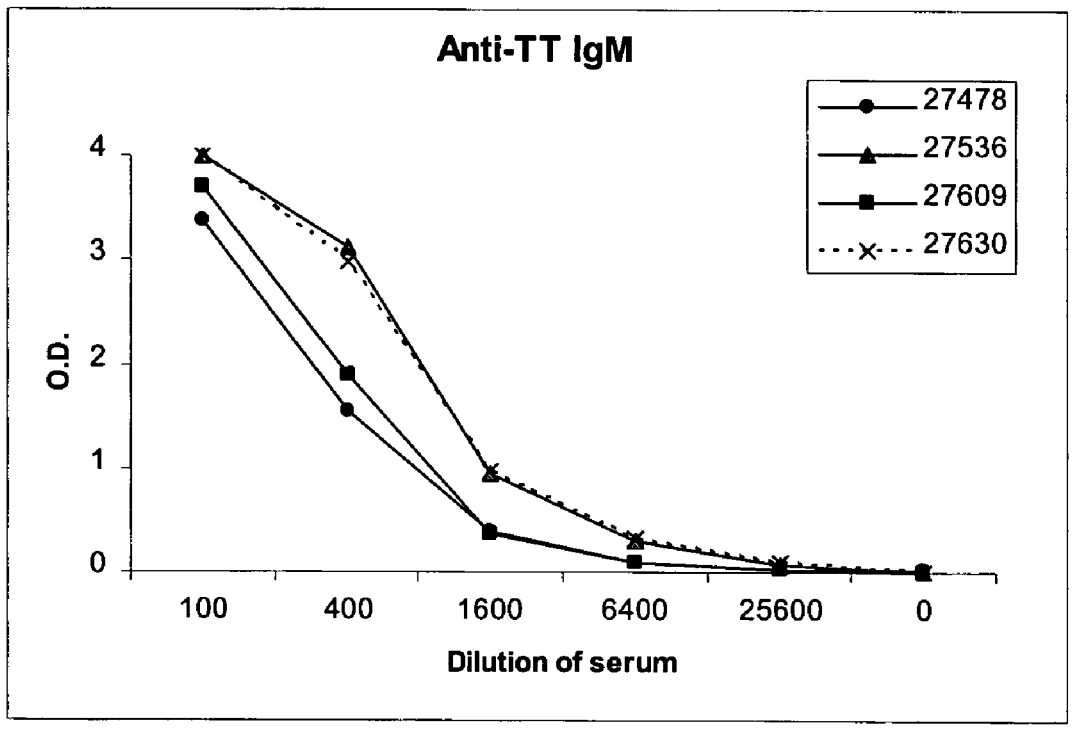
FIG. 2B shows reactivity of donor serum to TT by detection of donor anti-TT IgM.
Figure 3:
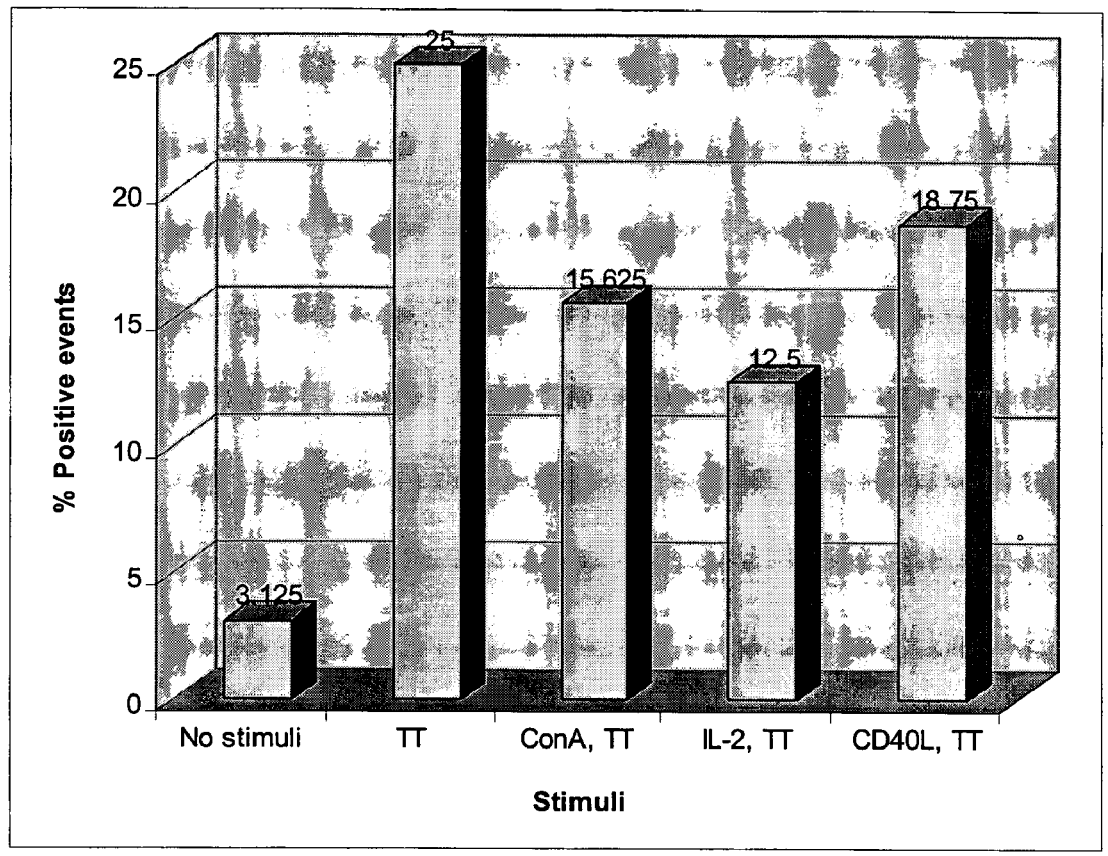
FIG. 3 shows the frequency of the anti-TT response of PBMCs upon in vitro immunization with TT, or with TT in combination with IL-2, or CD40L.
Figure 4:
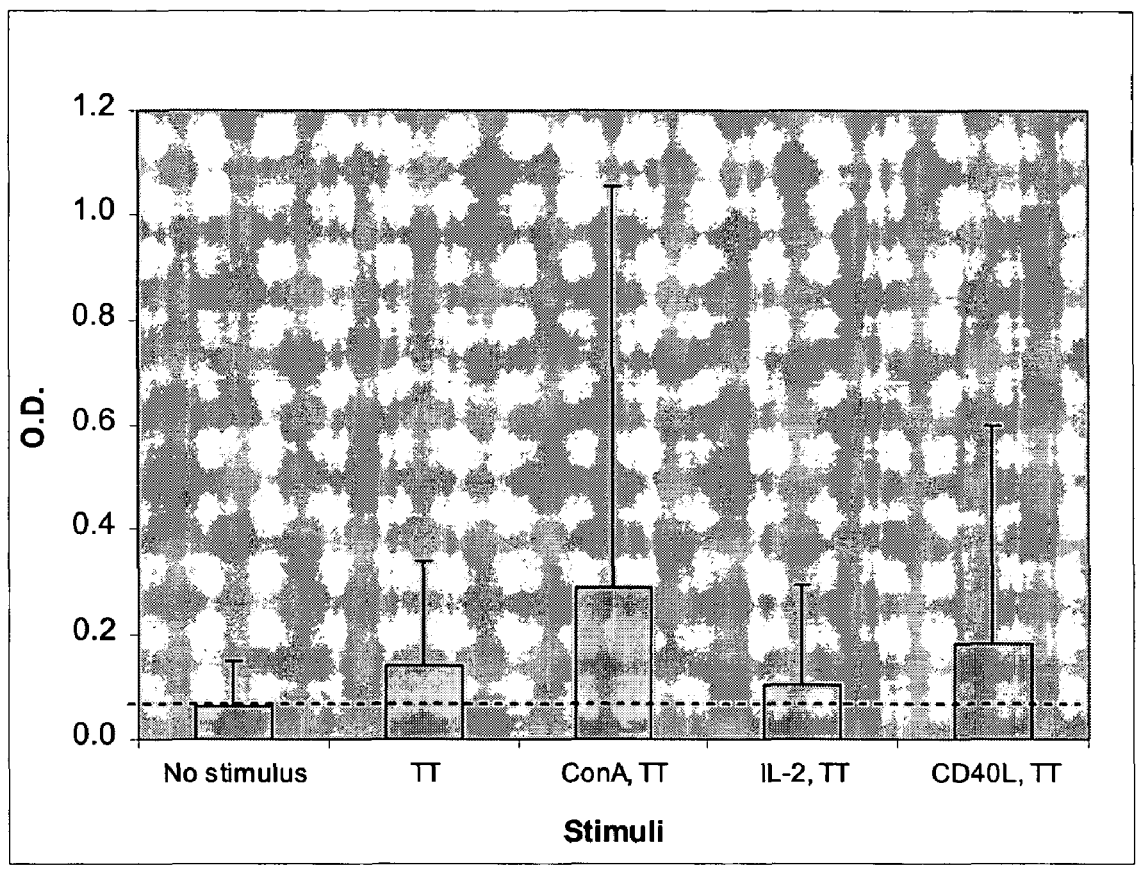
FIG. 4 shows the intensity of the response of PBMCs upon in vitro immunization with TT, or with TT in combination with IL-2, or CD40L.

Notably, peripheral blood mononuclear cells (PBMCs) from some donors contain a fraction of B cells that secret TT-specific antibodies in culture. This is due to the fact that about 90% of the population in the United States has been vaccinated against TT. Such sera also has a titer of higher than 1000 (FIG. 2). However, the percentage of positive events is greatly increased when PBMCs are immunized in vitro with TT (FIG. 3). The intensity of the PBMC response is also enhanced with the stimulation of TT alone or in combination with IL-2 or CD40L (FIG. 4). Similar effects were observed with other antigens (data not shown).

Generation of hybridomas secreting human antibodies. To prepare activated lymphocytes, cells were pooled and cultured in T flasks at $0.5\text{-}1\times10^6$ cells/ml in culture medium supplemented with 10% FBS one day prior to the fusion. To prepare the fusion partner, mouse myeloma NS0 cells were transfected with human PMS2-134 expression vector as described in Nicolaides et al. (1998) *Mol. Cell. Biol.* 18(3): 1635-1641. The cells were cultured in RPMI 1640 supplemented with 10% FBS and 2 mM glutamine (Complete Medium) and the culture was kept in log phase.

Next, lymphocytes were harvested and counted. An equal number of myeloma cells was harvested. Both types of cells were combined and washed three times with RPMI 1640 medium. Polyethylene glycol (PEG) was added dropwise to the loosened cell pellet, and the PEG was subsequently diluted out slowly with 25 ml of RPMI medium in a course of 2.5 minutes. After diluting out the PEG, fused cells were suspended in Complete Medium supplemented with HAT and 20% FBS, and seeded onto 96-well plates.

Figure 5:
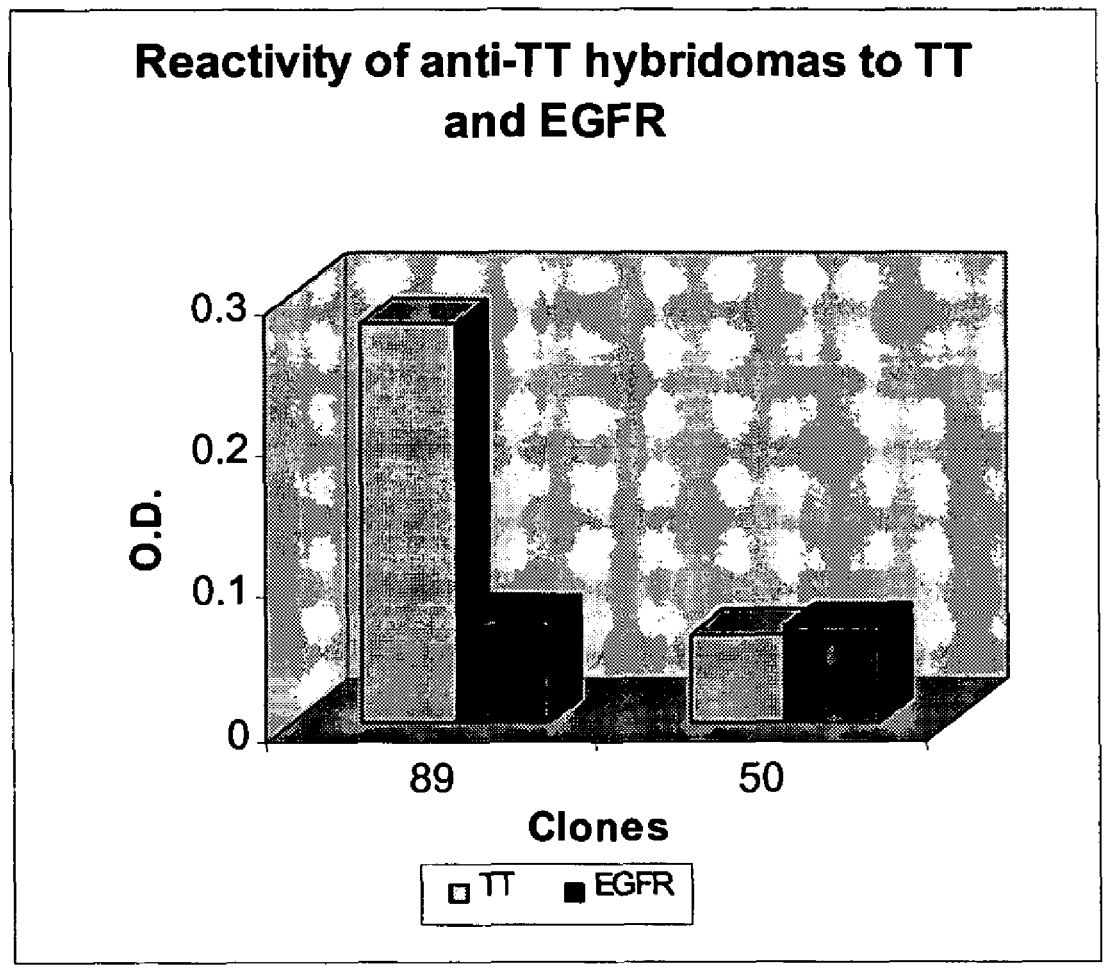
FIG. 5 shows the response of hybridomas expressing anti-TT antibodies.

Screening and characterization of antigen-specific hybridoma clones. When the hybridoma cells grew to semi-confluence, supernatants were collected and subjected to an ELISA for antigen-specific reactivity. As an example, hybridomas derived from TT-immunized lymphocytes were tested. Briefly, TT or BSA at 0.5 ug/ml in 0.05 M carbonate-bicarbonate buffer was immobilized onto the EIA plate. After blocking with 1% bovine serum albumen in PBS containing 0.05% Tween 20, the cell culture supernate was added to the wells. Antibodies bound to TT were detected with peroxidase-labeled goat anti-human IgG or anti-human IgM. TMB was used for color development. The plate was read in the Microplate reader with a 450 nm filter. A cell clone that showed reactivity to TT but not to BSA was considered positive (FIG. 5). Positive clones were expanded and subcloned by limiting dilution to generate monoclonal cells.

Example 2

Generation of Hybridomas Secreting Human Monoclonal Antibodies to Epidermal Growth Factor Receptor (EGFR) (Self Antigen)

A. Generation of EGFR-Specific B Lymphocytes

Preparation of Antigen. Human epidermal growth factor receptor (EGFR), purified from A431 cells, was purchased from Sigma. Previous studies found that immune responses to this antigen were very weak, most likely due to tolerance. In order to enhance immunization, we conjugated the EGFR to tetanus toxin C (EGFR-TT) and the conjugate was used as immunogen for in vitro immunization in order to overcome any immunotolerance.

Preparation of EGFR-TT conjugate. 100 ug of purified EGFR was reconstituted in 100 ul of sterile MilliQ-grade water. 1 mg of purified, lyophilized recombinant tetanus toxin C fragment (TT-C) was dissolved in sterile MilliQ-grade water to yield a 2 mg/ml TT-C solution. Crosslinking was performed in 50 mM sodium carbonate buffer pH 9.0 at equimolar ratios of EGFR to TT-C, using glutaraldehyde at a final concentration of 0.5% for 3 hours at room temperature, followed by 4° C. overnight. Glutaraldehyde was quenched by addition of a fresh 100 mg/ml solution of sodium borohydride in 50 mM sodium carbonate pH 9.0, under open atmosphere for 1 hour at 4° C. Crosslinked products were dialyzed against $Ca^{2+}$-, $Mg^{2+}$-free phosphate-buffered saline overnight at 4° C., using 3.5K MWCO Slide-A-Lyzer cassettes. The reaction was monitored by Western blotting, using commercial anti-EGFR (mAb-15) and anti-TT-C (Roche) monoclonal antibodies. By this method, greater than 70% of the components are crosslinked, and appear as immunoreactive species of greater MW than the starting material (data not shown).

In vitro stimulation of peripheral blood mononuclear cells (PBMC). LLOMe-pretreated PBMC were incubated at a density of $3\times10^6$ cells/ml in culture medium supplemented with 10% FBS and a stimuli mixture. The stimuli mixture was composed of EGFR-TT at a concentration of 50 ng/ml with or without recombinant human IL-2 at 20 IU, mouse anti-human CD40 antibody as CD40L at 0.5 ug/ml (used to enhance IgG class switching). After four days of culture, the cells were re-fed with complete medium, in the absence of added stimulus, every three or four days. Culture supernatants were collected on days 12-18 and tested for EGFR-specific antibodies.

Detection of EGFR-specific antibody response. The PBMC response to the stimulation was examined in a EGFR-specific ELISA. Briefly, EGFR, TT, or BSA at 0.5 ug/ml in 0.05 M carbonate-bicarbonate buffer, pH 9.6, was immobilized onto EIA plates. After blocking the plates with 5% non-fat dry milk in PBS containing 0.05% Tween 20, the supernatant was added to the wells. Antibodies from the supernatant bound to immobilized antigens were detected with peroxidase-labeled goat anti-human IgG+IgM (H+L). TMB substrate kit was used for color development. The plates were read in a Microplate reader with a 450 nm filter. A supernatant sample containing antibody that bound to EGFR, but not to TT and BSA, was considered positive. A robust response was observed in cultures immunized to the EGFR-TT as compared to controls. While anti-EGFR responses were observed in PBMCs for a small fraction of donors, the percentage of positive clones was greatly increased when PBMCs were immunized in vitro with EGFR complexed with TT (FIG. 6). Positive cells were pooled and used for hybridoma production.

Generation of Hybridomas. To prepare activated lymphocytes, cells were pooled and cultured in T flasks at $0.5\text{-}1\times10^6$ cells/ml in culture medium supplemented with 10% FBS one day prior to the fusion. To prepare the fusion partner, mouse myeloma NS0 cells were transfected with human PMS2-134 expression vector as described in Nicolaides et al. (1998) *Mol. Cell. Biol.* 18(3):1635-1641. The cells were cultured in RPMI 1640 supplemented with 10% FBS and 2 mM glutamine (Complete Medium) and the culture was kept in log phase.

Figure 7:
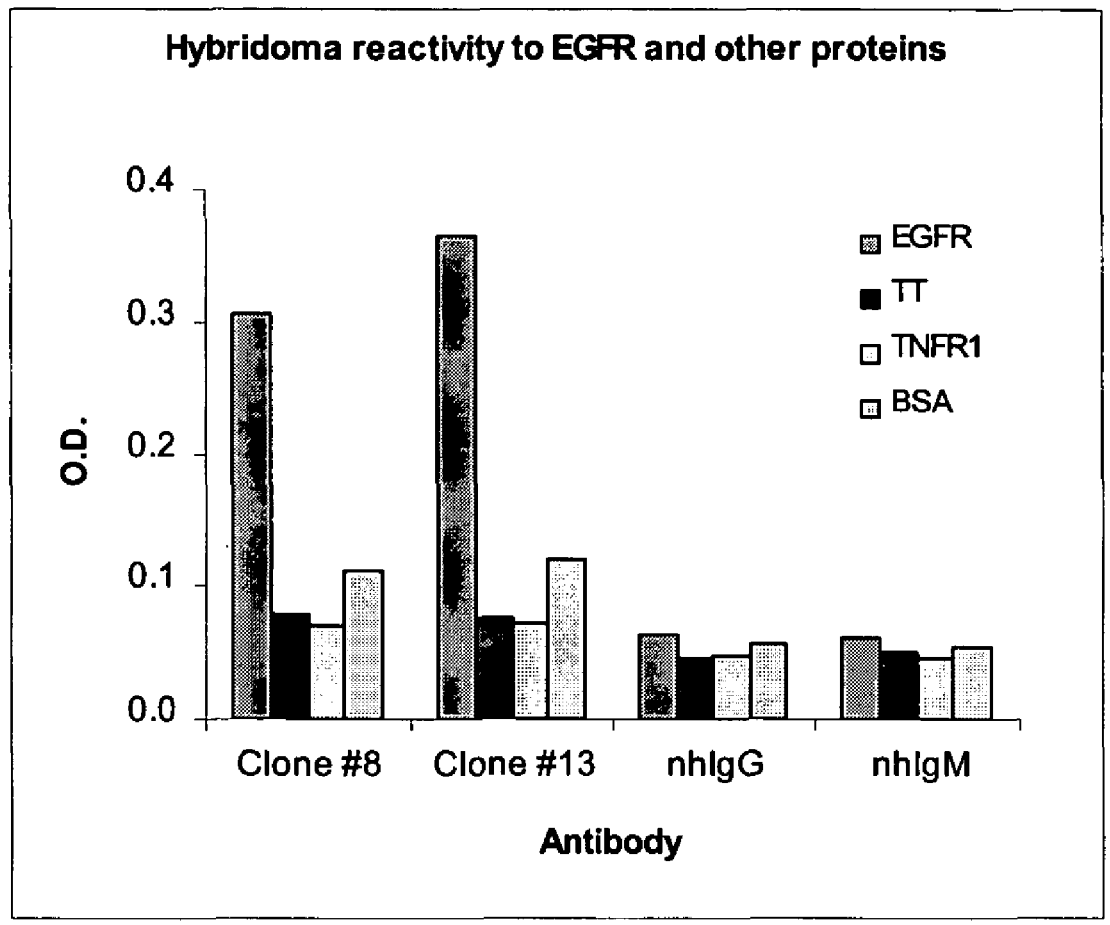
FIG. 7 shows the response of hybridomas expressing antibodies against human EGFR. Antibodies bound to EGFR or BSA (control) pre-coated on the solid phase were detected with HRP-labeled goat anti-human IgG or HRP-labeled goat anti-human IgM.

Screening and characterization of antigen-specific hybridoma clones. When the hybridoma cells grew to semi-confluence, supernatants were collected and subjected to an ELISA for antigen-specific reactivity. As an example, hybridomas derived from EGFR-immunized lymphocytes were tested. Briefly, EGFR, TT TNFR1 or BSA at 0.5 ug/ml in 0.05 M carbonate-bicarbonate buffer was immobilized onto the EIA plate. After blocking with 1% bovine serum albumen in PBS containing 0.05% Tween 20, the cell culture supernate was added to the wells. Antibodies bound were detected with peroxidase-labeled goat anti-human IgG or anti-human IgM. TMB was used for color development. Normal human IgG (nhIgG) and IgM (nhIgM) were used as controls. The plate was read in the Microplate reader with a 450 nm filter. A cell clone that showed reactivity to EGFR, but not to BSA was considered positive (FIG. 7).

Example 3

A. Isolation of PBMC from Whole Blood

Approximately 200 ml of whole blood mixed with 200 ml $PBS^{-/-}$ was centrifuged through Ficoll-Paque at 2000 rpm for 30 min. Serum was aspirated, the interface layer containing lymphocytes was collected and diluted 1:3 with $PBS^{-/-}$ and centrifuged at 2000 rpm for 10 min. The supernatant fluid was aspirated and the pellet was resuspended in 10 ml $PBS^{-/-}$. The cell suspension was split into two 50 ml conical tubes and PBS$^{-/-}$ was added to each tube to adjust the volume to 35 ml each. The tubes were centrifuged at 800 rpm for 7 minutes to remove the platelets. After aspirating the supernatant fluid, the pellet was resuspended in 10 ml ACK Lysing Buffer and incubated for 5 minutes at room temperature. Following lysis, 35 ml PBS$^{-/-}$ was added to the tubes and the tubes were centrifuged at 1000 rpm for 7 minutes. The cells were then washed with 45 ml RPMI medium.

B. Preparation of Dendritic Cells

Cells were centrifuged at 1000 rpm for 7 minutes and resuspended at $1 \times 10^8$ cells per 40 ml cRPMI for a density of $2.5 \times 10^6$ cells/ml. The cells were incubated at 37° C./8% $CO_2$ for 2 hours. Non-adherent cells were removed for further treatment (see Step C), and the adherent cells were carefully rinsed twice with PBS$^{-/-}$. Adherent cells were cultured in cRPMI supplemented with 400 IU/ml IL-4 and 50 ng/ml GM-CSF.

C. LLOMe Treatment and Cryopreservation of Non-Adherent Culture

The non-adherent cell culture was centrifuged at 1000 rpm for 7 minutes. The supernatant fluid was aspirated and the pellet was resuspended in 10 ml RPMI supplemented with 2% FBS and freshly thawed 85 µg/ml LLOMe. The cells were incubated for 15 minutes at room temperature. The cells were washed twice with cRPMI and resuspended in 45 ml cRPMI. The cells were transferred to an upright T25 flask at a density of $5 \times 10^6$ cells/ml in cRPMI supplemented with 2 µg/ml PHA and incubated at 37° C./8% $CO_2$ for 24 hours. The non-adherent cells were harvested, centrifuged at 1000 rpm for 7 minutes, and the cell pellet was resuspended in 5 ml cold cRPMI/5% DMSO. The tubes containing the cells were wrapped in paper towels and stored at −80° C. until needed.

D. Tumor Immunization

On day 6 of the procedure for isolation of dendritic cells, tumor cells were thawed in 2.5 ml pre-warmed medium at 37° C. The flask of dendritic cells was rinsed twice with 10 ml PBS$^{-/-}$. The dendritic cells were incubated with gentle rocking in 5 ml Cell Dissociation Buffer (Invitrogen Cat. No. 13151-014), and the solution was collected (scraping the remaining cells from the flask. The flask was rinsed with 10 ml cRPMI and the medium was collected. The cells were centrifuged at 1000 rpm for 7 minutes and the pellet was resuspended at $4 \times 10^6$ cells/ml cRPMI. Cells were distributed in a culture plate at a density of $1 \times 10^6$ cells/well. A tumor sample was chopped into fine pieces of approximately 1-3 mm$^3$. An aliquot of the tumor suspension was transferred to all but 1 well, titrating the amount of tumor per well. An aliquot of 0.25 ml cRPMI was added to the control well. The total volume in the wells was 0.5 ml/well. The dendritic cells and tumor cells were co-cultured at 37° C./8% $CO_2$ for 24 hours.

E. Co-Culture of PBMC with DC

Frozen PBMC were thawed by adding 40 ml cRPMI/30 IU/ml IL-2/600 IU/ml IL-4/0.75 µg/ml CD-40L pre-warmed to 50° C. to the frozen cells. When thawed, the cells were incubated for 1-2 hours at 37° C. The cells were centrifuged at 1000 rpm for 7 minutes and the pellet was resuspended in 5 ml of a 2× cocktail of cRPMI/60 IU/ml IL-2/1200 IU/ml IL-4/1.5 µg/ml CD-40L. The cell suspension was divided among wells in a tissue culture plate at 0.5 ml/well of suspension and diluted with 0.5 ml medium for a final concentration of 30 IU/ml IL-2, 600 IU/ml IL-4, and 0.75 µg/ml CD-40L. Cells were fed with cRPMI supplemented with 20 IU/ml IL-2, 400 IU/ml IL4, 100 IU/ml IL-10, and 0.5 µg/ml CD-40L.

F. Fusion

Figure 8:
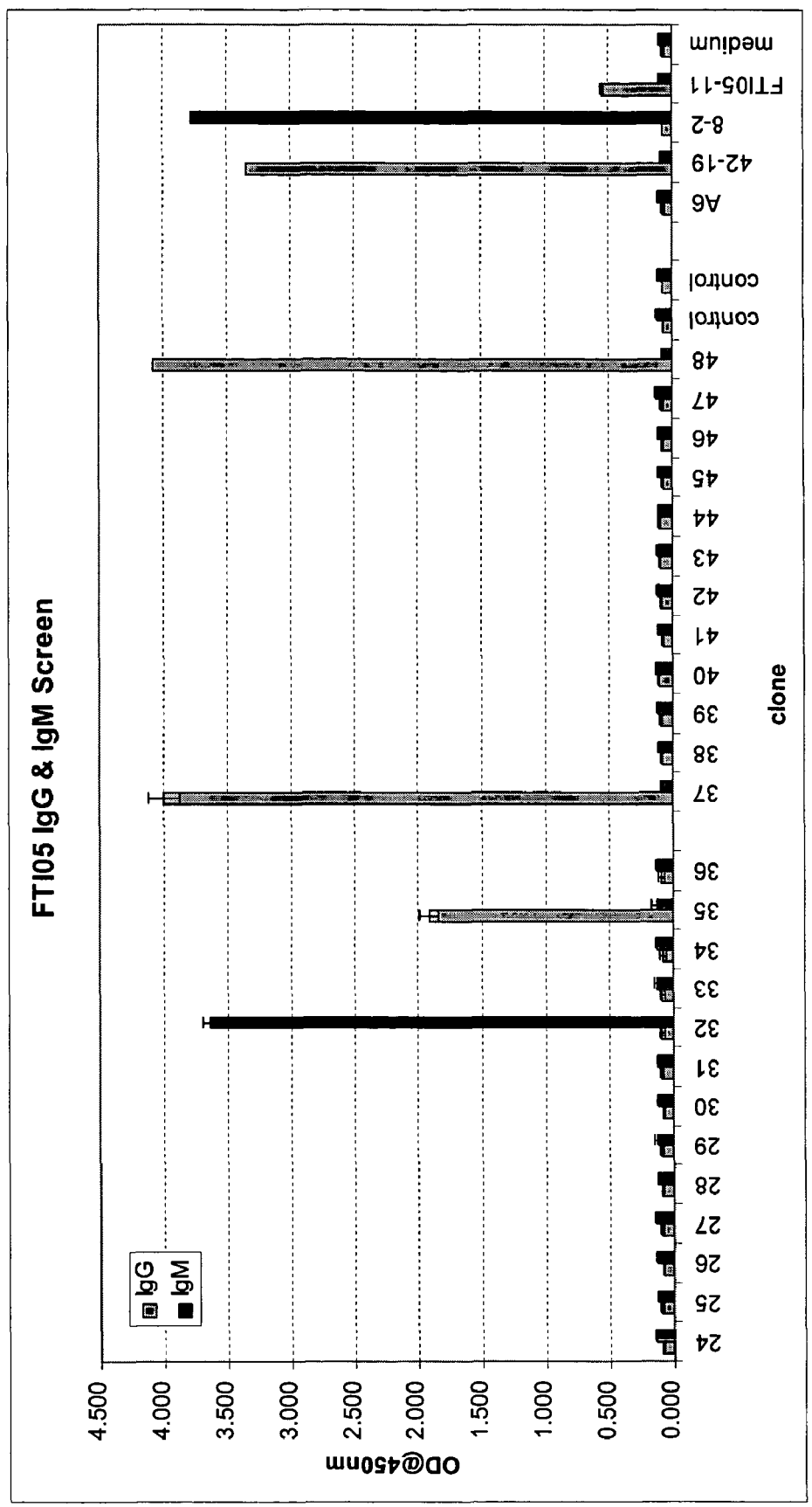
FIG. 8 shows the IgG and IgM responses of cells immunized with tumor cells in vitro.

Tumor-immunized PBMCs were then fused with A6 myeloma cells to generate hybridomas. Briefly, lymphocytes were harvested from 75% tumor and 100% tumor wells, rinsed with 1 ml RPMI, transfer to conical tubes, and the volume was adjusted to 5 ml with cRPMI. The cells were centrifuged through Ficoll-Paque, and the supernatant fluid was aspirated. Interfaces containing cells from all tubes were combined and the cells were rinsed with cRPMI. The cells were then resuspended in 7.5 ml cRPMI. Viable cells were assessed by trypan blue exclusion. A6 cell viability was also assessed by trypan blue exclusion. A6 cells and tumor-immunized lymphocytes were centrifuged separately at 1200 rpm for 10 minutes. The supernatant fluids were aspirated and the cells were washed with 10 ml DPBS$^{-/-}$/tube. Each cell line was washed three times with 2 ml cold Mannitol Fusion Medium (MFM) (0.3M Mannitol, 0.18 mM $MgCl_2$, 0.18 mM $CaCl_2$, 1 mM Hepes) and the cells were combined and resuspended in MFM at a density of $3 \times 10^6$ A6 cells and $3 \times 10^6$ PBMCs in 200 µl for a total of $6 \times 10^6$ cells in 200 µl. BTX 450 microslides were sterilized with 65 µL 100% EtOH and pre-wetted with 65 µl MFM. A 40 µl aliquot of cell suspension was distributed evenly onto a BTX 450-1 microslide. To fuse the cells, the ECM 2001 conditions were set as follows: alignment conditions, 20V for 30 seconds; pulse conditions, 150V for 30 µseconds (1×); compression conditions, 20V for 9 seconds. After fusion the cells were transferred to one well of a 24 well plate containing 1 ml phenol red-free cRPMI. The fusion steps were repeated for the remaining cell suspensions, rinsing slide between fusions with 65 µL MFM. The culture plate containing fused cell cultures was incubated overnight at 37° C./8% $CO_2$. The fused cells were cloned and assessed by ELISA for IgG and IgM production. The results are shown in FIG. 8.

Example 4

In Vitro Immunization

Purified GM-CSF from a Commercial Source is Administered In Vitro to Peripheral Blood Mononuclear Cells (PBMC).

A. Generation and Assaying of GM-CSF-Specific B Lymphocytes Isolation of Lymphocytes from Peripheral Blood.

Lymphocytes are isolated from whole blood by centrifugation through Ficoll-Paque according to the manufacturer's instructions. Isolated lymphocytes are incubated with 0.25 mM Leu-Leu methyl ester hydrobromide (LLOMe) prepared in RPMI 1640 medium containing 2% fetal bovine serum (FBS) for 15 minutes at room temperature. The cells are then washed three times with culture medium.

In Vitro Stimulation of Isolated Lymphocytes.

The cells are incubated at 37° C. in an incubator, supplied with 8% $CO_2$, at a density between 2.5 to $5 \times 10^6$ cells/ml in culture medium supplemented with 10% FBS and GM-CSF and IL-2 at various concentrations. After four days of culture, the cells are washed four times with medium and the culture was continued for additional eight days.

Measurement of the B Cell Response.

Lymphocyte culture supernatants are collected on day 12 of the culture and tested in an ELISA for the presence of anti-GM-CSF antibodies. Briefly, GM-CSF or BSA at 0.5 µg/ml in 0.05 M carbonate-bicarbonate buffer is immobilized onto an EIA plate. After blocking with 1% bovine serum albumin (BSA) in PBS containing 0.05% Tween 20, the supernatant is added to the wells. Antibodies bound to GM-CSF are detected with peroxidase-labeled goat anti-human IgG or anti-human IgM. TMB is used for color development. The plate is read using a Microplate reader with a 450 nm filter. A supernatant sample that had antibody bound to GM-CSF, but not to BSA, and in which the signal was two times the assay background is considered positive. The positive cells are pooled, and used for hybridoma production.

Generation of Hybridomas Secreting Human Antibodies.

To prepare activated lymphocytes, cells are pooled and cultured in T flasks at 05-1×10$^6$ cells/ml in culture medium supplemented with 10% FBS one day prior to the fusion. To prepare the fusion partner, mouse myeloma NS0 cells are transfected with human PMS2-134 expression vector as described in Nicolaides et al. (1998) *Mol. Cell. Biol.* 18(3): 1635-1641. The cells are cultured in RPMI 1640 supplemented with 10% FBS and 2 mM glutamine (Complete Medium) and the culture is kept in log phase.

Next, lymphocytes are harvested and counted. An equal number of myeloma cells is harvested. Both types of cells are combined and washed three times with RPMI 1640 medium. Polyethylene glycol (PEG) is added dropwise to the loosened cell pellet, and the PEG is subsequently diluted out slowly with 25 ml of RPMI medium in a course of 2.5 minutes. After diluting out the PEG, fused cells are suspended in Complete Medium supplemented with HAT and 20% FBS, and seeded onto 96-well plates.

Screening and Characterization of Antigen-Specific Hybridoma Clones.

When the hybridoma cells grew to semi-confluence, supernatants are collected and subjected to an ELISA for antigen-specific reactivity. As an example, hybridomas derived from TT-immunized lymphocytes are tested. Briefly, TT or BSA at 0.5 ug/ml in 0.05 M carbonate-bicarbonate buffer is immobilized onto the EIA plate. After blocking with 1% bovine serum albumin in PBS containing 0.05% Tween 20, the cell culture supernate is added to the wells. Antibodies bound to GM-CSF are detected with peroxidase-labeled goat anti-human IgG or anti-human IgM. TMB is used for color development. The plate is read in the Microplate reader with a 450 nm filter. A cell clone that showed reactivity to GM-CSF but not to BSA is considered positive. Positive clones are expanded and subcloned by limiting dilution to generate monoclonal cells.

Example 5

Generation of Hybridomas Secreting Human Monoclonal Antibodies to GM-CSF-KLH

A. Generation of GM-CSF-Specific B Lymphocytes

Preparation of Antigen.

Human GM-CSF was purchased from a vendor. In order to enhance immunization, GM-CSF was conjugated to keyhole limpet hemocyanin (KLH) (GM-CSF-KLH) and the conjugate was used as immunogen for in vitro immunization in order to overcome any immunotolerance.

Preparation of GM-CSF-KLH Conjugate.

Purified GM-CSF was reconstituted in sterile MilliQ-grade water to yield a 1 mg/ml solution. Purified, lyophilized recombinant KLH was dissolved in sterile MilliQ-grade water to yield a 1 mg/ml KLH solution. A 0.2% solution of glutaraldehyde in PBS was prepared. Crosslinking was performed by combining 25 ul of 1 mg/ml KLH, 25 ul of 1 mg/ml GM-CSF, and 50 ul 0.2% glutaraldehyde in a microcentrifuge tube wrapped in aluminum foil at room temperature, with shaking for 1 hour. Following cross-linking, 25 ul of 1 M glycine was added to the tube and the solution was incubated an additional 1 hour at room temperature with shaking. Crosslinked products were dialyzed against three changes of 300 ml PBS. The reaction was monitored by Western blotting, using a commercial anti-GM-CSF and anti-KLH monoclonal antibodies. By this method, greater than 80% of the components are crosslinked, and appeared as immunoreactive species of greater MW than the starting material (data not shown).

In Vitro Stimulation of Peripheral Blood Mononuclear Cells (PBMC).

LLOMe-pretreated PBMC were incubated at a density of 3×10$^6$ cells/ml in culture medium supplemented with 10% FBS and a stimuli mixture. The stimuli mixture was composed of GM-CSF-KLH at a concentration of 50 ng/ml with or without recombinant human IL-2 at 20 IU, mouse anti-human CD40 antibody as CD40L at 0.5 ug/ml (used to enhance IgG class switching). After four days of culture, the cells were re-fed with complete medium, in the absence of added stimulus, every three or four days. Culture supernatants were collected on days 12-18 and tested for GM-CSF-specific antibodies.

Detection of GM-CSF-Specific Antibody Response.

The PBMC response to the stimulation was examined in a GM-CSF-specific ELISA. Briefly, GM-CSF, KLH, or chick ovalbumin (CAB) at 0.5 ug/ml in 0.05 M carbonate-bicarbonate buffer, pH 9.6, was immobilized onto EIA plates. After blocking the plates with 1% BSA containing 0.05% Tween 20, the supernatant were added to the wells. Antibodies from the supernatant bound to immobilized antigens were detected with peroxidase-labeled goat anti-human IgG+IgM (H+L). TMB substrate kit was used for color development. The plates were read in a Microplate reader with a 450 nm filter. A supernatant sample containing antibody that bound to GM-CSF, but not to KLH and CAB, was considered positive. There was a robust response observed in cultures immunized to the GM-CSF-KLH as compared to controls. While anti-GM-CSF responses were observed in PBMCs for a small fraction of donors, the percentage of positive clones was greatly increased when PBMC were immunized in vitro with GM-CSF complexed with KLH. Positive cells were pooled and used for hybridoma production.

Generation of Hybridomas.

To prepare activated lymphocytes, cells were pooled and cultured in T flasks at 0.5-1×10$^6$ cells/ml in culture medium supplemented with 10% FBS one day prior to the fusion. To prepare the fusion partner, mouse myeloma NS0 cells were transfected with human PMS2-134 expression vector as described in Nicolaides et al. (1998) *Mol. Cell. Biol.* 18(3): 1635-1641. The cells were cultured in RPMI 1640 supplemented with 10% FBS and 2 mM glutamine (Complete Medium) and the culture was kept in log phase.

Screening and Characterization of Antigen-Specific Hybridoma Clones.

Figure 9:
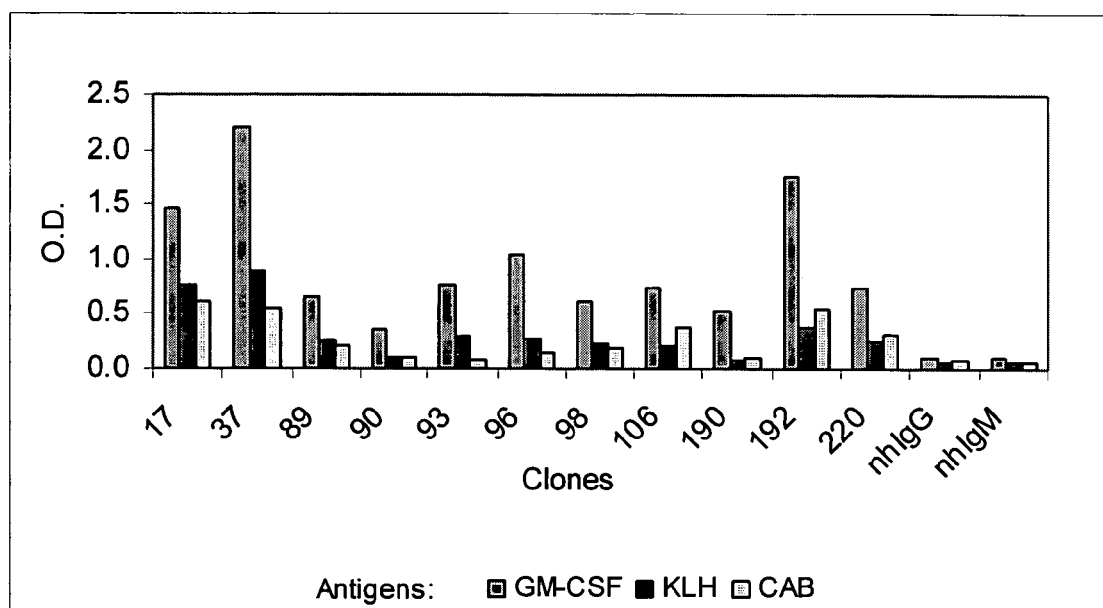
FIG. 9 shows reactivity of clones to GM-CSF, chick ovalbumin (CAB), or keyhole limpet hemocyanin.

When the hybridoma cells grew to semi-confluence, supernatants were collected and subjected to an ELISA for antigen-specific reactivity. As an example, hybridomas derived from GM-CSF-immunized lymphocytes were tested. Briefly, GM-CSF, KLH, or CAB at 0.5 ug/ml in 0.05 M carbonate-bicarbonate buffer was immobilized onto the EIA plate. After blocking with 1% bovine serum albumin in PBS containing 0.05% Tween 20, the cell culture supernate was added to the wells. Antibodies bound were detected with peroxidase-labeled goat anti-human IgG or anti-human IgM. TMB was used for color development. Normal human IgG (nhIgG) and IgM (nhIgM) were used as controls. The plate is read in the Microplate reader with a 450 nm filter. A cell clone that showed reactivity to GM-CSF, but not to CAB was considered positive. The results are shown in FIG. 9

Example 6

Inhibition of Proliferation Assays

Figure 10:
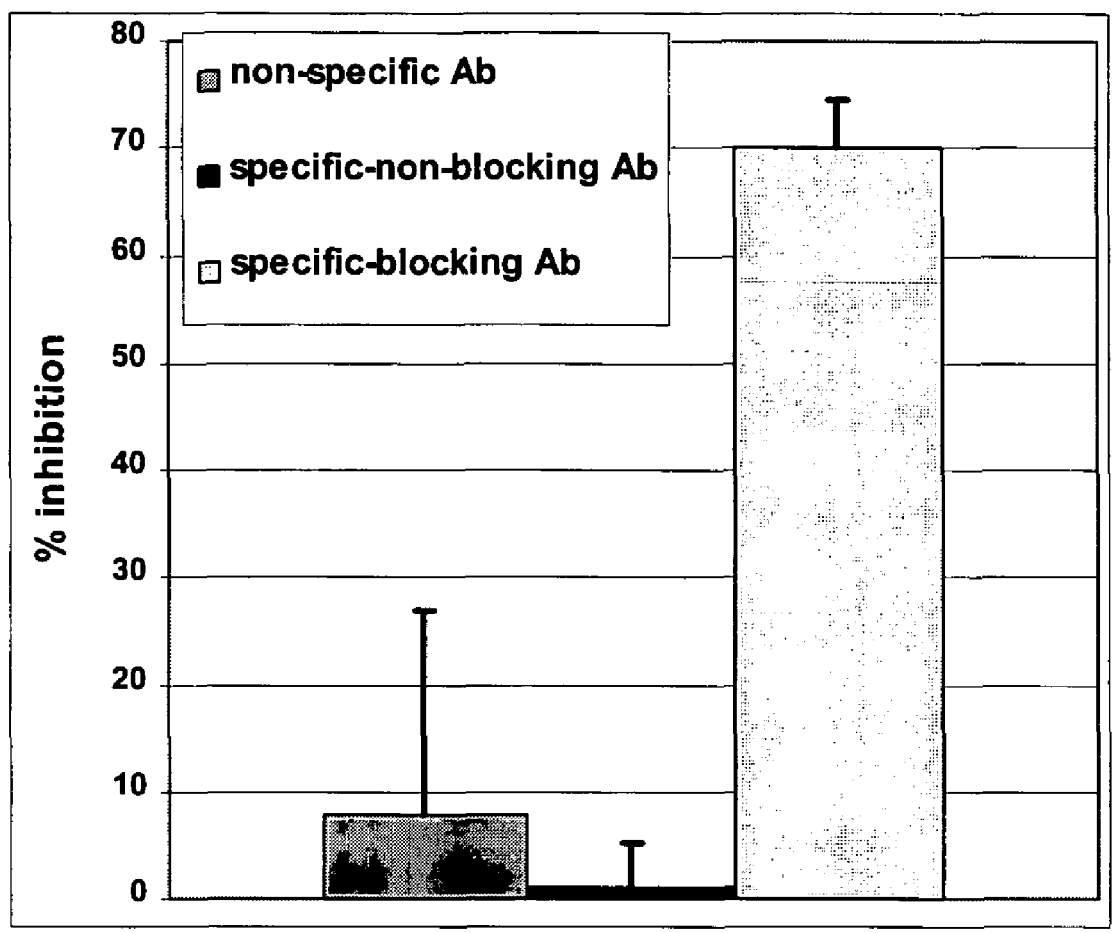
FIG. 10 shows inhibitory effect of anti-GM-CSF antibodies on proliferation of TF-1 cells. Shown are the effects of a GM-CSF-specific, blocking antibody; a GM-CSF-specific, non-blocking antibody; and a non-specific antibody.

TF-1 cells were seeded at $0.2 \times 10^6$/ml in RPMI supplemented with 10% FBS and 0.5 ng/ml recombinant human GM-CSF. TF-1 cells were serum starved for 24 hours in medium containing 0.5% BSA, without rhGM-CSF. Cells were then cultured in the presence of 0.275 ng/ml of GM-CSF for 3 days, with or without 4 ug/ml of various antibodies. Cell proliferation was measured using the ATPLite assay (Perkin Elmer). In this assay, ATP was released by lysis of viable cells and utilized by the enzyme luciferase to convert luciferin into oxyluciferin. Light was emitted (luminescence) as a result of the reaction, and the intensity of the emission was ultimately proportional to the ATP content and thus to the cell number. Counts per second (CPS) were obtained by reading the reactions with a luminometer and the percentage of inhibition was calculated according to the formula: 100-(CPS no Ab: CPS with Ab)×100%. The results are shown in FIG. 10.

The foregoing examples are merely illustrative of the invention and are not to be construed to limit the scope of the invention in any way. The scope of the invention is defined by the appended claims.

What is claimed is:

1. A method for producing hybridoma cells producing antibodies from in vitro immunized immunoglobulin-producing cells comprising:
   (a) combining donor cells comprising immunoglobulin-producing cells with an immunogenic antigen in vitro;
   (b) fusing said immunoglobulin-producing cells with myeloma cells to form parental hybridoma cells;
   (c) incubating said parental hybridoma cells in the presence of at least one chemical inhibitor of mismatch repair, thereby forming hypermutated hybridoma cells;
   (d) removing said chemical inhibitor of mismatch repair from said hypermutated hybridoma cells, thereby stabilizing the genome of said hypermutated hybridoma cells,
   (e) screening antibodies produced from said hypermutated hybridoma cells for binding to antigen; and
   (f) selecting hypermutated hybridoma cells that produce antibodies with higher affinity for said antigen than antibodies produced by said parental hybridoma cells;
   thereby producing hybridoma cells producing antibodies having higher affinity for said antigen than antibodies produced by said parental hybridoma cells.

2. The method of claim 1 wherein said chemical inhibitor of mismatch repair is an anthracene, ATPase inhibitor, a nuclease inhibitor, an RNA interference molecule, a polymerase inhibitor, or an antisense oligonucleotide that specifically hybridizes to a nucleotide encoding a mismatch repair protein.

3. A method for producing hybridoma cells producing antibodies from in vitro immunized immunoglobulin-producing cells comprising:
   (a) combining donor cells comprising immunoglobulin-producing cells with an immunogenic antigen in vitro;
   (b) fusing said immunoglobulin-producing cells with myeloma cells to form parental hybridoma cells;
   (c) incubating said parental hybridoma cells in the presence of at least one chemical inhibitor of mismatch repair, thereby forming hypermutated hybridoma cells, wherein said chemical inhibitor of mismatch repair is an anthracene having the formula:

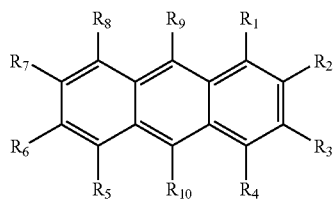

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or lower alkyl groups;

(d) screening antibodies produced from said hypermutated hybridoma cells for binding to antigen; and
(e) selecting hypermutated hybridoma cells that produce antibodies with higher affinity for said antigen than antibodies produced by said parental hybridoma cells;
thereby producing hybridoma cells producing antibodies having higher affinity for said antigen than antibodies produced by said parental hybridoma cells.

4. The method of claim 3 wherein $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl.

5. The method of claim 1 further comprising screening for hypermutated hybridoma cells that also produce antibodies in higher titers than said parental hybridoma cells.

6. The method of claim 3 further comprising the step of removing said chemical inhibitor of mismatch repair from said hypermutated hybridoma cells, thereby stabilizing the genome of said hypermutated hybridoma cells.

7. The method of claim 1 wherein said antibodies having higher affinity for said antigen than antibodies produced by said parental hybridoma cells have an affinity for said antigen of at least about $1 \times 10^7$ $M^{-1}$ to about $1 \times 10^{14}$ $M^{-1}$.

8. The method of claim 5 wherein said hypermutated hybridoma cells that produce antibodies in higher titers than said parental hybridoma cells have a titer that is at least about 1.5-8 fold greater than the titer produced by said parental hybridoma cells.

9. A method for producing hybridoma cells that produce antibodies from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form parental hybridoma cells;
(c) incubating said parental hybridoma cells in the presence of at least one chemical inhibitor of mismatch repair, thereby forming hypermutated hybridoma cells;
(d) removing said chemical inhibitor of mismatch repair from said hypermutated hybridoma cells, thereby stabilizing the genome of said hypermutated hybridoma cells; and
(e) selecting hypermutated hybridoma cells that produce higher titers of antigen-specific antibodies than said parental hybridoma cells;
thereby producing hybridoma cells that produce higher titers of antibodies than said parental hybridoma cells.

10. The method of claim 9 wherein said chemical inhibitor of mismatch repair is an anthracene, ATPase inhibitor, a nuclease inhibitor, an RNA interference molecule, a polymerase inhibitor, or an antisense oligonucleotide that specifically hybridizes to a nucleotide encoding a mismatch repair protein.

11. A method for producing hybridoma cells that produce antibodies from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form parental hybridoma cells;
(c) incubating said parental hybridoma cells in the presence of at least one chemical inhibitor of mismatch repair, thereby forming hypermutated hybridoma cells, wherein said chemical inhibitor of mismatch repair is an anthracene having the formula:

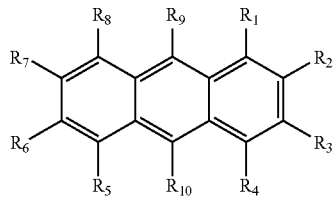

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;
wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and
wherein said amino groups are optionally substituted with an acyl group, or 1 to 3 aryl or lower alkyl groups; and
(d) selecting hypermutated hybridoma cells that produce higher titers of antigen-specific antibodies than said parental hybridoma cells;
thereby producing hybridoma cells that produce higher titers of antibodies than said parental hybridoma cells.

12. The method of claim 11 wherein $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl.

13. The method of claim 11 further comprising the step of removing said chemical inhibitor of mismatch repair from said hypermutated hybridoma cells, thereby stabilizing the genome of said hypermutated hybridoma cells.

14. The method of claim 9 wherein said higher titer of said antibodies is a titer of at least about 1.5-8 fold greater than the titer of said parental hybridoma cells.

15. A method for producing mammalian expression cells that produce antibodies comprising:
(a) combining donor cells comprising immunoglobulin-producing cells with an immunogenic antigen in vitro;
(b) fusing said immunoglobulin-producing cells with myeloma cells to form hybridoma cells;
(c) performing a screen for binding of antibodies produced from said hybridoma cells to antigen;
(d) cloning immunoglobulin genes from hybridoma cells that produce antibodies to said antigen into a mammalian expression cell;
(e) incubating said mammalian expression cell in the presence of at least one chemical inhibitor of mismatch repair, thereby forming hypermutated mammalian expression cells;
(f) removing said chemical inhibitor of mismatch repair from said hypermutated mammalian expression cells, thereby stabilizing the genome of said hypermutated mammalian expression cells; and
(g) performing a screen for hypermutated mammalian expression cells that secrete antibodies with higher affinity for antigen as compared to antibodies produced from said hybridoma cells that produce antibodies to said antigen;
thereby producing mammalian expression cells that produce antibodies having higher affinity for said antigen than said hybridoma cells that produce antibodies to said antigen.

16. The method of claim 15 wherein said chemical inhibitor of mismatch repair is an anthracene, ATPase inhibitor, a nuclease inhibitor, an RNA interference molecule, a polymerase inhibitor, or an antisense oligonucleotide that specifically hybridizes to a nucleotide encoding a mismatch repair protein.

17. A method for producing mammalian expression cells that produce antibodies comprising:
(a) combining donor cells comprising immunoglobulin-producing cells with an immunogenic antigen in vitro;
(b) fusing said immunoglobulin-producing cells with myeloma cells to form hybridoma cells;
(c) performing a screen for binding of antibodies produced from said hybridoma cells to antigen;
(d) cloning immunoglobulin genes from hybridoma cells that produce antibodies to said antigen into a mammalian expression cell;

(e) incubating said mammalian expression cell in the presence of at least one chemical inhibitor of mismatch repair, thereby forming hypermutated mammalian expression cells, wherein said chemical inhibitor of mismatch repair is an anthracene having the formula:

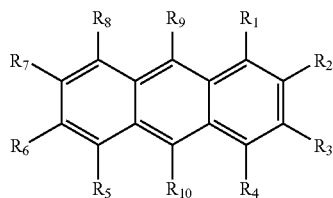

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or lower alkyl groups; and (f) performing a screen for hypermutated mammalian expression cells that secrete antibodies with higher affinity for antigen as compared to antibodies produced from said hybridoma cells that produce antibodies to said antigen;

thereby producing mammalian expression cells that produce antibodies having higher affinity for said antigen than said hybridoma cells that produce antibodies to said antigen.

18. The method of claim 17 wherein $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl.

19. The method of claim 15 further comprising performing a screen for hypermutated mammalian expression cells that also produce antibodies in higher titers than said hybridoma cells that produce antibodies to said antigen.

20. The method of claim 15 wherein said antibodies having higher affinity for said antigen than said hybridoma cells that produce antibodies to said antigen have an affinity for said antigen of at least about $1 \times 10^7$ $M^{-1}$ to about $1 \times 10^{14}$ $M^{-1}$.

21. The method of claim 19 wherein said higher titers of said antibodies is at least about 1.5-8 fold greater that the titer produced by said hybridoma cells that produce antibodies to said antigen.

22. The method of claim 17 further comprising removing said chemical inhibitor of mismatch repair from said hypermutated mammalian expression cells, thereby stabilizing the genome of said hypermutated mammalian expression cells.

23. A method for producing mammalian expression cells that produce antibodies to a selected antigen from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form parental hybridoma cells;
(c) incubating said parental hybridoma cells in the presence of at least one chemical inhibitor of mismatch repair to form hypermutated hybridoma cells;
(d) removing said chemical inhibitor of mismatch repair from said hypermutated hybridoma cells, thereby stabilizing the genome of said hypermutated hybridoma cells;
(e) performing a screen for binding of antigen for antibodies produced from said hypermutated hybridoma cells;
(f) selecting hypermutated hybridoma cells that produce antibodies with higher affinity for said antigen than antibodies produced by said parental hybridoma cells;
(g) cloning immunoglobulin genes from said hypermutated hybridoma cells that produce antibodies with higher affinity for said antigen than antibodies produced by said parental hybridoma cells into a mammalian expression cell, thereby forming parental mammalian expression cells;

thereby producing mammalian expression cells that produce antibodies having higher affinity for said antigen than said parental hybridoma cells from in vitro immunized immunoglobulin-producing cells.

24. The method of claim 23 wherein said chemical inhibitor of mismatch repair is an anthracene, ATPase inhibitor, a nuclease inhibitor, an RNA interference molecule, a polymerase inhibitor, or an antisense oligonucleotide that specifically hybridizes to a nucleotide encoding a mismatch repair protein.

25. A method for producing mammalian expression cells that produce antibodies to a selected antigen from in vitro immunized immunoglobulin-producing cells comprising:
(a) combining donor cells comprising immunoglobulin-producing cells with an immunogenic antigen in vitro;
(b) fusing said immunoglobulin-producing cells with myeloma cells to form parental hybridoma cells;
(c) incubating said parental hybridoma cells in the presence of at least one chemical inhibitor of mismatch repair to form hypermutated hybridoma cells, wherein said chemical inhibitor of mismatch repair is an anthracene having the formula:

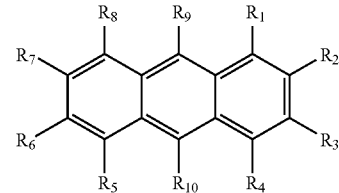

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroalkyl, heteroaryl, and substituted heteroaryl contain at least one heteroatom that is oxygen, sulfur, a metal atom, phosphorus, silicon or nitrogen; and wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkoxy, guanidino, alkoxycarbonyl, alkoxy, hydroxy, carboxy and amino; and wherein said amino groups are optionally substituted with an acyl group, or 1 to 3 aryl or lower alkyl groups;

(d) performing a screen for binding of antigen for antibodies produced from said hypermutated hybridoma cells;

(e) selecting hypermutated hybridoma cells that produce antibodies with higher affinity for said antigen than antibodies produced by said parental hybridoma cells; and (f) cloning immunoglobulin genes from said hypermutated hybridoma cells that produce antibodies with higher affinity for said antigen than antibodies produced by said parental hybridoma cells into a mammalian expression cell, thereby forming parental mammalian expression cells;

thereby producing mammalian expression cells that produce antibodies having higher affinity for said antigen than said parental hybridoma cells from in vitro immunized immunoglobulin-producing cells.

26. The method of claim 25 wherein $R_1$-$R_{10}$ are independently hydrogen, hydroxyl, methyl, ethyl, propyl, isopropyl, butyl, isobutyl, phenyl, tolyl, hydroxymethyl, hydroxypropyl, or hydroxybutyl.

27. The method of claim 23 wherein said antibodies having higher affinity for said antigen than said parental hybridoma cells have an affinity for said antigen of at least about $1\times10^7 M^{-1}$ to about $1\times10^{14} M^{-4}$.

28. The method of claim 23 further comprising the steps of:
incubating said parental mammalian expression cells in the presence of at least one chemical inhibitor of mismatch repair, thereby forming hypermutated mammalian expression cells; and
screening for hypermutated mammalian expression cells that produce a higher titer of antibodies than said parental mammalian expression cells.

29. The method of claim 25 further comprising removing said chemical inhibitor of mismatch repair from said hypermutated hybridoma cells, thereby stabilizing the genome of said hypermutated hybridoma cells.

30. The method of claim 28 further comprising removing said chemical inhibitor of mismatch repair from said hypermutated mammalian expression cells, thereby stabilizing the genome of said hypermutated mammalian expression cells.

31. The method of claim 28 wherein said higher titer of antibodies is at least about 1.5-8 fold greater than the titer produced by said parental mammalian expression cells.

32. The method of claim 1, 9, 15 or 23 wherein said chemical inhibitor of mismatch repair is an antisense molecule comprising at least 15 consecutive nucleotides of a sequence encoding a protein selected from the group consisting of SEQ ID NO:2; SEQ ID NO:4; SEQ ID NO:6; SEQ ID NO:8; SEQ ID NO:10; SEQ ID NO:12; SEQ ID NO:14; SEQ ID NO:16; SEQ ID NO:18; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; SEQ ID NO:38; SEQ ID NO:40; SEQ ID NO:42; SEQ ID NO:44; SEQ ID NO:46; SEQ ID NO:48; and SEQ ID NO:50.

33. The method of claim 1, 9, 15 or 23 wherein said chemical inhibitor of mismatch repair is an antisense molecule comprising at least 15 consecutive nucleotides of a sequence selected from the group consisting of SEQ ID NO:1; SEQ ID NO:3; SEQ ID NO:5; SEQ ID NO:7; SEQ ID NO:9; SEQ ID NO:11; SEQ ID NO:13; SEQ ID NO:15; SEQ ID NO:17; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; SEQ ID NO:41; SEQ ID NO:43; SEQ ID NO:45; SEQ ID NO:47; and SEQ ID NO:49.

34. The method of claim 25 wherein said antibodies having higher affinity for said antigen than said parental hybridoma cells have an affinity for said antigen of at least about $1\times10^7 M^{-1}$ to about $1\times10^{14} M^{-1}$.

35. The method of claim 25 further comprising the steps of:
incubating said parental mammalian expression cells in the presence of at least one chemical inhibitor of mismatch repair, thereby forming hypermutated mammalian expression cells; and
screening for hypermutated mammalian expression cells that produce a higher titer of antibodies than said parental mammalian expression cells.

36. The method of claim 35 further comprising removing said chemical inhibitor of mismatch repair from said hypermutated mammalian expression cells, thereby stabilizing the genome of said hypermutated mammalian expression cells.

37. The method of claim 35 wherein said higher titer of antibodies is at least about 1.5-8 fold greater than the titer produced by said parental mammalian expression cells.

38. The method of claim 17 further comprising performing a screen for hypermutated mammalian expression cells that also produce antibodies in higher titers than said hybridoma cells that produce antibodies to said antigen.

39. The method of claim 17 wherein said antibodies having higher affinity for said antigen than said hybridoma cells that produce antibodies to said antigen have an affinity for said antigen of at least about $1\times10^7 M^{-1}$ to about $1\times10^{14} M^{-1}$.

40. The method of claim 38 wherein said higher titers of said antibodies is at least about 1.5-8 fold greater that the titer produced by said hybridoma cells that produce antibodies to said antigen.

41. The method of claim 11 wherein said higher titer of said antibodies is a titer of at least about 1.5-8 fold greater than the titer of said parental hybridoma cells.

42. The method of claim 3 further comprising screening for hypermutated hybridoma cells that also produce antibodies in higher titers than said parental hybridoma cells.

43. The method of claim 42 further comprising removing said chemical inhibitor of mismatch repair from said hypermutated hybridoma cells, thereby stabilizing the genome of said hypermutated hybridoma cells.

44. The method of claim 3 wherein said antibodies having higher affinity for said antigen than antibodies produced by said parental hybridoma cells have an affinity for said antigen of at least about $1\times10^7 M^{-1}$ to about $1\times10^{14} M^{-1}$.

45. The method of claim 42 wherein said hypermutated hybridoma cells that produce antibodies in higher titers than said parental hybridoma cells have a titer that is at least about 1.5-8 fold greater than the titer produced by said parental hybridoma cells.

* * * * *

SEQUENCE LISTING

```
<160> NUMBER OF SEQ ID NOS: 50

<210> SEQ ID NO 1
<211> LENGTH: 3063
<212> TYPE: DNA
<213> ORGANISM: Homo sapiens

<400> SEQUENCE: 1
ggcacgagtg gctgcttgcg gctagtggat ggtaattgcc tgcctcgcgc tagcagcaag      60
ctgctctgtt aaaagcgaaa atgaaacaat tgcctgcggc aacagttcga ctccttcaa     120 gttctcagat catcacttcg gtggtcagtg ttgtaaaaga gcttattgaa aactccttgg     180
atgctggtgc cacaagcgta gatgttaaac tggagaacta tggatttgat aaaattgagg     240
tgcgagataa cggggagggt atcaaggctg ttgatgcacc tgtaatggca atgaagtact     300
acacctcaaa aataaatagt catgaagatc ttgaaaattt gacaacttac ggttttcgtg     360
gagaagcctt ggggtcaatt tgttgtatag ctgaggtttt aattacaaca agaacggctg     420
ctgataattt tagcacccag tatgttttag atggcagtgg ccacatactt tctcagaaac     480
cttcacatct tggtcaaggt acaactgtaa ctgctttaag attatttaag aatctacctg     540
taagaaagca gttttactca actgcaaaaa aatgtaaaga tgaaataaaa aagatccaag     600
atctcctcat gagctttggt atccttaaac ctgacttaag gattgtcttt gtacataaca     660
aggcagttat ttggcagaaa agcagagtat cagatcacaa gatggctctc atgtcagttc     720
tggggactgc tgttatgaac aatatggaat cctttcagta ccactctgaa gaatctcaga     780
tttatctcag tggatttctt ccaaagtgtg atgcagacca ctctttcact agtctttcaa     840
caccagaaag aagtttcatc ttcataaaca gtcgaccagt acatcaaaaa gatatcttaa     900
agttaatccg acatcattac aatgtgaaat gcctaaagga atctactcgt ttgtatcctg     960
ttttctttct gaaaatcgat gttcctacag ctgatgttga tgtaaattta acaccagata    1020
aaagccaagt attattacaa aataaggaat ctgttttaat tgctcttgaa aatctgatga    1080
```

```
cgacttgtta tggaccatta cctagtacaa attcttatga aaataataaa acagatgttt    1140
ccgcagctga catcgttctt agtaaaacag cagaaacaga tgtgctttt aataaagtgg     1200 aatcatctgg aaagaattat tcaaatgttg atacttcagt cattccattc caaaatgata    1260
tgcataatga tgaatctgga aaaaacactg atgattgttt aaatcaccag ataagtattg    1320
gtgactttgg ttatggtcat tgtagtagtg aaatttctaa cattgataaa aacactaaga    1380
atgcatttca ggacatttca atgagtaatg tatcatggga gaactctcag acggaatata    1440
gtaaaacttg ttttataagt tccgttaagc acacccagtc agaaaatggc aataaagacc    1500
atatagatga gagtggggaa aatgaggaag aagcaggtct tgaaaactct tcggaaattt    1560
ctgcagatga gtggagcagg ggaaatatac ttaaaaattc agtgggagag aatattgaac    1620
ctgtgaaaat tttagtgcct gaaaaaagtt taccatgtaa agtaagtaat aataattatc    1680
caatccctga acaaatgaat cttaatgaag attcatgtaa caaaaaatca aatgtaatag    1740
ataataaatc tggaaaagtt acagcttatg atttacttag caatcgagta atcaagaaac    1800
ccatgtcagc aagtgctctt tttgttcaag atcatcgtcc tcagtttctc atagaaaatc    1860
ctaagactag tttagaggat gcaacactac aaattgaaga actgtggaag acattgagtg    1920
aagaggaaaa actgaaatat gaagagaagg ctactaaaga cttggaacga tacaatagtc    1980
aaatgaagag agccattgaa caggagtcac aaatgtcact aaaagatggc agaaaaaga    2040 taaacccac cagcgcatgg aatttggccc agaagcacaa gttaaaaacc tcattatcta    2100
atcaaccaaa acttgatgaa ctccttcagt cccaaattga aaaagaagg agtcaaaata    2160 ttaaaatggt acagatcccc ttttctatga aaaacttaaa aataaatttt aagaaacaaa    2220
acaaagttga cttagaagag aaggatgaac cttgcttgat ccacaatctc aggttttcctg   2280 atgcatggct aatgacatcc aaaacagagg taatgttatt aaatccatat agagtagaag    2340
aagccctgct atttaaaaga cttcttgaga atcataaact tcctgcagag ccactggaaa    2400
agccaattat gttaacagag agtctttta atggatctca ttatttagac gtttatata     2460 aaatgacagc agatgaccaa agatacagtg gatcaactta cctgtctgat cctcgtctta    2520
cagcgaatgg tttcaagata aaattgatac caggagtttc aattactgaa aattacttgg    2580
aaatagaagg aatggctaat tgtctcccat tctatggagt agcagattta aaagaaattc    2640
ttaatgctat attaaacaga aatgcaaagg aagtttatga atgtagacct cgcaaagtga    2700
taagttattt agagggagaa gcagtgcgtc tatccagaca attacccatg tacttatcaa    2760
aagaggacat ccaagacatt atctacagaa tgaagcacca gtttggaaat gaaattaaag    2820
agtgtgttca tggtcgccca tttttttcatc atttaaccta tcttccagaa actacatgat    2880
taaatatgtt taagaagatt agttaccatt gaaattggtt ctgtcataaa acagcatgag    2940
tctggtttta aattatcttt gtattatgtg tcacatggtt attttttaaa tgaggattca    3000
ctgacttgtt tttatattga aaaagttcc acgtattgta gaaaacgtaa ataaactaat     3060
aac                                                                  3063
```

<210> SEQ ID NO 2
<211> LENGTH: 932
<212> TYPE: PRT
<213> ORGANISM: Homo sapiens

<400> SEQUENCE: 2

```
Met Lys Gln Leu Pro Ala Ala Thr Val Arg Leu Leu Ser Ser Ser Gln
1               5                   10                  15
```

-continued

```
Ile Ile Thr Ser Val Val Ser Val Val Lys Glu Leu Ile Glu Asn Ser
         20                  25                  30

Leu Asp Ala Gly Ala Thr Ser Val Asp Val Lys Leu Glu Asn Tyr Gly
     35                  40                  45

Phe Asp Lys Ile Glu Val Arg Asp Asn Gly Gly Ile Lys Ala Val
 50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
             85                  90                  95

Leu Gly Ser Ile Cys Cys Ile Ala Glu Val Leu Ile Thr Thr Arg Thr
             100                 105                 110

Ala Ala Asp Asn Phe Ser Thr Gln Tyr Val Leu Asp Gly Ser Gly His
             115                 120                 125

Ile Leu Ser Gln Lys Pro Ser His Leu Gly Gln Gly Thr Thr Val Thr
 130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
             165                 170                 175

Met Ser Phe Gly Ile Leu Lys Pro Asp Leu Arg Ile Val Phe Val His
             180                 185                 190

Asn Lys Ala Val Ile Trp Gln Lys Ser Arg Val Ser Asp His Lys Met
         195                 200                 205

Ala Leu Met Ser Val Leu Gly Thr Ala Val Met Asn Asn Met Glu Ser
         210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
             245                 250                 255

Arg Ser Phe Ile Phe Ile Asn Ser Arg Pro Val His Gln Lys Asp Ile
             260                 265                 270

Leu Lys Leu Ile Arg His His Tyr Asn Leu Lys Cys Leu Lys Glu Ser
             275                 280                 285

Thr Arg Leu Tyr Pro Val Phe Phe Leu Lys Ile Asp Val Pro Thr Ala
 290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
             325                 330                 335

Tyr Gly Pro Leu Pro Ser Thr Asn Ser Tyr Glu Asn Asn Lys Thr Asp
             340                 345                 350

Val Ser Ala Ala Asp Ile Val Leu Ser Lys Thr Ala Glu Thr Asp Val
             355                 360                 365

Leu Phe Asn Lys Val Glu Ser Ser Gly Lys Asn Tyr Ser Asn Val Asp
 370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
             405                 410                 415

Gly Tyr Gly His Cys Ser Ser Glu Ile Ser Asn Ile Asp Lys Asn Thr
             420                 425                 430

Lys Asn Ala Phe Gln Asp Ile Ser Met Ser Asn Val Ser Trp Glu Asn
```

-continued

```
            435                 440                 445
Ser Gln Thr Glu Tyr Ser Lys Thr Cys Phe Ile Ser Ser Val Lys His
    450                 455                 460
Thr Gln Ser Glu Asn Gly Asn Lys Asp His Ile Asp Glu Ser Gly Glu
465                 470                 475                 480
Asn Glu Glu Glu Ala Gly Leu Glu Asn Ser Ser Glu Ile Ser Ala Asp
                485                 490                 495
Glu Trp Ser Arg Gly Asn Ile Leu Lys Asn Ser Val Gly Glu Asn Ile
            500                 505                 510
Glu Pro Val Lys Ile Leu Val Pro Glu Lys Ser Leu Pro Cys Lys Val
            515                 520                 525
Ser Asn Asn Asn Tyr Pro Ile Pro Glu Gln Met Asn Leu Asn Glu Asp
    530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
                565                 570                 575
Ala Ser Ala Leu Phe Val Gln Asp His Arg Pro Gln Phe Leu Ile Glu
            580                 585                 590
Asn Pro Lys Thr Ser Leu Glu Asp Ala Thr Leu Gln Ile Glu Glu Leu
            595                 600                 605
Trp Lys Thr Leu Ser Glu Glu Glu Lys Leu Lys Tyr Glu Glu Lys Ala
            610                 615                 620
Thr Lys Asp Leu Glu Arg Tyr Asn Ser Gln Met Lys Arg Ala Ile Glu
625                 630                 635                 640
Gln Glu Ser Gln Met Ser Leu Lys Asp Gly Arg Lys Lys Ile Lys Pro
                645                 650                 655
Thr Ser Ala Trp Asn Leu Ala Gln Lys His Lys Leu Lys Thr Ser Leu
            660                 665                 670
Ser Asn Gln Pro Lys Leu Asp Glu Leu Leu Gln Ser Gln Ile Glu Lys
            675                 680                 685
Arg Arg Ser Gln Asn Ile Lys Met Val Gln Ile Pro Phe Ser Met Lys
            690                 695                 700
Asn Leu Lys Ile Asn Phe Lys Lys Gln Asn Lys Val Asp Leu Glu Glu
705                 710                 715                 720
Lys Asp Glu Pro Cys Leu Ile His Asn Leu Arg Phe Pro Asp Ala Trp
                725                 730                 735
Leu Met Thr Ser Lys Thr Glu Val Met Leu Leu Asn Pro Tyr Arg Val
            740                 745                 750
Glu Glu Ala Leu Leu Phe Lys Arg Leu Leu Glu Asn His Lys Leu Pro
            755                 760                 765
Ala Glu Pro Leu Glu Lys Pro Ile Met Leu Thr Glu Ser Leu Phe Asn
            770                 775                 780
Gly Ser His Tyr Leu Asp Val Leu Tyr Lys Met Thr Ala Asp Asp Gln
785                 790                 795                 800
Arg Tyr Ser Gly Ser Thr Tyr Leu Ser Asp Pro Arg Leu Thr Ala Asn
                805                 810                 815
Gly Phe Lys Ile Lys Leu Ile Pro Gly Val Ser Ile Thr Glu Asn Tyr
            820                 825                 830
Leu Glu Ile Glu Gly Met Ala Asn Cys Leu Pro Phe Tyr Gly Val Ala
            835                 840                 845
Asp Leu Lys Glu Ile Leu Asn Ala Ile Leu Asn Arg Asn Ala Lys Glu
            850                 855                 860
```

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
            885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His Leu Thr Tyr Leu
        915                 920                 925

Pro Glu Thr Thr
    930

<210> SEQ ID NO 3
<211> LENGTH: 2771
<212> TYPE: DNA
<213> ORGANISM: Homo sapiens

<400> SEQUENCE: 3

| | | | | | |
|---|---|---|---|---|---|
| cgaggcggat | cgggtgttgc | atccatggag | cgagctgaga | gctcgagtac | agaacctgct | 60 |
| aaggccatca | aacctattga | tcggaagtca | gtccatcaga | tttgctctgg | gcaggtggta | 120 |
| ctgagtctaa | gcactgcggt | aaaggagtta | gtagaaaaca | gtctggatgc | tggtgccact | 180 |
| aatattgatc | taaagcttaa | ggactatgga | gtggatctta | ttgaagtttc | agacaatgga | 240 |
| tgtgggtag | aagaagaaaa | cttcgaaggc | ttaactctga | acatcacac | atctaagatt | 300 |
| caagagtttg | ccgacctaac | tcaggttgaa | acttttggct | tcggggggga | agctctgagc | 360 |
| tcactttgtg | cactgagcga | tgtcaccatt | tctacctgcc | acgcatcggc | gaaggttgga | 420 |
| actcgactga | tgtttgatca | aatgggaaa | attatccaga | aaaccccta | ccccgcccc | 480 |
| agagggacca | cagtcagcgt | gcagcagtta | ttttccacac | tacctgtgcg | ccataaggaa | 540 |
| tttcaaagga | atattaagaa | ggagtatgcc | aaaatggtcc | aggtcttaca | tgcatactgt | 600 |
| atcatttcag | caggcatccg | tgtaagttgc | accaatcagc | ttggacaagg | aaaacgacag | 660 |
| cctgtggtat | gcacaggtgg | aagccccagc | ataaaggaaa | atatcggctc | tgtgtttggg | 720 |
| cagaagcagt | tgcaaagcct | cattcctttt | gttcagctgc | cccctagtga | ctccgtgtgt | 780 |
| gaagagtacg | gtttgagctg | ttcggatgct | ctgcataatc | ttttttacat | ctcaggtttc | 840 |
| atttcacaat | gcacgcatgg | agttggaagg | agttcaacag | acagacagtt | tttctttatc | 900 |
| aaccggcggc | cttgtgaccc | agcaaaggtc | tgcagactcg | tgaatgaggt | ctaccacatg | 960 |
| tataatcgac | accagtatcc | atttgttgtt | cttaacattt | ctgttgattc | agaatgcgtt | 1020 |
| gatatcaatg | ttactccaga | taaaaggcaa | attttgctac | aagaggaaaa | gcttttgttg | 1080 |
| gcagttttaa | agacctcttt | gataggaatg | tttgatagtg | atgtcaacaa | gctaaatgtc | 1140 |
| agtcagcagc | cactgctgga | tgttgaaggt | aacttaataa | aaatgcatgc | agcggatttg | 1200 |
| gaaaagccca | tggtagaaaa | gcaggatcaa | tcccttcat | taaggactgg | agaagaaaaa | 1260 |
| aaagacgtgt | ccatttccag | actgcgagag | gccttttctc | ttcgtcacac | aacagagaac | 1320 |
| aagcctcaca | gcccaaagac | tccagaacca | agaggagcc | ctctaggaca | gaaaggggt | 1380 |
| atgctgtctt | ctagcacttc | aggtgccatc | tctgacaaag | gcgtcctgag | acctcagaaa | 1440 |
| gaggcagtga | gttccagtca | cggacccagt | gaccctacgg | acagagcgga | ggtgagaag | 1500 |
| gactcggggc | acggcagcac | ttccgtggat | tctgaggggt | tcagcatccc | agacacgggc | 1560 |
| agtcactgca | gcagcgagta | tgcggccagc | tccccagggg | acaggggctc | gcaggaacat | 1620 |
| gtggactctc | aggagaaagc | gcctgaaact | gacgactctt | tttcagatgt | ggactgccat | 1680 |

-continued

```
tcaaaccagg aagataccgg atgtaaattt cgagttttgc ctcagccaac taatctcgca    1740
accccaaaca caaagcgttt taaaaagaa gaaattcttt ccagttctga catttgtcaa     1800
aagttagtaa atactcagga catgtcagcc tctcaggttg atgtagctgt gaaaattaat    1860
aagaaagttg tgcccctgga cttttctatg agttctttag ctaaacgaat aaagcagtta    1920
catcatgaag cacagcaaag tgaaggggaa cagaattaca ggaagtttag ggcaaagatt    1980
tgtcctggag aaaatcaagc agccgaagat gaactaagaa aagagataag taaaacgatg    2040
tttgcagaaa tggaaatcat tggtcagttt aacctgggat ttataataac aaactgaat    2100 gaggatatct tcatagtgga ccagcatgcc acggacgaga agtataactt cgagatgctg    2160
cagcagcaca ccgtgctcca ggggcagagg ctcatagcac ctcagactct caacttaact    2220
gctgttaatg aagctgttct gatagaaaat ctggaaatat ttagaaagaa tggctttgat    2280
tttgttatcg atgaaaatgc tccagtcact gaaagggcta aactgatttc cttgccaact    2340
agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520
cacatggggg agatggacca cccctggaac tgtccccatg gaaggccaac catgagacac    2580
atcgccaacc tgggtgtcat ttctcagaac tgaccgtagt cactgtatgg aataattggt    2640
tttatcgcag attttttatgt tttgaaagac agagtcttca ctaaccttt ttgttttaaa    2700 atgaaacctg ctacttaaaa aaaatacaca tcacacccat ttaaaagtga tcttgagaac    2760
cttttcaaac c                                                         2771
```

<210> SEQ ID NO 4
<211> LENGTH: 932
<212> TYPE: PRT
<213> ORGANISM: Homo sapiens

<400> SEQUENCE: 4

```
Met Lys Gln Leu Pro Ala Ala Thr Val Arg Leu Leu Ser Ser Ser Gln
1               5                   10                  15

Ile Ile Thr Ser Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175
```

```
Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
            195                 200                 205

Ala Leu Met Ser Val Leu Gly Thr Ala Val Met Asn Asn Met Glu Ser
210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
            275                 280                 285

Thr Arg Leu Tyr Pro Val Phe Phe Leu Lys Ile Asp Val Pro Thr Ala
            290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
            340                 345                 350

Val Ser Ala Ala Asp Ile Val Leu Ser Lys Thr Ala Glu Thr Asp Val
            355                 360                 365

Leu Phe Asn Lys Val Glu Ser Ser Gly Lys Asn Tyr Ser Asn Val Asp
            370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
            435                 440                 445

Ser Gln Thr Glu Tyr Ser Lys Thr Cys Phe Ile Ser Ser Val Lys His
            450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
            515                 520                 525

Ser Asn Asn Asn Tyr Pro Ile Pro Glu Gln Met Asn Leu Asn Glu Asp
530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590
```

```
Asn Pro Lys Thr Ser Leu Glu Asp Ala Thr Leu Gln Ile Glu Glu Leu
        595                 600                 605

Trp Lys Thr Leu Ser Glu Glu Lys Leu Lys Tyr Glu Glu Lys Ala
    610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Lys Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
            675                 680                 685

Arg Arg Ser Gln Asn Ile Lys Met Val Gln Ile Pro Phe Ser Met Lys
        690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
        755                 760                 765

Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
            820                 825                 830

Leu Glu Ile Glu Gly Met Ala Asn Cys Leu Pro Phe Tyr Gly Val Ala
        835                 840                 845

Asp Leu Lys Glu Ile Leu Asn Ala Ile Leu Asn Arg Asn Ala Lys Glu
    850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His Leu Thr Tyr Leu
        915                 920                 925

Pro Glu Thr Thr
    930

<210> SEQ ID NO 5
<211> LENGTH: 426
<212> TYPE: DNA
<213> ORGANISM: Homo sapiens

<400> SEQUENCE: 5
cgaggcggat cgggtgttgc atccatggag cgagctgaga gctcgagtac agaacctgct      60
aaggccatca aacctattga tcggaagtca gtccatcaga tttgctctgg gcaggtggta     120
ctgagtctaa gcactgcggt aaaggagtta gtagaaaaca gtctggatgc tggtgccact     180
```

```
aatattgatc taaagcttaa ggactatgga gtggatctta ttgaagtttc agacaatgga    240
tgtggggtag aagaagaaaa cttcgaaggc ttaactctga acatcacac atctaagatt    300 caagagtttg ccgacctaac tcaggttgaa acttttggct tcggggggga agctctgagc   360
tcactttgtg cactgagcga tgtcaccatt tctacctgcc acgcatcggc gaaggttgga   420
acttga                                                              426
```

<210> SEQ ID NO 6
<211> LENGTH: 133
<212> TYPE: PRT
<213> ORGANISM: Homo sapiens

<400> SEQUENCE: 6

```
Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys
    130
```

<210> SEQ ID NO 7
<211> LENGTH: 1408
<212> TYPE: DNA
<213> ORGANISM: Homo sapiens

<400> SEQUENCE: 7

```
ggcgctccta cctgcaagtg gctagtgcca agtgctgggc cgccgctcct gccgtgcatg    60
ttggggagcc agtacatgca ggtgggctcc acacggagag gggcgcagac ccggtgacag   120
ggctttacct ggtacatcgg catggcgcaa ccaaagcaag agagggtggc gcgtgccaga   180
caccaacggt cggaaaccgc cagacaccaa cggtcggaaa ccgccaagac accaacgctc   240
ggaaaccgcc agacaccaac gctcggaaac cgccagacac caaggctcgg aatccacgcc   300
aggccacgac ggagggcgac tacctccctt ctgaccctgc tgctggcgtt cggaaaaaac   360
gcagtccggt gtgctctgat tggtccaggc tctttgacgt cacggactcg acctttgaca   420
gagccactag gcgaaaagga gagacgggaa gtatttttc cgccccgccc ggaaagggtg   480 agcacaacg tcgaaagcag ccgttgggag cccaggaggc ggggcgcctg tgggagccgt   540
ggagggaact ttcccagtcc ccgaggcgga tccggtgttg catccttgga gcagctgag    600 aactcgagta cagaacctgc taaggccatc aaacctattg atcggaagtc agtccatcag   660
atttgctctg ggccggtggt accgagtcta aggccgaatg cggtgaagga ttagtagaa    720 aacagtctgg atgctggtgc cactaatgtt gatctaaagc ttaaggacta tggagtggat   780
```

```
ctcattgaag tttcaggcaa tggatgtggg gtagaagaag aaaacttcga aggctttact    840
ctgaaacatc acacatgtaa gattcaagag tttgccgacc taactcaggt ggaaactttt    900
ggctttcggg gggaagctct gagctcactt tgtgcactga gtgatgtcac catttctacc    960
tgccgtgtat cagcgaaggt tgggactcga ctggtgtttg atcactatgg gaaaatcatc   1020
cagaaaaccc cctaccccg ccccagaggg atgacagtca gcgtgaagca gttattttct    1080
acgctacctg tgcaccataa agaatttcaa aggaatatta agaagaaacg tgcctgcttc   1140
cccttcgcct tctgccgtga ttgtcagttt cctgaggcct ccccagccat gcttcctgta   1200
cagcctgtag aactgactcc tagaagtacc ccaccccacc cctgctcctt ggaggacaac   1260
gtgatcactg tattcagctc tgtcaagaat ggtccaggtt cttctagatg atctgcacaa   1320
atggttcctc tcctccttcc tgatgtctgc cattagcatt ggaataaagt tcctgctgaa   1380
aatccaaaaa aaaaaaaaaa aaaaaaaa                                       1408

<210> SEQ ID NO 8
<211> LENGTH: 389
<212> TYPE: PRT
<213> ORGANISM: Homo sapiens

<400> SEQUENCE: 8
```

Met Ala Gln Pro Lys Gln Glu Arg Val Ala Arg Ala Arg His Gln Arg
1               5                   10                  15

Ser Glu Thr Ala Arg His Gln Arg Ser Glu Thr Ala Lys Thr Pro Thr
            20                  25                  30

Leu Gly Asn Arg Gln Thr Pro Thr Leu Gly Asn Arg Gln Thr Pro Arg
        35                  40                  45

Leu Gly Ile His Ala Arg Pro Arg Arg Arg Ala Thr Thr Ser Leu Leu
    50                  55                  60

Thr Leu Leu Leu Ala Phe Gly Lys Asn Ala Val Arg Cys Ala Leu Ile
65                  70                  75                  80

Gly Pro Gly Ser Leu Thr Ser Arg Thr Arg Pro Leu Thr Glu Pro Leu
                85                  90                  95

Gly Glu Lys Glu Arg Arg Glu Val Phe Phe Pro Pro Arg Pro Glu Arg
            100                 105                 110

Val Glu His Asn Val Glu Ser Ser Arg Trp Glu Pro Arg Arg Arg Gly
        115                 120                 125

Ala Cys Gly Ser Arg Gly Gly Asn Phe Pro Ser Pro Arg Gly Gly Ser
    130                 135                 140

Gly Val Ala Ser Leu Glu Arg Ala Glu Asn Ser Ser Thr Glu Pro Ala
145                 150                 155                 160

Lys Ala Ile Lys Pro Ile Asp Arg Lys Ser Val His Gln Ile Cys Ser
                165                 170                 175

Gly Pro Val Val Pro Ser Leu Arg Pro Asn Ala Val Lys Glu Leu Val
            180                 185                 190

Glu Asn Ser Leu Asp Ala Gly Ala Thr Asn Val Asp Leu Lys Leu Lys
        195                 200                 205

Asp Tyr Gly Val Asp Leu Ile Glu Val Ser Gly Asn Gly Cys Gly Val
    210                 215                 220

Glu Glu Glu Asn Phe Glu Gly Phe Thr Leu Lys His His Thr Cys Lys
225                 230                 235                 240

Ile Gln Glu Phe Ala Asp Leu Thr Gln Val Glu Thr Phe Gly Phe Arg
                245                 250                 255

-continued

```
Gly Glu Ala Leu Ser Ser Leu Cys Ala Leu Ser Asp Val Thr Ile Ser
            260                 265                 270

Thr Cys Arg Val Ser Ala Lys Val Gly Thr Arg Leu Val Phe Asp His
        275                 280                 285

Tyr Gly Lys Ile Ile Gln Lys Thr Pro Tyr Pro Arg Pro Arg Gly Met
    290                 295                 300

Thr Val Ser Val Lys Gln Leu Phe Ser Thr Leu Pro Val His His Lys
305                 310                 315                 320

Glu Phe Gln Arg Asn Ile Lys Lys Arg Ala Cys Phe Pro Phe Ala
                325                 330                 335

Phe Cys Arg Asp Cys Gln Phe Pro Glu Ala Ser Pro Ala Met Leu Pro
            340                 345                 350

Val Gln Pro Val Glu Leu Thr Pro Arg Ser Thr Pro Pro His Pro Cys
        355                 360                 365

Ser Leu Glu Asp Asn Val Ile Thr Val Phe Ser Val Lys Asn Gly
    370                 375                 380

Pro Gly Ser Ser Arg
385
```

<210> SEQ ID NO 9
<211> LENGTH: 1785
<212> TYPE: DNA
<213> ORGANISM: Homo sapiens

<400> SEQUENCE: 9

```
tttttagaaa ctgatgttta ttttccatca accattttc catgctgctt aagagaatat      60
gcaagaacag cttaagacca gtcagtggtt gctcctaccc attcagtggc ctgagcagtg     120
gggagctgca gaccagtctt ccgtggcagg ctgagcgctc cagtcttcag tagggaattg     180
ctgaataggc acagagggca cctgtacacc ttcagaccag tctgcaacct caggctgagt     240
agcagtgaac tcaggagcgg gagcagtcca ttcaccctga aattcctcct tggtcactgc     300
cttctcagca gcagcctgct cttctttttc aatctcttca ggatctctgt agaagtacag     360
atcaggcatg acctcccatg ggtgttcacg ggaaatggtg ccacgcatgc gcagaacttc     420
ccgagccagc atccaccaca ttaaacccac tgagtgagct cccttgttgt tgcatgggat     480
ggcaatgtcc acatagcgca gaggagaatc tgtgttacac agcgcaatgg taggtaggtt     540
aacataagat gcctccgtga gaggcgaagg ggcggcggga cccgggcctg gcccgtatgt     600
gtccttggcg gcctagacta ggccgtcgct gtatggtgag cccagggag gcggatctgg     660
gcccccagaa ggacacccgc ctggatttgc cccgtagccc ggcccgggcc cctcgggagc     720
agaacagcct tggtgaggtg acaggaggg gacctcgcga gcagacgcgc gcgccagcga     780
cagcagcccc gccccggcct ctcgggagcc gggggcaga ggctgcggag ccccaggagg     840
gtctatcagc cacagtctct gcatgtttcc aagagcaaca ggaaatgaac acattgcagg     900
ggccagtgtc attcaaagat gtggctgtgg atttcaccca ggaggagtgg cggcaactgg     960
accctgatga agagatagca tacgggatg tgatgttgga gaactacagc catctagttt    1020
ctgtggggta tgattatcac caagccaaac atcatcatgg agtggaggtg aaggaagtgg    1080
agcagggaga ggagccgtgg ataatggaag gtgaatttcc atgtcaacat agtccagaac    1140
ctgctaaggc catcaaacct attgatcgga agtcagtcca tcagatttgc tctgggccag    1200
tggtactgag tctaagcact gcagtgaagg agttagtaga aaacagtctg gatgctggtg    1260
ccactaatat tgatctaaag cttaaggact atggagtgga tctcattgaa gtttcagaca    1320
```

-continued

```
atggatgtgg ggtagaagaa gaaaactttg aaggcttaat ctctttcagc tctgaaacat    1380
cacacatgta agattcaaga gtttgccgac ctaactgaag ttgaaacttt cggttttcag    1440
ggggaagctc tgagctcact gtgtgcactg agcgatgtca ccatttctac ctgccacgcg    1500
ttggtgaagg ttgggactcg actggtgttt gatcacgatg gaaaatcat  ccaggaaacc    1560 ccctaccccc accccagagg gaccacagtc agcgtgaagc agttattttc tacgctacct    1620
gtgcgccata aggaatttca aggaatatt  aagaagacgt gcctgcttcc ccttcgcctt    1680
ctgccgtgat tgtcagtttc tgaggcctc  cccagccatg cttcctgtac agcctgcaga    1740
actgtgagtc aattaaacct cttttcttca taaattaaaa aaaaa                    1785
```

<210> SEQ ID NO 10
<211> LENGTH: 264
<212> TYPE: PRT
<213> ORGANISM: Homo sapiens

<400> SEQUENCE: 10

```
Met Cys Pro Trp Arg Pro Arg Leu Gly Arg Arg Cys Met Val Ser Pro
1               5                  10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Asn Phe Glu Gly Leu Ile Ser
                245                 250                 255

Phe Ser Ser Glu Thr Ser His Met
            260
```

<210> SEQ ID NO 11
<211> LENGTH: 2271
<212> TYPE: DNA

<213> ORGANISM: Homo sapiens

<400> SEQUENCE: 11

```
atgtcgttcg tggcaggggt tattcggcgg ctggacgaga cagtggtgaa ccgcatcgcg      60
gcggggaag ttatccagcg gccagctaat gctatcaaag agatgattga gaactgttta     120
gatgcaaaat ccacaagtat tcaagtgatt gttaaagagg gaggcctgaa gttgattcag    180
atccaagaca atggcaccgg gatcaggaaa gaagatctgg atattgtatg tgaaaggttc    240
actactagta aactgcagtc ctttgaggat ttagccagta tttctaccta tggctttcga    300
ggtgaggctt tggccagcat aagccatgtg gctcatgtta ctattacaac gaaaacagct    360
gatggaaagt gtgcatacag agcaagttac tcagatggaa aactgaaagc ccctcctaaa    420
ccatgtgctg gcaatcaagg gacccagatc acggtggagg acctttttta caacatagcc    480
acgaggagaa aagctttaaa aaatccaagt gaagaatatg ggaaaatttt ggaagttgtt    540
ggcaggtatt cagtacacaa tgcaggcatt agtttctcag ttaaaaaaca aggagagaca    600
gtagctgatg ttaggacact acccaatgcc tcaaccgtgg acaatattcg ctccatcttt    660
ggaaatgctg ttagtcgaga actgatagaa attggatgtg aggataaaac cctagccttc    720
aaaatgaatg gttacatatc caatgcaaac tactcagtga agaagtgcat cttcttactc    780
ttcatcaacc atcgtctggt agaatcaact tccttgagaa aagccataga aacagtgtat    840
gcagcctatt tgcccaaaaa cacacaccca ttcctgtacc tcagtttaga aatcagtccc    900
cagaatgtgg atgttaatgt gcaccccaca aagcatgaag ttcacttcct gcacgaggag    960
agcatcctgg agcgggtgca gcagcacatc gagagcaagc tcctgggctc caattcctcc   1020
aggatgtact tcacccagac tttgctacca ggacttgctg gcccctctgg ggagatggtt   1080
aaatccacaa caagtctgac ctcgtcttct acttctggaa gtagtgataa ggtctatgcc   1140
caccagatgg ttcgtacaga ttcccgggaa cagaagcttg atgcatttct gcagcctctg   1200
agcaaacccc tgtccagtca gccccaggcc attgtcacag aggataagac agatatttct   1260
agtggcaggg ctaggcagca agatgaggag atgcttgaac tcccagcccc tgctgaagtg   1320
gctgccaaaa atcagagctt ggaggggat acaacaaagg ggacttcaga aatgtcagag   1380
aagagaggac ctacttccag caaccccaga aagagacatc gggaagattc tgatgtggaa   1440
atggtggaag atgattcccg aaaggaaatg actgcagctt gtaccccccg gagaaggatc   1500
attaacctca ctagtgtttt gagtctccag gaagaaatta atgagcaggg acatgaggtt   1560
ctccgggaga tgttgcataa ccactccttc gtgggctgtg tgaatcctca gtgggccttg   1620
gcacagcatc aaaccaagtt ataccttctc aacaccacca agcttagtga agaactgttc   1680
taccagatac tcatttatga ttttgccaat tttggtgttc tcaggttatc ggagccagca   1740
ccgctctttg accttgccat gcttgcctta gatagtccag agagtggctg acagaggaa   1800
gatggtccca agaaggact tgctgaatac attgttgagt ttctgaagaa gaaggctgag   1860
atgcttgcag actatttctc tttggaaatt gatgaggaag ggaacctgat tggattaccc   1920
cttctgattc acaactatgt gccccctttg gagggactgc ctatcttcat tcttcgacta   1980
gccactgagg tgaattggga cgaagaaaag gaatgttttg aaagcctcag taaagaatgc   2040
gctatgttct attccatccg gaagcagtac atatctgagg agtcgaccct ctcaggccag   2100
cagagtgaag tgcctggctc cattccaaac tcctggaagt ggactgtgga acacattgtc   2160
tataaagcct tgcgctcaca cattctgcct cctaaacatt tcacagaaga tggaaatatc   2220
ctgcagcttg ctaacctgcc tgatctatac aaagtctttg agaggtgtta a            2271
```

<210> SEQ ID NO 12
<211> LENGTH: 2484
<212> TYPE: PRT
<213> ORGANISM: Homo sapiens

<400> SEQUENCE: 12

```
Cys Thr Thr Gly Gly Cys Thr Cys Thr Thr Cys Thr Gly Gly Cys Gly
1               5                   10                  15

Cys Cys Ala Ala Ala Ala Thr Gly Thr Cys Gly Thr Thr Cys Gly Thr
                20                  25                  30

Gly Gly Cys Ala Gly Gly Gly Thr Thr Ala Thr Thr Cys Gly Gly
            35                  40                  45

Cys Gly Gly Cys Thr Gly Gly Ala Cys Gly Ala Gly Ala Cys Ala Gly
    50                  55                  60

Thr Gly Gly Thr Gly Ala Ala Cys Cys Gly Cys Ala Thr Cys Gly Cys
65                  70                  75                  80

Gly Gly Cys Gly Gly Gly Gly Ala Ala Gly Thr Thr Ala Thr Cys
            85                  90                  95

Cys Ala Gly Cys Gly Gly Cys Cys Ala Gly Thr Ala Ala Thr Gly
    100                 105                 110

Cys Thr Ala Thr Cys Ala Ala Gly Ala Gly Ala Thr Gly Ala Thr
        115                 120                 125

Thr Gly Ala Gly Ala Ala Cys Thr Gly Thr Thr Thr Ala Gly Ala Thr
    130                 135                 140

Gly Cys Ala Ala Ala Thr Cys Cys Ala Cys Ala Ala Gly Thr Ala
145                 150                 155                 160

Thr Thr Cys Ala Ala Gly Thr Gly Ala Thr Thr Gly Thr Thr Ala Ala
            165                 170                 175

Ala Gly Ala Gly Gly Gly Ala Gly Gly Cys Cys Thr Gly Ala Ala Gly
        180                 185                 190

Thr Thr Gly Ala Thr Thr Cys Ala Gly Ala Thr Cys Cys Ala Ala Gly
    195                 200                 205

Ala Cys Ala Ala Thr Gly Gly Cys Ala Cys Cys Gly Gly Gly Ala Thr
        210                 215                 220

Cys Ala Gly Gly Ala Ala Ala Gly Ala Ala Gly Ala Thr Cys Thr Gly
225                 230                 235                 240

Gly Ala Thr Ala Thr Thr Gly Thr Ala Thr Gly Thr Gly Ala Ala Ala
            245                 250                 255

Gly Gly Thr Thr Cys Ala Cys Thr Ala Cys Thr Ala Gly Thr Ala Ala
        260                 265                 270

Ala Cys Thr Gly Cys Ala Gly Thr Cys Cys Thr Thr Gly Ala Gly Gly
    275                 280                 285

Gly Ala Thr Thr Thr Ala Gly Cys Cys Ala Gly Thr Ala Thr Thr Thr
    290                 295                 300

Cys Thr Ala Cys Cys Thr Ala Thr Gly Gly Cys Thr Thr Cys Gly
305                 310                 315                 320

Ala Gly Gly Thr Gly Ala Gly Gly Cys Thr Thr Thr Gly Cys Cys
            325                 330                 335

Ala Gly Cys Ala Thr Ala Gly Cys Cys Ala Thr Gly Thr Gly Gly
        340                 345                 350

Cys Thr Cys Ala Thr Gly Thr Thr Ala Cys Thr Ala Thr Ala Cys
        355                 360                 365

Ala Ala Cys Gly Ala Ala Ala Ala Cys Ala Gly Cys Thr Gly Ala Thr
```

-continued

```
            370                 375                 380
Gly Gly Ala Ala Ala Gly Thr Gly Thr Gly Cys Ala Thr Ala Cys Ala
385                 390                 395                 400

Gly Ala Gly Cys Ala Ala Gly Thr Thr Ala Cys Thr Cys Ala Gly Ala
                405                 410                 415

Thr Gly Gly Ala Ala Ala Ala Cys Thr Gly Ala Ala Gly Cys Cys
            420                 425                 430

Cys Cys Thr Cys Cys Thr Ala Ala Cys Cys Ala Thr Gly Thr Gly
            435                 440                 445

Cys Thr Gly Gly Cys Ala Ala Thr Cys Ala Ala Gly Gly Ala Cys
        450                 455                 460

Cys Cys Ala Gly Ala Thr Cys Ala Cys Gly Gly Thr Gly Ala Gly
465                 470                 475                 480

Gly Ala Cys Cys Thr Thr Thr Thr Thr Ala Cys Ala Ala Cys Ala
                485                 490                 495

Thr Ala Gly Cys Cys Ala Cys Gly Ala Gly Gly Ala Gly Ala Ala Ala
            500                 505                 510

Ala Gly Cys Thr Thr Thr Ala Ala Ala Ala Thr Cys Cys Ala
            515                 520                 525

Ala Gly Thr Gly Ala Ala Gly Ala Ala Thr Ala Thr Gly Gly Ala
        530                 535                 540

Ala Ala Ala Thr Thr Thr Thr Gly Gly Ala Ala Gly Thr Thr Gly Thr
545                 550                 555                 560

Thr Gly Gly Cys Ala Gly Gly Thr Ala Thr Cys Ala Gly Thr Ala
                565                 570                 575

Cys Ala Cys Ala Ala Thr Gly Cys Ala Gly Gly Cys Ala Thr Thr Ala
            580                 585                 590

Gly Thr Thr Thr Cys Thr Cys Ala Gly Thr Ala Ala Ala Ala
        595                 600                 605

Ala Cys Ala Ala Gly Gly Gly Ala Gly Ala Cys Gly Thr Ala
610                 615                 620

Gly Cys Thr Gly Ala Thr Gly Thr Thr Ala Gly Gly Ala Cys Ala Cys
                625                 630                 635                 640

Thr Ala Cys Cys Cys Ala Ala Thr Gly Cys Cys Thr Cys Ala Ala Cys
            645                 650                 655

Cys Gly Thr Gly Gly Ala Cys Ala Ala Thr Ala Thr Cys Gly Cys
        660                 665                 670

Thr Cys Cys Ala Thr Cys Thr Thr Thr Gly Gly Ala Ala Ala Thr Gly
            675                 680                 685

Cys Thr Gly Thr Thr Ala Gly Thr Cys Gly Ala Gly Ala Ala Cys Thr
        690                 695                 700

Gly Ala Thr Ala Gly Ala Ala Ala Thr Thr Gly Gly Ala Thr Gly Thr
705                 710                 715                 720

Gly Ala Gly Gly Ala Thr Ala Ala Ala Cys Cys Thr Ala Gly
                725                 730                 735

Cys Cys Thr Thr Cys Ala Ala Ala Thr Gly Ala Ala Thr Gly Gly
            740                 745                 750

Thr Thr Ala Cys Ala Thr Ala Thr Cys Cys Ala Thr Gly Cys Ala
                755                 760                 765

Ala Ala Cys Thr Ala Cys Thr Cys Ala Gly Thr Gly Ala Ala Gly Ala
            770                 775                 780

Ala Gly Thr Gly Cys Ala Thr Cys Thr Thr Cys Thr Thr Ala Cys Thr
785                 790                 795                 800
```

-continued

```
Cys Thr Thr Cys Ala Thr Cys Ala Ala Cys Ala Thr Cys Gly Thr
                805                 810                 815
Cys Thr Gly Gly Thr Ala Gly Ala Ala Thr Cys Ala Ala Cys Thr Thr
                820                 825                 830
Cys Cys Thr Thr Gly Ala Gly Ala Ala Ala Ala Gly Cys Cys Ala Thr
                835                 840                 845
Ala Gly Ala Ala Ala Cys Ala Gly Thr Gly Thr Ala Thr Gly Cys Ala
                850                 855                 860
Gly Cys Cys Thr Ala Thr Thr Thr Gly Cys Cys Ala Ala Ala Ala
865                 870                 875                 880
Ala Cys Ala Cys Ala Cys Ala Cys Cys Ala Thr Thr Cys Cys Thr
                885                 890                 895
Gly Thr Ala Cys Cys Thr Cys Ala Gly Thr Thr Thr Ala Gly Ala Ala
                900                 905                 910
Ala Thr Cys Ala Gly Thr Cys Cys Cys Ala Gly Ala Ala Thr Gly
                915                 920                 925
Thr Gly Gly Ala Thr Gly Thr Thr Ala Ala Thr Gly Thr Gly Cys Ala
                930                 935                 940
Cys Cys Cys Cys Ala Cys Ala Ala Ala Gly Cys Ala Thr Gly Ala Ala
945                 950                 955                 960
Gly Thr Thr Cys Ala Cys Thr Thr Cys Thr Gly Cys Ala Cys Gly
                965                 970                 975
Ala Gly Gly Ala Gly Ala Gly Cys Ala Thr Cys Cys Thr Gly Gly Ala
                980                 985                 990
Gly Cys Gly Gly Gly Thr Gly Cys Ala Gly Cys Ala Gly Cys Ala Cys
                995                1000                1005
Ala Thr Cys Gly Ala Gly Ala Gly Cys Ala Ala Gly Cys Thr Cys
                1010                1015                1020
Cys Thr Gly Gly Gly Cys Thr Cys Cys Ala Ala Thr Thr Cys Cys
                1025                1030                1035
Thr Cys Cys Ala Gly Gly Ala Thr Gly Thr Ala Cys Thr Thr Cys
                1040                1045                1050
Ala Cys Cys Cys Ala Gly Ala Cys Thr Thr Thr Gly Cys Thr Ala
                1055                1060                1065
Cys Cys Ala Gly Gly Ala Cys Thr Thr Gly Cys Thr Gly Gly Cys
                1070                1075                1080
Cys Cys Cys Thr Cys Thr Gly Gly Gly Gly Ala Gly Ala Thr Gly
                1085                1090                1095
Gly Thr Thr Ala Ala Ala Thr Cys Cys Ala Cys Ala Ala Cys Ala
                1100                1105                1110
Ala Gly Thr Cys Thr Gly Ala Cys Cys Thr Cys Gly Thr Cys Thr
                1115                1120                1125
Thr Cys Thr Ala Cys Thr Thr Cys Thr Gly Gly Ala Ala Gly Thr
                1130                1135                1140
Ala Gly Thr Gly Ala Thr Ala Ala Gly Gly Thr Cys Thr Ala Thr
                1145                1150                1155
Gly Cys Cys Cys Ala Cys Cys Ala Gly Ala Thr Gly Gly Thr Thr
                1160                1165                1170
Cys Gly Thr Ala Cys Ala Gly Ala Thr Thr Cys Cys Cys Gly Gly
                1175                1180                1185
Gly Ala Ala Cys Ala Gly Ala Ala Gly Cys Thr Thr Gly Ala Thr
                1190                1195                1200
```

-continued

```
Gly Cys Ala Thr Thr Thr Cys Thr Gly Cys Ala Gly Cys Cys Thr
1205                1210                1215

Cys Thr Gly Ala Gly Cys Ala Ala Ala Cys Cys Cys Cys Thr Gly
1220                1225                1230

Thr Cys Cys Ala Gly Thr Cys Ala Gly Cys Cys Cys Ala Gly
1235                1240                1245

Gly Cys Cys Ala Thr Thr Gly Thr Cys Ala Cys Ala Gly Ala Gly
1250                1255                1260

Gly Ala Thr Ala Ala Gly Ala Cys Ala Gly Ala Thr Ala Thr Thr
1265                1270                1275

Thr Cys Thr Ala Gly Thr Gly Gly Cys Ala Gly Gly Gly Cys Thr
1280                1285                1290

Ala Gly Gly Cys Ala Gly Cys Ala Ala Gly Ala Thr Gly Ala Gly
1295                1300                1305

Gly Ala Gly Ala Thr Gly Cys Thr Thr Gly Ala Ala Cys Thr Cys
1310                1315                1320

Cys Cys Ala Gly Cys Cys Cys Thr Gly Cys Thr Gly Ala Ala
1325                1330                1335

Gly Thr Gly Gly Cys Thr Gly Cys Cys Ala Ala Ala Ala Ala Thr
1340                1345                1350

Cys Ala Gly Ala Gly Cys Thr Thr Gly Gly Ala Gly Gly Gly Gly
1355                1360                1365

Gly Ala Thr Ala Cys Ala Ala Cys Ala Ala Gly Gly Gly Gly
1370                1375                1380

Ala Cys Thr Thr Cys Ala Gly Ala Ala Ala Thr Gly Thr Cys Ala
1385                1390                1395

Gly Ala Gly Ala Ala Gly Ala Gly Ala Gly Gly Ala Cys Cys Thr
1400                1405                1410

Ala Cys Thr Thr Cys Ala Gly Cys Ala Ala Cys Cys Cys Cys
1415                1420                1425

Ala Gly Ala Ala Ala Gly Ala Gly Ala Cys Ala Thr Cys Gly Gly
1430                1435                1440

Gly Ala Ala Gly Ala Thr Thr Cys Thr Gly Ala Thr Gly Thr Gly
1445                1450                1455

Gly Ala Ala Ala Thr Gly Gly Thr Gly Gly Ala Ala Gly Ala Thr
1460                1465                1470

Gly Ala Thr Thr Cys Cys Cys Gly Ala Ala Ala Gly Gly Ala Ala
1475                1480                1485

Ala Thr Gly Ala Cys Thr Gly Cys Ala Gly Cys Thr Thr Gly Thr
1490                1495                1500

Ala Cys Cys Cys Cys Cys Gly Gly Ala Gly Ala Ala Gly Gly
1505                1510                1515

Ala Thr Cys Ala Thr Thr Ala Ala Cys Cys Thr Cys Ala Cys Thr
1520                1525                1530

Ala Gly Thr Gly Thr Thr Thr Gly Ala Gly Thr Cys Thr Cys
1535                1540                1545

Cys Ala Gly Gly Ala Ala Gly Ala Ala Ala Thr Thr Ala Ala Thr
1550                1555                1560

Gly Ala Gly Cys Ala Gly Gly Gly Ala Cys Ala Thr Gly Ala Gly
1565                1570                1575

Gly Thr Thr Cys Thr Cys Gly Gly Gly Ala Gly Ala Thr Gly
1580                1585                1590

Thr Thr Gly Cys Ala Thr Ala Ala Cys Cys Ala Cys Thr Cys Cys
```

-continued 1595 1600 1605

Thr Thr Cys Gly Thr Gly Gly Gly Cys Thr Gly Thr Gly Thr Gly
1610 1615 1620

Ala Ala Thr Cys Cys Thr Cys Ala Gly Thr Gly Gly Gly Cys Cys
1625 1630 1635

Thr Thr Gly Gly Cys Ala Cys Ala Gly Cys Ala Thr Cys Ala Ala
1640 1645 1650

Ala Cys Cys Ala Ala Gly Thr Thr Ala Thr Ala Cys Cys Thr Thr
1655 1660 1665

Cys Thr Cys Ala Ala Cys Ala Cys Cys Ala Cys Cys Ala Ala Gly
1670 1675 1680

Cys Thr Thr Ala Gly Thr Gly Ala Ala Gly Ala Ala Cys Thr Gly
1685 1690 1695

Thr Thr Cys Thr Ala Cys Cys Ala Gly Ala Thr Ala Cys Thr Cys
1700 1705 1710

Ala Thr Thr Thr Ala Thr Gly Ala Thr Thr Thr Thr Gly Cys Cys
1715 1720 1725

Ala Ala Thr Thr Thr Thr Gly Gly Thr Gly Thr Thr Cys Thr Cys
1730 1735 1740

Ala Gly Gly Thr Thr Ala Thr Cys Gly Gly Ala Gly Cys Cys Ala
1745 1750 1755

Gly Cys Ala Cys Cys Gly Cys Thr Cys Thr Thr Thr Gly Ala Cys
1760 1765 1770

Cys Thr Thr Gly Cys Cys Ala Thr Gly Cys Thr Thr Gly Cys Cys
1775 1780 1785

Thr Thr Ala Gly Ala Thr Ala Gly Thr Cys Cys Ala Gly Ala Gly
1790 1795 1800

Ala Gly Thr Gly Gly Cys Thr Gly Gly Ala Cys Ala Gly Ala Gly
1805 1810 1815

Gly Ala Ala Gly Ala Thr Gly Gly Thr Cys Cys Cys Ala Ala Ala
1820 1825 1830

Gly Ala Ala Gly Gly Ala Cys Thr Thr Gly Cys Thr Gly Ala Ala
1835 1840 1845

Thr Ala Cys Ala Thr Thr Gly Thr Thr Gly Ala Gly Thr Thr Thr
1850 1855 1860

Cys Thr Gly Ala Ala Gly Ala Ala Gly Ala Ala Gly Gly Cys Thr
1865 1870 1875

Gly Ala Gly Ala Thr Gly Cys Thr Thr Gly Cys Ala Gly Ala Cys
1880 1885 1890

Thr Ala Thr Thr Thr Cys Thr Cys Thr Thr Thr Gly Gly Ala Ala
1895 1900 1905

Ala Thr Thr Gly Ala Thr Gly Ala Gly Gly Ala Ala Gly Gly Gly
1910 1915 1920

Ala Ala Cys Cys Thr Gly Ala Thr Thr Gly Gly Ala Thr Thr Ala
1925 1930 1935

Cys Cys Cys Cys Thr Thr Cys Thr Gly Ala Thr Thr Gly Ala Cys
1940 1945 1950

Ala Ala Cys Thr Ala Thr Gly Thr Gly Cys Cys Cys Cys Cys Thr
1955 1960 1965

Thr Thr Gly Gly Ala Gly Gly Gly Ala Cys Thr Gly Cys Cys Thr
1970 1975 1980

Ala Thr Cys Thr Thr Cys Ala Thr Thr Cys Thr Thr Cys Gly Ala
1985 1990 1995

-continued

```
Cys Thr Ala Gly Cys Cys Ala Cys Thr Gly Ala Gly Gly Thr Gly
2000                2005                2010

Ala Ala Thr Thr Gly Gly Gly Ala Cys Gly Ala Ala Gly Ala Ala
2015                2020                2025

Ala Ala Gly Gly Ala Ala Thr Gly Thr Thr Thr Gly Ala Ala
2030                2035                2040

Ala Gly Cys Cys Thr Cys Ala Gly Thr Ala Ala Gly Ala Ala
2045                2050                2055

Thr Gly Cys Gly Cys Thr Ala Thr Gly Thr Thr Cys Thr Ala Thr
2060                2065                2070

Thr Cys Cys Ala Thr Cys Cys Gly Gly Ala Ala Gly Cys Ala Gly
2075                2080                2085

Thr Ala Cys Ala Thr Ala Thr Cys Thr Gly Ala Gly Gly Ala Gly
2090                2095                2100

Thr Cys Gly Ala Cys Cys Thr Cys Thr Cys Ala Gly Gly Cys
2105                2110                2115

Cys Ala Gly Cys Ala Gly Ala Gly Thr Gly Ala Ala Gly Thr Gly
2120                2125                2130

Cys Cys Thr Gly Gly Cys Thr Cys Cys Ala Thr Thr Cys Cys Ala
2135                2140                2145

Ala Ala Cys Thr Cys Cys Thr Gly Gly Ala Ala Gly Thr Gly Gly
2150                2155                2160

Ala Cys Thr Gly Thr Gly Gly Ala Ala Cys Ala Cys Ala Thr Thr
2165                2170                2175

Gly Thr Cys Thr Ala Thr Ala Ala Ala Gly Cys Cys Thr Thr Gly
2180                2185                2190

Cys Gly Cys Thr Cys Ala Cys Ala Cys Ala Thr Thr Cys Thr Gly
2195                2200                2205

Cys Cys Thr Cys Cys Thr Ala Ala Ala Cys Ala Thr Thr Thr Cys
2210                2215                2220

Ala Cys Ala Gly Ala Ala Gly Ala Thr Gly Gly Ala Ala Ala Thr
2225                2230                2235

Ala Thr Cys Cys Thr Gly Cys Ala Gly Cys Thr Thr Gly Cys Thr
2240                2245                2250

Ala Ala Cys Cys Thr Gly Cys Cys Thr Gly Ala Thr Cys Thr Ala
2255                2260                2265

Thr Ala Cys Ala Ala Ala Gly Thr Cys Thr Thr Thr Gly Ala Gly
2270                2275                2280

Ala Gly Gly Thr Gly Thr Thr Ala Ala Ala Thr Ala Thr Gly Gly
2285                2290                2295

Thr Thr Ala Thr Thr Thr Ala Thr Gly Cys Ala Cys Thr Gly Thr
2300                2305                2310

Gly Gly Gly Ala Thr Gly Thr Gly Thr Thr Cys Thr Thr Cys Thr
2315                2320                2325

Thr Thr Cys Thr Cys Thr Gly Thr Ala Thr Thr Cys Cys Gly Ala
2330                2335                2340

Thr Ala Cys Ala Ala Ala Gly Thr Gly Thr Thr Gly Thr Ala Thr
2345                2350                2355

Cys Ala Ala Ala Gly Thr Gly Thr Gly Ala Thr Ala Thr Ala Cys
2360                2365                2370

Ala Ala Ala Gly Thr Gly Thr Ala Cys Cys Ala Ala Cys Ala Thr
2375                2380                2385
```

```
Ala Ala Gly Thr Gly Thr Gly Gly Thr Ala Gly Cys Ala Cys
    2390            2395            2400

Thr Thr Ala Ala Gly Ala Cys Thr Thr Ala Thr Ala Cys Thr Thr
    2405            2410            2415

Gly Cys Cys Thr Thr Cys Thr Gly Ala Thr Ala Gly Thr Ala Thr
    2420            2425            2430

Thr Cys Cys Thr Thr Ala Thr Ala Cys Ala Cys Ala Gly Thr
    2435            2440            2445

Gly Gly Ala Thr Thr Gly Ala Thr Thr Ala Thr Ala Ala Ala Thr
    2450            2455            2460

Ala Ala Ala Thr Ala Gly Ala Thr Gly Thr Gly Thr Cys Thr Thr
    2465            2470            2475

Ala Ala Cys Ala Thr Ala
    2480

<210> SEQ ID NO 13
<211> LENGTH: 4895
<212> TYPE: DNA
<213> ORGANISM: Homo sapiens

<400> SEQUENCE: 13
gtcggcgtcc gaggcggttg gtgtcggaga atttgttaag cgggactcca ggcaattatt    60
tccagtcaga gaaggaaacc agtgcctggc attctcacca tctttctacc taccatgatc   120
aagtgcttgt cagttgaagt acaagccaaa ttgcgttctg gtttggccat aagctccttg   180
ggccaatgtg ttgaggaact tgccctcaac agtattgatc tgaagcaaa atgtgtggct    240 gtcagggtga atatggaaac cttccaagtt caagtgatag acaatggatt tgggatgggg   300
agtgatgatg tagagaaagt gggaaatcgt tatttcacca gtaaatgcca ctcggtacag   360
gacttggaga atccaaggtt ttatggtttc cgaggagagg ccttggcaaa tattgctgac   420
atggccagtg ctgtgaaaat ttcgtccaag aaaaacagga caatgaaaac ttttgtgaaa   480
ctgtttcaga gtggaaaagc cctgaaagct tgtgaagctg atgtgactag agcaagcgct   540
gggactactg taacagtgta taacctattt taccagcttc ctgtaaggag gaaatgcatg   600
gacccctaga ctggagtttga aaggttaggg cagagaatag aagctctctc actcatgcac   660
ccttccattt cttttctctt gagaaatgat gtttctggtt ccatggttct tcagctccct   720
aaaaccaaag acgtatgttc ccgattttgt caaatttatg gattgggaaa gtcccaaaag   780
ctaagagaaa taagttttaa atataaagag tttgagctta gtggctatat cagctctgaa   840
gcacattaca acaagaatat gcagttttg tttgtgaaca aaagactagt tttaaggaca   900
aagctacata aactcattga cttttatta aggaaagaaa gtattatatg caagccaaag   960
aatggtccca ccagtaggca aatgaattca agtcttcggc accggtctac cccagaactc  1020
tatggcatat atgtaattaa tgtgcagtgc caattctgtg agtatgatgt gtgcatggag  1080
ccagccaaaa ctctgattga atttcagaac tgggacactc tcttgttttg cattcaggaa  1140
ggagtgaaaa tgttttaaa gcaagaaaaa ttatttgtgg aattatcagg tgaggatatt  1200
aaggaattta gtgaagataa tggttttagt ttatttgatg ctactcttca gaagcgtgtg  1260
acttccgatg agaggagcaa tttccaggaa gcatgtaata atattttaga ttcctatgag  1320
atgtttaatt tgcagtcaaa agctgtgaaa agaaaaacta ctgcagaaaa cgtaaacaca  1380
cagagttcta gggattcaga agctaccaga aaaatacaa atgatgcatt tttgtacatt  1440
tatgaatcag gtggtccagg ccatagcaaa atgacagagc catctttaca aacaaagac   1500
```

```
agctcttgct cagaatcaaa gatgttagaa caagagacaa ttgtagcatc agaagctggt    1560
gaaaatgaga aacataaaaa atctttcctg gaacgtagct ctttagaaaa tccgtgtgga    1620
accagtttag aaatgttttt aagccctttt cagacaccat gtcactttga ggagagtggg    1680
caggatctag aaatatggaa agaaagtact actgttaatg gcatggctgc caacatcttg    1740
aaaaataata gaattcagaa tcaaccaaag agatttaaag atgctactga agtgggatgc    1800
cagcctctgc cttttgcaac aacattatgg ggagtacata gtgctcagac agagaaagag    1860
aaaaaaaaag aatctagcaa ttgtggaaga agaaatgttt ttagttatgg gcgagttaaa    1920
ttatgttcca ctggctttat aactcatgta gtacaaaata aaaaaactaa atcaactgaa    1980
acagaacatt catttaaaaa ttatgttaga cctggtccca cacgtgccca agaaacattt    2040
ggaaatagaa cacgtcattc agttgaaact ccagacatca agatttagc cagcacttta     2100 agtaaagaat ctggtcaatt gcccaacaaa aaaaattgca gaacgaatat aagttatggg    2160
ctagagaatg aacctacagc aacttataca atgttttctg cttttcagga aggtagcaaa    2220
aaatcacaaa cagattgcat attatctgat acatcccct cttcccctg gtatagacac      2280 gtttccaatg atagtaggaa acagataaaa ttaattggtt ctccaaacc aatcgtccgt     2340 aagaagctaa gcttgagttc acagctagga tctttagaga gtttaagag gcaatatggg     2400 aaggttgaaa atcctctgga tacagaagta gaggaaagta atggagtcac taccaatctc    2460
agtcttcaag ttgaacctga cattctgctg aaggacaaga accgcttaga gaactctgat    2520
gtttgtaaaa tcactactat ggagcatagt gattcagata gtagttgtca accagcaagc    2580
cacatccttg actcagagaa gtttccattc tccaaggatg aagattgttt agaacaacag    2640
atgcctagtt tgagagaaag tcctatgacc ctgaaggagt tatctctctt taatagaaaa    2700
cctttggacc ttgagaagtc atctgaatca ctagcctcta aattatccag actgaagggt    2760
tccgaaagag aaactcaaac aatggggatg atgagtcgtt ttaatgaact tccaaattca    2820
gattccagta ggaaagacag caagttgtgc agtgtgttaa cacaagattt ttgtatgtta    2880
tttaacaaca agcatgaaaa aacagagaat ggtgtcatcc caacatcaga ttctgccaca    2940
caggataatt cctttaataa aaatagtaaa acacattcta acagcaatac aacagagaac    3000
tgtgtgatat cagaaactcc tttggtattg ccctataata attctaaagt taccggtaaa    3060
gattcagatg ttcttatcag agcctcgaa caacagatag gaagtcttga ctctcccagt     3120
ggaatgttaa tgaatccggt agaagatgcc acaggtgacc aaaatggaat tgttttcag    3180 agtgaggaat ctaaagcaag agcttgttct gaaactgaag agtcaaacac gtgttgttca    3240
gattggcagc ggcatttcga gtagccctg ggaagaatgg tttatgtcaa caaaatgact    3300
ggactcagca cattcattgc cccaactgag gacattcagg ctgcttgtac taaagacctg    3360
acaactgtgg ctgtggatgt tgtacttgag aatgggtctc agtacaggtg tcaaccttttt   3420 agaagcgacc ttgttcttcc tttccttccg agagctcgag cagagaggac tgtgatgaga    3480
caggataaca gagatactgt ggatgatact gttagtagcg aatcgcttca gtctttgttc    3540
tcagaatggg acaatccagt atttgcccgt tatccagagg ttgctgttga tgtaagcagt    3600
ggccaggctg agagcttagc agttaaaatt cacaacatct gtatcccta tcgtttcacc     3660 aaaggaatga ttcattcaat gcaggttctc cagcaagtag ataacaagtt tattgcctgt    3720
ttgatgagca ctaagactga agagaatggc gaggcagatt cctacgagaa gcaacaggca    3780
caaggctctg tcggaaaaaa attactgtct tctactctaa ttcctccgct agagataaca    3840
gtgacagagg aacaaaggag actcttatgg tgttaccaca aaaatctgga agatctgggc    3900
```

```
cttgaatttg tatttccaga cactagtgat tctctggtcc ttgtgggaaa agtaccacta    3960
tgttttgtgg aaagagaagc caatgaactt cggagaggaa gatctactgt gaccaagagt    4020
attgtggagg aatttatccg agaacaactg gagctactcc agaccaccgg aggcatccaa    4080
gggacattgc cactgactgt ccagaaggtg ttggcatccc aagcctgcca tggggccatt    4140
aagtttaatg atggcctgag cttacaggaa agttgccgcc ttattgaagc tctgtcctca    4200
tgccagctgc cattccagtg tgctcacggg agaccttcta tgctgccgtt agctgacata    4260
gaccacttgg aacaggaaaa acagattaaa cccaacctca ctaaacttcg caaaatggcc    4320
caggcctggc gtctctttgg aaaagcagag tgtgatacaa ggcagagcct gcagcagtcc    4380
atgcctccct gtgagccacc atgagaacag aatcactggt ctaaaaggaa caaagggatg    4440
ttcactgtat gcctctgagc agagagcagc agcagcaggt accagcacgg ccctgactga    4500
atcagcccag tgtccctgag cagcttagac agcagggctc tctgtatcag tctttcttga    4560
gcagatgatt cccctagttg agtagccaga tgaaattcaa gcctaaagac aattcattca    4620
tttgcatcca tgggcacaga aggttgctat atagtatcta ccttttgcta cttatttaat    4680
gataaaattt aatgacagtt taaaaaaaaa aaaaaaaaaa attatttgaa ggggtgggtg    4740 attttttgttt ttgtacagtt tttttttcaag cttcacattt gcgtgtatct aattcagctg    4800
atgctcaagt ccaaggggta gtctgccttc ccaggctgcc cccagggttt ctgcactggt    4860
cccctctttt cccttcagtc ttcttcactt ccctt                               4895
```

<210> SEQ ID NO 14
<211> LENGTH: 1429
<212> TYPE: PRT
<213> ORGANISM: Homo sapiens

<400> SEQUENCE: 14

```
Met Ile Lys Cys Leu Ser Val Glu Val Gln Ala Lys Leu Arg Ser Gly
1               5                   10                  15

Leu Ala Ile Ser Ser Leu Gly Gln Cys Val Glu Glu Leu Ala Leu Asn
            20                  25                  30

Ser Ile Asp Ala Glu Ala Lys Cys Val Ala Val Arg Val Asn Met Glu
        35                  40                  45

Thr Phe Gln Val Gln Val Ile Asp Asn Gly Phe Gly Met Gly Ser Asp
    50                  55                  60

Asp Val Glu Lys Val Gly Asn Arg Tyr Phe Thr Ser Lys Cys His Ser
65                  70                  75                  80

Val Gln Asp Leu Glu Asn Pro Arg Phe Tyr Gly Phe Arg Gly Glu Ala
                85                  90                  95

Leu Ala Asn Ile Ala Asp Met Ala Ser Ala Val Glu Ile Ser Ser Lys
            100                 105                 110

Lys Asn Arg Thr Met Lys Thr Phe Val Lys Leu Phe Gln Ser Gly Lys
        115                 120                 125

Ala Leu Lys Ala Cys Glu Ala Asp Val Thr Arg Ala Ser Ala Gly Thr
    130                 135                 140

Thr Val Thr Val Tyr Asn Leu Phe Tyr Gln Leu Pro Val Arg Arg Lys
145                 150                 155                 160

Cys Met Asp Pro Arg Leu Glu Phe Glu Lys Val Arg Gln Arg Ile Glu
                165                 170                 175

Ala Leu Ser Leu Met His Pro Ser Ile Ser Phe Ser Leu Arg Asn Asp
            180                 185                 190
```

-continued

```
Val Ser Gly Ser Met Val Leu Gln Leu Pro Lys Thr Lys Asp Val Cys
        195                 200                 205
Ser Arg Phe Cys Gln Ile Tyr Gly Leu Gly Lys Ser Gln Lys Leu Arg
    210                 215                 220
Glu Ile Ser Phe Lys Tyr Lys Glu Phe Glu Leu Ser Gly Tyr Ile Ser
225                 230                 235                 240
Ser Glu Ala His Tyr Asn Lys Asn Met Gln Phe Leu Phe Val Asn Lys
                245                 250                 255
Arg Leu Val Leu Arg Thr Lys Leu His Lys Leu Ile Asp Phe Leu Leu
            260                 265                 270
Arg Lys Glu Ser Ile Ile Cys Lys Pro Lys Asn Gly Pro Thr Ser Arg
        275                 280                 285
Gln Met Asn Ser Ser Leu Arg His Arg Ser Thr Pro Glu Leu Tyr Gly
    290                 295                 300
Ile Tyr Val Ile Asn Val Gln Cys Gln Phe Cys Glu Tyr Asp Val Cys
305                 310                 315                 320
Met Glu Pro Ala Lys Thr Leu Ile Glu Phe Gln Asn Trp Asp Thr Leu
                325                 330                 335
Leu Phe Cys Ile Gln Glu Gly Val Lys Met Phe Leu Lys Gln Glu Lys
            340                 345                 350
Leu Phe Val Glu Leu Ser Gly Glu Asp Ile Lys Glu Phe Ser Glu Asp
        355                 360                 365
Asn Gly Phe Ser Leu Phe Asp Ala Thr Leu Gln Lys Arg Val Thr Ser
    370                 375                 380
Asp Glu Arg Ser Asn Phe Gln Glu Ala Cys Asn Asn Ile Leu Asp Ser
385                 390                 395                 400
Tyr Glu Met Phe Asn Leu Gln Ser Lys Ala Val Lys Arg Lys Thr Thr
                405                 410                 415
Ala Glu Asn Val Asn Thr Gln Ser Ser Arg Asp Ser Glu Ala Thr Arg
            420                 425                 430
Lys Asn Thr Asn Asp Ala Phe Leu Tyr Ile Tyr Glu Ser Gly Gly Pro
        435                 440                 445
Gly His Ser Lys Met Thr Glu Pro Ser Leu Gln Asn Lys Asp Ser Ser
    450                 455                 460
Cys Ser Glu Ser Lys Met Leu Glu Gln Glu Thr Ile Val Ala Ser Glu
465                 470                 475                 480
Ala Gly Glu Asn Glu Lys His Lys Lys Ser Phe Leu Glu Arg Ser Ser
                485                 490                 495
Leu Glu Asn Pro Cys Gly Thr Ser Leu Glu Met Phe Leu Ser Pro Phe
            500                 505                 510
Gln Thr Pro Cys His Phe Glu Ser Gly Gln Asp Leu Glu Ile Trp
        515                 520                 525
Lys Glu Ser Thr Thr Val Asn Gly Met Ala Ala Asn Ile Leu Lys Asn
    530                 535                 540
Asn Arg Ile Gln Asn Gln Pro Lys Arg Phe Lys Asp Ala Thr Glu Val
545                 550                 555                 560
Gly Cys Gln Pro Leu Pro Phe Ala Thr Thr Leu Trp Gly Val His Ser
                565                 570                 575
Ala Gln Thr Glu Lys Glu Lys Lys Glu Ser Ser Asn Cys Gly Arg
            580                 585                 590
Arg Asn Val Phe Ser Tyr Gly Arg Val Lys Leu Cys Ser Thr Gly Phe
        595                 600                 605
Ile Thr His Val Val Gln Asn Glu Lys Thr Lys Ser Thr Glu Thr Glu
```

-continued

```
                610                615                620
His Ser Phe Lys Asn Tyr Val Arg Pro Gly Pro Thr Arg Ala Gln Glu
625                     630                     635                     640

Thr Phe Gly Asn Arg Thr Arg His Ser Val Glu Thr Pro Asp Ile Lys
            645                     650                     655

Asp Leu Ala Ser Thr Leu Ser Lys Glu Ser Gly Gln Leu Pro Asn Lys
            660                     665                     670

Lys Asn Cys Arg Thr Asn Ile Ser Tyr Gly Leu Glu Asn Glu Pro Thr
            675                     680                     685

Ala Thr Tyr Thr Met Phe Ser Ala Phe Gln Gly Ser Lys Lys Ser
            690                     695                     700

Gln Thr Asp Cys Ile Leu Ser Asp Thr Ser Pro Ser Phe Pro Trp Tyr
705                     710                     715                     720

Arg His Val Ser Asn Asp Ser Arg Lys Thr Asp Lys Leu Ile Gly Phe
            725                     730                     735

Ser Lys Pro Ile Val Arg Lys Lys Ser Leu Ser Ser Gln Leu Gly
            740                     745                     750

Ser Leu Glu Lys Phe Lys Arg Gln Tyr Gly Lys Val Glu Asn Pro Leu
            755                     760                     765

Asp Thr Glu Val Glu Glu Ser Asn Gly Val Thr Thr Asn Leu Ser Leu
            770                     775                     780

Gln Val Glu Pro Asp Ile Leu Leu Lys Asp Lys Asn Arg Leu Glu Asn
785                     790                     795                     800

Ser Asp Val Cys Lys Ile Thr Thr Met Glu His Ser Asp Ser Asp Ser
            805                     810                     815

Ser Cys Gln Pro Ala Ser His Ile Leu Asp Ser Glu Lys Phe Pro Phe
            820                     825                     830

Ser Lys Asp Glu Asp Cys Leu Glu Gln Gln Met Pro Ser Leu Arg Glu
            835                     840                     845

Ser Pro Met Thr Leu Lys Glu Leu Ser Leu Phe Asn Arg Lys Pro Leu
            850                     855                     860

Asp Leu Glu Lys Ser Ser Glu Ser Leu Ala Ser Lys Leu Ser Arg Leu
865                     870                     875                     880

Lys Gly Ser Glu Arg Glu Thr Gln Thr Met Gly Met Met Ser Arg Phe
            885                     890                     895

Asn Glu Leu Pro Asn Ser Asp Ser Ser Arg Lys Asp Ser Lys Leu Cys
            900                     905                     910

Ser Val Leu Thr Gln Asp Phe Cys Met Leu Phe Asn Asn Lys His Glu
            915                     920                     925

Lys Thr Glu Asn Gly Val Ile Pro Thr Ser Asp Ser Ala Thr Gln Asp
            930                     935                     940

Asn Ser Phe Asn Lys Asn Ser Lys Thr His Ser Asn Ser Asn Thr Thr
945                     950                     955                     960

Glu Asn Cys Val Ile Ser Glu Thr Pro Leu Val Leu Pro Tyr Asn Asn
            965                     970                     975

Ser Lys Val Thr Gly Lys Asp Ser Asp Val Leu Ile Arg Ala Ser Glu
            980                     985                     990

Gln Gln Ile Gly Ser Leu Asp Ser  Pro Ser Gly Met Leu  Met Asn Pro
            995                     1000                    1005

Val Glu  Asp Ala Thr Gly Asp  Gln Asn Gly Ile Cys  Phe Gln Ser
        1010                    1015                     1020

Glu Glu  Ser Lys Ala Arg Ala  Cys Ser Glu Thr Glu  Glu Ser Asn
        1025                    1030                     1035
```

-continued

```
Thr Cys Cys Ser Asp Trp Gln Arg His Phe Asp Val Ala Leu Gly
    1040                1045                1050

Arg Met Val Tyr Val Asn Lys Met Thr Gly Leu Ser Thr Phe Ile
    1055                1060                1065

Ala Pro Thr Glu Asp Ile Gln Ala Ala Cys Thr Lys Asp Leu Thr
    1070                1075                1080

Thr Val Ala Val Asp Val Val Leu Glu Asn Gly Ser Gln Tyr Arg
    1085                1090                1095

Cys Gln Pro Phe Arg Ser Asp Leu Val Leu Pro Phe Leu Pro Arg
    1100                1105                1110

Ala Arg Ala Glu Arg Thr Val Met Arg Gln Asp Asn Arg Asp Thr
    1115                1120                1125

Val Asp Asp Thr Val Ser Ser Glu Ser Leu Gln Ser Leu Phe Ser
    1130                1135                1140

Glu Trp Asp Asn Pro Val Phe Ala Arg Tyr Pro Glu Val Ala Val
    1145                1150                1155

Asp Val Ser Ser Gly Gln Ala Glu Ser Leu Ala Val Lys Ile His
    1160                1165                1170

Asn Ile Leu Tyr Pro Tyr Arg Phe Thr Lys Gly Met Ile His Ser
    1175                1180                1185

Met Gln Val Leu Gln Gln Val Asp Asn Lys Phe Ile Ala Cys Leu
    1190                1195                1200

Met Ser Thr Lys Thr Glu Glu Asn Gly Glu Ala Asp Ser Tyr Glu
    1205                1210                1215

Lys Gln Gln Ala Gln Gly Ser Gly Arg Lys Lys Leu Leu Ser Ser
    1220                1225                1230

Thr Leu Ile Pro Pro Leu Glu Ile Thr Val Thr Glu Glu Gln Arg
    1235                1240                1245

Arg Leu Leu Trp Cys Tyr His Lys Asn Leu Glu Asp Leu Gly Leu
    1250                1255                1260

Glu Phe Val Phe Pro Asp Thr Ser Asp Ser Leu Val Leu Val Gly
    1265                1270                1275

Lys Val Pro Leu Cys Phe Val Glu Arg Glu Ala Asn Glu Leu Arg
    1280                1285                1290

Arg Gly Arg Ser Thr Val Thr Lys Ser Ile Val Glu Glu Phe Ile
    1295                1300                1305

Arg Glu Gln Leu Glu Leu Leu Gln Thr Thr Gly Gly Ile Gln Gly
    1310                1315                1320

Thr Leu Pro Leu Thr Val Gln Lys Val Leu Ala Ser Gln Ala Cys
    1325                1330                1335

His Gly Ala Ile Lys Phe Asn Asp Gly Leu Ser Leu Gln Glu Ser
    1340                1345                1350

Cys Arg Leu Ile Glu Ala Leu Ser Ser Cys Gln Leu Pro Phe Gln
    1355                1360                1365

Cys Ala His Gly Arg Pro Ser Met Leu Pro Leu Ala Asp Ile Asp
    1370                1375                1380

His Leu Glu Gln Glu Lys Gln Ile Lys Pro Asn Leu Thr Lys Leu
    1385                1390                1395

Arg Lys Met Ala Gln Ala Trp Arg Leu Phe Gly Lys Ala Glu Cys
    1400                1405                1410

Asp Thr Arg Gln Ser Leu Gln Ser Met Pro Pro Cys Glu Pro
    1415                1420                1425
```

Pro

<210> SEQ ID NO 15
<211> LENGTH: 3145
<212> TYPE: DNA
<213> ORGANISM: Homo sapiens

<400> SEQUENCE: 15

| | | | | | |
|---|---|---|---|---|---|
| ggcgggaaac | agcttagtgg | gtgtggggtc | gcgcatttc | ttcaaccagg | aggtgaggag | 60 |
| gtttcgacat | ggcggtgcag | ccgaaggaga | cgctgcagtt | ggagagcgcg | gccgaggtcg | 120 |
| gcttcgtgcg | cttctttcag | ggcatgccgg | agaagccgac | caccacagtg | cgccttttcg | 180 |
| accggggcga | cttctatacg | gcgcacggcg | aggacgcgct | gctggccgcc | cgggaggtgt | 240 |
| tcaagaccca | gggggtgatc | aagtacatgg | ggccggcagg | agcaaagaat | ctgcagagtg | 300 |
| ttgtgcttag | taaaatgaat | tttgaatctt | ttgtaaaaga | tcttcttctg | gttcgtcagt | 360 |
| atagagttga | agtttataag | aatagagctg | gaaataaggc | atccaaggag | aatgattggt | 420 |
| atttggcata | taaggcttct | cctggcaatc | tctctcagtt | tgaagacatt | ctctttggta | 480 |
| acaatgatat | gtcagcttcc | attggtgttg | tgggtgttaa | aatgtccgca | gttgatggcc | 540 |
| agagacaggt | tggagttggg | tatgtggatt | ccatacagag | gaaactagga | ctgtgtgaat | 600 |
| tccctgataa | tgatcagttc | tccaatcttg | aggctctcct | catccagatt | ggaccaaagg | 660 |
| aatgtgtttt | acccggagga | gagactgctg | gagacatggg | gaaactgaga | cagataattc | 720 |
| aaagaggagg | aattctgatc | acagaaagaa | aaaaagctga | cttttccaca | aaagacattt | 780 |
| atcaggacct | caaccggttg | ttgaaaggca | aaagggaga | gcagatgaat | agtgctgtat | 840 |
| tgccagaaat | ggagaatcag | gttgcagttt | catcactgtc | tgcggtaatc | aagtttttag | 900 |
| aactcttatc | agatgattcc | aactttggac | agtttgaact | gactactttt | gacttcagcc | 960 |
| agtatatgaa | attggatatt | gcagcagtca | gagcccttaa | ccttttttcag | ggttctgttg | 1020 |
| aagataccac | tggctctcag | tctctggctg | ccttgctgaa | taagtgtaaa | acccctcaag | 1080 |
| gacaaagact | tgttaaccag | tggattaagc | agcctctcat | ggataagaac | agaatagagg | 1140 |
| agagattgaa | tttagtggaa | gcttttgtag | aagatgcaga | attgaggcag | actttacaag | 1200 |
| aagatttact | tcgtcgattc | ccagatctta | accgacttgc | caagaagttt | caaagacaag | 1260 |
| cagcaaactt | acaagattgt | taccgactct | atcagggtat | aaatcaacta | cctaatgtta | 1320 |
| tacaggctct | ggaaaaacat | gaaggaaaac | accagaaatt | attgttggca | gttttttgtga | 1380 |
| ctcctcttac | tgatcttcgt | tctgacttct | ccaagtttca | ggaaatgata | gaaacaactt | 1440 |
| tagatatgga | tcaggtggaa | aaccatgaat | tccttgtaaa | accttcattt | gatcctaatc | 1500 |
| tcagtgaatt | aagagaaata | atgaatgact | tggaaaagaa | gatgcagtca | acattaataa | 1560 |
| gtgcagccag | agatcttggc | ttggaccctg | gcaaacagat | taaactggat | tccagtgcac | 1620 |
| agtttggata | ttactttcgt | gtaacctgta | aggaagaaaa | agtccttcgt | aacaataaaa | 1680 |
| actttagtac | tgtagatatc | cagaagaatg | gtgttaaatt | taccaacagc | aaattgactt | 1740 |
| cttttaaatga | agagtatacc | aaaaataaaa | cagaatatga | agaagcccag | gatgccattg | 1800 |
| ttaaagaaat | tgtcaatatt | cttcaggct | atgtagaacc | aatgcagaca | ctcaatgatg | 1860 |
| tgttagctca | gctagatgct | gttgtcagct | ttgctcacgt | gtcaaatgga | gcacctgttc | 1920 |
| catatgtacg | accagccatt | ttggagaaag | acaaggaag | aattatatta | aaagcatcca | 1980 |
| ggcatgcttg | tgttgaagtt | caagatgaaa | ttgcatttat | tcctaatgac | gtatactttg | 2040 |
| aaaaagataa | acagatgttc | cacatcatta | ctggccccaa | tatgggaggt | aaatcaacat | 2100 |

-continued

```
atattcgaca aactggggtg atagtactca tggcccaaat tgggtgtttt gtgccatgtg    2160
agtcagcaga agtgtccatt gtggactgca tcttagcccg agtaggggct ggtgacagtc    2220
aattgaaagg agtctccacg ttcatggctg aaatgttgga aactgcttct atcctcaggt    2280
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa agttttggga ttcatgttgc agagcttgct aatttcccta    2580
agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaaattatt caggagttcc tgtccaaggt gaaacaaatg cccttactg     2760 aaatgtcaga agaaaacatc acaataaagt taaaacagct aaaagctgaa gtaatagcaa    2820
agaataatag ctttgtaaat gaatcattt cacgaataaa agttactacg tgaaaaatcc     2880
cagtaatgga atgaaggtaa tattgataag ctattgtctg taatagtttt atattgtttt    2940
atattaaccc ttttttccata gtgttaactg tcagtgccca tgggctatca acttaataag   3000
atatttagta atattttact ttgaggacat tttcaaagat ttttatttg aaaaatgaga     3060 gctgtaactg aggactgttt gcaattgaca taggcaataa taagtgatgt gctgaatttt    3120
ataaataaaa tcatgtagtt tgtgg                                          3145
```

<210> SEQ ID NO 16
<211> LENGTH: 934
<212> TYPE: PRT
<213> ORGANISM: Homo sapiens

<400> SEQUENCE: 16

```
Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
```

-continued

```
            180                 185                 190
Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
        355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
        435                 440                 445

Lys Phe Gln Glu Met Ile Glu Thr Thr Leu Asp Met Asp Gln Val Glu
    450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
        515                 520                 525

Glu Glu Lys Val Leu Arg Asn Asn Lys Asn Phe Ser Thr Val Asp Ile
    530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
        595                 600                 605
```

Ala His Val Ser Asn Gly Ala Pro Val Pro Tyr Val Arg Pro Ala Ile
        610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
            645                 650                 655

Phe Glu Lys Asp Lys Gln Met Phe His Ile Ile Thr Gly Pro Asn Met
        660                 665                 670

Gly Gly Lys Ser Thr Tyr Ile Arg Gln Thr Gly Val Ile Val Leu Met
    675                 680                 685

Ala Gln Ile Gly Cys Phe Val Pro Cys Glu Ser Ala Glu Val Ser Ile
690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
            725                 730                 735

Arg Ser Ala Thr Lys Asp Ser Leu Ile Ile Ile Asp Glu Leu Gly Arg
        740                 745                 750

Gly Thr Ser Thr Tyr Asp Gly Phe Gly Leu Ala Trp Ala Ile Ser Glu
    755                 760                 765

Tyr Ile Ala Thr Lys Ile Gly Ala Phe Cys Met Phe Ala Thr His Phe
770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
            805                 810                 815

Val Lys Lys Gly Val Cys Asp Gln Ser Phe Gly Ile His Val Ala Glu
        820                 825                 830

Leu Ala Asn Phe Pro Lys His Val Ile Glu Cys Ala Lys Gln Lys Ala
    835                 840                 845

Leu Glu Leu Glu Glu Phe Gln Tyr Ile Gly Glu Ser Gln Gly Tyr Asp
850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
            885                 890                 895

Thr Glu Met Ser Glu Glu Asn Ile Thr Ile Lys Leu Lys Gln Leu Lys
        900                 905                 910

Ala Glu Val Ile Ala Lys Asn Asn Ser Phe Val Asn Glu Ile Ile Ser
    915                 920                 925

Arg Ile Lys Val Thr Thr
    930

<210> SEQ ID NO 17
<211> LENGTH: 4374
<212> TYPE: DNA
<213> ORGANISM: Homo sapiens

<400> SEQUENCE: 17
gggcacgagc cctgccatgt ctcgccggaa gcctgcgtcg gcggcctcg ctgcctccag      60 ctcagcccct gcgaggcaag cggttttgag ccgattcttc cagtctacgg gaagcctgaa     120
atccacctcc tcctccacag gtgcagccga ccaggtggac cctggcgctg cagcggccgc     180
agcgccccca gcgcccgcct tcccgcccca gctgccgccg cacgtagcta cagaaattga     240

```
cagaagaaag aagagaccat tggaaaatga tgggcctgtt aaaaagaaag taaagaaagt      300
ccaacaaaag gaaggaggaa gtgatctggg aatgtctggc aactctgagc caaagaaatg      360
tctgaggacc aggaatgttt caaagtctct ggaaaaattg aaagaattct gctgcgattc      420
tgcccttcct caaagtagag tccagacaga atctctgcag gagagatttg cagttctgcc      480
aaaatgtact gattttgatg atatcagtct tctacacgca aagaatgcag tttcttctga      540
agattcgaaa cgtcaaatta atcaaaagga cacaacactt tttgatctca gtcagtttgg      600
atcatcaaat acaagtcatg aaaatttaca gaaaactgct tccaaatcag ctaacaaacg      660
gtccaaaagc atctatacgc cgctagaatt acaatacata gaaatgaagc agcagcacaa      720
agatgcagtt ttgtgtgtgg aatgtggata taagtataga ttctttgggg aagatgcaga      780
gattgcagcc cgagagctca atatttattg ccatttagat cacaacttta tgacagcaag      840
tatacctact cacagactgt tgttcatgt acgccgcctg gtggcaaaag gatataaggt       900
gggagttgtg aagcaaactg aaactgcagc attaaaggcc attggagaca acagaagttc      960
actcttttcc cggaaattga ctgccccttta tacaaaatct acacttattg gagaagatgt     1020
gaatccccta atcaagctgg atgatgctgt aaatgttgat gagataatga ctgatacttc     1080
taccagctat cttctgtgca tctctgaaaa taaggaaaat gttagggaca aaaaaaaggg     1140
caacattttt attggcattg tgggagtgca gcctgccaca ggcgaggttg tgtttgatag     1200
tttccaggac tctgcttctc gttcagagct agaaacccgg atgtcaagcc tgcagccagt     1260
agagctgctg cttccttcgg ccttgtccga gcaaacagag gcgctcatcc acagagccac     1320
atctgttagt gtgcaggatg acagaattcg agtcgaaagg atggataaca tttattttga     1380
atacagccat gctttccagg cagttacaga gtttttatgca aaagatacag ttgacatcaa     1440
aggttctcaa attatttctg gcattgttaa cttagagaag cctgtgattt gctctttggc     1500
tgccatcata aaatacctca agaattcaa cttggaaaag atgctctcca acctgagaa       1560
ttttaaacag ctatcaagta aaatggaatt tatgacaatt aatggaacaa cattaaggaa     1620
tctggaaatc ctacagaatc agactgatat gaaaaccaaa ggaagtttgc tgtgggtttt     1680
agaccacact aaaacttcat tgggagacg gaagttaaag aagtgggtga cccagccact      1740
ccttaaaatta agggaaataa atgcccggct tgatgctgta tcggaagttc tccattcaga    1800
atctagtgtg tttggtcaga tagaaaatca tctacgtaaa ttgcccgaca tagagagggg     1860
actctgtagc atttatcaca aaaatgttc tacccaagag ttcttcttga ttgtcaaaac      1920
tttatatcac ctaaagtcag aatttcaagc aataatacct gctgttaatt cccacattca    1980
gtcagacttg ctccggaccg ttattttaga aattcctgaa ctcctcagtc cagtggagca    2040
ttacttaaag atactcaatg aacaagctgc caaagttggg gataaaactg aattatttaa    2100
agacctttct gacttccctt taataaaaaa gaggaaggat gaaattcaag gtgttattga    2160
cgagatccga atgcatttgc aagaaatacg aaaaatacta aaaaatcctt ctgcacaata    2220
tgtgacagta tcaggacagg agtttatgat agaaataaag aactctgctg tatcttgtat    2280
accaactgat tgggtaaagg ttggaagcac aaaagctgtg agccgctttc actctccttt    2340
tattgtagaa aattacagac atctgaatca gctccgggag cagctagtcc ttgactgcag    2400
tgctgaatgg cttgattttc tagagaaatt cagtgaacat tatcactcct tgtgtaaagc    2460
agtgcatcac ctagcaactg ttgactgcat tttctcctg gccaaggtcg ctaagcaagg     2520
agattactgc agaccaactg tacaagaaga agaaaaaatt gtaataaaaa atggaaggca    2580
```

-continued

```
ccctgtgatt gatgtgttgc tgggagaaca ggatcaatat gtcccaaata atacagattt    2640
atcagaggac tcagagagag taatgataat taccggacca acatgggtg gaaagagctc     2700 ctacataaaa caagttgcat tgattaccat catggctcag attggctcct atgttcctgc    2760
agaagaagcg acaattggga ttgtggatgg cattttcaca aggatgggtg ctgcagacaa    2820
tatatataaa ggacggagta catttatgga agaactgact gacacagcag aaataatcag    2880
aaaagcaaca tcacagtcct tggttatctt ggatgaacta ggaagaggga cgagcactca    2940
tgatggaatt gccattgcct atgctacact tgagtatttc atcagagatg tgaaatcctt    3000
aaccctgttt gtcacccatt atccgccagt ttgtgaacta gaaaaaaatt actcacacca    3060
ggtggggaat taccacatgg gattcttggt cagtgaggat gaaagcaaac tggatccagg    3120
cgcagcagaa caagtccctg attttgtcac cttcctttac caataacta gaggaattgc     3180 agcaaggagt tatggattaa atgtggctaa actagcagat gttcctggag aaattttgaa    3240
gaaagcagct cacaagtcaa aagagctgga aggattaata aatacgaaaa gaaagagact    3300
caagtatttt gcaaagttat ggacgatgca taatgcacaa gacctgcaga gtggacaga     3360 ggagttcaac atggaagaaa cacagacttc tcttcttcat taaaatgaag actacatttg    3420
tgaacaaaaa atggagaatt aaaaatacca actgtacaaa ataactctcc agtaacagcc    3480
tatctttgtg tgacatgtga gcataaaatt atgaccatgg tatattccta ttggaaacag    3540
agaggttttt ctgaagacag tcttttttcaa gtttctgtct tcctaacttt tctacgtata    3600
aacactcttg aatagacttc cacttttgtaa ttagaaaatt ttatgacag taagtccagt     3660 aaagccttaa gtggcagaat ataattccca agcttttgga gggtgatata aaaatttact    3720
tgatattttt atttgtttca gttcagataa ttggcaactg ggtgaatctg caggaatct     3780 atccattgaa ctaaaataat tttattatgc aaccagttta tccaccaaga acataagaat    3840 ttttttataag tagaaagaat tggccaggca tggtggctca tgcctgtaat cccagcactt    3900
tgggaggcca aggtaggcag atcacctgag gtcaggagtt caagaccagc ctggccaaca    3960
tggcaaaacc ccatctttac taaaaatata agtacatct ctactaaaaa tacgaaaaaa     4020
ttagctgggc atggtggcgc acacctgtag tcccagctac tccggaggct gaggcaggag    4080
aatctcttga acctgggagg cggaggttgc aatgagccga gatcacgtca ctgcactcca    4140
gcttgggcaa cagagcaaga ctccatctca aaaagaaaa agaaaagaa atagaattat       4200 caagctttta aaaactagag cacagaagga ataaggtcat gaaatttaaa aggttaaata    4260
ttgtcatagg attaagcagt ttaaagattg ttggatgaaa ttatttgtca ttcattcaag    4320
taataaatat ttaatgaata cttgctataa aaaaaaaaa aaaaaaaaa aaaa             4374
```

<210> SEQ ID NO 18
<211> LENGTH: 1128
<212> TYPE: PRT
<213> ORGANISM: Homo sapiens

<400> SEQUENCE: 18

```
Met Ser Arg Arg Lys Pro Ala Ser Gly Gly Leu Ala Ala Ser Ser Ser
1               5                   10                  15

Ala Pro Ala Arg Gln Ala Val Leu Ser Arg Phe Phe Gln Ser Thr Gly
            20                  25                  30

Ser Leu Lys Ser Thr Ser Ser Thr Gly Ala Ala Asp Gln Val Asp
        35                  40                  45

Pro Gly Ala Ala Ala Ala Ala Pro Pro Ala Pro Ala Phe Pro Pro
    50                  55                  60
```

-continued

```
Gln Leu Pro Pro His Val Ala Thr Glu Ile Asp Arg Arg Lys Lys Arg
 65                  70                  75                  80

Pro Leu Glu Asn Asp Gly Pro Val Lys Lys Val Lys Lys Val Gln
                 85                  90                  95

Gln Lys Glu Gly Gly Ser Asp Leu Gly Met Ser Gly Asn Ser Glu Pro
            100                 105                 110

Lys Lys Cys Leu Arg Thr Arg Asn Val Ser Lys Ser Leu Glu Lys Leu
        115                 120                 125

Lys Glu Phe Cys Cys Asp Ser Ala Leu Pro Gln Ser Arg Val Gln Thr
    130                 135                 140

Glu Ser Leu Gln Glu Arg Phe Ala Val Leu Pro Lys Cys Thr Asp Phe
145                 150                 155                 160

Asp Asp Ile Ser Leu Leu His Ala Lys Asn Ala Val Ser Ser Glu Asp
                165                 170                 175

Ser Lys Arg Gln Ile Asn Gln Lys Asp Thr Thr Leu Phe Asp Leu Ser
            180                 185                 190

Gln Phe Gly Ser Ser Asn Thr Ser His Glu Asn Leu Gln Lys Thr Ala
        195                 200                 205

Ser Lys Ser Ala Asn Lys Arg Ser Lys Ser Ile Tyr Thr Pro Leu Glu
    210                 215                 220

Leu Gln Tyr Ile Glu Met Lys Gln Gln His Lys Asp Ala Val Leu Cys
225                 230                 235                 240

Val Glu Cys Gly Tyr Lys Tyr Arg Phe Phe Gly Glu Asp Ala Glu Ile
                245                 250                 255

Ala Ala Arg Glu Leu Asn Ile Tyr Cys His Leu Asp His Asn Phe Met
            260                 265                 270

Thr Ala Ser Ile Pro Thr His Arg Leu Phe Val His Val Arg Arg Leu
        275                 280                 285

Val Ala Lys Gly Tyr Lys Val Gly Val Val Lys Gln Thr Glu Thr Ala
    290                 295                 300

Ala Leu Lys Ala Ile Gly Asp Asn Arg Ser Ser Leu Phe Ser Arg Lys
305                 310                 315                 320

Leu Thr Ala Leu Tyr Thr Lys Ser Thr Leu Ile Gly Glu Asp Val Asn
                325                 330                 335

Pro Leu Ile Lys Leu Asp Asp Ala Val Asn Val Asp Glu Ile Met Thr
            340                 345                 350

Asp Thr Ser Thr Ser Tyr Leu Leu Cys Ile Ser Glu Asn Lys Glu Asn
        355                 360                 365

Val Arg Asp Lys Lys Lys Gly Asn Ile Phe Ile Gly Ile Val Gly Val
    370                 375                 380

Gln Pro Ala Thr Gly Glu Val Val Phe Asp Ser Phe Gln Asp Ser Ala
385                 390                 395                 400

Ser Arg Ser Glu Leu Glu Thr Arg Met Ser Ser Leu Gln Pro Val Glu
                405                 410                 415

Leu Leu Leu Pro Ser Ala Leu Ser Glu Gln Thr Glu Ala Leu Ile His
            420                 425                 430

Arg Ala Thr Ser Val Ser Val Gln Asp Asp Arg Ile Arg Val Glu Arg
        435                 440                 445

Met Asp Asn Ile Tyr Phe Glu Tyr Ser His Ala Phe Gln Ala Val Thr
    450                 455                 460

Glu Phe Tyr Ala Lys Asp Thr Val Asp Ile Lys Gly Ser Gln Ile Ile
465                 470                 475                 480
```

-continued

```
Ser Gly Ile Val Asn Leu Glu Lys Pro Val Ile Cys Ser Leu Ala Ala
            485                 490                 495
Ile Ile Lys Tyr Leu Lys Glu Phe Asn Leu Glu Lys Met Leu Ser Lys
            500                 505                 510
Pro Glu Asn Phe Lys Gln Leu Ser Ser Lys Met Glu Phe Met Thr Ile
            515                 520                 525
Asn Gly Thr Thr Leu Arg Asn Leu Glu Ile Leu Gln Asn Gln Thr Asp
            530                 535                 540
Met Lys Thr Lys Gly Ser Leu Leu Trp Val Leu Asp His Thr Lys Thr
545                 550                 555                 560
Ser Phe Gly Arg Arg Lys Leu Lys Lys Trp Val Thr Gln Pro Leu Leu
                565                 570                 575
Lys Leu Arg Glu Ile Asn Ala Arg Leu Asp Ala Val Ser Glu Val Leu
            580                 585                 590
His Ser Glu Ser Ser Val Phe Gly Gln Ile Glu Asn His Leu Arg Lys
            595                 600                 605
Leu Pro Asp Ile Glu Arg Gly Leu Cys Ser Ile Tyr His Lys Lys Cys
            610                 615                 620
Ser Thr Gln Glu Phe Phe Leu Ile Val Lys Thr Leu Tyr His Leu Lys
625                 630                 635                 640
Ser Glu Phe Gln Ala Ile Ile Pro Ala Val Asn Ser His Ile Gln Ser
                645                 650                 655
Asp Leu Leu Arg Thr Val Ile Leu Glu Ile Pro Glu Leu Leu Ser Pro
            660                 665                 670
Val Glu His Tyr Leu Lys Ile Leu Asn Glu Gln Ala Ala Lys Val Gly
            675                 680                 685
Asp Lys Thr Glu Leu Phe Lys Asp Leu Ser Asp Phe Pro Leu Ile Lys
            690                 695                 700
Lys Arg Lys Asp Glu Ile Gln Gly Val Ile Asp Glu Ile Arg Met His
705                 710                 715                 720
Leu Gln Glu Ile Arg Lys Ile Leu Lys Asn Pro Ser Ala Gln Tyr Val
                725                 730                 735
Thr Val Ser Gly Gln Glu Phe Met Ile Glu Ile Lys Asn Ser Ala Val
            740                 745                 750
Ser Cys Ile Pro Thr Asp Trp Val Lys Val Gly Ser Thr Lys Ala Val
            755                 760                 765
Ser Arg Phe His Ser Pro Phe Ile Val Glu Asn Tyr Arg His Leu Asn
            770                 775                 780
Gln Leu Arg Glu Gln Leu Val Leu Asp Cys Ser Ala Glu Trp Leu Asp
785                 790                 795                 800
Phe Leu Glu Lys Phe Ser Glu His Tyr His Ser Leu Cys Lys Ala Val
                805                 810                 815
His His Leu Ala Thr Val Asp Cys Ile Phe Ser Leu Ala Lys Val Ala
            820                 825                 830
Lys Gln Gly Asp Tyr Cys Arg Pro Thr Val Gln Glu Glu Arg Lys Ile
            835                 840                 845
Val Ile Lys Asn Gly Arg His Pro Val Ile Asp Val Leu Leu Gly Glu
            850                 855                 860
Gln Asp Gln Tyr Val Pro Asn Asn Thr Asp Leu Ser Glu Asp Ser Glu
865                 870                 875                 880
Arg Val Met Ile Ile Thr Gly Pro Asn Met Gly Gly Lys Ser Ser Tyr
                885                 890                 895
Ile Lys Gln Val Ala Leu Ile Thr Ile Met Ala Gln Ile Gly Ser Tyr
```

-continued

```
                    900              905              910
Val Pro Ala Glu Glu Ala Thr Ile Gly Ile Val Asp Gly Ile Phe Thr
            915              920              925

Arg Met Gly Ala Ala Asp Asn Ile Tyr Lys Gly Arg Ser Thr Phe Met
        930              935              940

Glu Glu Leu Thr Asp Thr Ala Glu Ile Ile Arg Lys Ala Thr Ser Gln
945              950              955              960

Ser Leu Val Ile Leu Asp Glu Leu Gly Arg Gly Thr Ser Thr His Asp
                965              970              975

Gly Ile Ala Ile Ala Tyr Ala Thr Leu Glu Tyr Phe Ile Arg Asp Val
            980              985              990

Lys Ser Leu Thr Leu Phe Val Thr His Tyr Pro Pro Val Cys Glu Leu
        995             1000             1005

Glu Lys Asn Tyr Ser His Gln Val Gly Asn Tyr His Met Gly Phe
   1010             1015             1020

Leu Val Ser Glu Asp Glu Ser Lys Leu Asp Pro Gly Ala Ala Glu
   1025             1030             1035

Gln Val Pro Asp Phe Val Thr Phe Leu Tyr Gln Ile Thr Arg Gly
   1040             1045             1050

Ile Ala Ala Arg Ser Tyr Gly Leu Asn Val Ala Lys Leu Ala Asp
   1055             1060             1065

Val Pro Gly Glu Ile Leu Lys Lys Ala Ala His Lys Ser Lys Glu
   1070             1075             1080

Leu Glu Gly Leu Ile Asn Thr Lys Arg Lys Arg Leu Lys Tyr Phe
   1085             1090             1095

Ala Lys Leu Trp Thr Met His Asn Ala Gln Asp Leu Gln Lys Trp
   1100             1105             1110

Thr Glu Glu Phe Asn Met Glu Glu Thr Gln Thr Ser Leu Leu His
   1115             1120             1125
```

<210> SEQ ID NO 19
<211> LENGTH: 3095
<212> TYPE: DNA
<213> ORGANISM: Homo sapiens

<400> SEQUENCE: 19

```
cagaaacctc atacttctcg ggtcagggaa ggtttgggag gatgctgagg cctgagatct    60
catcaacctc gccttctgcc ccggcggttt cccccgtcgt cggagaaacc cgctcacctc   120
agggtccccg ctacaatttc ggactccagg agactccaca gagccgccct tcggtccagg   180
tggtctctgc atccacctgt cctggcacgt caggagctgc gggcgaccgg agcagcagca   240
gcagcagcct tccctgcccc gcgccaaact cccggccagc tcaaggttca tactttggaa   300
acaaagagc ttatgcagaa aacacagttg catcaaattt tactttggt gcaagctcat    360
cttctgcacg atatactaat tatcctcaaa cacttaaaac tccattgtct actgaaaatc   420
ctcagagatc aggttataag agctggacac cacaagtggg atattcagct tcatcctcat   480
ctgcgatttc tgcacactcc ccatcagtta ttgtagctgt tgtagaaggg agaggacttg   540
ccagaggtga ataggaatg gcaagtattg atttaaaaaa ccccaaatt atactatccc    600
agtttgcaga caacacaaca tatgcaaagg tgatcactaa acttaaaatt ttatcacctt   660
tggaaataat aatgtcaaat actgcttgtg ctgtgggaa ttccaccaag ttgttcactc   720
tgatcacaga aaatttcaag aatgttaatt tcactactat ccaaaggaaa tacttcaatg   780
aaacaaaagg attagagtac attgaacagt tatgcatagc agaattcagc actgtcctaa   840
```

```
tggaggttca gtccaagtat tactgccttg cagctgttgc agctttgtta aaatatgttg    900
aatttattca aaattcagtt tatgcaccaa atcactgaa gatttgtttc cagggtagtg    960
aacagacagc catgatagat tcatcatcag cccaaaacct tgaattgtta attaataatc   1020
aagactatag gaataatcac actctctttg gtgttctaaa ttatactaag actcctggag   1080
ggagtagacg acttcgttct aatatattag agcctctagt tgatattgaa accattaaca   1140
tgcgcttaga ttgtgttcaa gaactacttc aagatgagga actattttt ggacttcaat    1200
cagttatatc aagatttctt gatacagagc agcttctttc tgttttagtc caaattccag   1260
agcaagacac ggtcaatgct gctgaatcaa agataacaaa tttaatatac ttaaaacata   1320
ccttggaact tgtggatcct ttaaagattg ctatgaagaa ctgtaacaca cctttattaa   1380
gagcttacta tggttccttg aagacaaga ggtttggaat catacttgaa aagattaaaa    1440
cagtaattaa tgatgatgca agatacatga aaggatgcct aaacatgagg actcagaagt   1500
gctatgcagt gaggtctaac ataaatgaat tcttgacat agcaagaaga acatacacag    1560
agattgtaga tgacatagca ggaatgatat cacaacttgg agaaaatat agtctacctt    1620
taaggacaag tcttagctct gttcgaggat ttttcatcca gatgactaca gattgtatag   1680
ccctacctag tgatcaactt ccttcagaat ttattaagat ttctaaagtg aaaaattctt   1740
acagctttac atcagcagat ttaattaaaa tgaatgaaag atgccaagaa tctttgagag   1800
aaatctatca catgacttat atgatagtgt gcaaactgct tagtgagatt tatgaacata   1860
ttcattgctt atataaacta tctgacactg tgtcaatgct ggatatgcta ctgtcatttg   1920
ctcatgcctg cactctttct gactatgttc gaccagaatt tactgatact ttagcaatca   1980
aacagggatg gcatcctatt cttgaaaaaa tatctgcgga aaaacctatt gccaacaata   2040
cctatgttac agaagggagt aattttttga tcataactgg accaaacatg agtggaaaat   2100
ccacatattt aaaacagatt gctctttgtc agattatggc ccagattgga tcatatgttc   2160
cagcagaata ttcttccttt agaattgcta acagattt tacaagaatt agtactgatg    2220
atgatatcga aacaaattca tcaacattta tgaaagaaat gaaagagata gcatatattc   2280
tacataatgc taatgacaaa tcgctcatat taattgatga acttggcaga ggtactaata   2340
cggaagaagg tattggcatt tgttatgctg tttgtaata tctactgagc ttaaaggcat    2400
ttacactgtt tgctacacat ttcctggaac tatgccatat tgatgccctg tatcctaatg   2460
tagaaaacat gcattttgaa gttcaacatg taaagaatac ctcaagaaat aaagaagcaa   2520
ttttgtatac ctacaaactt tctaagggac tcacagaaga gaaaaattat ggattaaaag   2580
ctgcagaggt gtcatcactt ccaccatcaa ttgtcttgga tgccaaggaa atcacaactc   2640
aaattacgag acaaatttg caaaaccaaa ggagtacccc tgagatggaa agacagagag    2700
ctgtgtacca tctagccact aggcttgttc aaactgctcg aaactctcaa ttggatccag   2760
acagtttacg aatatattta agtaacctca agaagaagta caagaagat tttcccagga    2820
ccgaacaagt tccagaaaag actgaagaat aatcacaatt ctaatgtaat aatatatctt   2880
aattcaagga acctagaatt tatttttctc cttagagata aggaaaataa catttgccaa   2940
atttcatatt ttaattgaaa attacattat attaacatca caattgtcat ctatatattc   3000
tatatgaaaa atatttatta taacttaaca aatgagaact acttaaagga atggttttta   3060
tgttaggaga aaatacaata caccacaaaa aaaaa                              3095
```

<210> SEQ ID NO 20

<211> LENGTH: 936
<212> TYPE: PRT
<213> ORGANISM: Homo sapiens

<400> SEQUENCE: 20

```
Met Leu Arg Pro Glu Ile Ser Ser Thr Ser Pro Ser Ala Pro Ala Val
1               5                   10                  15

Ser Pro Val Val Gly Glu Thr Arg Ser Pro Gln Gly Pro Arg Tyr Asn
            20                  25                  30

Phe Gly Leu Gln Glu Thr Pro Gln Ser Arg Pro Ser Val Gln Val Val
        35                  40                  45

Ser Ala Ser Thr Cys Pro Gly Thr Ser Gly Ala Ala Gly Asp Arg Ser
50                  55                  60

Ser Ser Ser Ser Leu Pro Cys Pro Ala Pro Asn Ser Arg Pro Ala
65                  70                  75                  80

Gln Gly Ser Tyr Phe Gly Asn Lys Arg Ala Tyr Ala Glu Asn Thr Val
                85                  90                  95

Ala Ser Asn Phe Thr Phe Gly Ala Ser Ser Ser Ala Arg Asp Thr
                100                 105                 110

Asn Tyr Pro Gln Thr Leu Lys Thr Pro Leu Ser Thr Gly Asn Pro Gln
            115                 120                 125

Arg Ser Gly Tyr Lys Ser Trp Thr Pro Gln Val Gly Tyr Ser Ala Ser
130                 135                 140

Ser Ser Ser Ala Ile Ser Ala His Ser Pro Ser Val Ile Val Ala Val
145                 150                 155                 160

Val Glu Gly Arg Gly Leu Ala Arg Gly Glu Ile Gly Met Ala Ser Ile
                165                 170                 175

Asp Leu Lys Asn Pro Gln Ile Ile Leu Ser Gln Phe Ala Asp Asn Thr
            180                 185                 190

Thr Tyr Ala Lys Val Ile Thr Lys Leu Lys Ile Leu Ser Pro Leu Glu
        195                 200                 205

Ile Ile Met Ser Asn Thr Ala Cys Ala Val Gly Asn Ser Thr Lys Leu
210                 215                 220

Phe Thr Leu Ile Thr Glu Asn Phe Lys Asn Val Asn Phe Thr Thr Ile
225                 230                 235                 240

Gln Arg Lys Tyr Phe Asn Glu Thr Lys Gly Leu Glu Tyr Ile Glu Gln
                245                 250                 255

Leu Cys Ile Ala Glu Phe Ser Thr Val Leu Met Glu Val Gln Ser Lys
            260                 265                 270

Tyr Tyr Cys Leu Ala Ala Val Ala Ala Leu Leu Lys Tyr Val Glu Phe
        275                 280                 285

Ile Gln Asn Ser Val Tyr Ala Pro Lys Ser Leu Lys Ile Cys Phe Gln
290                 295                 300

Gly Ser Glu Gln Thr Ala Met Ile Asp Ser Ser Ala Gln Asn Leu
305                 310                 315                 320

Glu Leu Leu Ile Asn Asn Gln Asp Tyr Arg Asn Asn His Thr Leu Phe
                325                 330                 335

Gly Val Leu Asn Tyr Thr Lys Thr Pro Gly Gly Ser Arg Arg Leu Arg
            340                 345                 350

Ser Asn Ile Leu Glu Pro Leu Val Asp Ile Glu Thr Ile Asn Met Arg
        355                 360                 365

Leu Asp Cys Val Gln Glu Leu Leu Gln Asp Glu Glu Leu Phe Phe Gly
370                 375                 380

Leu Gln Ser Val Ile Ser Arg Phe Leu Asp Thr Glu Gln Leu Leu Ser
```

```
            385                 390                 395                 400
    Val Leu Val Gln Ile Pro Glu Gln Asp Thr Val Asn Ala Ala Glu Ser
                        405                 410                 415
    Lys Ile Thr Asn Leu Ile Tyr Leu Lys His Thr Leu Glu Leu Val Asp
                        420                 425                 430
    Pro Leu Lys Ile Ala Met Lys Asn Cys Asn Thr Pro Leu Leu Arg Ala
                        435                 440                 445
    Tyr Tyr Gly Ser Leu Glu Asp Lys Arg Phe Gly Ile Ile Leu Glu Lys
                        450                 455                 460
    Ile Lys Thr Val Ile Asn Asp Asp Ala Arg Tyr Met Lys Gly Cys Leu
    465                 470                 475                 480
    Asn Met Arg Thr Gln Lys Cys Tyr Ala Val Arg Ser Asn Ile Asn Glu
                        485                 490                 495
    Phe Leu Asp Ile Ala Arg Arg Thr Tyr Thr Glu Ile Val Asp Asp Ile
                        500                 505                 510
    Ala Gly Met Ile Ser Gln Leu Gly Glu Lys Tyr Ser Leu Pro Leu Arg
                        515                 520                 525
    Thr Ser Leu Ser Ser Val Arg Gly Phe Phe Ile Gln Met Thr Thr Asp
                        530                 535                 540
    Cys Ile Ala Leu Pro Ser Asp Gln Leu Pro Ser Glu Phe Ile Lys Ile
    545                 550                 555                 560
    Ser Lys Val Lys Asn Ser Tyr Ser Phe Thr Ser Ala Asp Leu Ile Lys
                        565                 570                 575
    Met Asn Glu Arg Cys Gln Glu Ser Leu Arg Glu Ile Tyr His Met Thr
                        580                 585                 590
    Tyr Met Ile Val Cys Lys Leu Leu Ser Glu Ile Tyr Glu His Ile His
                        595                 600                 605
    Cys Leu Tyr Lys Leu Ser Asp Thr Val Ser Met Leu Asp Met Leu Leu
                        610                 615                 620
    Ser Phe Ala His Ala Cys Thr Leu Ser Asp Tyr Val Arg Pro Glu Phe
    625                 630                 635                 640
    Thr Asp Thr Leu Ala Ile Lys Gln Gly Trp His Pro Ile Leu Glu Lys
                        645                 650                 655
    Ile Ser Ala Glu Lys Pro Ile Ala Asn Asn Thr Tyr Val Thr Glu Gly
                        660                 665                 670
    Ser Asn Phe Leu Ile Ile Thr Gly Pro Asn Met Ser Gly Lys Ser Thr
                        675                 680                 685
    Tyr Leu Lys Gln Ile Ala Leu Cys Gln Ile Met Ala Gln Ile Gly Ser
                        690                 695                 700
    Tyr Val Pro Ala Glu Tyr Ser Ser Phe Arg Ile Ala Lys Gln Ile Phe
    705                 710                 715                 720
    Thr Arg Ile Ser Thr Asp Asp Ile Glu Thr Asn Ser Ser Thr Phe
                        725                 730                 735
    Met Lys Glu Met Lys Glu Ile Ala Tyr Ile Leu His Asn Ala Asn Asp
                        740                 745                 750
    Lys Ser Leu Ile Leu Ile Asp Glu Leu Gly Arg Gly Thr Asn Thr Glu
                        755                 760                 765
    Glu Gly Ile Gly Ile Cys Tyr Ala Val Cys Glu Tyr Leu Leu Ser Leu
                        770                 775                 780
    Lys Ala Phe Thr Leu Phe Ala Thr His Phe Leu Glu Leu Cys His Ile
    785                 790                 795                 800
    Asp Ala Leu Tyr Pro Asn Val Glu Asn Met His Phe Glu Val Gln His
                        805                 810                 815
```

```
Val Lys Asn Thr Ser Arg Asn Lys Glu Ala Ile Leu Tyr Thr Tyr Lys
            820                 825                 830

Leu Ser Lys Gly Leu Thr Glu Glu Lys Asn Tyr Gly Leu Lys Ala Ala
            835                 840                 845

Glu Val Ser Ser Leu Pro Pro Ser Ile Val Leu Asp Ala Lys Glu Ile
            850                 855                 860

Thr Thr Gln Ile Thr Arg Gln Ile Leu Gln Asn Gln Arg Ser Thr Pro
865                 870                 875                 880

Glu Met Glu Arg Gln Arg Ala Val Tyr His Leu Ala Thr Arg Leu Val
                885                 890                 895

Gln Thr Ala Arg Asn Ser Gln Leu Asp Pro Asp Ser Leu Arg Ile Tyr
            900                 905                 910

Leu Ser Asn Leu Lys Lys Lys Tyr Lys Glu Asp Phe Pro Arg Thr Glu
            915                 920                 925

Gln Val Pro Glu Lys Thr Glu Glu
            930                 935

<210> SEQ ID NO 21
<211> LENGTH: 2726
<212> TYPE: DNA
<213> ORGANISM: Homo sapiens

<400> SEQUENCE: 21
```

| | | | | | |
|---|---|---|---|---|---|
| gcggtcggtc | agcggggcgt | tctcccacct | gtagcgactc | agagcctcca | agctcatggc | 60 |
| ctccttagga | gcgaacccaa | ggaggacacc | gcagggaccg | agacctgggg | cggcctcctc | 120 |
| cggcttcccc | agcccggccc | cagtgccggg | ccccagggag | gccgaggagg | aggaagtcga | 180 |
| ggaggaggag | gagctggccg | agatccatct | gtgtgtgctg | tggaattcag | gatacttggg | 240 |
| cattgcctac | tatgatacta | gtgactccac | tatccacttc | atgccagatg | ccccagacca | 300 |
| cgagagcctc | aagcttctcc | agagagttct | ggatgagatc | aatccccagt | ctgttgttac | 360 |
| gagtgccaaa | caggatgaga | atatgactcg | atttctggga | aagcttgcct | cccaggagca | 420 |
| cagagagcct | aaaagacctg | aaatcatatt | tttgccaagt | gtggattttg | gtctggagat | 480 |
| aagcaaacaa | cgcctccttt | ctggaaacta | ctccttcatc | ccagacgcca | tgactgccac | 540 |
| tgagaaaatc | ctcttcctct | cttccattat | tccctttgac | tgcctcctca | cagttcgagc | 600 |
| acttggaggg | ctgctgaagt | tcctgggtcg | aagaagaatc | ggggttgaac | tggaagacta | 660 |
| taatgtcagc | gtccccatcc | tgggctttaa | gaaatttatg | ttgactcatc | tggtgaacat | 720 |
| agatcaagac | acttacagtg | ttctacagat | ttttaagagt | gagtctcacc | cctcagtgta | 780 |
| caaagtggcc | agtggactga | ggagggggct | cagcctcttt | ggaatcctca | acagatgcca | 840 |
| ctgtaagtgg | ggagagaagc | tgctcaggct | atggttcaca | cgtccgactc | atgacctggg | 900 |
| ggagctcagt | tctcgtctgg | acgtcattca | gttttttctg | ctgccccaga | atctggacat | 960 |
| ggctcagatg | ctgcatcggc | tcctgggtca | catcaagaac | gtgcctctga | ttctgaaacg | 1020 |
| catgaagttg | tccacacca | aggtcagcga | ctggcaggtt | ctctacaaga | ctgtgtacag | 1080 |
| tgccctgggc | ctgagggatg | cctgccgctc | cctgccgcag | tccatccagc | tctttcggga | 1140 |
| cattgcccaa | gagttctctg | atgacctgca | ccatatcgcc | agcctcattg | ggaaagtagt | 1200 |
| ggactttgag | ggcagccttg | ctgaaaatcg | cttcacagtc | ctccccaaca | tagatcctga | 1260 |
| aattgatgag | aaaaagcgaa | gactgatggg | acttcccagt | ttccttactg | aggttgcccg | 1320 |
| caaggagctg | gagaatctgg | actcccgtat | tccttcatgc | agtgtcatct | acatccctct | 1380 |

```
gattggcttc cttctttcta ttccccgcct gccttccatg gtagaggcca gtgactttga    1440
gattaatgga ctggacttca tgtttctctc agaggagaag ctgcactatc gtagtgcccg    1500
aaccaaggag ctggatgcat tgctggggga cctgcactgc gagatccggg accaggagac    1560
gctgctgatg taccagctac agtgccaggt gctggcacga gcagctgtct taacccgagt    1620
attggacctt gcctcccgcc tggacgtcct gctggctctt gccagtgctg cccgggacta    1680
tggctactca aggccgcgtt actccccaca gtccttggg gtacgaatcc agaatggcag     1740
acatcctctg atggaactct gtgcccgaac ctttgtgccc aactccacag aatgtggtgg    1800
ggacaaaggg agggtcaaag tcatcactgg acccaactca tcaggaaga gcatataccct   1860 caaacaggta ggcttgatca cattcatggc cctggtaggc agctttgtgc cagcagagga   1920
ggccgaaatt ggggcagtag acgccatctt cacacgaatt catagctgcg aatccatctc   1980
ccttggcctc tccaccttca tgatcgacct caaccagcag gtggcgaaag cagtgaacaa   2040
tgccactgca cagtcgctgg tccttattga tgaatttgga aagggaacca acacggtgga   2100
tgggctcgcg cttctggccg ctgtgctccg acactggctg gcacgtggac ccacatgccc   2160
ccacatcttt gtggccacca actttctgag ccttgttcag ctacaactgc tgccacaagg   2220
gcccctggtg cagtatttga ccatggagac ctgtgaggat ggcaacgatc ttgtcttctt   2280
ctatcaggtt tgcgaaggtg ttgcgaaggc cagccatgcc tcccacacag ctgcccaggc   2340
tgggcttcct gacaagcttg tggctcgtgg caaggaggtc tcagacttga tccgcagtgg   2400
aaaacccatc aagcctgtca aggatttgct aagaagaac caaatggaaa attgccagac    2460
attagtggat aagtttatga aactggattt ggaagatcct aacctggact tgaacgtttt   2520
catgagccag gaagtgctgc ctgctgccac cagcatcctc tgagagtcct tccagtgtcc   2580
tccccagcct cctgagactc cggtgggctg ccatgccctc tttgtttcct tatctccctc   2640
agacgcagag tttttagttt ctctagaaat tttgtttcat attaggaata aagtttattt   2700
tgaagaaaaa aaaaaaaaa aaaaaa                                         2726
```

<210> SEQ ID NO 22
<211> LENGTH: 835
<212> TYPE: PRT
<213> ORGANISM: Homo sapiens

<400> SEQUENCE: 22

```
Met Ala Ser Leu Gly Ala Asn Pro Arg Arg Thr Pro Gln Gly Pro Arg
1               5                   10                  15

Pro Gly Ala Ala Ser Ser Gly Phe Pro Ser Pro Ala Pro Val Pro Gly
                20                  25                  30

Pro Arg Glu Ala Glu Glu Glu Val Glu Glu Glu Glu Leu Ala
            35                  40                  45

Glu Ile His Leu Cys Val Leu Trp Asn Ser Gly Tyr Leu Gly Ile Ala
        50                  55                  60

Tyr Tyr Asp Thr Ser Asp Ser Thr Ile His Phe Met Pro Asp Ala Pro
65                  70                  75                  80

Asp His Glu Ser Leu Lys Leu Leu Gln Arg Val Leu Asp Glu Ile Asn
                85                  90                  95

Pro Gln Ser Val Val Thr Ser Ala Lys Gln Asp Glu Asn Met Thr Arg
            100                 105                 110

Phe Leu Gly Lys Leu Ala Ser Gln Glu His Arg Glu Pro Lys Arg Pro
        115                 120                 125

Glu Ile Ile Phe Leu Pro Ser Val Asp Phe Gly Leu Glu Ile Ser Lys
```

-continued

```
            130                 135                 140
Gln Arg Leu Leu Ser Gly Asn Tyr Ser Phe Ile Pro Asp Ala Met Thr
145                 150                 155                 160
Ala Thr Glu Lys Ile Leu Phe Leu Ser Ser Ile Ile Pro Phe Asp Cys
                    165                 170                 175
Leu Leu Thr Val Arg Ala Leu Gly Gly Leu Leu Lys Phe Leu Gly Arg
                180                 185                 190
Arg Arg Ile Gly Val Glu Leu Glu Asp Tyr Asn Val Ser Val Pro Ile
            195                 200                 205
Leu Gly Phe Lys Lys Phe Met Leu Thr His Leu Val Asn Ile Asp Gln
210                 215                 220
Asp Thr Tyr Ser Val Leu Gln Ile Phe Lys Ser Glu Ser His Pro Ser
225                 230                 235                 240
Val Tyr Lys Val Ala Ser Gly Leu Lys Glu Gly Leu Ser Leu Phe Gly
                245                 250                 255
Ile Leu Asn Arg Cys His Cys Lys Trp Gly Glu Lys Leu Leu Arg Leu
            260                 265                 270
Trp Phe Thr Arg Pro Thr His Asp Leu Gly Glu Leu Ser Ser Arg Leu
        275                 280                 285
Asp Val Ile Gln Phe Phe Leu Leu Pro Gln Asn Leu Asp Met Ala Gln
    290                 295                 300
Met Leu His Arg Leu Leu Gly His Ile Lys Asn Val Pro Leu Ile Leu
305                 310                 315                 320
Lys Arg Met Lys Leu Ser His Thr Lys Val Ser Asp Trp Gln Val Leu
                325                 330                 335
Tyr Lys Thr Val Tyr Ser Ala Leu Gly Leu Arg Asp Ala Cys Arg Ser
                340                 345                 350
Leu Pro Gln Ser Ile Gln Leu Phe Arg Asp Ile Ala Gln Glu Phe Ser
            355                 360                 365
Asp Asp Leu His His Ile Ala Ser Leu Ile Gly Lys Val Val Asp Phe
        370                 375                 380
Glu Gly Ser Leu Ala Glu Asn Arg Phe Thr Val Leu Pro Asn Ile Asp
385                 390                 395                 400
Pro Glu Ile Asp Glu Lys Lys Arg Arg Leu Met Gly Leu Pro Ser Phe
                405                 410                 415
Leu Thr Glu Val Ala Arg Lys Glu Leu Glu Asn Leu Asp Ser Arg Ile
                420                 425                 430
Pro Ser Cys Ser Val Ile Tyr Ile Pro Leu Ile Gly Phe Leu Leu Ser
            435                 440                 445
Ile Pro Arg Leu Pro Ser Met Val Glu Ala Ser Asp Phe Glu Ile Asn
450                 455                 460
Gly Leu Asp Phe Met Phe Leu Ser Glu Glu Lys Leu His Tyr Arg Ser
465                 470                 475                 480
Ala Arg Thr Lys Glu Leu Asp Ala Leu Leu Gly Asp Leu His Cys Glu
                485                 490                 495
Ile Arg Asp Gln Glu Thr Leu Leu Met Tyr Gln Leu Gln Cys Gln Val
            500                 505                 510
Leu Ala Arg Ala Ala Val Leu Thr Arg Val Leu Asp Leu Ala Ser Arg
        515                 520                 525
Leu Asp Val Leu Leu Ala Leu Ala Ser Ala Ala Arg Asp Tyr Gly Tyr
    530                 535                 540
Ser Arg Pro Arg Tyr Ser Pro Gln Val Leu Gly Val Arg Ile Gln Asn
545                 550                 555                 560
```

```
Gly Arg His Pro Leu Met Glu Leu Cys Ala Arg Thr Phe Val Pro Asn
                565                 570                 575

Ser Thr Glu Cys Gly Gly Asp Lys Gly Arg Val Lys Val Ile Thr Gly
            580                 585                 590

Pro Asn Ser Ser Gly Lys Ser Ile Tyr Leu Lys Gln Val Gly Leu Ile
        595                 600                 605

Thr Phe Met Ala Leu Val Gly Ser Phe Val Pro Ala Glu Glu Ala Glu
    610                 615                 620

Ile Gly Ala Val Asp Ala Ile Phe Thr Arg Ile His Ser Cys Glu Ser
625                 630                 635                 640

Ile Ser Leu Gly Leu Ser Thr Phe Met Ile Asp Leu Asn Gln Gln Val
                645                 650                 655

Ala Lys Ala Val Asn Asn Ala Thr Gln Ser Leu Val Leu Ile Asp
            660                 665                 670

Glu Phe Gly Lys Gly Thr Asn Thr Val Asp Gly Leu Ala Leu Leu Ala
        675                 680                 685

Ala Val Leu Arg His Trp Leu Ala Arg Gly Pro Thr Cys Pro His Ile
    690                 695                 700

Phe Val Ala Thr Asn Phe Leu Ser Leu Val Gln Leu Gln Leu Leu Pro
705                 710                 715                 720

Gln Gly Pro Leu Val Gln Tyr Leu Thr Met Glu Thr Cys Glu Asp Gly
                725                 730                 735

Asn Asp Leu Val Phe Phe Tyr Gln Val Cys Glu Gly Val Ala Lys Ala
            740                 745                 750

Ser His Ala Ser His Thr Ala Ala Gln Ala Gly Leu Pro Asp Lys Leu
        755                 760                 765

Val Ala Arg Gly Lys Glu Val Ser Asp Leu Ile Arg Ser Gly Lys Pro
    770                 775                 780

Ile Lys Pro Val Lys Asp Leu Leu Lys Asn Gln Met Glu Asn Cys
785                 790                 795                 800

Gln Thr Leu Val Asp Lys Phe Met Lys Leu Asp Leu Glu Asp Pro Asn
                805                 810                 815

Leu Asp Leu Asn Val Phe Met Ser Gln Glu Val Leu Pro Ala Ala Thr
            820                 825                 830

Ser Ile Leu
        835

<210> SEQ ID NO 23
<211> LENGTH: 4264
<212> TYPE: DNA
<213> ORGANISM: Homo sapiens

<400> SEQUENCE: 23
atttcccgcc agcaggagcc gcgcggtaga tgcggtgctt ttaggagctc cgtccgacag      60
aacggttggg ccttgccggc tgtcggtatg tcgcgacaga gcaccctgta cagcttcttc     120
cccaagtctc cggcgctgag tgatgccaac aaggcctcgg ccagggcctc acgcgaaggc     180
ggccgtgccg ccgctgcccc cggggcctct ccttccccag gcgggatgc ggcctggagc      240 gaggctgggc ctgggcccag gcccttggcg cgatccgcgt caccgcccaa ggcgaagaac     300
ctcaacggag ggctgcggag atcggtagcg cctgctgccc ccaccagttg tgacttctca     360
ccaggagatt tggtttgggc caagatggag ggttacccct ggtggccttg tctggtttac     420 aaccaccccct ttgatggaac attcatccgc gagaaaggga atcagtccg tgttcatgta     480
```

```
cagttttttg atgacagccc aacaaggggc tgggttagca aaaggctttt aaagccatat    540
acaggttcaa aatcaaagga agcccagaag ggaggtcatt tttacagtgc aaagcctgaa    600
atactgagag caatgcaacg tgcagatgaa gccttaaata aagacaagat taagaggctt    660
gaattggcag tttgtgatga gccctcagag ccagaagagg aagaagagat ggaggtaggc    720
acaacttacg taacagataa gagtgaagaa gataatgaaa ttgagagtga agaggaagta    780
cagcctaaga cacaaggatc taggcgaagt agccgccaaa taaaaaaacg aagggtcata    840
tcagattctg agagtgacat tggtggctct gatgtggaat ttaagccaga cactaaggag    900
gaaggaagca gtgatgaaat aagcagtgga gtggggtata tgagagtga aggcctgaac     960 agccctgtca agttgctcg aaagcggaag agaatggtga ctggaaatgg ctctcttaaa    1020
aggaaaagct ctaggaagga aacgccctca gccaccaaac aagcaactag catttcatca    1080
gaaaccaaga atactttgag agctttctct gcccctcaaa attctgaatc ccaagcccac    1140
gttagtggag gtggtgatga cagtagtcgc cctactgttt ggtatcatga aactttagaa    1200
tggcttaagg aggaaaagag aagagatgag cacaggagga ggcctgatca ccccgatttt    1260
gatgcatcta cactctatgt gcctgaggat ttcctcaatt cttgtactcc tgggatgagg    1320
aagtggtggc agattaagtc tcagaacttt gatcttgtca tctgttacaa ggtggggaaa    1380
ttttatgagc tgtaccacat ggatgctctt attggagtca gtgaactggg gctggtattc    1440
atgaaaggca actgggccca ttctggcttt cctgaaattg catttggccg ttattcagat    1500
tccctggtgc agaagggcta taaagtagca cgagtggaac agactgagac tccagaaatg    1560
atggaggcac gatgtagaaa gatggcacat atatccaagt atgatagagt ggtgaggagg    1620
gagatctgta ggatcattac caagggtaca cagacttaca gtgtgctgga aggtgatccc    1680
tctgagaact acagtaagta tcttcttagc ctcaaagaaa aagaggaaga ttcttctggc    1740
catactcgtg catatggtgt gtgctttgtt gatacttcac tgggaaagtt tttcataggt    1800 cagtttttcag atgatcgcca ttgttcgaga tttaggactc tagtggcaca ctatccccca    1860
gtacaagttt tatttgaaaa aggaaatctc tcaaaggaaa ctaaaacaat tctaaagagt    1920
tcattgtcct gttctcttca ggaaggtctg atacccggct cccagttttg ggatgcatcc    1980
aaaactttga gaactctcct tgaggaagaa tattttaggg aaaagctaag tgatggcatt    2040
ggggtgatgt taccccaggt gcttaaaggt atgacttcag agtctgattc cattgggttg    2100
acaccaggag agaaaagtga attggccctc tctgctctag gtggttgtgt cttctacctc    2160
aaaaaatgcc ttattgatca ggagctttta tcaatggcta atttttgaaga atatattccc    2220 ttggattctg acacagtcag cactacaaga tctggtgcta tcttcaccaa agcctatcaa    2280
cgaatggtgc tagatgcagt gacattaaac aacttggaga ttttttctgaa tggaacaaat    2340 ggttctactg aaggaaccct actagagagg gttgatactt gccatactcc ttttggtaag    2400
cggctcctaa agcaatggct ttgtgcccca ctctgtaacc attatgctat taatgatcgt    2460
ctagatgcca tagaagacct catggttgtg cctgacaaaa tctccgaagt tgtagagctt    2520
ctaaagaagc ttccagatct tgagaggcta ctcagtaaaa ttcataatgt tgggtctccc    2580
ctgaagagtc agaaccaccc agacagcagg gctataatgt atgaagaaac tacatacagc    2640
aagaagaaga ttattgattt tcttttctgct ctggaaggat tcaaagtaat gtgtaaaatt    2700
atagggatca tggaagaagt tgctgatggt tttaagtcta aaatccttaa gcaggtcatc    2760
tctctgcaga caaaaaatcc tgaaggtcgt tttcctgatt tgactgtaga attgaaccga    2820
tgggatacag ccttttgacca tgaaaaggct cgaaagactg gacttattac tcccaaagca    2880
```

```
ggctttgact ctgattatga ccaagctctt gctgacataa agaaaatga acagagcctc    2940 ctggaatacc tagagaaaca gcgcaacaga attggctgta ggaccatagt ctattggggg    3000
attggtagga accgttacca gctggaaatt cctgagaatt tcaccactcg caatttgcca    3060
gaagaatacg agttgaaatc taccaagaag ggctgtaaac gatactggac caaaactatt    3120
gaaaagaagt tggctaatct cataaatgct gaagaacgga gggatgtatc attgaaggac    3180
tgcatgcggc gactgttcta taactttgat aaaaattaca aggactggca gtctgctgta    3240
gagtgtatcg cagtgttgga tgttttactg tgcctggcta actatagtcg aggggggtgat    3300 ggtcctatgt gtcgcccagt aattctgttg ccggaagata cccccccctt cttagagctt    3360
aaaggatcac gccatccttg cattacgaag acttttttg gagatgattt tattcctaat    3420
gacattctaa taggctgtga ggaagaggag caggaaaatg gcaaagccta ttgtgtgctt    3480
gttactggac caaatatggg gggcaagtct acgcttatga cacaggctgg cttattagct    3540
gtaatggccc agatgggttg ttacgtccct gctgaagtgt gcaggctcac accaattgat    3600
agagtgttta ctagacttgg tgcctcagac agaataatgt caggtgaaag tacattttt    3660 gttgaattaa gtgaaactgc cagcatactc atgcatgcaa cagcacattc tctggtgctt    3720
gtggatgaat taggaagagg tactgcaaca tttgatggga cggcaatagc aaatgcagtt    3780
gttaaagaac ttgctgagac tataaaatgt cgtacattat tttcaactca ctaccattca    3840
ttagtagaag attattctca aaatgttgct gtgcgcctag gacatatggc atgcatggta    3900
gaaaatgaat gtgaagaccc cagccaggag actattacgt tcctctataa attcattaag    3960
ggagcttgtc ctaaaagcta tggctttaat gcagcaaggc ttgctaatct cccagaggaa    4020
gttattcaaa agggacatag aaaagcaaga gaatttgaga gatgaatca gtcactacga    4080 ttatttcggg aagtttgcct ggctagtgaa aggtcaactg tagatgctga agctgtccat    4140
aaattgctga ctttgattaa ggaattatag actgactaca ttggaagctt tgagttgact    4200
tctgaccaaa ggtggtaaat tcagacaaca ttatgatcta ataaacttta ttttttaaaa    4260
atga                                                                4264
```

<210> SEQ ID NO 24
<211> LENGTH: 1360
<212> TYPE: PRT
<213> ORGANISM: Homo sapiens

<400> SEQUENCE: 24

Met Ser Arg Gln Ser Thr Leu Tyr Ser Phe Phe Pro Lys Ser Pro Ala
1               5                   10                  15

Leu Ser Asp Ala Asn Lys Ala Ser Ala Arg Ala Ser Arg Glu Gly Gly
            20                  25                  30

Arg Ala Ala Ala Ala Pro Gly Ala Ser Pro Ser Pro Gly Gly Asp Ala
        35                  40                  45

Ala Trp Ser Glu Ala Gly Pro Gly Pro Arg Pro Leu Ala Arg Ser Ala
    50                  55                  60

Ser Pro Pro Lys Ala Lys Asn Leu Asn Gly Gly Leu Arg Arg Ser Val
65                  70                  75                  80

Ala Pro Ala Ala Pro Thr Ser Cys Asp Phe Ser Pro Gly Asp Leu Val
                85                  90                  95

Trp Ala Lys Met Glu Gly Tyr Pro Trp Trp Pro Cys Leu Val Tyr Asn
            100                 105                 110

His Pro Phe Asp Gly Thr Phe Ile Arg Glu Lys Gly Lys Ser Val Arg

-continued

```
            115                 120                 125
Val His Val Gln Phe Phe Asp Asp Ser Pro Thr Arg Gly Trp Val Ser
    130                 135                 140
Lys Arg Leu Leu Lys Pro Tyr Thr Gly Ser Lys Ser Lys Glu Ala Gln
145                 150                 155                 160
Lys Gly Gly His Phe Tyr Ser Ala Lys Pro Glu Ile Leu Arg Ala Met
                165                 170                 175
Gln Arg Ala Asp Glu Ala Leu Asn Lys Asp Lys Ile Lys Arg Leu Glu
            180                 185                 190
Leu Ala Val Cys Asp Glu Pro Ser Glu Pro Glu Glu Glu Glu Glu Met
            195                 200                 205
Glu Val Gly Thr Thr Tyr Val Thr Asp Lys Ser Glu Glu Asp Asn Glu
    210                 215                 220
Ile Glu Ser Glu Glu Glu Val Gln Pro Lys Thr Gln Gly Ser Arg Arg
225                 230                 235                 240
Ser Ser Arg Gln Ile Lys Lys Arg Val Ile Ser Asp Ser Glu Ser
                245                 250                 255
Asp Ile Gly Gly Ser Asp Val Glu Phe Lys Pro Asp Thr Lys Glu Glu
            260                 265                 270
Gly Ser Ser Asp Glu Ile Ser Ser Gly Val Gly Asp Ser Glu Ser Glu
        275                 280                 285
Gly Leu Asn Ser Pro Val Lys Val Ala Arg Lys Arg Lys Arg Met Val
        290                 295                 300
Thr Gly Asn Gly Ser Leu Lys Arg Lys Ser Ser Arg Lys Glu Thr Pro
305                 310                 315                 320
Ser Ala Thr Lys Gln Ala Thr Ser Ile Ser Ser Glu Thr Lys Asn Thr
                325                 330                 335
Leu Arg Ala Phe Ser Ala Pro Gln Asn Ser Glu Ser Gln Ala His Val
            340                 345                 350
Ser Gly Gly Gly Asp Asp Ser Ser Arg Pro Thr Val Trp Tyr His Glu
        355                 360                 365
Thr Leu Glu Trp Leu Lys Glu Glu Lys Arg Arg Asp Glu His Arg Arg
    370                 375                 380
Arg Pro Asp His Pro Asp Phe Asp Ala Ser Thr Leu Tyr Val Pro Glu
385                 390                 395                 400
Asp Phe Leu Asn Ser Cys Thr Pro Gly Met Arg Lys Trp Trp Gln Ile
                405                 410                 415
Lys Ser Gln Asn Phe Asp Leu Val Ile Cys Tyr Lys Val Gly Lys Phe
            420                 425                 430
Tyr Glu Leu Tyr His Met Asp Ala Leu Ile Gly Val Ser Glu Leu Gly
        435                 440                 445
Leu Val Phe Met Lys Gly Asn Trp Ala His Ser Gly Phe Pro Glu Ile
    450                 455                 460
Ala Phe Gly Arg Tyr Ser Asp Ser Leu Val Gln Lys Gly Tyr Lys Val
465                 470                 475                 480
Ala Arg Val Glu Gln Thr Glu Thr Pro Glu Met Met Glu Ala Arg Cys
                485                 490                 495
Arg Lys Met Ala His Ile Ser Lys Tyr Asp Arg Val Val Arg Arg Glu
            500                 505                 510
Ile Cys Arg Ile Ile Thr Lys Gly Thr Gln Thr Tyr Ser Val Leu Glu
        515                 520                 525
Gly Asp Pro Ser Glu Asn Tyr Ser Lys Tyr Leu Leu Ser Leu Lys Glu
    530                 535                 540
```

```
Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
                565                 570                 575

Arg His Cys Ser Arg Phe Arg Thr Leu Val Ala His Tyr Pro Pro Val
                580                 585                 590

Gln Val Leu Phe Glu Lys Gly Asn Leu Ser Lys Glu Thr Lys Thr Ile
                595                 600                 605

Leu Lys Ser Ser Leu Ser Cys Ser Leu Gln Glu Gly Leu Ile Pro Gly
                610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
                660                 665                 670

Pro Gly Glu Lys Ser Glu Leu Ala Leu Ser Ala Leu Gly Gly Cys Val
                675                 680                 685

Phe Tyr Leu Lys Lys Cys Leu Ile Asp Gln Glu Leu Leu Ser Met Ala
690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
                725                 730                 735

Ala Val Thr Leu Asn Asn Leu Glu Ile Phe Leu Asn Gly Thr Asn Gly
                740                 745                 750

Ser Thr Glu Gly Thr Leu Leu Glu Arg Val Asp Thr Cys His Thr Pro
                755                 760                 765

Phe Gly Lys Arg Leu Leu Lys Gln Trp Leu Cys Ala Pro Leu Cys Asn
                770                 775                 780

His Tyr Ala Ile Asn Asp Arg Leu Asp Ala Ile Glu Asp Leu Met Val
785                 790                 795                 800

Val Pro Asp Lys Ile Ser Glu Val Val Glu Leu Leu Lys Lys Leu Pro
                805                 810                 815

Asp Leu Glu Arg Leu Leu Ser Lys Ile His Asn Val Gly Ser Pro Leu
                820                 825                 830

Lys Ser Gln Asn His Pro Asp Ser Arg Ala Ile Met Tyr Glu Glu Thr
                835                 840                 845

Thr Tyr Ser Lys Lys Lys Ile Ile Asp Phe Leu Ser Ala Leu Glu Gly
850                 855                 860

Phe Lys Val Met Cys Lys Ile Ile Gly Ile Met Glu Glu Val Ala Asp
865                 870                 875                 880

Gly Phe Lys Ser Lys Ile Leu Lys Gln Val Ile Ser Leu Gln Thr Lys
                885                 890                 895

Asn Pro Glu Gly Arg Phe Pro Asp Leu Thr Val Glu Leu Asn Arg Trp
                900                 905                 910

Asp Thr Ala Phe Asp His Glu Lys Ala Arg Lys Thr Gly Leu Ile Thr
                915                 920                 925

Pro Lys Ala Gly Phe Asp Ser Asp Tyr Asp Gln Ala Leu Ala Asp Ile
                930                 935                 940

Arg Glu Asn Glu Gln Ser Leu Leu Glu Tyr Leu Glu Lys Gln Arg Asn
945                 950                 955                 960
```

-continued

```
Arg Ile Gly Cys Arg Thr Ile Val Tyr Trp Gly Ile Gly Arg Asn Arg
            965                 970                 975

Tyr Gln Leu Glu Ile Pro Glu Asn Phe Thr Thr Arg Asn Leu Pro Glu
            980                 985                 990

Glu Tyr Glu Leu Lys Ser Thr Lys Lys Gly Cys Lys Arg Tyr Trp Thr
            995                 1000                1005

Lys Thr Ile Glu Lys Lys Leu Ala Asn Leu Ile Asn Ala Glu Glu
            1010                1015                1020

Arg Arg Asp Val Ser Leu Lys Asp Cys Met Arg Arg Leu Phe Tyr
            1025                1030                1035

Asn Phe Asp Lys Asn Tyr Lys Asp Trp Gln Ser Ala Val Glu Cys
            1040                1045                1050

Ile Ala Val Leu Asp Val Leu Leu Cys Leu Ala Asn Tyr Ser Arg
            1055                1060                1065

Gly Gly Asp Gly Pro Met Cys Arg Pro Val Ile Leu Leu Pro Glu
            1070                1075                1080

Asp Thr Pro Pro Phe Leu Glu Leu Lys Gly Ser Arg His Pro Cys
            1085                1090                1095

Ile Thr Lys Thr Phe Phe Gly Asp Asp Phe Ile Pro Asn Asp Ile
            1100                1105                1110

Leu Ile Gly Cys Glu Glu Glu Glu Gln Glu Asn Gly Lys Ala Tyr
            1115                1120                1125

Cys Val Leu Val Thr Gly Pro Asn Met Gly Gly Lys Ser Thr Leu
            1130                1135                1140

Met Arg Gln Ala Gly Leu Leu Ala Val Met Ala Gln Met Gly Cys
            1145                1150                1155

Tyr Val Pro Ala Glu Val Cys Arg Leu Thr Pro Ile Asp Arg Val
            1160                1165                1170

Phe Thr Arg Leu Gly Ala Ser Asp Arg Ile Met Ser Gly Glu Ser
            1175                1180                1185

Thr Phe Phe Val Glu Leu Ser Glu Thr Ala Ser Ile Leu Met His
            1190                1195                1200

Ala Thr Ala His Ser Leu Val Leu Val Asp Glu Leu Gly Arg Gly
            1205                1210                1215

Thr Ala Thr Phe Asp Gly Thr Ala Ile Ala Asn Ala Val Val Lys
            1220                1225                1230

Glu Leu Ala Glu Thr Ile Lys Cys Arg Thr Leu Phe Ser Thr His
            1235                1240                1245

Tyr His Ser Leu Val Glu Asp Tyr Ser Gln Asn Val Ala Val Arg
            1250                1255                1260

Leu Gly His Met Ala Cys Met Val Glu Asn Glu Cys Glu Asp Pro
            1265                1270                1275

Ser Gln Glu Thr Ile Thr Phe Leu Tyr Lys Phe Ile Lys Gly Ala
            1280                1285                1290

Cys Pro Lys Ser Tyr Gly Phe Asn Ala Ala Arg Leu Ala Asn Leu
            1295                1300                1305

Pro Glu Glu Val Ile Gln Lys Gly His Arg Lys Ala Arg Glu Phe
            1310                1315                1320

Glu Lys Met Asn Gln Ser Leu Arg Leu Phe Arg Glu Val Cys Leu
            1325                1330                1335

Ala Ser Glu Arg Ser Thr Val Asp Ala Glu Ala Val His Lys Leu
            1340                1345                1350

Leu Thr Leu Ile Lys Glu Leu
```

<210> SEQ ID NO 25
<211> LENGTH: 1445
<212> TYPE: DNA
<213> ORGANISM: Homo sapiens

<400> SEQUENCE: 25

```
tttttttttt tgatgttctc cagtgcctca gtggcagcag aactggccct gtatcaggcc      60
gctaccgcca ctccatgacc aacctccctg catacccccc ccccagcac ccctcccaca     120
ggaccgcttc tgtgtttggg acccaccagg cctttgcacc atacaacaaa ccctcactct     180
ccggggcccg gtctgcgccc aggctgaaca ccacgaacgc ctgggacgca gctcctcctt     240
ccctggggag ccagcccctc taccgctcca gcctctccca cctgggaccg cagcacctgc     300
ccccaggatc ctccacctcc ggtgcagtca gtgcctccct cccagcggt ccctcaagca     360
gcccaggcga gcgtccctgc cactgtgccc atgcagatgc caagccagca gagtcagcag     420
gcgctcgctg agcgacccg aagccagagc agagcagagc aggtcataaa actacacgga     480
agagctgaaa gtgcccccag atgaggactg catcatctgc atggagaagc tgtccgcagc     540
gtctggatac agcgatgtga ctgacagcaa ggcaatgggg ccctggctg tgggctgcct     600
caccaagtgc agccacgcct tccacctgct gtgcctcctg gccatgtact gcaacggcaa     660
taagggccct gagcacccca tcccggaaa gccgttcact gccagagggt ttcccgccag     720
tgctaccttc cagacaacgc cagggccgca agcctccagg ggcttccaga acccggagac     780
actggctgac attccggcct ccccacagct gctgaccgat ggccactaca tgacgctgcc     840
cgtgtctccg gaccagctgc cctgtgacga ccccatgggcg ggcagcggag gcgccccccgt     900
gctgcgggtg ggccatgacc acggctgcca ccagcagcca cgtatctgca cgcgcccct     960
cccctggccct ggaccctatc gtacagaacc tgctaaggcc atcaaaccta ttgatcggaa    1020
gtcagtccat cagatttgct ctgggccagt ggtactgagt ctaagcactg cagtgaagga    1080
gttagtagaa aacagtctgg atgctggtgc cactaatatt gatctaaagc ttaaggacta    1140
tggaatggat ctcattgaag tttcaggcaa tggatgtggg gtagaagaag aaaacttcga    1200
aggcttaatg atgtcaccat ttctacctgc cacgtctcgg cgaaggttgg gactcgactg    1260
gtgtttgatc acgatgggaa aatcatccag aagaccccct accccaccc cagagggacc    1320
acagtcagcg tgaagcagtt attttctacg ctacctgtgc gccataagga atttcaaagg    1380
aatattaaga agaaacatgc tgcttcccct tcgccttctg ccgtgattgt cagttttaac    1440
cggaa                                                                1445
```

<210> SEQ ID NO 26
<211> LENGTH: 270
<212> TYPE: PRT
<213> ORGANISM: Homo sapiens

<400> SEQUENCE: 26

```
Met Glu Lys Leu Ser Ala Ala Ser Gly Tyr Ser Asp Val Thr Asp Ser
1               5                   10                  15

Lys Ala Met Gly Pro Leu Ala Val Gly Cys Leu Thr Lys Cys Ser His
            20                  25                  30

Ala Phe His Leu Leu Cys Leu Leu Ala Met Tyr Cys Asn Gly Asn Lys
        35                  40                  45

Gly Pro Glu His Pro Asn Pro Gly Lys Pro Phe Thr Ala Arg Gly Phe
    50                  55                  60
```

Pro Ala Ser Ala Thr Phe Gln Thr Thr Pro Gly Pro Gln Ala Ser Arg
65                  70                  75                  80

Gly Phe Gln Asn Pro Glu Thr Leu Ala Asp Ile Pro Ala Ser Pro Gln
                85                  90                  95

Leu Leu Thr Asp Gly His Tyr Met Thr Leu Pro Val Ser Pro Asp Gln
            100                 105                 110

Leu Pro Cys Asp Asp Pro Met Ala Gly Ser Gly Ala Pro Val Leu
            115                 120                 125

Arg Val Gly His Asp His Gly Cys His Gln Gln Pro Arg Ile Cys Asn
            130                 135                 140

Ala Pro Leu Pro Gly Pro Gly Pro Tyr Arg Thr Glu Pro Ala Lys Ala
145                 150                 155                 160

Ile Lys Pro Ile Asp Arg Lys Ser Val His Gln Ile Cys Ser Gly Pro
                165                 170                 175

Val Val Leu Ser Leu Ser Thr Ala Val Lys Glu Leu Val Glu Asn Ser
            180                 185                 190

Leu Asp Ala Gly Ala Thr Asn Ile Asp Leu Lys Leu Lys Asp Tyr Gly
            195                 200                 205

Met Asp Leu Ile Glu Val Ser Gly Asn Gly Cys Gly Val Glu Glu Glu
            210                 215                 220

Asn Phe Glu Gly Leu Met Met Ser Pro Phe Leu Pro Ala Thr Ser Arg
225                 230                 235                 240

Arg Arg Leu Gly Leu Asp Trp Cys Leu Ile Thr Met Gly Lys Ser Ser
                245                 250                 255

Arg Arg Pro Pro Thr Pro Thr Pro Glu Gly Pro Gln Ser Ala
                260                 265                 270

<210> SEQ ID NO 27
<211> LENGTH: 795
<212> TYPE: DNA
<213> ORGANISM: Homo sapiens

<400> SEQUENCE: 27

```
atgtgtcctt ggcggcctag actaggccgt cgctgtatgg tgagcccag  ggaggcggat      60
ctgggccccc agaaggacac ccgcctggat tgccccgta gcccggcccg ggcccctcgg     120
gagcagaaca gccttggtga ggtggacagg aggggacctc gcgagcagac gcgcgcgcca     180
gcgacagcag ccccgccccg gcctctcggg agccggggg cagaggctgc ggagccccag     240
gagggtctat cagccacagt ctctgcatgt ttccaagagc aacaggaaat gaacacattg     300
caggggccag tgtcattcaa agatgtggct gtggatttca cccaggagga gtggcggcaa     360
ctggaccctg atgagaagat agcatacggg gatgtgatgt ggagaactca gccatcta     420
gtttctgtgg gtatgatta tcaccaagcc aaacatcatc atggagtgga ggtgaaggaa     480
gtggagcagg gagaggagcc gtggataatg aaggtgaat tccatgtca acatagtcca     540
gaacctgcta aggccatcaa acctattgat cggaagtcag tccatcagat ttgctctggg     600
ccagtggtac tgagtctaag cactgcagtg aaggagttag tagaaaacag tctggatgct     660
ggtgccacta atattgatct aaagcttaag gactatggag tggatctcat tgaagtttca     720
gacaatggat gtgggataga agaagaaaac tttgaaggct taatctcttt cagctctgaa     780
acatcacaca tgtaa                                                      795
```

<210> SEQ ID NO 28
<211> LENGTH: 260

```
<212> TYPE: PRT
<213> ORGANISM: Homo sapiens

<400> SEQUENCE: 28

Met Cys Pro Trp Arg Pro Arg Leu Gly Arg Arg Cys Met Val Ser Pro
1               5                  10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Asn Phe Glu Gly Leu Ile Ser
                245                 250                 255

Phe Ser Ser Glu
            260

<210> SEQ ID NO 29
<211> LENGTH: 3218
<212> TYPE: DNA
<213> ORGANISM: Saccharomyces cerevisiae

<400> SEQUENCE: 29
aaataggaat gtgataacctt ctattgcatg caaagatagt gtaggaggcg ctgctattgc      60
caaagacttt tgagaccgct tgctgtttca ttatagttga ggagttctcg aagacgagaa     120
attagcagtt ttcggtgttt agtaatcgcg ctagcatgct aggacaattt aactgcaaaa     180
ttttgatacg atagtgatag taaatggaag gtaaaaataa catagaccta tcaataagca     240
atgtctctca gaataaaagc acttgatgca tcagtggtta acaaaattgc tgcaggtgag     300
atcataatat cccccgtaaa tgctctcaaa gaaatgatgg agaattccat cgatgcgaat     360
gctacaatga ttgatattct agtcaaggaa ggaggaatta aggtacttca ataacagat      420 aacggatctg gaattaataa agcagacctg ccaatcttat gtgagcgatt cacgacgtcc     480
```

-continued

```
aaattacaaa aattcgaaga tttgagtcag attcaaacgt atggattccg aggagaagct    540
ttagccagta tctcacatgt ggcaagagtc acagtaacga caaaagttaa agaagacaga    600
tgtgcatgga gagtttcata tgcagaaggt aagatgttgg aaagccccaa acctgttgct    660
ggaaaagacg gtaccacgat cctagttgaa gaccttttt tcaatattcc ttctagatta     720
agggccttga ggtcccataa tgatgaatac tctaaaatat tagatgttgt cgggcgatac    780
gccattcatt ccaaggacat tggcttttct tgtaaaaagt tcggagactc taattattct    840
ttatcagtta aaccttcata tacagtccag gataggatta ggactgtgtt caataaatct    900
gtggcttcga atttaattac ttttcatatc agcaaagtag aagatttaaa cctggaaagc    960
gttgatggaa aggtgtgtaa tttgaatttc atatccaaaa agtccatttc attaattttt   1020
ttcattaata atagactagt gacatgtgat cttctaagaa gagctttgaa cagcgtttac   1080
tccaattatc tgccaaaggg cttcagacct tttatttatt tgggaattgt tatagatccg   1140
gcggctgttg atgttaacgt tcacccgaca aagagagagg ttcgtttcct gagccaagat   1200
gagatcatag agaaaatcgc caatcaattg cacgccgaat tatctgccat tgatacttca   1260
cgtactttca aggcttcttc aatttcaaca aacaagccag agtcattgat accatttaat   1320
gacaccatag aaagtgatag gaataggaag agtctccgac aagcccaagt ggtagagaat   1380
tcatatacga cagccaatag tcaactaagg aaagcgaaaa gacaagagaa taaactagtc   1440
agaatagatg cttcacaagc taaaattacg tcatttttat cctcaagtca acagttcaac   1500
tttgaaggat cgtctacaaa gcgacaactg agtgaaccca agtaacaaa tgtaagccac    1560
tcccaagagg cagaaaagct gacactaaat gaaagcgaac aaccgcgtga tgccaataca   1620
atcaatgata atgacttgaa ggatcaacct aagaagaaac aaaagttggg ggattataaa   1680
gttccaagca ttgccgatga cgaaaagaat gcactcccga tttcaaaaga cgggtatatt   1740
agagtaccta aggagcgagt taatgttaat cttacgagta tcaagaaatt gcgtgaaaaa   1800
gtagatgatt cgatacatcg agaactaaca gacattttg caaatttgaa ttacgttggg   1860
gttgtagatg aggaaagaag attagccgct attcagcatg acttaaagct ttttttaata   1920
gattacggat ctgtgtgcta tgagctattc tatcagattg gtttgacaga cttcgcaaac   1980
tttggtaaga taaacctaca gagtacaaat gtgtcagatg atatagtttt gtataatctc   2040
ctatcagaat ttgacgagtt aaatgacgat gcttccaaag aaaaaataat tagtaaaata   2100
tgggacatga gcagtatgct aaatgagtac tattccatag aattggtgaa tgatggtcta   2160
gataatgact taaagtctgt gaagctaaaa tctctaccac tacttttaaa aggctacatt   2220
ccatctctgg tcaagttacc attttttata tatcgcctgg gtaaagaagt tgattgggag   2280
gatgaacaag agtgtctaga tggtatttta agagagattg cattactcta tatacctgat   2340
atggttccga aagtcgatac actcgatgca tcgttgtcag aagacgaaaa agcccagttt   2400
ataaatagaa aggaacacat atcctcatta ctagaacacg ttctcttccc ttgtatcaaa   2460
cgaaggttcc tggcccctag acacattctc aaggatgtcg tggaaatagc caaccttcca   2520
gatctataca agttttttga gaggtgttaa ctttaaaacg ttttggctgt aataccaaag   2580
tttttgttta tttcctgagt gtgattgtgt ttcatttgaa agtgtatgcc ctttcctta    2640
acgattcatc cgcgagattt caaaggatat gaaatatggt tgcagttagg aaagtatgtc   2700
agaaatgtat attcggattg aaactcttct aatagttctg aagtcacttg gttccgtatt   2760
gttttcgtcc tcttcctcaa gcaacgattc ttgtctaagc ttattcaacg gtaccaaaga   2820
```

```
cccgagtcct tttatgagag aaaacatttc atcattttc aactcaatta tcttaatatc   2880
attttgtagt attttgaaaa caggatggta aaacgaatca cctgaatcta gaagctgtac   2940
cttgtcccat aaaagtttta atttactgag cctttcggtc aagtaaacta gtttatctag   3000
ttttgaaccg aatattgtgg gcagatttgc agtaagttca gttagatcta ctaaaagttg   3060
tttgacagca gccgattcca caaaaatttg gtaaaaggag atgaaagaga cctcgcgcgt   3120
aatggtttgc atcaccatcg gatgtctgtt gaaaaactca cttttttgcat ggaagttatt   3180 aacaataaga ctaatgatta ccttagaata atgtataa                           3218
```

<210> SEQ ID NO 30
<211> LENGTH: 769
<212> TYPE: PRT
<213> ORGANISM: Saccharomyces cerevisiae

<400> SEQUENCE: 30

```
Met Ser Leu Arg Ile Lys Ala Leu Asp Ala Ser Val Val Asn Lys Ile
1               5                   10                  15

Ala Ala Gly Glu Ile Ile Ile Ser Pro Val Asn Ala Leu Lys Glu Met
            20                  25                  30

Met Glu Asn Ser Ile Asp Ala Asn Ala Thr Met Ile Asp Ile Leu Val
        35                  40                  45

Lys Glu Gly Gly Ile Lys Val Leu Gln Ile Thr Asp Asn Gly Ser Gly
    50                  55                  60

Ile Asn Lys Ala Asp Leu Pro Ile Leu Cys Glu Arg Phe Thr Thr Ser
65                  70                  75                  80

Lys Leu Gln Lys Phe Glu Asp Leu Ser Gln Ile Gln Thr Tyr Gly Phe
                85                  90                  95

Arg Gly Glu Ala Leu Ala Ser Ile Ser His Val Ala Arg Val Thr Val
            100                 105                 110

Thr Thr Lys Val Lys Glu Asp Arg Cys Ala Trp Arg Val Ser Tyr Ala
        115                 120                 125

Glu Gly Lys Met Leu Glu Ser Pro Lys Pro Val Ala Gly Lys Asp Gly
    130                 135                 140

Thr Thr Ile Leu Val Glu Asp Leu Phe Phe Asn Ile Pro Ser Arg Leu
145                 150                 155                 160

Arg Ala Leu Arg Ser His Asn Asp Glu Tyr Ser Lys Ile Leu Asp Val
                165                 170                 175

Val Gly Arg Tyr Ala Ile His Ser Lys Asp Ile Gly Phe Ser Cys Lys
            180                 185                 190

Lys Phe Gly Asp Ser Asn Tyr Ser Leu Ser Val Lys Pro Ser Tyr Thr
        195                 200                 205

Val Gln Asp Arg Ile Arg Thr Val Phe Asn Lys Ser Val Ala Ser Asn
    210                 215                 220

Leu Ile Thr Phe His Ile Ser Lys Val Glu Asp Leu Asn Leu Glu Ser
225                 230                 235                 240

Val Asp Gly Lys Val Cys Asn Leu Asn Phe Ile Ser Lys Lys Ser Ile
                245                 250                 255

Ser Leu Ile Phe Phe Ile Asn Asn Arg Leu Val Thr Cys Asp Leu Leu
            260                 265                 270

Arg Arg Ala Leu Asn Ser Val Tyr Ser Asn Tyr Leu Pro Lys Gly Phe
        275                 280                 285

Arg Pro Phe Ile Tyr Leu Gly Ile Val Ile Asp Pro Ala Ala Val Asp
    290                 295                 300
```

```
Val Asn Val His Pro Thr Lys Arg Glu Val Arg Phe Leu Ser Gln Asp
305                 310                 315                 320

Glu Ile Ile Glu Lys Ile Ala Asn Gln Leu His Ala Glu Leu Ser Ala
                325                 330                 335

Ile Asp Thr Ser Arg Thr Phe Lys Ala Ser Ser Ile Ser Thr Asn Lys
            340                 345                 350

Pro Glu Ser Leu Ile Pro Phe Asn Asp Thr Ile Glu Ser Asp Arg Asn
        355                 360                 365

Arg Lys Ser Leu Arg Gln Ala Gln Val Val Glu Asn Ser Tyr Thr Thr
    370                 375                 380

Ala Asn Ser Gln Leu Arg Lys Ala Lys Arg Gln Glu Asn Lys Leu Val
385                 390                 395                 400

Arg Ile Asp Ala Ser Gln Ala Lys Ile Thr Ser Phe Leu Ser Ser Ser
                405                 410                 415

Gln Gln Phe Asn Phe Glu Gly Ser Ser Thr Lys Arg Gln Leu Ser Glu
            420                 425                 430

Pro Lys Val Thr Asn Val Ser His Ser Gln Glu Ala Glu Lys Leu Thr
        435                 440                 445

Leu Asn Glu Ser Glu Gln Pro Arg Asp Ala Asn Thr Ile Asn Asp Asn
    450                 455                 460

Asp Leu Lys Asp Gln Pro Lys Lys Gln Lys Leu Gly Asp Tyr Lys
465                 470                 475                 480

Val Pro Ser Ile Ala Asp Asp Glu Lys Asn Ala Leu Pro Ile Ser Lys
                485                 490                 495

Asp Gly Tyr Ile Arg Val Pro Lys Glu Arg Val Asn Val Asn Leu Thr
            500                 505                 510

Ser Ile Lys Lys Leu Arg Glu Lys Val Asp Asp Ser Ile His Arg Glu
        515                 520                 525

Leu Thr Asp Ile Phe Ala Asn Leu Asn Tyr Val Gly Val Val Asp Glu
    530                 535                 540

Glu Arg Arg Leu Ala Ala Ile Gln His Asp Leu Lys Leu Phe Leu Ile
545                 550                 555                 560

Asp Tyr Gly Ser Val Cys Tyr Glu Leu Phe Tyr Gln Ile Gly Leu Thr
                565                 570                 575

Asp Phe Ala Asn Phe Gly Lys Ile Asn Leu Gln Ser Thr Asn Val Ser
            580                 585                 590

Asp Asp Ile Val Leu Tyr Asn Leu Leu Ser Glu Phe Asp Glu Leu Asn
        595                 600                 605

Asp Asp Ala Ser Lys Glu Lys Ile Ile Ser Lys Ile Trp Asp Met Ser
    610                 615                 620

Ser Met Leu Asn Glu Tyr Tyr Ser Ile Glu Leu Val Asn Asp Gly Leu
625                 630                 635                 640

Asp Asn Asp Leu Lys Ser Val Lys Leu Lys Ser Leu Pro Leu Leu Leu
                645                 650                 655

Lys Gly Tyr Ile Pro Ser Leu Val Lys Leu Pro Phe Phe Ile Tyr Arg
            660                 665                 670

Leu Gly Lys Glu Val Asp Trp Glu Asp Glu Gln Glu Cys Leu Asp Gly
        675                 680                 685

Ile Leu Arg Glu Ile Ala Leu Leu Tyr Ile Pro Asp Met Val Pro Lys
    690                 695                 700

Val Asp Thr Leu Asp Ala Ser Leu Ser Glu Asp Glu Lys Ala Gln Phe
705                 710                 715                 720

Ile Asn Arg Lys Glu His Ile Ser Ser Leu Leu Glu His Val Leu Phe
```

```
            725                 730                 735
Pro Cys Ile Lys Arg Arg Phe Leu Ala Pro Arg His Ile Leu Lys Asp
        740                 745                 750

Val Val Glu Ile Ala Asn Leu Pro Asp Leu Tyr Lys Val Phe Glu Arg
        755                 760                 765

Cys

<210> SEQ ID NO 31
<211> LENGTH: 3056
<212> TYPE: DNA
<213> ORGANISM: Mus musculus

<400> SEQUENCE: 31
```

| | | | | | |
|---|---|---|---|---|---|
| gaattccggt | gaaggtcctg | aagaatttcc | agattcctga | gtatcattgg | aggagacaga | 60 |
| taacctgtcg | tcaggtaacg | atggtgtata | tgcaacagaa | atgggtgttc | ctggagacgc | 120 |
| gtcttttccc | gagagcggca | ccgcaactct | cccgcggtga | ctgtgactgg | aggagtcctg | 180 |
| catccatgga | gcaaaccgaa | ggcgtgagta | cagaatgtgc | taaggccatc | aagcctattg | 240 |
| atgggaagtc | agtccatcaa | atttgttctg | ggcaggtgat | actcagttta | agcaccgctg | 300 |
| tgaaggagtt | gatagaaaat | agtgtagatg | ctggtgctac | tactattgat | ctaaggctta | 360 |
| aagactatgg | ggtggacctc | attgaagttt | cagacaatgg | atgtggggta | gaagaagaaa | 420 |
| actttgaagg | tctagctctg | aaacatcaca | catctaagat | tcaagagttt | gccgacctca | 480 |
| cgcaggttga | aactttcggc | tttcgggggg | aagctctgag | ctctctgtgt | gcactaagtg | 540 |
| atgtcactat | atctacctgc | cacgggtctg | caagcgttgg | gactcgactg | gtgtttgacc | 600 |
| ataatgggaa | aatcacccag | aaaactccct | accccgacc | taaaggaacc | acagtcagtg | 660 |
| tgcagcactt | attttataca | ctacccgtgc | gttacaaaga | gtttcagagg | aacattaaaa | 720 |
| aggagtattc | caaaatggtg | caggtcttac | aggcgtactg | tatcatctca | gcaggcgtcc | 780 |
| gtgtaagctg | cactaatcag | ctcggacagg | ggaagcggca | cgctgtggtg | tgcacaagcg | 840 |
| gcacgtctgg | catgaaggaa | aatatcgggt | ctgtgtttgg | ccagaagcag | ttgcaaagcc | 900 |
| tcattccttt | tgttcagctg | cccccctagtg | acgctgtgtg | tgaagagtac | ggcctgagca | 960 |
| cttcaggacg | ccacaaaacc | ttttctacgt | ttcgggcttc | atttcacagt | gcacgcacgg | 1020 |
| cgccgggagg | agtgcaacag | acaggcagtt | tttcttcatc | aatcagaggc | cctgtgaccc | 1080 |
| agcaaaggtc | tctaagcttg | tcaatgaggt | tttatcacat | gtataaccgg | catcagtacc | 1140 |
| catttgtcgt | ccttaacgtt | tccgttgact | cagaatgtgt | ggatattaat | gtaactccag | 1200 |
| ataaaaggca | aattctacta | caagaagaga | agctattgct | ggccgtttta | aagacctcct | 1260 |
| tgataggaat | gtttgacagt | gatgcaaaca | agcttaatgt | caaccagcag | ccactgctag | 1320 |
| atgttgaagg | taacttagta | aagctgcata | ctgcagaact | agaaaagcct | gtgccaggaa | 1380 |
| agcaagataa | ctctccttca | ctgaagagca | cagcagacga | gaaaagggta | gcatccatct | 1440 |
| ccaggctgag | agaggccttt | tctcttcatc | ctactaaaga | gatcaagtct | aggggtccag | 1500 |
| agactgctga | actgacacgg | agttttccaa | gtgagaaaag | gggcgtgtta | tcctcttatc | 1560 |
| cttcagacgt | catctcttac | agaggcctcc | gtggctcgca | ggacaaattg | gtgagtccca | 1620 |
| cggacagccc | tggtgactgt | atggacagag | agaaaataga | aaaagactca | gggctcagca | 1680 |
| gcacctcagc | tggctctgag | gaagagttca | gcaccccaga | agtggccagt | agctttagca | 1740 |
| gtgactataa | cgtgagctcc | ctagaagaca | gaccttctca | ggaaaccata | aactgtggtg | 1800 |
| acctggactg | ccgtcctcca | ggtacaggac | agtccttgaa | gccagaagac | catggatatc | 1860 |

-continued

```
aatgcaaagc tctacctcta gctcgtctgt cacccacaaa tgccaagcgc ttcaagacag    1920
aggaaagacc ctcaaatgtc aacatttctc aaagattgcc tggtcctcag agcacctcag    1980
cagctgaggt cgatgtagcc ataaaaatga ataagagaat cgtgctcctc gagttctctc    2040
tgagttctct agctaagcga atgaagcagt tacagcacct aaaggcgcag aacaaacatg    2100
aactgagtta cagaaaattt agggccaaga tttgccctgg agaaaaccaa gcagcagaag    2160
atgaactcag aaagagatt agtaaatcga tgtttgcaga gatggagatc ttgggtcagt     2220
ttaacctggg attatatagta accaaactga agaggacct cttcctggtg gaccagcatg    2280
ctgcggatga gaagtacaac tttgagatgc tgcagcagca cacggtgctc caggcgcaga    2340
ggctcatcac accccagact ctgaacttaa ctgctgtcaa tgaagctgta ctgatagaaa    2400
atctggaaat attcagaaag aatggctttg actttgtcat tgatgaggat gctccagtca    2460
ctgaaagggc taaattgatt tccttaccaa ctagtaaaaa ctggacctt ggaccccaag     2520 atatagatga actgatcttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagatggac caccccctgga   2700 actgccccca cggcaggcca accatgaggc acgttgccaa tctggatgtc atctctcaga    2760
actgacacac cccttgtagc atagagttta ttacagattg ttcggtttgc aaagagaagg    2820
ttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc cacattcatg    3000
agactcaatt caaggacaaa aaaaaaaaga tattttttgaa gcctttaaa aaaaaa       3056
```

<210> SEQ ID NO 32
<211> LENGTH: 859
<212> TYPE: PRT
<213> ORGANISM: Mus musculus

<400> SEQUENCE: 32

```
Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160
```

-continued

```
His Leu Phe Tyr Thr Leu Pro Val Arg Tyr Lys Glu Phe Gln Arg Asn
            165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
            195                 200                 205

Gly Lys Arg His Ala Val Val Cys Thr Ser Gly Thr Ser Gly Met Lys
        210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
                260                 265                 270

Phe His Ser Ala Arg Thr Ala Pro Gly Gly Val Gln Gln Thr Gly Ser
        275                 280                 285

Phe Ser Ser Ser Ile Arg Gly Pro Val Thr Gln Gln Arg Ser Leu Ser
        290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Glu Lys Leu Leu Leu
                340                 345                 350

Ala Val Leu Lys Thr Ser Leu Ile Gly Met Phe Asp Ser Asp Ala Asn
            355                 360                 365

Lys Leu Asn Val Asn Gln Gln Pro Leu Leu Asp Val Glu Gly Asn Leu
        370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
        435                 440                 445

Ser Glu Lys Arg Gly Val Leu Ser Ser Tyr Pro Ser Asp Val Ile Ser
    450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
                500                 505                 510

Val Ala Ser Ser Phe Ser Ser Asp Tyr Asn Val Ser Ser Leu Glu Asp
            515                 520                 525

Arg Pro Ser Gln Glu Thr Ile Asn Cys Gly Asp Leu Asp Cys Arg Pro
        530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
```

-continued

```
              580             585             590
Gly Pro Gln Ser Thr Ser Ala Ala Glu Val Asp Val Ala Ile Lys Met
        595                 600                 605

Asn Lys Arg Ile Val Leu Leu Glu Phe Ser Leu Ser Ser Leu Ala Lys
    610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Gly Ile Ser Lys Ser Met Phe Ala Glu
            660                 665                 670

Met Glu Ile Leu Gly Gln Phe Asn Leu Gly Phe Ile Val Thr Lys Leu
        675                 680                 685

Lys Glu Asp Leu Phe Leu Val Asp Gln His Ala Ala Asp Glu Lys Tyr
    690                 695                 700

Asn Phe Glu Met Leu Gln His Thr Val Leu Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750

Asp Glu Asp Ala Pro Val Thr Glu Arg Ala Lys Leu Ile Ser Leu Pro
        755                 760                 765

Thr Ser Lys Asn Trp Thr Phe Gly Pro Gln Asp Ile Asp Glu Leu Ile
    770                 775                 780

Phe Met Leu Ser Asp Ser Pro Gly Val Met Cys Arg Pro Ser Arg Val
785                 790                 795                 800

Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
            820                 825                 830

Glu Met Asp His Pro Trp Asn Cys Pro His Gly Arg Pro Thr Met Arg
        835                 840                 845

His Val Ala Asn Leu Asp Val Ile Ser Gln Asn
    850                 855
```

<210> SEQ ID NO 33
<211> LENGTH: 399
<212> TYPE: DNA
<213> ORGANISM: Mus musculus

<400> SEQUENCE: 33

| | | | | | |
|---|---|---|---|---|---|
| atggagcaaa | ccgaaggcgt | gagtacagaa | tgtgctaagg | ccatcaagcc | tattgatggg | 60 |
| aagtcagtcc | atcaaatttg | ttctgggcag | gtgatactca | gtttaagcac | cgctgtgaag | 120 |
| gagttgatag | aaaatagtgt | agatgctggt | gctactacta | ttgatctaag | gcttaaagac | 180 |
| tatggggtgg | acctcattga | agtttcagac | aatggatgtg | gggtagaaga | agaaaacttt | 240 |
| gaaggtctag | ctctgaaaca | tcacacatct | aagattcaag | agtttgccga | cctcacgcag | 300 |
| gttgaaactt | tcggctttcg | gggggaagct | ctgagctctc | tgtgtgcact | aagtgatgtc | 360 |
| actatatcta | cctgccacgg | gtctgcaagc | gttgggact | | | 399 |

<210> SEQ ID NO 34
<211> LENGTH: 133
<212> TYPE: PRT

<213> ORGANISM: Mus musculus

<400> SEQUENCE: 34

```
Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr
    130
```

<210> SEQ ID NO 35
<211> LENGTH: 3099
<212> TYPE: DNA
<213> ORGANISM: Arabidopsis thaliana

<400> SEQUENCE: 35

| | |
|---|---|
| gtcttcttct tcatccttgt ctcaccttcg attttggcgg caaaacataa accctaaggg | 60 |
| ttttctcact ctctctctct cttctcacac acacagtccc agagtacggt ggtgttgatt | 120 |
| cgattgagga gattcatctg tttatagggt ttagcaaatg caaggagatt cttctccgtc | 180 |
| tccgacgact actagctctc ctttgataag acctataaac agaaacgtaa ttcacagaat | 240 |
| ctgttccggt caagtcatct tagacctctc ttcggccgtc aaggagcttg tcgagaatag | 300 |
| tctcgacgcc ggcgccacca gtatagagat taacctccga gactacggcg aagactattt | 360 |
| tcaggtcatt gacaatggtt gtggcatttc cccaaccaat ttcaaggttc ttgcacttaa | 420 |
| gcatcatact tctaaattag aggatttcac agatcttttg aatttgacta cttatggttt | 480 |
| tagaggagaa gccttgagct ctctctgtgc attgggaaat ctcactgtgg aaacaagaac | 540 |
| aaagaatgag ccagttgcta cgctcttgac gtttgatcat tctggtttgc ttactgctga | 600 |
| aaagaagact gctcgccaaa ttggtaccac tgtcactgtt aggaagttgt tctctaattt | 660 |
| acctgtacga agcaaagagt ttaagcggaa atacgcaaa gaatatggga agcttgtatc | 720 |
| tttattgaac gcatatgcgc ttattgcgaa aggagtgcgg tttgtctgct ctaacacgac | 780 |
| tgggaaaaac ccaaagtctg ttgtgctgaa cacacaaggg aggggttcac ttaaagataa | 840 |
| tatcataaca gttttcggca ttagtacctt tacaagtcta cagcctgtaa gtatatgtgt | 900 |
| atcagaagat tgtagagttg aagggtttct ttccaagcct ggacagggta ctggacgcaa | 960 |
| tttagcagat cgacagtatt tctttataaa tggtcggcct gtagatatgc caaaagtcag | 1020 |
| caagttggtg aatgagttat ataaagatac aagttctcgg aaatatccag ttaccattct | 1080 |
| ggattttatt gtgcctggtg gagcatgtga tttgaatgtc acgcccgata aaagaaaggt | 1140 |
| gttcttttct gacgagactt ctgttatcgg ttctttgagg gaaggtctga acgagatata | 1200 |

```
ttcctccagt aatgcgtctt atattgttaa taggttcgag gagaattcgg agcaaccaga   1260
taaggctgga gtttcgtcgt ttcagaagaa atcaaatctt ttgtcagaag ggatagttct   1320
ggatgtcagt tctaaaacaa gactagggga agctattgag aaagaaaatc catccttaag   1380
ggaggttgaa attgataata gttcgccaat ggagaagttt aagtttgaga tcaaggcatg   1440
tgggacgaag aaaggggaag gttctttatc agtccatgat gtaactcacc ttgacaagac   1500
acctagcaaa ggtttgcctc agttaaatgt gactgagaaa gttactgatg caagtaaaga   1560
cttgagcagc cgctctagct ttgcccagtc aactttgaat acttttgtta ccatgggaaa   1620
aagaaaacat gaaacataa gcaccatcct ctctgaaaca cctgtcctca gaaaccaaac   1680
ttctagttat cgtgtggaga aaagcaaatt tgaagttcgt gccttagctt caaggtgtct   1740
cgtggaaggc gatcaacttg atgatatggt catctcaaag gaagatatga caccaagcga   1800
aagagattct gaactaggca atcggatttc tcctggaaca caagctgata atgttgaaag   1860
acatgagaga gaacatgaaa agcctataag gtttgaagaa ccaacatcag ataacacact   1920
caccaagggg gatgtggaaa gggtttcaga ggacaatcca cggtgcagtc agccactgcg   1980
atctgtggcc acagtgctgg attccccagc tcagtcaacc ggtcctaaaa tgttttccac   2040
attagaattt agtttccaaa acctcaggac aaggaggtta gagaggctgt cgagattgca   2100
gtccacaggt tatgtatcta atgtatgaa acgccacag cctaaaaagt gctttgccgc   2160
tgcaacatta gagttatctc aaccggatga tgaagagcga aaagcaaggg ctttagctgc   2220
agctacttct gagctggaaa ggcttttttcg aaaagaggat ttcaggagaa tgcaggtact   2280
cgggcaattc aatcttgggt tcatcattgc aaaattggag cgagatctgt tcattgtgga   2340
tcagcatgca gctgatgaga aattcaactt cgaacattta gcaaggtcaa ctgtcctgaa   2400
ccagcaaccc ttactccagc ctttgaactt ggaactctct ccagaagaag aagtaactgt   2460
gttaatgcac atggatatta tcagggaaaa tggctttctt ctagaggaga atccaagtgc   2520
tcctcccgga aaacacttta gactacgagc cattccttat agcaagaata tcacctttgg   2580
agtcgaagat cttaaagacc tgatctcaac tctaggagat aaccatgggg aatgttcggt   2640
tgctagtagc tacaaaacca gcaaaacaga ttcgatttgt ccatcacgag tccgtgcaat   2700
gctagcatcc cgagcatgca gatcatctgt gatgatcgga gatccactca gaaaaaacga   2760
aatgcagaag atagtagaac acttggcaga tctcgaatct ccttggaatt gcccacacgg   2820
acgaccaaca atgcgtcatc ttgtggactt gacaacttta ctcacattac ctgatgacga   2880
caatgtcaat gatgatgatg atgatgatgc aaccatctca ttggcatgaa cactcaaaag   2940
tcttaacgta tttagatgtg agaatcctta agattaacat tgaggaacac tcggttataa   3000
ctacaatcgt aaatgtaaat tgtcttagtc tatatgatct ttttggtcac aacaggtaat   3060
ttcattttcc tttgattact ctcgtgaaaa aacaaatt                          3099
```

<210> SEQ ID NO 36
<211> LENGTH: 923
<212> TYPE: PRT
<213> ORGANISM: Arabidopsis thaliana

<400> SEQUENCE: 36

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
            20                  25                  30

Val Ile Leu Asp Leu Ser Ser Ala Val Lys Glu Leu Val Glu Asn Ser

-continued

```
                35                  40                  45
Leu Asp Ala Gly Ala Thr Ser Ile Glu Ile Asn Leu Arg Asp Tyr Gly
 50                  55                  60

Glu Asp Tyr Phe Gln Val Ile Asp Asn Gly Cys Gly Ile Ser Pro Thr
 65                  70                  75                  80

Asn Phe Lys Val Leu Ala Leu Lys His His Thr Ser Lys Leu Glu Asp
                 85                  90                  95

Phe Thr Asp Leu Leu Asn Leu Thr Thr Tyr Gly Phe Arg Gly Glu Ala
            100                 105                 110

Leu Ser Ser Leu Cys Ala Leu Gly Asn Leu Thr Val Glu Thr Arg Thr
            115                 120                 125

Lys Asn Glu Pro Val Ala Thr Leu Leu Thr Phe Asp His Ser Gly Leu
130                 135                 140

Leu Thr Ala Glu Lys Lys Thr Ala Arg Gln Ile Gly Thr Thr Val Thr
145                 150                 155                 160

Val Arg Lys Leu Phe Ser Asn Leu Pro Val Arg Ser Lys Glu Phe Lys
                165                 170                 175

Arg Asn Ile Arg Lys Glu Tyr Gly Lys Leu Val Ser Leu Leu Asn Ala
            180                 185                 190

Tyr Ala Leu Ile Ala Lys Gly Val Arg Phe Val Cys Ser Asn Thr Thr
            195                 200                 205

Gly Lys Asn Pro Lys Ser Val Val Leu Asn Thr Gln Gly Arg Gly Ser
210                 215                 220

Leu Lys Asp Asn Ile Ile Thr Val Phe Gly Ile Ser Thr Phe Thr Ser
225                 230                 235                 240

Leu Gln Pro Val Ser Ile Cys Val Ser Glu Asp Cys Arg Val Glu Gly
                245                 250                 255

Phe Leu Ser Lys Pro Gly Gln Gly Thr Gly Arg Asn Leu Ala Asp Arg
            260                 265                 270

Gln Tyr Phe Phe Ile Asn Gly Arg Pro Val Asp Met Pro Lys Val Ser
            275                 280                 285

Lys Leu Val Asn Glu Leu Tyr Lys Asp Thr Ser Ser Arg Lys Tyr Pro
290                 295                 300

Val Thr Ile Leu Asp Phe Ile Val Pro Gly Gly Ala Cys Asp Leu Asn
305                 310                 315                 320

Val Thr Pro Asp Lys Arg Lys Val Phe Phe Ser Asp Glu Thr Ser Val
                325                 330                 335

Ile Gly Ser Leu Arg Glu Gly Leu Asn Glu Ile Tyr Ser Ser Ser Asn
            340                 345                 350

Ala Ser Tyr Ile Val Asn Arg Phe Glu Glu Asn Ser Glu Gln Pro Asp
            355                 360                 365

Lys Ala Gly Val Ser Ser Phe Gln Lys Lys Ser Asn Leu Leu Ser Glu
370                 375                 380

Gly Ile Val Leu Asp Val Ser Ser Lys Thr Arg Leu Gly Glu Ala Ile
385                 390                 395                 400

Glu Lys Glu Asn Pro Ser Leu Arg Glu Val Glu Ile Asp Asn Ser Ser
                405                 410                 415

Pro Met Glu Lys Phe Lys Phe Glu Ile Lys Ala Cys Gly Thr Lys Lys
            420                 425                 430

Gly Glu Gly Ser Leu Ser Val His Asp Val Thr His Leu Asp Lys Thr
            435                 440                 445

Pro Ser Lys Gly Leu Pro Gln Leu Asn Val Thr Glu Lys Val Thr Asp
450                 455                 460
```

```
Ala Ser Lys Asp Leu Ser Ser Arg Ser Ser Phe Ala Gln Ser Thr Leu
465                 470                 475                 480

Asn Thr Phe Val Thr Met Gly Lys Arg Lys His Glu Asn Ile Ser Thr
                485                 490                 495

Ile Leu Ser Glu Thr Pro Val Leu Arg Asn Gln Thr Ser Ser Tyr Arg
                500                 505                 510

Val Glu Lys Ser Lys Phe Glu Val Arg Ala Leu Ala Ser Arg Cys Leu
                515                 520                 525

Val Glu Gly Asp Gln Leu Asp Asp Met Val Ile Ser Lys Glu Asp Met
                530                 535                 540

Thr Pro Ser Glu Arg Asp Ser Glu Leu Gly Asn Arg Ile Ser Pro Gly
545                 550                 555                 560

Thr Gln Ala Asp Asn Val Glu Arg His Arg Glu His Glu Lys Pro
                565                 570                 575

Ile Arg Phe Glu Glu Pro Thr Ser Asp Asn Thr Leu Thr Lys Gly Asp
                580                 585                 590

Val Glu Arg Val Ser Glu Asp Asn Pro Arg Cys Ser Gln Pro Leu Arg
                595                 600                 605

Ser Val Ala Thr Val Leu Asp Ser Pro Ala Gln Ser Thr Gly Pro Lys
                610                 615                 620

Met Phe Ser Thr Leu Glu Phe Ser Phe Gln Asn Leu Arg Thr Arg Arg
625                 630                 635                 640

Leu Glu Arg Leu Ser Arg Leu Gln Ser Thr Gly Tyr Val Ser Lys Cys
                645                 650                 655

Met Asn Thr Pro Gln Pro Lys Lys Cys Phe Ala Ala Ala Thr Leu Glu
                660                 665                 670

Leu Ser Gln Pro Asp Asp Glu Glu Arg Lys Ala Arg Ala Leu Ala Ala
                675                 680                 685

Ala Thr Ser Glu Leu Glu Arg Leu Phe Arg Lys Glu Asp Phe Arg Arg
                690                 695                 700

Met Gln Val Leu Gly Gln Phe Asn Leu Gly Phe Ile Ile Ala Lys Leu
705                 710                 715                 720

Glu Arg Asp Leu Phe Ile Val Asp Gln His Ala Ala Asp Glu Lys Phe
                725                 730                 735

Asn Phe Glu His Leu Ala Arg Ser Thr Val Leu Asn Gln Gln Pro Leu
                740                 745                 750

Leu Gln Pro Leu Asn Leu Glu Leu Ser Pro Glu Glu Val Thr Val
                755                 760                 765

Leu Met His Met Asp Ile Ile Arg Glu Asn Gly Phe Leu Leu Glu Glu
770                 775                 780

Asn Pro Ser Ala Pro Pro Gly Lys His Phe Arg Leu Arg Ala Ile Pro
785                 790                 795                 800

Tyr Ser Lys Asn Ile Thr Phe Gly Val Glu Asp Leu Lys Asp Leu Ile
                805                 810                 815

Ser Thr Leu Gly Asp Asn His Gly Glu Cys Ser Val Ala Ser Ser Tyr
                820                 825                 830

Lys Thr Ser Lys Thr Asp Ser Ile Cys Pro Ser Arg Val Arg Ala Met
                835                 840                 845

Leu Ala Ser Arg Ala Cys Arg Ser Ser Val Met Ile Gly Asp Pro Leu
                850                 855                 860

Arg Lys Asn Glu Met Gln Lys Ile Val Glu His Leu Ala Asp Leu Glu
865                 870                 875                 880
```

```
Ser Pro Trp Asn Cys Pro His Gly Arg Pro Thr Met Arg His Leu Val
            885                 890                 895

Asp Leu Thr Thr Leu Leu Thr Leu Pro Asp Asp Asn Val Asn Asp
            900                 905                 910

Asp Asp Asp Asp Ala Thr Ile Ser Leu Ala
        915                 920

<210> SEQ ID NO 37
<211> LENGTH: 399
<212> TYPE: DNA
<213> ORGANISM: Arabidopsis thaliana

<400> SEQUENCE: 37
atgcaaggag attcttctcc gtctccgacg actactagct ctcctttgat aagacctata      60
aacagaaacg taattcacag aatctgttcc ggtcaagtca tcttagacct ctcttcggcc     120
gtcaaggagc ttgtcgagaa tagtctcgac gccggcgcca ccagtataga gattaacctc     180
cgagactacg gcgaagacta ttttcaggtc attgacaatg gttgtggcat tccccaacc      240 aatttcaagg ttcttgcact taagcatcat acttctaaat tagaggattt cacagatctt     300
ttgaatttga ctacttatgg ttttagagga gaagccttga gctctctctg tgcattggga     360
aatctcactg tggaaacaag aacaaagaat gagccagtt                            399

<210> SEQ ID NO 38
<211> LENGTH: 133
<212> TYPE: PRT
<213> ORGANISM: Arabidopsis thaliana

<400> SEQUENCE: 38

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
            20                  25                  30

Val Ile Leu Asp Leu Ser Ser Ala Val Lys Glu Leu Val Glu Asn Ser
        35                  40                  45

Leu Asp Ala Gly Ala Thr Ser Ile Glu Ile Asn Leu Arg Asp Tyr Gly
    50                  55                  60

Glu Asp Tyr Phe Gln Val Ile Asp Asn Gly Cys Gly Ile Ser Pro Thr
65                  70                  75                  80

Asn Phe Lys Val Leu Ala Leu Lys His His Thr Ser Lys Leu Glu Asp
                85                  90                  95

Phe Thr Asp Leu Leu Asn Leu Thr Thr Tyr Gly Phe Arg Gly Glu Ala
            100                 105                 110

Leu Ser Leu Cys Ala Leu Gly Asn Leu Thr Val Glu Thr Arg Thr
        115                 120                 125

Lys Asn Glu Pro Val
    130

<210> SEQ ID NO 39
<211> LENGTH: 2772
<212> TYPE: DNA
<213> ORGANISM: Arabidopsis thaliana

<400> SEQUENCE: 39
atgcaaggag attcttctcc gtctccgacg actactagct ctcctttgat aagacctata      60
aacagaaacg taattcacag aatctgttcc ggtcaagtca tcttagacct ctcttcggcc     120
gtcaaggagc ttgtcgagaa tagtctcgac gccggcgcca ccagtataga gattaacctc     180
```

-continued

| | | |
|---|---|---|
| cgagactacg gcgaagacta ttttcaggtc attgacaatg gttgtggcat ttccccaacc | 240 | |
| aatttcaagg ttcttgcact taagcatcat acttctaaat tagaggattt cacagatctt | 300 | |
| ttgaatttga ctacttatgg ttttagagga gaagccttga gctctctctg tgcattggga | 360 | |
| aatctcactg tggaaacaag aacaaagaat gagccagttg ctacgctctt gacgtttgat | 420 | |
| cattctggtt tgcttactgc tgaaaagaag actgctcgcc aaattggtac cactgtcact | 480 | |
| gttaggaagt tgttctctaa tttacctgta cgaagcaaag agtttaagcg aatatacgc | 540 | |
| aaagaatatg ggaagcttgt atctttattg aacgcatatg cgcttattgc gaaaggagtg | 600 | |
| cggtttgtct gctctaacac gactgggaaa acccaaagt ctgttgtgct gaacacacaa | 660 | |
| gggagggggtt cacttaaaga taatatcata acagttttcg gcattagtac ctttacaagt | 720 | |
| ctacagcctg taagtatatg tgtatcagaa gattgtagag ttgaagggtt tctttccaag | 780 | |
| cctggacagg gtactggacg caatttagca gatcgacagt atttctttat aaatggtcgg | 840 | |
| cctgtagata tgccaaaagt cagcaagttg gtgaatgagt tatataaaga tacaagttct | 900 | |
| cggaaatatc cagttaccat tctggatttt attgtgcctg gtggagcatg tgatttgaat | 960 | |
| gtcacgcccg ataaaagaaa ggtgttcttt tctgacgaga cttctgttat cggttctttg | 1020 | |
| agggaaggtc tgaacgagat atattcctcc agtaatgcgt cttatattgt taataggttc | 1080 | |
| gaggagaatt cggagcaacc agataaggct ggagtttcgt cgtttcagaa gaaatcaaat | 1140 | |
| cttttgtcag aagggatagt tctgatgtc agttctaaaa caagactagg ggaagctatt | 1200 | |
| gagaaagaaa atccatcctt aagggaggtt gaaattgata atagttcgcc aatggagaag | 1260 | |
| tttaagtttg agatcaaggc atgtgggacg aagaaagggg aaggttcttt atcagtccat | 1320 | |
| gatgtaactc accttgacaa gacacctagc aaaggtttgc ctcagttaaa tgtgactgag | 1380 | |
| aaagttactg atgcaagtaa agacttgagc agccgctcta gctttgccca gtcaactttg | 1440 | |
| aatactttgg ttaccatggg aaaaagaaaa catgaaaaca taagcaccat cctctctgaa | 1500 | |
| acacctgtcc tcagaaacca aacttctagt tatcgtgtgg agaaaagcaa atttgaagtt | 1560 | |
| cgtgccttag cttcaaggtg tctcgtggaa ggcgatcaac ttgatgatat ggtcatctca | 1620 | |
| aaggaagata tgacaccaag cgaaagagat tctgaactag gcaatcggat ttctcctgga | 1680 | |
| acacaagctg ataatgttga aagacatgag agagaacatg aaaagcctat aaggtttgaa | 1740 | |
| gaaccaacat cagataacac actcaccaag ggggatgtgg aaagggtttc agaggacaat | 1800 | |
| ccacggtgca gtcagccact gcgatctgtg gccacagtgc tggattcccc agctcagtca | 1860 | |
| accggtccta aaatgttttc cacattagaa tttagtttcc aaaacctcag gacaaggagg | 1920 | |
| ttagagaggc tgtcgagatt gcagtccaca ggttatgtat ctaaatgtat gaatacgcca | 1980 | |
| cagcctaaaa agtgctttgc cgctgcaaca ttagagttat ctcaaccgga tgatgaagag | 2040 | |
| cgaaaagcaa gggctttagc tgcagctact tctgagctgg aaaggctttt tcgaaaagag | 2100 | |
| gatttcagga gaatgcaggt actcgggcaa ttcaatcttg ggttcatcat tgcaaaattg | 2160 | |
| gagcgagatc tgttcattgt ggatcagcat gcagctgatg agaaattcaa cttcgaacat | 2220 | |
| ttagcaaggt caactgtcct gaaccagcaa cccttactcc agcctttgaa cttggaactc | 2280 | |
| tctccagaag aagaagtaac tgtgttaatg cacatggata ttatcaggga aaatggcttt | 2340 | |
| cttctagagg agaatccaag tgctcctccc ggaaaacact ttagactacg agccattcct | 2400 | |
| tatagcaaga atatcacctt tggagtcgaa gatcttaaag acctgatctc aactctagga | 2460 | |
| gataaccatg gggaatgttc ggttgctagt agctacaaaa ccagcaaaac agattcgatt | 2520 | |

-continued

```
tgtccatcac gagtccgtgc aatgctagca tcccgagcat gcagatcatc tgtgatgatc    2580
ggagatccac tcagaaaaaa cgaaatgcag aagatagtag aacacttggc agatctcgaa    2640
tctccttgga attgcccaca cggacgacca acaatgcgtc atcttgtgga cttgacaact    2700
ttactcacat tacctgatga cgacaatgtc aatgatgatg atgatgatga tgcaaccatc    2760
tcattggcat ga                                                        2772
```

```
<210> SEQ ID NO 40
<211> LENGTH: 923
<212> TYPE: PRT
<213> ORGANISM: Arabidopsis thaliana

<400> SEQUENCE: 40
```

| | | | | | | | | | | | | | | |
|---|---|---|---|---|---|---|---|---|---|---|---|---|---|---|
| Met | Gln | Gly | Asp | Ser | Ser | Pro | Ser | Pro | Thr | Thr | Thr | Ser | Ser | Pro | Leu |
| 1 | | | | 5 | | | | | 10 | | | | | 15 | |
| Ile | Arg | Pro | Ile | Asn | Arg | Asn | Val | Ile | His | Arg | Ile | Cys | Ser | Gly | Gln |
| | | | 20 | | | | | 25 | | | | | 30 | | |
| Val | Ile | Leu | Asp | Leu | Ser | Ser | Ala | Val | Lys | Glu | Leu | Val | Glu | Asn | Ser |
| | | 35 | | | | | 40 | | | | | 45 | | | |
| Leu | Asp | Ala | Gly | Ala | Thr | Ser | Ile | Glu | Ile | Asn | Leu | Arg | Asp | Tyr | Gly |
| | 50 | | | | | 55 | | | | | 60 | | | | |
| Glu | Asp | Tyr | Phe | Gln | Val | Ile | Asp | Asn | Gly | Cys | Gly | Ile | Ser | Pro | Thr |
| 65 | | | | | 70 | | | | | 75 | | | | | 80 |
| Asn | Phe | Lys | Val | Leu | Ala | Leu | Lys | His | His | Thr | Ser | Lys | Leu | Glu | Asp |
| | | | | 85 | | | | | 90 | | | | | 95 | |
| Phe | Thr | Asp | Leu | Leu | Asn | Leu | Thr | Thr | Tyr | Gly | Phe | Arg | Gly | Glu | Ala |
| | | | 100 | | | | | 105 | | | | | 110 | | |
| Leu | Ser | Ser | Leu | Cys | Ala | Leu | Gly | Asn | Leu | Thr | Val | Glu | Thr | Arg | Thr |
| | | 115 | | | | | 120 | | | | | 125 | | | |
| Lys | Asn | Glu | Pro | Val | Ala | Thr | Leu | Leu | Thr | Phe | Asp | His | Ser | Gly | Leu |
| | 130 | | | | | 135 | | | | | 140 | | | | |
| Leu | Thr | Ala | Glu | Lys | Lys | Thr | Ala | Arg | Gln | Ile | Gly | Thr | Thr | Val | Thr |
| 145 | | | | | 150 | | | | | 155 | | | | | 160 |
| Val | Arg | Lys | Leu | Phe | Ser | Asn | Leu | Pro | Val | Arg | Ser | Lys | Glu | Phe | Lys |
| | | | | 165 | | | | | 170 | | | | | 175 | |
| Arg | Asn | Ile | Arg | Lys | Glu | Tyr | Gly | Lys | Leu | Val | Ser | Leu | Leu | Asn | Ala |
| | | | 180 | | | | | 185 | | | | | 190 | | |
| Tyr | Ala | Leu | Ile | Ala | Lys | Gly | Val | Arg | Phe | Val | Cys | Ser | Asn | Thr | Thr |
| | | 195 | | | | | 200 | | | | | 205 | | | |
| Gly | Lys | Asn | Pro | Lys | Ser | Val | Val | Leu | Asn | Thr | Gln | Gly | Arg | Gly | Ser |
| | 210 | | | | | 215 | | | | | 220 | | | | |
| Leu | Lys | Asp | Asn | Ile | Ile | Thr | Val | Phe | Gly | Ile | Ser | Thr | Phe | Thr | Ser |
| 225 | | | | | 230 | | | | | 235 | | | | | 240 |
| Leu | Gln | Pro | Val | Ser | Ile | Cys | Val | Ser | Glu | Asp | Cys | Arg | Val | Glu | Gly |
| | | | | 245 | | | | | 250 | | | | | 255 | |
| Phe | Leu | Ser | Lys | Pro | Gly | Gln | Gly | Thr | Gly | Arg | Asn | Leu | Ala | Asp | Arg |
| | | | 260 | | | | | 265 | | | | | 270 | | |
| Gln | Tyr | Phe | Phe | Ile | Asn | Gly | Arg | Pro | Val | Asp | Met | Pro | Lys | Val | Ser |
| | | 275 | | | | | 280 | | | | | 285 | | | |
| Lys | Leu | Val | Asn | Glu | Leu | Tyr | Lys | Asp | Thr | Ser | Ser | Arg | Lys | Tyr | Pro |
| | 290 | | | | | 295 | | | | | 300 | | | | |
| Val | Thr | Ile | Leu | Asp | Phe | Ile | Val | Pro | Gly | Gly | Ala | Cys | Asp | Leu | Asn |
| 305 | | | | | 310 | | | | | 315 | | | | | 320 |
| Val | Thr | Pro | Asp | Lys | Arg | Lys | Val | Phe | Phe | Ser | Asp | Glu | Thr | Ser | Val |

-continued

```
                325                 330                 335
Ile Gly Ser Leu Arg Glu Gly Leu Asn Glu Ile Tyr Ser Ser Asn
            340                 345                 350

Ala Ser Tyr Ile Val Asn Arg Phe Glu Glu Asn Ser Glu Gln Pro Asp
            355                 360                 365

Lys Ala Gly Val Ser Ser Phe Gln Lys Lys Ser Asn Leu Leu Ser Glu
            370                 375             380

Gly Ile Val Leu Asp Val Ser Ser Lys Thr Arg Leu Gly Glu Ala Ile
385                 390                 395                 400

Glu Lys Glu Asn Pro Ser Leu Arg Glu Val Glu Ile Asp Asn Ser Ser
                405                 410                 415

Pro Met Glu Lys Phe Lys Phe Glu Ile Lys Ala Cys Gly Thr Lys Lys
            420                 425                 430

Gly Glu Gly Ser Leu Ser Val His Asp Val Thr His Leu Asp Lys Thr
            435                 440                 445

Pro Ser Lys Gly Leu Pro Gln Leu Asn Val Thr Glu Lys Val Thr Asp
            450                 455                 460

Ala Ser Lys Asp Leu Ser Ser Arg Ser Ser Phe Ala Gln Ser Thr Leu
465                 470                 475                 480

Asn Thr Phe Val Thr Met Gly Lys Arg Lys His Glu Asn Ile Ser Thr
                485                 490                 495

Ile Leu Ser Glu Thr Pro Val Leu Arg Asn Gln Thr Ser Ser Tyr Arg
            500                 505                 510

Val Glu Lys Ser Lys Phe Glu Val Arg Ala Leu Ala Ser Arg Cys Leu
            515                 520                 525

Val Glu Gly Asp Gln Leu Asp Asp Met Val Ile Ser Lys Glu Asp Met
            530                 535                 540

Thr Pro Ser Glu Arg Asp Ser Glu Leu Gly Asn Arg Ile Ser Pro Gly
545                 550                 555                 560

Thr Gln Ala Asp Asn Val Glu Arg His Glu Arg Glu His Glu Lys Pro
                565                 570                 575

Ile Arg Phe Glu Glu Pro Thr Ser Asp Asn Thr Leu Thr Lys Gly Asp
            580                 585                 590

Val Glu Arg Val Ser Glu Asp Asn Pro Arg Cys Ser Gln Pro Leu Arg
            595                 600                 605

Ser Val Ala Thr Val Leu Asp Ser Pro Ala Gln Ser Thr Gly Pro Lys
            610                 615                 620

Met Phe Ser Thr Leu Glu Phe Ser Phe Gln Asn Leu Arg Thr Arg Arg
625                 630                 635                 640

Leu Glu Arg Leu Ser Arg Leu Gln Ser Thr Gly Tyr Val Ser Lys Cys
                645                 650                 655

Met Asn Thr Pro Gln Pro Lys Lys Cys Phe Ala Ala Ala Thr Leu Glu
            660                 665                 670

Leu Ser Gln Pro Asp Asp Glu Arg Lys Ala Arg Ala Leu Ala Ala
            675                 680                 685

Ala Thr Ser Glu Leu Glu Arg Leu Phe Arg Lys Glu Asp Phe Arg Arg
            690                 695                 700

Met Gln Val Leu Gly Gln Phe Asn Leu Gly Phe Ile Ile Ala Lys Leu
705                 710                 715                 720

Glu Arg Asp Leu Phe Ile Val Asp Gln His Ala Ala Asp Glu Lys Phe
                725                 730                 735

Asn Phe Glu His Leu Ala Arg Ser Thr Val Leu Asn Gln Gln Pro Leu
            740                 745                 750
```

-continued

```
Leu Gln Pro Leu Asn Leu Glu Leu Ser Pro Glu Glu Val Thr Val
        755                 760                 765
Leu Met His Met Asp Ile Ile Arg Glu Asn Gly Phe Leu Glu Glu
    770                 775                 780
Asn Pro Ser Ala Pro Pro Gly Lys His Phe Arg Leu Arg Ala Ile Pro
785                 790                 795                 800
Tyr Ser Lys Asn Ile Thr Phe Gly Val Glu Asp Leu Lys Asp Leu Ile
                805                 810                 815
Ser Thr Leu Gly Asp Asn His Gly Glu Cys Ser Val Ala Ser Ser Tyr
            820                 825                 830
Lys Thr Ser Lys Thr Asp Ser Ile Cys Pro Ser Arg Val Arg Ala Met
        835                 840                 845
Leu Ala Ser Arg Ala Cys Arg Ser Ser Val Met Ile Gly Asp Pro Leu
    850                 855                 860
Arg Lys Asn Glu Met Gln Lys Ile Val Glu His Leu Ala Asp Leu Glu
865                 870                 875                 880
Ser Pro Trp Asn Cys Pro His Gly Arg Pro Thr Met Arg His Leu Val
                885                 890                 895
Asp Leu Thr Thr Leu Leu Thr Leu Pro Asp Asp Asn Val Asn Asp
            900                 905                 910
Asp Asp Asp Asp Asp Ala Thr Ile Ser Leu Ala
        915                 920
```

<210> SEQ ID NO 41
<211> LENGTH: 3466
<212> TYPE: DNA
<213> ORGANISM: Arabidopsis thaliana

<400> SEQUENCE: 41

```
ttcgaattct ctcagctcaa acatcgtttt ctctctcact ctctctcaca attccaaaaa      60
atgcagcgcc agagatcgat tttgtctttc ttccaaaaac ccacggcggc gactacgaag     120
ggtttggttt ccggcgatgc tgctagcggc gggggcggca gcggaggacc acgatttaat     180
gtgaaggaag gggatgctaa aggcgacgct tctgtacgtt ttgctgtttc gaaatctgtc     240
gatgaggtta gaggaacgga tactccaccg gagaaggttc cgcgtcgtgt cctgccgtct     300
ggatttaagc cggctgaatc cgccggtgat gcttcgtccc tgttctccaa tattatgcat     360
aagtttgtaa aagtcgatga tcgagattgt tctggagaga ggagccgaga agatgttgtt     420
ccgctgaatg attcatctct atgtatgaag gctaatgatg ttattcctca atttcgttcc     480
aataatggta aaactcaaga agaaaccat gcttttagtt tcagtgggag agctgaactt     540
agatcagtag aagatatagg agtagatggc gatgttcctg gtccagaaac accagggatg     600
cgtccacgtg cttctcgctt gaagcgagtt ctggaggatg aaatgacttt taaggaggat     660
aaggttcctg tattggactc taacaaaagg ctgaaaatgc tccaggatcc ggtttgtgga     720
gagaagaaag aagtaaacga aggaaccaaa tttgaatggc ttgagtcttc tcgaatcagg     780
gatgccaata gaagacgtcc tgatgatccc ctttacgata gaaagacctt acacatacca     840
cctgatgttt tcaagaaaat gtctgcatca caaaagcaat attggagtgt taagagtgaa     900
tatatggaca ttgtgctttt ctttaaagtg gggaatttt atgagctgta tgagctagat     960
gcggaattag gtcacaagga gcttgactgg aagatgacca tgagtggtgt gggaaaatgc    1020
agacaggttg gtatctctga aagtgggata gatgaggcag tgcaaaagct attagctcgt    1080
ggatataaag ttggacgaat cgagcagcta gaaacatctg accaagcaaa agccagaggt    1140
```

```
gctaatacta taattccaag gaagctagtt caggtattaa ctccatcaac agcaagcgag    1200
ggaaacatcg ggcctgatgc cgtccatctt cttgctataa aagagatcaa aatggagcta    1260
caaaagtgtt caactgtgta tggatttgct tttgttgact gtgctgcctt gaggttttgg    1320
gttgggtcca tcagcgatga tgcatcatgt gctgctcttg gagcgttatt gatgcaggtt    1380
tctccaaagg aagtgttata tgacagtaaa gggctatcaa gagaagcaca aaaggctcta    1440
aggaaatata cgttgacagg gtctacggcg gtacagttgg ctccagtacc acaagtaatg    1500
ggggatacag atgctgctgg agttagaaat ataatagaat ctaacggata ctttaaaggt    1560
tcttctgaat catggaactg tgctgttgat ggtctaaatg aatgtgatgt tgcccttagt    1620
gctcttggag agctaattaa tcatctgtct aggctaaagc tagaagatgt acttaagcat    1680
ggggatattt ttccatacca agtttacagg ggttgtctca gaattgatgg ccagacgatg    1740
gtaaatcttg agatatttaa caatagctgt gatggtgtcc ttcagggacc cttgaacaaa    1800
tatcttgaaa actgtgttag tccaactggt aagcgactct aaggaattg gatctgccat    1860 ccactcaaag atgtagaaag catcaataaa cggcttgatg tagttgaaga attcacggca    1920
aactcagaaa gtatgcaaat cactggccag tatctccaca aacttccaga cttagaaaga    1980
ctgctcggac gcatcaagtc tagcgttcga tcatcagcct ctgtgttgcc tgctcttctg    2040
gggaaaaaag tgctgaaaca acgagttaaa gcatttgggc aaattgtgaa agggttcaga    2100
agtggaattg atctgttgtt ggctctacag aaggaatcaa atatgatgag tttgctttat    2160
aaactctgta aacttcctat attagtagga aaaagcgggc tagagttatt tctttctcaa    2220
ttcgaagcag ccatagatag cgactttcca aattatcaga accaagatgt gacagatgaa    2280
aacgctgaaa ctctcacaat acttatcgaa cttttatcg aaagagcaac tcaatggtct    2340
gaggtcattc acaccataag ctgcctagat gtcctgagat cttttgcaat cgcagcaagt    2400
ctctctgctg gaagcatggc caggcctgtt attttcccg aatcagaagc tacagatcag    2460
aatcagaaaa caaagggcc aatacttaaa atccaaggac tatggcatcc atttgcagtt    2520
gcagccgatg gtcaattgcc tgttccgaat gatatactcc ttggcgaggc tagaagaagc    2580
agtggcagca ttcatcctcg gtcattgtta ctgacgggac caaacatggg cggaaaatca    2640
actcttcttc gtgcaacatg tctggccgtt atctttgccc aacttggctg ctacgtgccg    2700
tgtgagtctt gcgaaatctc cctcgtggat actatcttca caaggcttgg cgcatctgat    2760
agaatcatga caggagagag tacctttttg gtagaatgca ctgagacagc gtcagttctt    2820
cagaatgcaa ctcaggattc actagtaatc cttgacgaac tgggcagagg aactagtact    2880
ttcgatggat acgccattgc atactcggtt tttcgtcacc tggtagagaa agttcaatgt    2940
cggatgctct ttgcaacaca ttaccaccct ctcaccaagg aattcgcgtc tcacccacgt    3000
gtcacctcga aacacatggc ttgcgcattc aaatcaagat ctgattatca accacgtggt    3060
tgtgatcaag acctagtgtt cttgtaccgt ttaaccgagg agcttgtcc tgagagctac    3120 ggacttcaag tggcactcat ggctggaata ccaaaccaag tggttgaaac agcatcaggt    3180
gctgctcaag ccatgaagag atcaattggg gaaaacttca agtcaagtga gctaagatct    3240
gagttctcaa gtctgcatga agactggctc aagtcattgg tgggtatttc tcgagtcgcc    3300
cacaacaatg ccccccattgg cgaagatgac tacgacactt tgttttgctt atggcatgag    3360
atcaaatcct cttactgtgt tcccaaataa atggctatga cataacacta tctgaagctc    3420
gttaagtctt ttgcttctct gatgtttatt cctcttaaaa aatgcg              3466
```

<210> SEQ ID NO 42
<211> LENGTH: 1109
<212> TYPE: PRT
<213> ORGANISM: Arabidopsis thaliana

<400> SEQUENCE: 42

```
Met Gln Arg Gln Arg Ser Ile Leu Ser Phe Phe Gln Lys Pro Thr Ala
1               5                   10                  15

Ala Thr Thr Lys Gly Leu Val Ser Gly Asp Ala Ala Ser Gly Gly Gly
            20                  25                  30

Gly Ser Gly Gly Pro Arg Phe Asn Val Lys Glu Gly Asp Ala Lys Gly
        35                  40                  45

Asp Ala Ser Val Arg Phe Ala Val Ser Lys Ser Val Asp Glu Val Arg
    50                  55                  60

Gly Thr Asp Thr Pro Pro Glu Lys Val Pro Arg Arg Val Leu Pro Ser
65                  70                  75                  80

Gly Phe Lys Pro Ala Glu Ser Ala Gly Asp Ala Ser Ser Leu Phe Ser
                85                  90                  95

Asn Ile Met His Lys Phe Val Lys Val Asp Asp Arg Asp Cys Ser Gly
            100                 105                 110

Glu Arg Ser Arg Glu Asp Val Val Pro Leu Asn Asp Ser Ser Leu Cys
        115                 120                 125

Met Lys Ala Asn Asp Val Ile Pro Gln Phe Arg Ser Asn Asn Gly Lys
    130                 135                 140

Thr Gln Glu Arg Asn His Ala Phe Ser Phe Ser Gly Arg Ala Glu Leu
145                 150                 155                 160

Arg Ser Val Glu Asp Ile Gly Val Asp Gly Asp Val Pro Gly Pro Glu
                165                 170                 175

Thr Pro Gly Met Arg Pro Arg Ala Ser Arg Leu Lys Arg Val Leu Glu
            180                 185                 190

Asp Glu Met Thr Phe Lys Glu Asp Lys Val Pro Val Leu Asp Ser Asn
        195                 200                 205

Lys Arg Leu Lys Met Leu Gln Asp Pro Val Cys Gly Glu Lys Lys Glu
    210                 215                 220

Val Asn Glu Gly Thr Lys Phe Glu Trp Leu Glu Ser Ser Arg Ile Arg
225                 230                 235                 240

Asp Ala Asn Arg Arg Pro Asp Asp Pro Leu Tyr Asp Arg Lys Thr
                245                 250                 255

Leu His Ile Pro Pro Asp Val Phe Lys Lys Met Ser Ala Ser Gln Lys
            260                 265                 270

Gln Tyr Trp Ser Val Lys Ser Glu Tyr Met Asp Ile Val Leu Phe Phe
        275                 280                 285

Lys Val Gly Lys Phe Tyr Glu Leu Tyr Glu Leu Asp Ala Glu Leu Gly
    290                 295                 300

His Lys Glu Leu Asp Trp Lys Met Thr Met Ser Gly Val Gly Lys Cys
305                 310                 315                 320

Arg Gln Val Gly Ile Ser Glu Ser Gly Ile Asp Glu Ala Val Gln Lys
                325                 330                 335

Leu Leu Ala Arg Gly Tyr Lys Val Gly Arg Ile Glu Gln Leu Glu Thr
            340                 345                 350

Ser Asp Gln Ala Lys Ala Arg Gly Ala Asn Thr Ile Ile Pro Arg Lys
        355                 360                 365

Leu Val Gln Val Leu Thr Pro Ser Thr Ala Ser Glu Gly Asn Ile Gly
    370                 375                 380
```

```
Pro Asp Ala Val His Leu Leu Ala Ile Lys Glu Ile Lys Met Glu Leu
385                 390                 395                 400

Gln Lys Cys Ser Thr Val Tyr Gly Phe Ala Phe Val Asp Cys Ala Ala
            405                 410                 415

Leu Arg Phe Trp Val Gly Ser Ile Ser Asp Asp Ala Ser Cys Ala Ala
            420                 425                 430

Leu Gly Ala Leu Leu Met Gln Val Ser Pro Lys Glu Val Leu Tyr Asp
            435                 440                 445

Ser Lys Gly Leu Ser Arg Glu Ala Gln Lys Ala Leu Arg Lys Tyr Thr
        450                 455                 460

Leu Thr Gly Ser Thr Ala Val Gln Leu Ala Pro Val Pro Gln Val Met
465                 470                 475                 480

Gly Asp Thr Asp Ala Ala Gly Val Arg Asn Ile Ile Glu Ser Asn Gly
                485                 490                 495

Tyr Phe Lys Gly Ser Ser Glu Ser Trp Asn Cys Ala Val Asp Gly Leu
            500                 505                 510

Asn Glu Cys Asp Val Ala Leu Ser Ala Leu Gly Glu Leu Ile Asn His
            515                 520                 525

Leu Ser Arg Leu Lys Leu Glu Asp Val Leu Lys His Gly Asp Ile Phe
        530                 535                 540

Pro Tyr Gln Val Tyr Arg Gly Cys Leu Arg Ile Asp Gly Gln Thr Met
545                 550                 555                 560

Val Asn Leu Glu Ile Phe Asn Asn Ser Cys Asp Gly Val Leu Gln Gly
                565                 570                 575

Pro Leu Asn Lys Tyr Leu Glu Asn Cys Val Ser Pro Thr Gly Lys Arg
            580                 585                 590

Leu Leu Arg Asn Trp Ile Cys His Pro Leu Lys Asp Val Glu Ser Ile
        595                 600                 605

Asn Lys Arg Leu Asp Val Val Glu Glu Phe Thr Ala Asn Ser Glu Ser
610                 615                 620

Met Gln Ile Thr Gly Gln Tyr Leu His Lys Leu Pro Asp Leu Glu Arg
625                 630                 635                 640

Leu Leu Gly Arg Ile Lys Ser Ser Val Arg Ser Ser Ala Ser Val Leu
                645                 650                 655

Pro Ala Leu Leu Gly Lys Lys Val Leu Lys Gln Arg Val Lys Ala Phe
            660                 665                 670

Gly Gln Ile Val Lys Gly Phe Arg Ser Gly Ile Asp Leu Leu Leu Ala
            675                 680                 685

Leu Gln Lys Glu Ser Asn Met Met Ser Leu Leu Tyr Lys Leu Cys Lys
        690                 695                 700

Leu Pro Ile Leu Val Gly Lys Ser Gly Leu Glu Leu Phe Leu Ser Gln
705                 710                 715                 720

Phe Glu Ala Ala Ile Asp Ser Asp Phe Pro Asn Tyr Gln Asn Gln Asp
                725                 730                 735

Val Thr Asp Glu Asn Ala Glu Thr Leu Thr Ile Leu Glu Leu Phe
            740                 745                 750

Ile Glu Arg Ala Thr Gln Trp Ser Glu Val Ile His Thr Ile Ser Cys
            755                 760                 765

Leu Asp Val Leu Arg Ser Phe Ala Ile Ala Ala Ser Leu Ser Ala Gly
        770                 775                 780

Ser Met Ala Arg Pro Val Ile Phe Pro Glu Ser Glu Ala Thr Asp Gln
785                 790                 795                 800
```

```
Asn Gln Lys Thr Lys Gly Pro Ile Leu Lys Ile Gln Gly Leu Trp His
                805                 810                 815
Pro Phe Ala Val Ala Ala Asp Gly Gln Leu Pro Val Pro Asn Asp Ile
            820                 825                 830
Leu Leu Gly Glu Ala Arg Arg Ser Ser Gly Ser Ile His Pro Arg Ser
        835                 840                 845
Leu Leu Leu Thr Gly Pro Asn Met Gly Gly Lys Ser Thr Leu Leu Arg
    850                 855                 860
Ala Thr Cys Leu Ala Val Ile Phe Ala Gln Leu Gly Cys Tyr Val Pro
865                 870                 875                 880
Cys Glu Ser Cys Glu Ile Ser Leu Val Asp Thr Ile Phe Thr Arg Leu
                885                 890                 895
Gly Ala Ser Asp Arg Ile Met Thr Gly Glu Ser Thr Phe Leu Val Glu
            900                 905                 910
Cys Thr Glu Thr Ala Ser Val Leu Gln Asn Ala Thr Gln Asp Ser Leu
        915                 920                 925
Val Ile Leu Asp Glu Leu Gly Arg Gly Thr Ser Thr Phe Asp Gly Tyr
    930                 935                 940
Ala Ile Ala Tyr Ser Val Phe Arg His Leu Val Glu Lys Val Gln Cys
945                 950                 955                 960
Arg Met Leu Phe Ala Thr His Tyr His Pro Leu Thr Lys Glu Phe Ala
                965                 970                 975
Ser His Pro Arg Val Thr Ser Lys His Met Ala Cys Ala Phe Lys Ser
            980                 985                 990
Arg Ser Asp Tyr Gln Pro Arg Gly Cys Asp Gln Asp Leu Val Phe Leu
        995                 1000                1005
Tyr Arg Leu Thr Glu Gly Ala Cys Pro Glu Ser Tyr Gly Leu Gln
    1010                1015                1020
Val Ala Leu Met Ala Gly Ile Pro Asn Gln Val Val Glu Thr Ala
    1025                1030                1035
Ser Gly Ala Ala Gln Ala Met Lys Arg Ser Ile Gly Glu Asn Phe
    1040                1045                1050
Lys Ser Ser Glu Leu Arg Ser Glu Phe Ser Leu His Glu Asp
    1055                1060                1065
Trp Leu Lys Ser Leu Val Gly Ile Ser Arg Val Ala His Asn Asn
    1070                1075                1080
Ala Pro Ile Gly Glu Asp Asp Tyr Asp Thr Leu Phe Cys Leu Trp
    1085                1090                1095
His Glu Ile Lys Ser Ser Tyr Cys Val Pro Lys
    1100                1105

<210> SEQ ID NO 43
<211> LENGTH: 5307
<212> TYPE: DNA
<213> ORGANISM: Arabidopsis thaliana

<400> SEQUENCE: 43
aaagataagt tcatcgact  tttgtggctc atcaaaggcc atcatcgtcc tctatataca      60
atttagtgct ttatagtaca aaaccttcca cttcccttg  tccaaagttt tccaatttaa     120
tttataaaca ggaataatat tatctatata ataaagtgaa aaataactat cattgtccaa    180
ataatttggt cgttgatcat gttactacaa agaaatgaaa tccttagtag aagtatatat    240
atatatatat ttgtaacaca ctcaaaatgg taggtgttgt tacagacaga tgttcgttag    300
cccagtaagc ccaatatgag atttaatggg ccttgatatt ttatagacca aacattgaaa    360
```

```
cattgcacgc ctggtctcaa agaacgttaa tacacgcgcc gccggttgcc gccaatccgc    420
tttcccgcca aattcgacac cataaatttc ttctagtcgc tttcgattcc agttccactg    480
aaaaaccacg aaagaagaac atttgcaccg tagttgcaga aggtaggtga aggatttagc    540
tttctctatc ttccaatgga gggtaatttc gaggaacaga acaagcttcc ggagctgaaa    600
ttgggtaatg ttaaacccta gtttttttt tctttctcat tttcgtattc gatttcccaa    660
ttgggtttat gggttttgta aaggtctga tatttgttat gcattttttt tttaattttt    720
ggaagatgca aagcaagctc aagggtttct ctcgttctac aaaaccctac caaatgtaag    780
ttctcgtttt ctttcgattt ctgggagaag ttagagcttg tacagtgcct ctaattgcaa    840
taaataacac caattctagt cggaaagtag atgctttaaa attagggttt gaagcaattg    900
tagacatttt gttcattggg aagcgaatta ggaaaaaagg cttaagatt tttagcaatt    960
tctcgatctt tgcttatgtg ggttttgatt gttctttgct tcaggatacg agagctgtta   1020
gattctttga tcgcaaggtg agttcattgt tctcaaatgg tctagacttt ggttgtttaa   1080
atgtcgtcat tgatttatgg aaatttttg aatgcatttg caggattatt atacagctca   1140
tggtgaaaat tcagttttca ttgcaaagac ttattatcat acaaccactg ctctacgtca   1200
gctcgggagt ggttcaaatg ctctttcaag cgtaagcatt agtaggaaca tgttcgaaac   1260
gattgctagg gatcttctcc tggagcgtaa tgatcatact gtagaacttt atgaaggaag   1320
cggatcgaat tggagacttg tgaaaacagg ttctcctgga acattggaa gctttgaaga   1380
tgttttgttt gcaaacaatg aaatgcagga cacaccagtt gttgtctcca tatttccaag   1440
ttttcacgat ggcagatgcg ttattgggat ggcctatgtt gatctgacta ggcgagttct   1500
tggactagct gagtttcttg atgatagccg cttcaccaat ctggagtctt cgttgattgc   1560
tctaggcgca aaagaatgca ttttccagc tgaatccggc aaatccaatg aatgcaaaag   1620
cctgtatgat tccctggaga ggtgtgccgt gatgataaca gagaggaaga aacacgagtt   1680
caaaggaaga gatttagatt cagatcttaa gagattggtg aagggaata ttgagcctgt   1740
tagagatttg gtatccgggt ttgaccttgc gactcctgct ctaggtgcat tactctcgtt   1800
ttctgaactt ctctcaaatg aggataacta tgggaacttc acaatccgca gatatgatat   1860
tggcggattc atgagacttg actctgcagc tatgagggcg ttgaatgtga tggagagcaa   1920
aactgatgct aataagaatt tcagtttgtt tggtctcatg aacagaacat gtaccgcagg   1980
gatgggtaag agactgcttc atatgtggct gaagcaaccc ctcgtggatt tgaatgagat   2040
taagacgaga ttagatatag ttcagtgctt tgttgaagaa gctgggttaa ggcaggatct   2100
tagacagcat ctgaagcgaa tctcagatgt tgagaggctt ttgcgcagtc tcgagagaag   2160
aagaggtggg ttacagcaca ttattaaact ctatcaggta cttccgcac ttcaatctgc   2220
ttctctcaat gttaacaaaa ttgcattttc attgtcctaa atgtgtttat gcaactctga   2280
agttataggt atgttattaa gttcattact aattaagtct tcatcttttc tctgcagtca   2340
gctataaggc ttcccttcat caaaacagct atgcaacagt acaccggaga attcgcatca   2400
ctcatcagcg agaggtacct gaaaaagctt gaggctttat cagatcaaga tcaccttgga   2460
aagttcatcg atttggttga gtgctctgta gatcttgacc agctagaaaa tggagaatac   2520
atgatatctt caaactacga caccaaattg gcatctctga aagatcagaa agaattgctg   2580
gagcagcaga ttcacgaatt gcacaaaaag acagcgatag aacttgatct tcaggtcgac   2640
aaggctctta aacttgacaa agcagcgcaa tttgggcatg tcttcaggat cacgaagaag   2700
```

```
gaagagccaa agatcaggaa gaagctgacg acacagttta tagtgctgga gactcgcaaa   2760
gacggagtga agttcacaaa cacaaagcta aaaaaactgg gcgaccagta ccaaagtgtt   2820
gtggatgatt ataggagctg tcaaaaggag ctcgttgatc gtgtagttga gactgttacc   2880
agcttctctg aggtatgttt agttattcat attaagcatt ggactgttac agaattggtt   2940
gtttaaaatc atagtaaact atatgtgaaa tttatatgta tatttgtatgg ttataggtat   3000 ttgaggactt agctgggtta cttttctgaaa tggatgtttt gttaagcttt gctgatttgg   3060
ctgccagttg ccctactcca tactgtaggc cagaaatcac ctctttggtt agtacaatct   3120
caagttgatt attttgttct gaaaatgaat agttttttct ttccaagttt atgacataat   3180
gttgagagca cggttaataa attgtaggat gctggagata ttgtactaga aggaagcaga   3240
catccatgtg tagaagctca agattgggtg aatttcatac caaatgattg cagactcgta   3300
agtattgaat gtggtaaata aactgagacg tctttgtttt tcttgtttcc cttttgactt   3360
gaacaaatac ttgtttgccc tttactgttc tttgaaatca gatgagaggg aagagttggt   3420
ttcaaatagt aacagggcct aacatgggag ggaagtccac tttcatccgc caggtatgat   3480
gatttcctct agttcagttt tgcttcatag acgtatgact aaagtcggtt tccggccatt   3540
ataaatccca ggttggtgtg attgtgctga tggctcaagt tggttccttt gttccttgtg   3600
ataaagcatc aatttccata agagactgca tcttgcccg tgtaggagca ggcgattgcc   3660
aagtgagttt aagtttagcc ctcaatgaac gaaaaactgc tgatatcctg aacacccta   3720 ttccaacttt ttttccttg gtgtgttagc tgcgtggagt gtcaactttt atgcaagaaa   3780
tgcttgaaac cgcatcgata ttgaaaggcg ctactgataa gtcactgata attatcgatg   3840
aacttggtcg tggaacatca acttatgatg gttttggtta gtttctctgc aatttctctt   3900
ctttcatttg gatgttttta gtaagttttc tattatatat tcatttttat ggtcatatgt   3960
gagatttcag tgctcttgac atcatcgtgg tgaatatatc aggtttagct tgggctatat   4020
gtgagcatct ggttcaagtg aaaagagcac caactctgtt tgctactcac ttccatgaac   4080
ttactgcctt ggctcaagca aactctgagg tctctggtaa cactgttggt gtggcaaact   4140
tccatgtcag cgctcacatt gacactgaaa gccgcaaact caccatgctt tacaaggtct   4200
ggtttataaa ttaaaaaatt gctgatctgt tgcagttaaa agtgtctctg tttttatgtt   4260
taatctaaat tacttatttg attttcttac aaagatgaaa ttgaaattaa ttttgtgtgg   4320
tgtgttgttt gtctggttag gttgaaccag gggcctgtga ccagagcttt gggattcatg   4380
tggcggaatt tgccaacttc cctgaaagcg tcgtggccct cgcaagagag aaagctgcag   4440
agctggaaga tttctctccc tcctcgatga taatcaacaa tgaggtcttg attcatttcc   4500
ccctttgttt ttggttgatg atggaatcat tctatcattc acccattctg cagtttatgc   4560
tatattatta taaatctatg tgacaaagat ttaattctcg tattgttgtt tgcaggagag   4620
tgggaagaga aagagcagag aagatgatcc agatgaagta tcaagagggg cagagcgagc   4680
tcacaagttt ctgaaagagt ttgcagcgat gccacttgat aaaatggagc ttaaagattc   4740
acttcaacgg gtacgtgaga tgaaagatga gctagagaaa gatgctgcag actgccactg   4800
gctcaggcag tttctgtgaa gaacccctga cgttttttgg ttttggtttt tgtaaatagc   4860
ttaaatcggt tcttgtagtt gtggtcgttg cttgggatga aactaaatga gggcaaaaac   4920
ataattctac attttttgtt agtaaagctc gttaatttac tccctagtgc tatcaattat   4980
tttgcctatt ataattgttg atcaagtact tagagcaacc ccaatggttt ctaaacataa   5040
gtttcttatt ttatagagag aaattttatt ataaaaaaat gtgtgggttt cttgattagt   5100
```

-continued

```
gaagaaacca tctccaaaat accttatatt cttatataag gtattttgga gagaatttct    5160
aactattcaa gaaacttaca taattaaata ctattatttt tattgtttta atgttaagaa    5220
acttatattt aaaaccacc aatggaattg ctcttagcta ccatacaaat aattataaaa     5280
atatatcgaa aagtagaaga gccattt                                        5307
```

<210> SEQ ID NO 44
<211> LENGTH: 937
<212> TYPE: PRT
<213> ORGANISM: Arabidopsis thaliana

<400> SEQUENCE: 44

```
Met Glu Gly Asn Phe Glu Glu Gln Asn Lys Leu Pro Glu Leu Lys Leu
1               5                   10                  15

Asp Ala Lys Gln Ala Gln Gly Phe Leu Ser Phe Tyr Lys Thr Leu Pro
            20                  25                  30

Asn Asp Thr Arg Ala Val Arg Phe Phe Asp Arg Lys Asp Tyr Tyr Thr
        35                  40                  45

Ala His Gly Glu Asn Ser Val Phe Ile Ala Lys Thr Tyr Tyr His Thr
    50                  55                  60

Thr Thr Ala Leu Arg Gln Leu Gly Ser Gly Ser Asn Ala Leu Ser Ser
65                  70                  75                  80

Val Ser Ile Ser Arg Asn Met Phe Glu Thr Ile Ala Arg Asp Leu Leu
                85                  90                  95

Leu Glu Arg Asn Asp His Thr Val Glu Leu Tyr Glu Gly Ser Gly Ser
            100                 105                 110

Asn Trp Arg Leu Val Lys Thr Gly Ser Pro Gly Asn Ile Gly Ser Phe
        115                 120                 125

Glu Asp Val Leu Phe Ala Asn Asn Glu Met Gln Asp Thr Pro Val Val
    130                 135                 140

Val Ser Ile Phe Pro Ser Phe His Asp Gly Arg Cys Val Ile Gly Met
145                 150                 155                 160

Ala Tyr Val Asp Leu Thr Arg Arg Val Leu Gly Leu Ala Glu Phe Leu
                165                 170                 175

Asp Asp Ser Arg Phe Thr Asn Leu Glu Ser Ser Leu Ile Ala Leu Gly
            180                 185                 190

Ala Lys Glu Cys Ile Phe Pro Ala Glu Ser Gly Lys Ser Asn Glu Cys
        195                 200                 205

Lys Ser Leu Tyr Asp Ser Leu Arg Cys Ala Val Met Ile Thr Glu
    210                 215                 220

Arg Lys His Glu Phe Lys Gly Arg Asp Leu Asp Ser Asp Leu Lys
225                 230                 235                 240

Arg Leu Val Lys Gly Asn Ile Glu Pro Val Arg Asp Leu Val Ser Gly
                245                 250                 255

Phe Asp Leu Ala Thr Pro Ala Leu Gly Ala Leu Leu Ser Phe Ser Glu
            260                 265                 270

Leu Leu Ser Asn Glu Asp Asn Tyr Gly Asn Phe Thr Ile Arg Arg Tyr
        275                 280                 285

Asp Ile Gly Gly Phe Met Arg Leu Asp Ser Ala Ala Met Arg Ala Leu
    290                 295                 300

Asn Val Met Glu Ser Lys Thr Asp Ala Asn Lys Asn Phe Ser Leu Phe
305                 310                 315                 320

Gly Leu Met Asn Arg Thr Cys Thr Ala Gly Met Gly Lys Arg Leu Leu
                325                 330                 335
```

-continued

His Met Trp Leu Lys Gln Pro Leu Val Asp Leu Asn Glu Ile Lys Thr
            340                 345                 350

Arg Leu Asp Ile Val Gln Cys Phe Val Glu Glu Ala Gly Leu Arg Gln
            355                 360                 365

Asp Leu Arg Gln His Leu Lys Arg Ile Ser Asp Val Glu Arg Leu Leu
            370                 375                 380

Arg Ser Leu Glu Arg Arg Gly Gly Leu Gln His Ile Ile Lys Leu
385                 390                 395                 400

Tyr Gln Ser Ala Ile Arg Leu Pro Phe Ile Lys Thr Ala Met Gln Gln
                405                 410                 415

Tyr Thr Gly Glu Phe Ala Ser Leu Ile Ser Glu Arg Tyr Leu Lys Lys
            420                 425                 430

Leu Glu Ala Leu Ser Asp Gln Asp His Leu Gly Lys Phe Ile Asp Leu
            435                 440                 445

Val Glu Cys Ser Val Asp Leu Asp Gln Leu Glu Asn Gly Glu Tyr Met
450                 455                 460

Ile Ser Ser Asn Tyr Asp Thr Lys Leu Ala Ser Leu Lys Asp Gln Lys
465                 470                 475                 480

Glu Leu Leu Glu Gln Gln Ile His Glu Leu His Lys Lys Thr Ala Ile
                485                 490                 495

Glu Leu Asp Leu Gln Val Asp Lys Ala Leu Lys Leu Asp Lys Ala Ala
            500                 505                 510

Gln Phe Gly His Val Phe Arg Ile Thr Lys Lys Glu Pro Lys Ile
            515                 520                 525

Arg Lys Lys Leu Thr Thr Gln Phe Ile Val Leu Glu Thr Arg Lys Asp
530                 535                 540

Gly Val Lys Phe Thr Asn Thr Lys Leu Lys Lys Leu Gly Asp Gln Tyr
545                 550                 555                 560

Gln Ser Val Val Asp Asp Tyr Arg Ser Cys Gln Lys Glu Leu Val Asp
                565                 570                 575

Arg Val Val Glu Thr Val Thr Ser Phe Ser Glu Val Phe Glu Asp Leu
            580                 585                 590

Ala Gly Leu Leu Ser Glu Met Asp Val Leu Leu Ser Phe Ala Asp Leu
            595                 600                 605

Ala Ala Ser Cys Pro Thr Pro Tyr Cys Arg Pro Glu Ile Thr Ser Leu
            610                 615                 620

Asp Ala Gly Asp Ile Val Leu Glu Gly Ser Arg His Pro Cys Val Glu
625                 630                 635                 640

Ala Gln Asp Trp Val Asn Phe Ile Pro Asn Asp Cys Arg Leu Met Arg
                645                 650                 655

Gly Lys Ser Trp Phe Gln Ile Val Thr Gly Pro Asn Met Gly Gly Lys
            660                 665                 670

Ser Thr Phe Ile Arg Gln Val Gly Val Ile Val Leu Met Ala Gln Val
            675                 680                 685

Gly Ser Phe Val Pro Cys Asp Lys Ala Ser Ile Ser Ile Arg Asp Cys
            690                 695                 700

Ile Phe Ala Arg Val Gly Ala Gly Asp Cys Gln Leu Arg Gly Val Ser
705                 710                 715                 720

Thr Phe Met Gln Glu Met Leu Glu Thr Ala Ser Ile Leu Lys Gly Ala
                725                 730                 735

Thr Asp Lys Ser Leu Ile Ile Ile Asp Glu Leu Gly Arg Gly Thr Ser
            740                 745                 750

```
Thr Tyr Asp Gly Phe Gly Leu Ala Trp Ala Ile Cys Glu His Leu Val
        755                 760                 765
Gln Val Lys Arg Ala Pro Thr Leu Phe Ala Thr His Phe His Glu Leu
    770                 775                 780
Thr Ala Leu Ala Gln Ala Asn Ser Glu Val Ser Gly Asn Thr Val Gly
785                 790                 795                 800
Val Ala Asn Phe His Val Ser Ala His Ile Asp Thr Glu Ser Arg Lys
                805                 810                 815
Leu Thr Met Leu Tyr Lys Val Glu Pro Gly Ala Cys Asp Gln Ser Phe
            820                 825                 830
Gly Ile His Val Ala Glu Phe Ala Asn Phe Pro Glu Ser Val Val Ala
        835                 840                 845
Leu Ala Arg Glu Lys Ala Ala Glu Leu Glu Asp Phe Ser Pro Ser Ser
    850                 855                 860
Met Ile Ile Asn Asn Glu Glu Ser Gly Lys Arg Lys Ser Arg Glu Asp
865                 870                 875                 880
Asp Pro Asp Glu Val Ser Arg Gly Ala Glu Arg Ala His Lys Phe Leu
                885                 890                 895
Lys Glu Phe Ala Ala Met Pro Leu Asp Lys Met Glu Leu Lys Asp Ser
            900                 905                 910
Leu Gln Arg Val Arg Glu Met Lys Asp Glu Leu Glu Lys Asp Ala Ala
        915                 920                 925
Asp Cys His Trp Leu Arg Gln Phe Leu
    930                 935

<210> SEQ ID NO 45
<211> LENGTH: 3521
<212> TYPE: DNA
<213> ORGANISM: Arabidopsis thaliana

<400> SEQUENCE: 45
ctaagaaagc gcgcgaaaat tggcaaccca agttcgccat agccacgacc acgaccttcc     60
atttctctta aacggaggag attacgaata aagcaattat gggcaagcaa aagcagcaga    120
cgatttctcg tttcttcgct cccaaaccca atccccgac tcacgaaccg aatccggtag    180
ccgaatcatc aacaccgcca ccgaagatat ccgccactgt atccttctct ccttccaagc    240
gtaagcttct ctccgaccac ctcgccgccg cgtcacccaa aaagcctaaa ctttctcctc    300
acactcaaaa cccagtaccc gatcccaatt tacaccaaag atttctccag agatttctgg    360
aaccctcgcc ggaggaatat gttccgaaa cgtcatcatc gaggaaatac acaccattgg    420
aacagcaagt ggtggagcta aagagcaagt acccagatgt ggttttgatg gtggaagttg    480
gttacaggta cagattcttc ggagaagacg cggagatcgc agcacgcgtg ttgggtattt    540
acgctcatat ggatcacaat ttcatgacgg cgagtgtgcc aacatttcga ttgaatttcc    600
atgtgagaag actggtgaat gcaggataca agattggtgt agtgaagcag actgaaactg    660
cagccattaa gtcccatggt gcaaaccgga ccggcccttt tttccgggga ctgtcggcgt    720
tgtataccaa agccacgctt gaagcggctg aggataaag tggtggttgt ggtggtgaag    780
aaggttttgg ttcacagagt aatttcttgg tttgtgttgt ggatgagaga gttaagtcgg    840
agacattagg ctgtggtatt gaatgagtt ttgatgttag agtcggtgtt gttggcgttg    900
aaatttcgac aggtgaagtt gtttatgaag agttcaatga taatttcatg agaagtggat    960
tagaggctgt gattttgagc ttgtcaccag ctgagctgtt gcttggccag cctcttttcac   1020 aacaaactga gaagtttttg gtggcacatg ctggacctac ctcaaacgtt cgagtggaac   1080
```

```
gtgcctcact ggattgtttc agcaatggta atgcagtaga tgaggttatt tcattatgtg   1140
aaaaaatcag cgcaggtaac ttagaagatg ataaagaaat gaagctggag gctgctgaaa   1200
aaggaatgtc ttgcttgaca gttcatacaa ttatgaacat gccacatctg actgttcaag   1260
ccctcgccct aacgttttgc catctcaaac agtttggatt tgaaaggatc ctttaccaag   1320
gggcctcatt tcgctctttg tcaagtaaca cagagatgac tctctcagcc aatactctgc   1380
aacagttgga ggttgtgaaa ataattcag atggatcgga atctggctcc ttattccata   1440
atatgaatca cacacttaca gtatatggtt ccaggcttct tagacactgg gtgactcatc   1500
ctctatgcga tagaaatttg atatctgctc ggcttgatgc tgtttctgag atttctgctt   1560
gcatgggatc tcatagttct tcccagctca gcagtgagtt ggttgaagaa ggttctgaga   1620
gagcaattgt atcacctgag ttttatctcg tgctctcctc agtcttgaca gctatgtcta   1680
gatcatctga tattcaacgt ggaataacaa gaatctttca tcggactgct aaagccacag   1740
agttcattgc agttatggaa gctattttac ttgcggggaa gcaaattcag cggcttggca   1800
taaagcaaga ctctgaaatg aggagtatgc aatctgcaac tgtgcgatct actcttttga   1860
gaaaattgat ttctgttatt tcatcccctg ttgtggttga caatgccgga aaacttctct   1920
ctgccctaaa taaggaagcg gctgttcgag gtgacttgct cgacatacta atcacttcca   1980
gcgaccaatt tcctgagctt gctgaagctc gccaagcagt tttagtcatc agggaaaagc   2040
tggattcctc gatagcttca tttcgcaaga agctcgctat tcgaaatttg gaatttcttc   2100
aagtgtcggg gatcacacat tgatagagc tgcccgttga ttccaaggtc cctatgaatt   2160
gggtgaaagt aaatagcacc aagaagacta ttcgatatca tcccccagaa atagtagctg   2220
gcttggatga gctagctcta gcaactgaac atcttgccat tgtgaaccga gcttcgtggg   2280
atagtttcct caagagtttc agtagatact acacagattt taaggctgcc gttcaagctc   2340
ttgctgcact ggactgtttg cactcccttt caactctatc tagaaacaag aactatgtcc   2400
gtcccgagtt tgtggatgac tgtgaaccag ttgagataaa catacagtct ggtcgtcatc   2460
ctgtactgga gactatatta caagataact tcgtcccaaa tgacacaatt ttgcatgcag   2520
aaggggaata ttgccaaatt atcaccggac taacatggg aggaaagagc tgctatatcc   2580
gtcaagttgc tttaatttcc ataatggctc aggttggttc cttttgtacca gcgtcattcg   2640 ccaagctgca cgtgcttgat ggtgttttca ctcggatggg tgcttcagac agtatccagc   2700
atggcagaag tacctttcta gaagaattaa gtgaagcgtc acacataatc agaacctgtt   2760
cttctcgttc gcttgttata ttagatgagc ttggaagagg cactagcaca cacgacggtg   2820
tagccattgc ctatgcaaca ttacagcatc tcctagcaga aaagagatgt ttggttcttt   2880
ttgtcacgca ttaccctgaa atagctgaga tcagtaacgg attcccaggt tctgttggga   2940
cataccatgt ctcgtatctg acattgcaga aggataaagg cagttatgat catgatgatg   3000
tgacctacct atataagctt gtgcgtggtc tttgcagcag gagctttggt tttaaggttg   3060
ctcagcttgc ccagatacct ccatcatgta tacgtcgagc catttcaatg gctgcaaaat   3120
tggaagctga ggtacgtgca agagagagaa atacacgcat gggagaacca gaaggacatg   3180
aagaaccgag aggcgcagaa gaatctattt cggctctagg tgacttgttt gcagacctga   3240
aatttgctct ctctgaagag gacccttgga aagcattcga gttttttaaag catgcttgga   3300 agattgctgg caaaatcaga ctaaaaccaa cttgttcatt ttgatttaat cttaacatta   3360
tagcaactgc aaggtcttga tcatctgtta gttgcgtact aacttatgtg tattagtata   3420
```

```
acaagaaaag agaattagag agatggattc taatccggtg ttgcagtaca tcttttctcc    3480
acccgcataa aaaaaaaaaa aaaaaaaaaa aaaaaaaaa a                         3521
```

<210> SEQ ID NO 46
<211> LENGTH: 1081
<212> TYPE: PRT
<213> ORGANISM: Arabidopsis thaliana

<400> SEQUENCE: 46

```
Met Gly Lys Gln Lys Gln Gln Thr Ile Ser Arg Phe Phe Ala Pro Lys
 1               5                  10                  15

Pro Lys Ser Pro Thr His Glu Pro Asn Pro Val Ala Glu Ser Ser Thr
            20                  25                  30

Pro Pro Pro Lys Ile Ser Ala Thr Val Ser Phe Ser Pro Ser Lys Arg
        35                  40                  45

Lys Leu Leu Ser Asp His Leu Ala Ala Ala Ser Pro Lys Lys Pro Lys
    50                  55                  60

Leu Ser Pro His Thr Gln Asn Pro Val Pro Asp Pro Asn Leu His Gln
65                  70                  75                  80

Arg Phe Leu Gln Arg Phe Leu Glu Pro Ser Pro Glu Glu Tyr Val Pro
                85                  90                  95

Glu Thr Ser Ser Ser Arg Lys Tyr Thr Pro Leu Glu Gln Gln Val Val
            100                 105                 110

Glu Leu Lys Ser Lys Tyr Pro Asp Val Val Leu Met Val Glu Val Gly
        115                 120                 125

Tyr Arg Tyr Arg Phe Phe Gly Glu Asp Ala Glu Ile Ala Ala Arg Val
130                 135                 140

Leu Gly Ile Tyr Ala His Met Asp His Asn Phe Met Thr Ala Ser Val
145                 150                 155                 160

Pro Thr Phe Arg Leu Asn Phe His Val Arg Arg Leu Val Asn Ala Gly
                165                 170                 175

Tyr Lys Ile Gly Val Val Lys Gln Thr Glu Thr Ala Ala Ile Lys Ser
            180                 185                 190

His Gly Ala Asn Arg Thr Gly Pro Phe Phe Arg Gly Leu Ser Ala Leu
        195                 200                 205

Tyr Thr Lys Ala Thr Leu Glu Ala Ala Glu Asp Ile Ser Gly Gly Cys
    210                 215                 220

Gly Gly Glu Glu Gly Phe Gly Ser Gln Ser Asn Phe Leu Val Cys Val
225                 230                 235                 240

Val Asp Glu Arg Val Lys Ser Glu Thr Leu Gly Cys Gly Ile Glu Met
                245                 250                 255

Ser Phe Asp Val Arg Val Gly Val Gly Val Glu Ile Ser Thr Gly
            260                 265                 270

Glu Val Val Tyr Glu Glu Phe Asn Asp Asn Phe Met Arg Ser Gly Leu
        275                 280                 285

Glu Ala Val Ile Leu Ser Leu Ser Pro Ala Glu Leu Leu Leu Gly Gln
    290                 295                 300

Pro Leu Ser Gln Gln Thr Glu Lys Phe Leu Val Ala His Ala Gly Pro
305                 310                 315                 320

Thr Ser Asn Val Arg Val Glu Arg Ala Ser Leu Asp Cys Phe Ser Asn
                325                 330                 335

Gly Asn Ala Val Asp Glu Val Ile Ser Leu Cys Glu Lys Ile Ser Ala
            340                 345                 350

Gly Asn Leu Glu Asp Asp Lys Glu Met Lys Leu Glu Ala Ala Glu Lys
```

-continued

```
               355                 360                 365
Gly Met Ser Cys Leu Thr Val His Thr Ile Met Asn Met Pro His Leu
        370                 375                 380
Thr Val Gln Ala Leu Ala Leu Thr Phe Cys His Leu Lys Gln Phe Gly
385                 390                 395                 400
Phe Glu Arg Ile Leu Tyr Gln Gly Ala Ser Phe Arg Ser Leu Ser Ser
                405                 410                 415
Asn Thr Glu Met Thr Leu Ser Ala Asn Thr Leu Gln Gln Leu Glu Val
            420                 425                 430
Val Lys Asn Asn Ser Asp Gly Ser Glu Ser Gly Ser Leu Phe His Asn
        435                 440                 445
Met Asn His Thr Leu Thr Val Tyr Gly Ser Arg Leu Leu Arg His Trp
    450                 455                 460
Val Thr His Pro Leu Cys Asp Arg Asn Leu Ile Ser Ala Arg Leu Asp
465                 470                 475                 480
Ala Val Ser Glu Ile Ser Ala Cys Met Gly Ser His Ser Ser Ser Gln
                485                 490                 495
Leu Ser Ser Glu Leu Val Glu Glu Gly Ser Glu Arg Ala Ile Val Ser
            500                 505                 510
Pro Glu Phe Tyr Leu Val Leu Ser Ser Val Leu Thr Ala Met Ser Arg
        515                 520                 525
Ser Ser Asp Ile Gln Arg Gly Ile Thr Arg Ile Phe His Arg Thr Ala
    530                 535                 540
Lys Ala Thr Glu Phe Ile Ala Val Met Glu Ala Ile Leu Leu Ala Gly
545                 550                 555                 560
Lys Gln Ile Gln Arg Leu Gly Ile Lys Gln Asp Ser Glu Met Arg Ser
                565                 570                 575
Met Gln Ser Ala Thr Val Arg Ser Thr Leu Leu Arg Lys Leu Ile Ser
            580                 585                 590
Val Ile Ser Ser Pro Val Val Asp Asn Ala Gly Lys Leu Leu Ser
        595                 600                 605
Ala Leu Asn Lys Glu Ala Ala Val Arg Gly Asp Leu Leu Asp Ile Leu
    610                 615                 620
Ile Thr Ser Ser Asp Gln Phe Pro Glu Leu Ala Glu Ala Arg Gln Ala
625                 630                 635                 640
Val Leu Val Ile Arg Glu Lys Leu Asp Ser Ser Ile Ala Ser Phe Arg
                645                 650                 655
Lys Lys Leu Ala Ile Arg Asn Leu Glu Phe Leu Gln Val Ser Gly Ile
            660                 665                 670
Thr His Leu Ile Glu Leu Pro Val Asp Ser Lys Val Pro Met Asn Trp
        675                 680                 685
Val Lys Val Asn Ser Thr Lys Lys Thr Ile Arg Tyr His Pro Pro Glu
    690                 695                 700
Ile Val Ala Gly Leu Asp Glu Leu Ala Leu Ala Thr Glu His Leu Ala
705                 710                 715                 720
Ile Val Asn Arg Ala Ser Trp Asp Ser Phe Leu Lys Ser Phe Ser Arg
                725                 730                 735
Tyr Tyr Thr Asp Phe Lys Ala Val Gln Ala Leu Ala Ala Leu Asp
            740                 745                 750
Cys Leu His Ser Leu Ser Thr Leu Ser Arg Asn Lys Asn Tyr Val Arg
        755                 760                 765
Pro Glu Phe Val Asp Asp Cys Glu Pro Val Glu Ile Asn Ile Gln Ser
    770                 775                 780
```

-continued

Gly Arg His Pro Val Leu Glu Thr Ile Leu Gln Asp Asn Phe Val Pro
785                 790                 795                 800

Asn Asp Thr Ile Leu His Ala Glu Gly Glu Tyr Cys Gln Ile Ile Thr
                805                 810                 815

Gly Pro Asn Met Gly Gly Lys Ser Cys Tyr Ile Arg Gln Val Ala Leu
                820                 825                 830

Ile Ser Ile Met Ala Gln Val Gly Ser Phe Val Pro Ala Ser Phe Ala
            835                 840                 845

Lys Leu His Val Leu Asp Gly Val Phe Thr Arg Met Gly Ala Ser Asp
        850                 855                 860

Ser Ile Gln His Gly Arg Ser Thr Phe Leu Glu Glu Leu Ser Glu Ala
865                 870                 875                 880

Ser His Ile Ile Arg Thr Cys Ser Ser Arg Ser Leu Val Ile Leu Asp
                885                 890                 895

Glu Leu Gly Arg Gly Thr Ser Thr His Asp Gly Val Ala Ile Ala Tyr
            900                 905                 910

Ala Thr Leu Gln His Leu Leu Ala Glu Lys Arg Cys Leu Val Leu Phe
        915                 920                 925

Val Thr His Tyr Pro Glu Ile Ala Glu Ile Ser Asn Gly Phe Pro Gly
        930                 935                 940

Ser Val Gly Thr Tyr His Val Ser Tyr Leu Thr Leu Gln Lys Asp Lys
945                 950                 955                 960

Gly Ser Tyr Asp His Asp Asp Val Thr Tyr Leu Tyr Lys Leu Val Arg
                965                 970                 975

Gly Leu Cys Ser Arg Ser Phe Gly Phe Lys Val Ala Gln Leu Ala Gln
            980                 985                 990

Ile Pro Pro Ser Cys Ile Arg Arg  Ala Ile Ser Met Ala  Ala Lys Leu
        995                 1000                1005

Glu Ala  Glu Val Arg Ala  Arg  Glu Arg Asn Thr Arg  Met Gly Glu
    1010                1015                1020

Pro Glu  Gly His Glu Glu Pro  Arg Gly Ala Glu Glu  Ser Ile Ser
    1025                1030                1035

Ala Leu  Gly Asp Leu Phe Ala  Asp Leu Lys Phe Ala  Leu Ser Glu
    1040                1045                1050

Glu Asp  Pro Trp Lys Ala Phe  Glu Phe Leu Lys His  Ala Trp Lys
    1055                1060                1065

Ile Ala  Gly Lys Ile Arg Leu  Lys Pro Thr Cys Ser  Phe
    1070                1075                1080

<210> SEQ ID NO 47
<211> LENGTH: 7080
<212> TYPE: DNA
<213> ORGANISM: Arabidopsis thaliana

<400> SEQUENCE: 47
ctcttcgccg actgtttcac tccccttctc tctcactctc tgtgcgcttt attccactct      60
ccgatggctc cgtctcgccg acagatcagc ggaagatctc cgttggtgaa ccagcagcgt     120
caaatcacct ccttctttgg gaaatctgct tcatcatctt cttctccgtc tccatctcct     180
tcaccatctc tctccaataa gaaaccccca aatctaaaca acctaaccc taaatctccg      240 tctccgtcac catctccgcc taagaaaacc cccaaattga accctaaccc tagttctaat     300
cttcctgctc gtagtcctag ccctggtcct gatactcctt ctcctgtaca gtccaagttt     360
aagaagcccc ttctcgtcat cggacagaca ccttcgcctc ctcaatcggt ggtaattact     420

-continued

```
tacggtgacg aggtggtggg gaagcaagtt agggtttatt ggcctttgga taaaaaatgg      480
tatgatggga gcgtgacgtt ttatgataag ggtgagggta agcatgtggt tgagtatgaa      540
gatggggaag aagagtcttt ggatttggga aaggagaaga ctgagtgggt ggttggggaa      600
aaatcaggag ataggtttaa tcgattgaaa cgaggcgctt cggctttgag aaaagttgtg      660
acggatagtg atgatgatgt ggagatgggt aatgtggaag aagataaaag tgacggtgat      720
gattctagcg atgaggattg gggaaagaat gttgggaagg aggtttgtga gagtgaagaa      780
gatgatgtgg agttggttga tgagaatgaa atggatgaag aagagttggt ggaagagaaa      840
gatgaagaaa cttctaaagt taatagagta tccaaaactg actctagaaa gcggaagact      900
agtgaagtaa cgaaatcagg tggtgagaag aaaagcaaga ctgatacagg cactatcttg      960
aaaggtttta aggcttctgt tgtggagcct gcgaagaaga ttggacaagg taaaccgaag     1020
agtctcttgt tgtaatcata tgcttgtatt tgcattgttt tagtttgtgg tatgtctctt     1080
gcactgactt ttgtttcaga tagtgtatgt tgttggttgc ttaatattat ttgtgtctta     1140
ctacagctga tagggtggtc aagggtttgg aagataacgt gttggatggg gatgctcttg     1200
ctagatttgg tgctcgtgat tctgagaaat tccgcttttt gggagtgtaa gtctttcaca     1260
aaaaaaattc catcttagag gctatttgct acggtggtta ggagtagaga atgtaaattt     1320
gtgtcttaag caatattgac ttctctactg gcaggagcat ctctggtttt cttttatctt     1380
catgatgtat tagtaggctg catgatccct attctagcta agttagttct gttaattatt     1440
tttggtgaac agagaccgaa gggatgctaa aaggagacgc cctactgatg agaattatga     1500
tccgaggaca ctctacctcc ctcctgattt tgtgaaaaaa ttaactggag gccaggtcag     1560
aagagcgcat ggaaatctgg ttcaggattt ttggtgaagc taatcaactt tcacttatat     1620
gattttgtgg cctttttca gagacaatgg tgggagttta aagcaaagca tatggacaaa     1680
gttgtattct tcaaggtaga acgataatta cttatttcgt tataacttat ttattgatgg     1740
gagattctag gataaatggt cttcttttgt ggcaagcaga tgggtaaatt ctatgagctt     1800
tttgagatgg atgcacatgt cggagctaag gaactggata tacaatacat gaaggtaact     1860
gtttgttatg actcataact aggtgatgca tttgaagaca tctgttaaaa atgttaaaaa     1920
accgaaaatt tggcatcaga ttatgctaaa agggttcttt tcattggtgt tacattacaa     1980
atttctcctg tattgtctct aatgtatctc tctttacaag cccctgacat atgcatttat     2040
tttgtaggga gagcaacctc attgtggatt tccgagaaga aatttttctg taaacattga     2100
gaaattagtt agaaaggttt gtttccagaa atatagcaac tccagttcaa gcgtgatcta     2160
tttcttgtta cgtgtagaga aattacattc atggcaaatg ctgtactttg ggtagaaata     2220
aagttgattg aattgaatgg aacagggcta tcgggtttta gttgtcgaac aaacagaaac     2280
acctgatcag ctggagcaac gccgaaaaga gacaggttcc aaggataaag tatgtcccac     2340
tatgaatcta atttagttgg cattatcagt tcaagtcaat ttgtttgctc ttgaaactaa     2400
aatttgttca ctttgggtga tgcctatgta gaaaaattat gatagggagg gctcatagtg     2460
acagaacttc tgtttttata ggttgtgaag cgcgaagtat gtgcagttgt tacaaaaggc     2520
acgctgacag atggggagat gctattaact aatccggatg catcttatct aatggccttg     2580
actgaaggag gagaaagttt aactaatcct acagcagagc acaattttgg tgtatgtttg     2640
gttgatgttg cgacacagaa gataaactgg ggccaggtga gttctagttg atgaatggta     2700
cctggttgca cttatacgta acatttctcg gtgtatattg atggcatttt ttttcattc     2760
```

```
gtaccagttt aaggatgatc aagattgcag tgcattatct tgcctgctat ctgagatgag   2820
gccggtggaa attattaaac cagctaaggt gttgagttat gcaacagaga gaacaatagt   2880
tagacaaacc agaaatccct tagtaaataa tctcgttcca ctttctgaat tttgggattc   2940
ggagaagacc atatatgaag ttggaattat ctacaagcga atcaattgtc aaccgtcttc   3000
tgcttattct agtgagggaa agattctagg tgatggttca agctttcttc caaaaatgtt   3060
gtctgaatta gcaactgaag ataagaatgg tagcctggca ctctctgctc ttggtggtgc   3120
catttactac ctgcgacaag cattcttgga tgagagtctg cttagatttg caaagtttga   3180
atccctgcct tactgtgatt tcagcaacgt taatgagaag cagcacatgg ttcttgatgc   3240
tgctgctctt gaaaaccttg agatatttga aaacagtaga atggaggct attcagggta   3300 aagtttctct atcttaccat gtattattaa acataattga tgtgttctaa atctagagtg   3360
ttgtcttttg aagaacgctg tatgctcaac tgaatcaatg tatcactgca tctgggaaac   3420
ggttactgaa acatggctg gcaagacctt tatataatac ggaactgatc aaggaacgac   3480
aagatgctgt agcaattctg cgggtgagtc tttcaacaag ttgtttgact ttgctgctgt   3540
catttctctg tctctcaact agacaataac ttggcatctt ggtttcacat ttgatcattt   3600
ttcatgtctg tttcgctatc catggatctc tcctcagaat tacactattt ccccattatg   3660
ggtgttcaag accattttg ccactgtttc actggcaaag atgatgtttt cctatgcgtt   3720
caactaacca tctatttcta gaacttattc cctaagatta taaaacttac tctgcttctt   3780
cagcatgtca aggctttcgt ttacactatc catctgacaa tgtattatgg tactgtccct   3840
tccctcaggg tgaaaatctt ccgtactcac tggaattccg gaagtcgttg tccagacttc   3900
cagacatgga acggttgatt gcacgtatgt tttctagcat gtaagggatt agctagattg   3960
agatgttaat tcttacatta tatgtttata ccaaagactt actaaacata tttgttaaac   4020
ttgtgttacg tgttatagtg aagctagtgg aagaaatggc gataaagtgg tgctatatga   4080
agatacagct aagaagcagg tacaggaatt catatcaact ctacgtggtt gtgaaacaat   4140
ggcagaagca tgctcttctc tccgtgctat cttgaagcat gatacatcca ggcggctgct   4200
tcatttacta actcctggta taatcaattt gctccatatt cacattctta tactggcaaa   4260
ttgcacagca tctcatatca tttctctgcc aggtcaaagt cttccaaata tatcatcctc   4320
cataaagtat ttcaaggatg cttttgactg ggtagaagct cacaattctg gacgtgtaat   4380
accccatgaa ggagcagatg aagagtatga ttgtgcctgc aaaacagtag aagaatttga   4440
gtccagtttg aaaaaacatc tgaaagagca acggaaatta ctcggagatg catcagtgag   4500
aattacttca ctattttttt ttactcctta aatggctaat caaccgaggg ttttctgatc   4560
agatctttgg tgctcttttg tcttcttatc cagataaact atgttacagt tggaaaagat   4620
gaatacctct tggaagttcc tgaaagttta agtgggagtg ttcctcatga ttatgaatta   4680
tgctcatcga aaaaggtaaa agttgtacca agtttcacat tctaaagaaa ttggcatttc   4740
gctttcgtca taacaagtcg atagtcttct cgtaattgct gtctgctgat atatttacta   4800
tatagagacc cttaattta aacatgagat tttcttactt tttactctct ttcagggtgt   4860
ctctcgatat tggactccta ccataaagaa attattaaaa gagctatcac aagcaaaatc   4920
tgaaaaagag tcgccctga agagcatttc acagagattg attggacgtt tctgcgagca   4980
tcaagaaaaa tggagacaat tggtttctgc aacagctggt atggacaagt tcatgtttta   5040
aaaaaaaaaa attgtttaag gaattttcag catcttcctt cagaatatgt atcttgctta   5100
tccaattcct gttaattact gtcacccagt gttagctttg tgggtcgtcg cttggaccct   5160
```

-continued

| | |
|---|---|
| tttcgttgtg aacatttgtt gagctagtta gaattgagtt tgatcccaca ctttatagat | 5220 |
| tgagttagaa gtaggcatgc agaagaaaat gaatcttagg cagacgtata gttcaatcac | 5280 |
| atcttataag caagaggttt cttgggtgga agattgtttt atagaattag gcatgcaaac | 5340 |
| aactttgcac ttagaccttt atgtggatac attttttgaca tgaattcttt ctattgcaga | 5400 |
| gctggacgtg ttgatcagcc tcgcttttgc aagtgattct tatgaaggag taagatgccg | 5460 |
| cccagtaata tctggttcta catctgatgg tgttccacac ttgtctgcca ctggtctagg | 5520 |
| gcatccagtt ctaagggtg attcgttagg cagaggctct tttgtaccaa ataatgtaaa | 5580 |
| gataggtggt gctgagaaag ccagtttcat cctcctcaca ggccctaata tgggtggaaa | 5640 |
| atcaacccctt cttcgccaag tttgcttggc tgtaatcttg gctcaggtaa gctatcattt | 5700 |
| gaaaaaactt tgtaggcaat gggctttgac ccgtttaatt ttgatgaaag aaactcaagc | 5760 |
| aatgatgatc ttttcacaga ttggagcaga gtcccagca gaacctttg aggtttcgcc | 5820 |
| tgttgacaaa atttgtgtcc ggatgggtgc aaaagatcat atcatggcag acaaagcac | 5880 |
| gttttaaca gaactttcag aaactgcggt aatgttggta agtaatgttc attctgtttg | 5940 |
| tcaaattgat tacatgaagc tttctaagat aaatgtgaaa cttgccacag tggttaccct | 6000 |
| tttgagagtt ggtcacaggc tttgttaaac tatgcgaatg ccaacaaacg cactgataga | 6060 |
| atgttttata ttaataatat gcagacatca gccacccgaa actcgctggt ggtgctagat | 6120 |
| gagcttggac gaggaacagc cacatcagat gggcaagcca ttgcgtatgt tgaatcaatt | 6180 |
| attgcgtatc atgtttttttg ggacttactg ttattgttca ctttatctaa aatatcttaa | 6240 |
| ctatttacag ggaatccgta cttgagcact tcatagaaaa ggtgcagtgt agaggattct | 6300 |
| tctctactca ttatcatcgt ctctctgtgg attatcaaac caatccaaag gtattgtgaa | 6360 |
| aagtgtctgc ttcagtttct gggtttgaaa gacttgagaa ctatcaataa taatctgatt | 6420 |
| gtttgtgtac attctgaaac ttgtcaaaaa ccgatcagtc ttgaatattt gtttggatag | 6480 |
| gtctcacttt gccatatggc atgtcaaata ggagaaggaa tcggtggagt agaagaagtt | 6540 |
| acatttctct atagattgac tcctggtgca tgtcctaaaa gttatggagt taacgttgct | 6600 |
| cggttagctg gtaagaacac tgaattctct actccatcac ctctactcag ttaaacagaa | 6660 |
| gcagtcactc atcaaattgt tttggtttta atctccatag gtcttccaga ttacgtactc | 6720 |
| cagagagccg tgataaaatc ccaagaattc gaggctttgt acggtaaaaa ccatagaaaa | 6780 |
| accgatcata aattagcagc aatgataaag cagatcatca gcagtgttgc atcagattct | 6840 |
| gattactcag cttcaaagga ctcattgtgt gagctacact ccatggccaa tacatttctc | 6900 |
| cggttaacca actaatttaa cagctctacg cctttccggt ttgtcgttct tcttgtaact | 6960 |
| cttaaccaa ggtcaatcca cgagcttcgt cgtgtcaaat actaaaacct gagtcagcct | 7020 |
| gaaactaaac tcctgagtag agactcagtt ttgaggtgtg ggtttagctt ctgagtcttt | 7080 |

<210> SEQ ID NO 48
<211> LENGTH: 1324
<212> TYPE: PRT
<213> ORGANISM: Arabidopsis thaliana

<400> SEQUENCE: 48

Met Ala Pro Ser Arg Arg Gln Ile Ser Gly Arg Ser Pro Leu Val Asn
1               5                   10                  15

Gln Gln Arg Gln Ile Thr Ser Phe Phe Gly Lys Ser Ala Ser Ser Ser
            20                  25                  30

```
Ser Ser Pro Ser Pro Ser Pro Ser Leu Ser Asn Lys Lys Thr
    35              40              45

Pro Lys Ser Asn Asn Pro Asn Pro Lys Ser Pro Ser Pro Ser
    50              55              60

Pro Pro Lys Lys Thr Pro Lys Leu Asn Pro Asn Pro Ser Ser Asn Leu
65               70              75                  80

Pro Ala Arg Ser Pro Ser Pro Gly Pro Asp Thr Pro Ser Pro Val Gln
            85              90              95

Ser Lys Phe Lys Lys Pro Leu Leu Val Ile Gly Gln Thr Pro Ser Pro
            100             105             110

Pro Gln Ser Val Val Ile Thr Tyr Gly Asp Glu Val Gly Lys Gln
            115             120             125

Val Arg Val Tyr Trp Pro Leu Asp Lys Lys Trp Tyr Asp Gly Ser Val
    130             135             140

Thr Phe Tyr Asp Lys Gly Glu Gly Lys His Val Val Glu Tyr Glu Asp
145             150             155                 160

Gly Glu Glu Glu Ser Leu Asp Leu Gly Lys Glu Lys Thr Glu Trp Val
                165             170             175

Val Gly Glu Lys Ser Gly Asp Arg Phe Asn Arg Leu Lys Arg Gly Ala
            180             185             190

Ser Ala Leu Arg Lys Val Val Thr Asp Ser Asp Asp Val Glu Met
            195             200             205

Gly Asn Val Glu Glu Asp Lys Ser Asp Gly Asp Ser Ser Asp Glu
    210             215             220

Asp Trp Gly Lys Asn Val Gly Lys Glu Val Cys Glu Ser Glu Glu Asp
225             230             235                 240

Asp Val Glu Leu Val Asp Glu Asn Glu Met Asp Glu Glu Leu Val
            245             250             255

Glu Glu Lys Asp Glu Glu Thr Ser Lys Val Asn Arg Val Ser Lys Thr
            260             265             270

Asp Ser Arg Lys Arg Lys Thr Ser Glu Val Thr Lys Ser Gly Gly Glu
    275             280             285

Lys Lys Ser Lys Thr Asp Thr Gly Thr Ile Leu Lys Gly Phe Lys Ala
    290             295             300

Ser Val Val Glu Pro Ala Lys Lys Ile Gly Gln Ala Asp Arg Val Val
305             310             315                 320

Lys Gly Leu Glu Asp Asn Val Leu Asp Gly Asp Ala Leu Ala Arg Phe
            325             330             335

Gly Ala Arg Asp Ser Glu Lys Phe Arg Phe Leu Gly Val Asp Arg Arg
            340             345             350

Asp Ala Lys Arg Arg Arg Pro Thr Asp Glu Asn Tyr Asp Pro Arg Thr
            355             360             365

Leu Tyr Leu Pro Pro Asp Phe Val Lys Lys Leu Thr Gly Gly Gln Arg
    370             375             380

Gln Trp Trp Glu Phe Lys Ala Lys His Met Asp Lys Val Val Phe Phe
385             390             395                 400

Lys Met Gly Lys Phe Tyr Glu Leu Phe Glu Met Asp Ala His Val Gly
            405             410             415

Ala Lys Glu Leu Asp Ile Gln Tyr Met Lys Gly Glu Gln Pro His Cys
            420             425             430

Gly Phe Pro Glu Lys Asn Phe Ser Val Asn Ile Glu Lys Leu Val Arg
            435             440             445

Lys Gly Tyr Arg Val Leu Val Val Glu Gln Thr Glu Thr Pro Asp Gln
```

-continued

```
            450                 455                 460
Leu Glu Gln Arg Arg Lys Glu Thr Gly Ser Lys Asp Lys Val Val Lys
465                 470                 475                 480

Arg Glu Val Cys Ala Val Val Thr Lys Gly Thr Leu Thr Asp Gly Glu
                485                 490                 495

Met Leu Leu Thr Asn Pro Asp Ala Ser Tyr Leu Met Ala Leu Thr Glu
            500                 505                 510

Gly Gly Glu Ser Leu Thr Asn Pro Thr Ala Glu His Asn Phe Gly Val
            515                 520                 525

Cys Leu Val Asp Val Ala Thr Gln Lys Ile Ile Leu Gly Gln Phe Lys
530                 535                 540

Asp Asp Gln Asp Cys Ser Ala Leu Ser Cys Leu Leu Ser Glu Met Arg
545                 550                 555                 560

Pro Val Glu Ile Ile Lys Pro Ala Lys Val Leu Ser Tyr Ala Thr Glu
                565                 570                 575

Arg Thr Ile Val Arg Gln Thr Arg Asn Pro Leu Val Asn Asn Leu Val
                580                 585                 590

Pro Leu Ser Glu Phe Trp Asp Ser Glu Lys Thr Ile Tyr Glu Val Gly
            595                 600                 605

Ile Ile Tyr Lys Arg Ile Asn Cys Gln Pro Ser Ser Ala Tyr Ser Ser
            610                 615                 620

Glu Gly Lys Ile Leu Gly Asp Gly Ser Ser Phe Leu Pro Lys Met Leu
625                 630                 635                 640

Ser Glu Leu Ala Thr Glu Asp Lys Asn Gly Ser Leu Ala Leu Ser Ala
                645                 650                 655

Leu Gly Gly Ala Ile Tyr Tyr Leu Arg Gln Ala Phe Leu Asp Glu Ser
                660                 665                 670

Leu Leu Arg Phe Ala Lys Phe Glu Ser Leu Pro Tyr Cys Asp Phe Ser
            675                 680                 685

Asn Val Asn Glu Lys Gln His Met Val Leu Asp Ala Ala Leu Glu
            690                 695                 700

Asn Leu Glu Ile Phe Glu Asn Ser Arg Asn Gly Gly Tyr Ser Gly Thr
705                 710                 715                 720

Leu Tyr Ala Gln Leu Asn Gln Cys Ile Thr Ala Ser Gly Lys Arg Leu
                725                 730                 735

Leu Lys Thr Trp Leu Ala Arg Pro Leu Tyr Asn Thr Glu Leu Ile Lys
            740                 745                 750

Glu Arg Gln Asp Ala Val Ala Ile Leu Arg Gly Glu Asn Leu Pro Tyr
            755                 760                 765

Ser Leu Glu Phe Arg Lys Ser Leu Ser Arg Leu Pro Asp Met Glu Arg
770                 775                 780

Leu Ile Ala Arg Met Phe Ser Ser Ile Glu Ala Ser Gly Arg Asn Gly
785                 790                 795                 800

Asp Lys Val Val Leu Tyr Glu Asp Thr Ala Lys Lys Gln Val Gln Glu
                805                 810                 815

Phe Ile Ser Thr Leu Arg Gly Cys Glu Thr Met Ala Glu Ala Cys Ser
            820                 825                 830

Ser Leu Arg Ala Ile Leu Lys His Asp Thr Ser Arg Leu Leu His
            835                 840                 845

Leu Leu Thr Pro Gly Gln Ser Leu Pro Asn Ile Ser Ser Ser Ile Lys
850                 855                 860

Tyr Phe Lys Asp Ala Phe Asp Trp Val Glu Ala His Asn Ser Gly Arg
865                 870                 875                 880
```

```
Val Ile Pro His Glu Gly Ala Asp Glu Tyr Asp Cys Ala Cys Lys
            885                 890                 895

Thr Val Glu Glu Phe Glu Ser Ser Leu Lys Lys His Leu Lys Glu Gln
            900                 905                 910

Arg Lys Leu Leu Gly Asp Ala Ser Ile Asn Tyr Val Thr Val Gly Lys
            915                 920                 925

Asp Glu Tyr Leu Leu Glu Val Pro Glu Ser Leu Ser Gly Ser Val Pro
    930                 935                 940

His Asp Tyr Glu Leu Cys Ser Ser Lys Lys Gly Val Ser Arg Tyr Trp
945                 950                 955                 960

Thr Pro Thr Ile Lys Lys Leu Lys Glu Leu Ser Gln Ala Lys Ser
            965                 970                 975

Glu Lys Glu Ser Ala Leu Lys Ser Ile Ser Gln Arg Leu Ile Gly Arg
            980                 985                 990

Phe Cys Glu His Gln Glu Lys Trp Arg Gln Leu Val Ser Ala Thr Ala
            995                 1000                1005

Glu Leu Asp Val Leu Ile Ser Leu Ala Phe Ala Ser Asp Ser Tyr
    1010                1015                1020

Glu Gly Val Arg Cys Arg Pro Val Ile Ser Gly Ser Thr Ser Asp
    1025                1030                1035

Gly Val Pro His Leu Ser Ala Thr Gly Leu Gly His Pro Val Leu
    1040                1045                1050

Arg Gly Asp Ser Leu Gly Arg Gly Ser Phe Val Pro Asn Asn Val
    1055                1060                1065

Lys Ile Gly Gly Ala Glu Lys Ala Ser Phe Ile Leu Leu Thr Gly
    1070                1075                1080

Pro Asn Met Gly Gly Lys Ser Thr Leu Leu Arg Gln Val Cys Leu
    1085                1090                1095

Ala Val Ile Leu Ala Gln Ile Gly Ala Asp Val Pro Ala Glu Thr
    1100                1105                1110

Phe Glu Val Ser Pro Val Asp Lys Ile Cys Val Arg Met Gly Ala
    1115                1120                1125

Lys Asp His Ile Met Ala Gly Gln Ser Thr Phe Leu Thr Glu Leu
    1130                1135                1140

Ser Glu Thr Ala Val Met Leu Thr Ser Ala Thr Arg Asn Ser Leu
    1145                1150                1155

Val Val Leu Asp Glu Leu Gly Arg Gly Thr Ala Thr Ser Asp Gly
    1160                1165                1170

Gln Ala Ile Ala Glu Ser Val Leu Glu His Phe Ile Glu Lys Val
    1175                1180                1185

Gln Cys Arg Gly Phe Phe Ser Thr His Tyr His Arg Leu Ser Val
    1190                1195                1200

Asp Tyr Gln Thr Asn Pro Lys Val Ser Leu Cys His Met Ala Cys
    1205                1210                1215

Gln Ile Gly Glu Gly Ile Gly Gly Val Glu Glu Val Thr Phe Leu
    1220                1225                1230

Tyr Arg Leu Thr Pro Gly Ala Cys Pro Lys Ser Tyr Gly Val Asn
    1235                1240                1245

Val Ala Arg Leu Ala Gly Leu Pro Asp Tyr Val Leu Gln Arg Ala
    1250                1255                1260

Val Ile Lys Ser Gln Glu Phe Glu Ala Leu Tyr Gly Lys Asn His
    1265                1270                1275
```

| Arg | Lys | Thr | Asp | His | Lys | Leu | Ala | Ala | Met | Ile | Lys | Gln | Ile | Ile |
|-----|-----|-----|-----|-----|-----|-----|-----|-----|-----|-----|-----|-----|-----|-----|
| 1280 | | | | | 1285 | | | | 1290 | | | | | |

| Ser | Ser | Val | Ala | Ser | Asp | Ser | Asp | Tyr | Ser | Ala | Ser | Lys | Asp | Ser |
|-----|-----|-----|-----|-----|-----|-----|-----|-----|-----|-----|-----|-----|-----|-----|
| 1295 | | | | | 1300 | | | | | 1305 | | | | |

| Leu | Cys | Glu | Leu | His | Ser | Met | Ala | Asn | Thr | Phe | Leu | Arg | Leu | Thr |
|-----|-----|-----|-----|-----|-----|-----|-----|-----|-----|-----|-----|-----|-----|-----|
| 1310 | | | | | 1315 | | | | | 1320 | | | | |

Asn

<210> SEQ ID NO 49
<211> LENGTH: 2501
<212> TYPE: DNA
<213> ORGANISM: Oryza sativa

<400> SEQUENCE: 49

```
cggcacgaga ttttgcagtc tcctctcctc ctccgctcga gcgagtgagt cccgaccacg      60
tcgctgccct cgcctcaccg ccggccaacc gccgtgacga gagatcgagc agggcggggc     120
atggacgagc cttcgccgcg cggaggtggg tgcgccgggg agccgccccg catccggagg     180
ttggaggagt cggtggtgaa ccgcatcgcg gcggggagg tgatccagcg gccgtcgtcg      240
gcggtgaagg agctcatcga gaacagcctc gacgctggcg cctccagcgt ctccgttgcg     300
gtgaaggacg gtggcctcaa gctcatccag gtctccgatg acggccatgg catcaggttt     360
gaggatttgg caatattgtg cgaaaggcat actacctcaa agttatctgc atacgaggat     420
ctgcagacca taaatcgat ggggttcaga ggggaggctt tggctagtat gacttatgtt      480
ggccatgtta ccgtgacaac gataacagaa ggccaattgc acggctacag ggtttcttac     540
agagatggtg taatggagaa tgagcctaag ccttgcgctg cggtgaaagg aactcaagtc     600
atggttgaaa atctatttta caacatggta gcccgcaaga aaacattgca gaactccaat     660
gatgactacc ccaagatcgt agacttcatc agtcggtttg cagtccatca catcaacgtt     720
accttctctt gcagaaagca tggagccaat agagcagatg ttcatagtgc aagtacatcc     780
tcaaggttag atgctatcag gagtgtctat ggggcttctg tcgttcgtga tctcatagaa     840
ataaaggttt catatgagga tgctgcagat tcaatcttca agatggatgg ttacatctca     900
aatgcaaatt atgtggcaaa gaagattaca atgattcttt tcataaatga taggcttgta     960
gactgtactg ctttgaaaag agctattgaa tttgtgtact ctgcaacatt gcctcaagca    1020
tccaaacctt tcatatacat gtccatacat cttccatcag aacacgtgga tgttaatata    1080
cacccaacca agaaagaggt tagccttttg aatcaagagc gtattattga acaataagaa    1140
aatgctattg aggaaaaact gatgaattct aatacaacca ggatattcca aactcaggca    1200
ttaaacttat cagggattgc tcaagctaac ccacaaaagg ataaggtttc tgaggccagt    1260
atgggttctg gaacaaaatc tcaaaaaatt cctgtgagcc aaatggtcag aacagatcca    1320
cgcaatccat ctggaagatt gcacacctac tggcacgggc aatcttcaaa tcttgaaaag    1380
aaatttgatc ttgtatctgt aagaaatgtt gtaagatcaa ggagaaacca aaagatgct    1440
ggtgatttgt caagccgtca tgagctcctt gtggaaatag attctagctt ccatcctggc    1500
cttttggaca ttgtcaagaa ctgcacatat gttggacttg ccgatgaagc ctttgctttg    1560
atacaacaca ataccgcctt ataccttgta aatgtggtaa atattagtaa agaacttatg    1620
taccagcaag ctttgtgccg ttttgggaac ttcaatgcta ttcagctcag tgaaccagct    1680
ccacttcagg agttgctggt gatggcactg aaagacgatg aattgatgag tgatgaaaag    1740
gatgatgaga aactggagat tgcagaagta aacactgaga tactaaaaga aatgctgag    1800
```

-continued

```
atgattaatg agtactttc tattcacatt gatcaagatg gcaaattgac aagacttcct      1860
gttgtactgg accagtacac ccctgatatg gaccgtcttc cagaatttgt gttggcttta      1920
ggaaatgatg ttacttggga tgacgagaaa gagtgcttca gaacagtagc ttctgctgta      1980
ggaaacttct atgcacttca tcccccaatc cttccaaatc catctgggaa tggcattcat      2040
ttatacaaga aaatagaga ttcaatggct gatgaacatg ctgagaatga tctaatatca      2100
gatgaaaatg acgttgatca agaacttctt gcggaagcag aagcagcatg ggcccaacgt      2160
gagtggacca ttcagcatgt cttgtttcca tccatgcgac ttttcctcaa gcccccgaag      2220
tcaatggcaa cagatggaac gtttgtgcag gttgcttcct tggagaaact ctacaagatt      2280
tttgaaaggt gttagctcat aagtgagaaa atgaaggcag agtaagatca tgattcatgg      2340 agtgttttg aaaatgtgta taatttcacc gtattatgta ctttgatagt gtctgtagaa      2400
actgaagaaa gaaagatggc tttacttctg aattgaaagt taacgatgcc agcaattgta      2460
tattctgatc aaccaaaaaa aaaaaaaaaa aaaaaaaaa a                           2501
```

<210> SEQ ID NO 50
<211> LENGTH: 724
<212> TYPE: PRT
<213> ORGANISM: Oryza sativa

<400> SEQUENCE: 50

```
Met Asp Glu Pro Ser Pro Arg Gly Gly Gly Cys Ala Gly Glu Pro Pro
1               5                   10                  15

Arg Ile Arg Arg Leu Glu Glu Ser Val Val Asn Arg Ile Ala Ala Gly
            20                  25                  30

Glu Val Ile Gln Arg Pro Ser Ser Ala Val Lys Glu Leu Ile Glu Asn
        35                  40                  45

Ser Leu Asp Ala Gly Ala Ser Ser Val Ser Val Ala Val Lys Asp Gly
    50                  55                  60

Gly Leu Lys Leu Ile Gln Val Ser Asp Asp Gly His Gly Ile Arg Phe
65                  70                  75                  80

Glu Asp Leu Ala Ile Leu Cys Glu Arg His Thr Thr Ser Lys Leu Ser
                85                  90                  95

Ala Tyr Glu Asp Leu Gln Thr Ile Lys Ser Met Gly Phe Arg Gly Glu
            100                 105                 110

Ala Leu Ala Ser Met Thr Tyr Val Gly His Val Thr Val Thr Thr Ile
        115                 120                 125

Thr Glu Gly Gln Leu His Gly Tyr Arg Val Ser Tyr Arg Asp Gly Val
    130                 135                 140

Met Glu Asn Glu Pro Lys Pro Cys Ala Ala Val Lys Gly Thr Gln Val
145                 150                 155                 160

Met Val Glu Asn Leu Phe Tyr Asn Met Val Ala Arg Lys Lys Thr Leu
                165                 170                 175

Gln Asn Ser Asn Asp Asp Tyr Pro Lys Ile Val Asp Phe Ile Ser Arg
            180                 185                 190

Phe Ala Val His His Ile Asn Val Thr Phe Ser Cys Arg Lys His Gly
        195                 200                 205

Ala Asn Arg Ala Asp Val His Ser Ala Ser Thr Ser Ser Arg Leu Asp
    210                 215                 220

Ala Ile Arg Ser Val Tyr Gly Ala Ser Val Val Arg Asp Leu Ile Glu
225                 230                 235                 240

Ile Lys Val Ser Tyr Glu Asp Ala Ala Asp Ser Ile Phe Lys Met Asp
                245                 250                 255
```

```
Gly Tyr Ile Ser Asn Ala Asn Tyr Val Ala Lys Lys Ile Thr Met Ile
            260                 265                 270

Leu Phe Ile Asn Asp Arg Leu Val Asp Cys Thr Ala Leu Lys Arg Ala
        275                 280                 285

Ile Glu Phe Val Tyr Ser Ala Thr Leu Pro Gln Ala Ser Lys Pro Phe
    290                 295                 300

Ile Tyr Met Ser Ile His Leu Pro Ser Glu His Val Asp Val Asn Ile
305                 310                 315                 320

His Pro Thr Lys Lys Glu Val Ser Leu Leu Asn Gln Glu Arg Ile Ile
                325                 330                 335

Glu Thr Ile Arg Asn Ala Ile Glu Glu Lys Leu Met Asn Ser Asn Thr
            340                 345                 350

Thr Arg Ile Phe Gln Thr Gln Ala Leu Asn Leu Ser Gly Ile Ala Gln
        355                 360                 365

Ala Asn Pro Gln Lys Asp Lys Val Ser Glu Ala Ser Met Gly Ser Gly
    370                 375                 380

Thr Lys Ser Gln Lys Ile Pro Val Ser Gln Met Val Arg Thr Asp Pro
385                 390                 395                 400

Arg Asn Pro Ser Gly Arg Leu His Thr Tyr Trp His Gly Gln Ser Ser
                405                 410                 415

Asn Leu Glu Lys Lys Phe Asp Leu Val Ser Val Arg Asn Val Val Arg
            420                 425                 430

Ser Arg Arg Asn Gln Lys Asp Ala Gly Asp Leu Ser Ser Arg His Glu
        435                 440                 445

Leu Leu Val Glu Ile Asp Ser Ser Phe His Pro Gly Leu Leu Asp Ile
    450                 455                 460

Val Lys Asn Cys Thr Tyr Val Gly Leu Ala Asp Glu Ala Phe Ala Leu
465                 470                 475                 480

Ile Gln His Asn Thr Arg Leu Tyr Leu Val Asn Val Val Asn Ile Ser
                485                 490                 495

Lys Glu Leu Met Tyr Gln Gln Ala Leu Cys Arg Phe Gly Asn Phe Asn
            500                 505                 510

Ala Ile Gln Leu Ser Glu Pro Ala Pro Leu Gln Glu Leu Leu Val Met
        515                 520                 525

Ala Leu Lys Asp Asp Glu Leu Met Ser Asp Glu Lys Asp Glu Lys
    530                 535                 540

Leu Glu Ile Ala Glu Val Asn Thr Glu Ile Leu Lys Glu Asn Ala Glu
545                 550                 555                 560

Met Ile Asn Glu Tyr Phe Ser Ile His Ile Asp Gln Asp Gly Lys Leu
                565                 570                 575

Thr Arg Leu Pro Val Val Leu Asp Gln Tyr Thr Pro Asp Met Asp Arg
            580                 585                 590

Leu Pro Glu Phe Val Leu Ala Leu Gly Asn Asp Val Thr Trp Asp Asp
        595                 600                 605

Glu Lys Glu Cys Phe Arg Thr Val Ala Ser Ala Val Gly Asn Phe Tyr
    610                 615                 620

Ala Leu His Pro Pro Ile Leu Pro Asn Pro Ser Gly Asn Gly Ile His
625                 630                 635                 640

Leu Tyr Lys Lys Asn Arg Asp Ser Met Ala Asp Glu His Ala Glu Asn
                645                 650                 655

Asp Leu Ile Ser Asp Glu Asn Asp Val Asp Gln Glu Leu Leu Ala Glu
            660                 665                 670
```

```
Ala Glu Ala Ala Trp Ala Gln Arg Glu Trp Thr Ile Gln His Val Leu
        675                 680                 685

Phe Pro Ser Met Arg Leu Phe Leu Lys Pro Pro Lys Ser Met Ala Thr
    690                 695                 700

Asp Gly Thr Phe Val Gln Val Ala Ser Leu Glu Lys Leu Tyr Lys Ile
705                 710                 715                 720

Phe Glu Arg Cys
```